(12) United States Patent
Tomita et al.

(10) Patent No.: US 9,278,931 B2
(45) Date of Patent: Mar. 8, 2016

(54) CYCLOPROPANEAMINE COMPOUND

(75) Inventors: Naoki Tomita, Tokyo (JP); Shigeo Kajii, Kanagawa (JP); Douglas Robert Cary, Kanagawa (JP); Daisuke Tomita, Kanagawa (JP); Shinichi Imamura, Kanagawa (JP); Ken Tsuchida, Kanagawa (JP); Satoru Matsuda, Kanagawa (JP); Ryujiro Hara, Kanagawa (JP); Yusuke Tominari, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/237,440

(22) PCT Filed: Aug. 8, 2012

(86) PCT No.: PCT/JP2012/070267
§ 371 (c)(1),
(2), (4) Date: Apr. 9, 2014

(87) PCT Pub. No.: WO2013/022047
PCT Pub. Date: Feb. 14, 2013

(65) Prior Publication Data
US 2014/0228405 A1    Aug. 14, 2014

(30) Foreign Application Priority Data

Aug. 9, 2011   (JP) ................... 2011-174305

(51) Int. Cl.
*A61K 31/167*   (2006.01)
*A61K 31/435*   (2006.01)
(Continued)

(52) U.S. Cl.
CPC ............ *C07D 211/98* (2013.01); *A61K 31/167* (2013.01); *A61K 31/36* (2013.01); *A61K 31/366* (2013.01); *A61K 31/381* (2013.01); *A61K 31/40* (2013.01); *A61K 31/402* (2013.01); *A61K 31/404* (2013.01); *A61K 31/4035* (2013.01); *A61K 31/4184* (2013.01); *A61K 31/42* (2013.01); *A61K 31/421* (2013.01); *A61K 31/426* (2013.01); *A61K 31/428* (2013.01); *A61K 31/429* (2013.01); *A61K 31/433* (2013.01); *A61K 31/4406* (2013.01); *A61K 31/4409* (2013.01); *A61K 31/4453* (2013.01); *A61K 31/4468* (2013.01); *A61K 31/451* (2013.01); *A61K 31/495* (2013.01);
(Continued)

(58) Field of Classification Search
CPC . A61K 31/167; A61K 31/435; A61K 31/415; A61K 31/382; C07D 231/22; C07D 231/20; C07D 231/56; C07D 231/14; C07D 295/14; C07C 233/80; C07C 271/22; C07C 235/56; C07C 237/40
See application file for complete search history.

(56) References Cited

U.S. PATENT DOCUMENTS
2010/0324147 A1    12/2010   McCafferty et al.

FOREIGN PATENT DOCUMENTS
WO   2005/014552    2/2005
WO   2010/043721    4/2010
(Continued)

OTHER PUBLICATIONS

Binda, et al., "Biochemical, Structural, and Biological Evaluation of Tranylcypromine Derivatives as Inhibitors of Histone Demethylases LSD1 and LSD2", J. Am. Chem. Soc. 2010, vol. 132, pp. 6827-3833.
(Continued)

*Primary Examiner* — Samantha Shterengarts
(74) *Attorney, Agent, or Firm* — Hamre, Schumann, Mueller & Larson, P.C.

(57) ABSTRACT

The present invention provides a compound having a lysine-specific demethylase 1 inhibitory action, and useful as a medicament such as a prophylactic or therapeutic agent for cancer, and central nervous system diseases, and the like. The present invention relates to a compound represented by the formula

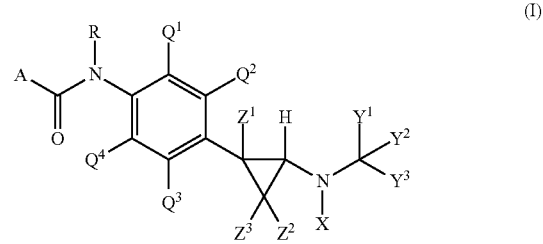

(I)

wherein A is a hydrocarbon group or heterocyclic group optionally having substituent(s); R is H, a hydrocarbon group or heterocyclic group optionally having substituent(s); A and R are optionally bonded to each other to form a ring optionally having substituent(s); $Q^1$, $Q^2$, $Q^3$ and $Q^4$ are each a hydrogen atom or a substituent; $Q^1$ and $Q^2$, and $Q^3$ and $Q^4$, are each optionally bonded to each other to form a ring optionally having substituent(s); X is H, an acyclic hydrocarbon group or saturated cyclic group optionally having substituent(s); $Y^1$, $Y^2$ and $Y^3$ are each H, a hydrocarbon group or heterocyclic group optionally having substituent(s); X and $Y^1$, and $Y^1$ and $Y^2$, are each optionally bonded to each other to form a ring optionally having substituent(s); and $Z^1$, $Z^2$ and $Z^3$ are each H or a substituent, or a salt thereof.

21 Claims, No Drawings

(51) Int. Cl.

| | |
|---|---|
| A61K 31/415 | (2006.01) |
| A61K 31/382 | (2006.01) |
| C07D 295/14 | (2006.01) |
| C07D 231/14 | (2006.01) |
| C07D 231/56 | (2006.01) |
| C07D 231/20 | (2006.01) |
| C07D 231/22 | (2006.01) |
| C07C 233/80 | (2006.01) |
| C07C 271/22 | (2006.01) |
| C07C 235/56 | (2006.01) |
| C07C 237/40 | (2006.01) |
| C07D 211/98 | (2006.01) |
| A61K 31/36 | (2006.01) |
| A61K 31/366 | (2006.01) |
| A61K 31/381 | (2006.01) |
| A61K 31/40 | (2006.01) |
| A61K 31/402 | (2006.01) |
| A61K 31/4035 | (2006.01) |
| A61K 31/404 | (2006.01) |
| A61K 31/4184 | (2006.01) |
| A61K 31/42 | (2006.01) |
| A61K 31/421 | (2006.01) |
| A61K 31/426 | (2006.01) |
| A61K 31/428 | (2006.01) |
| A61K 31/429 | (2006.01) |
| A61K 31/433 | (2006.01) |
| A61K 31/4406 | (2006.01) |
| A61K 31/4409 | (2006.01) |
| A61K 31/4453 | (2006.01) |
| A61K 31/4468 | (2006.01) |
| A61K 31/451 | (2006.01) |
| A61K 31/495 | (2006.01) |
| A61K 31/55 | (2006.01) |
| C07D 309/14 | (2006.01) |
| C07D 317/58 | (2006.01) |
| C07D 223/16 | (2006.01) |
| C07D 333/20 | (2006.01) |
| C07D 233/61 | (2006.01) |
| C07D 233/64 | (2006.01) |
| C07D 405/04 | (2006.01) |
| C07D 239/36 | (2006.01) |
| C07D 409/04 | (2006.01) |
| C07D 471/04 | (2006.01) |
| C07D 261/08 | (2006.01) |
| C07D 261/10 | (2006.01) |
| C07D 263/32 | (2006.01) |
| C07D 263/34 | (2006.01) |
| C07D 207/06 | (2006.01) |
| C07D 495/04 | (2006.01) |
| C07D 207/337 | (2006.01) |
| C07D 277/20 | (2006.01) |
| C07D 277/28 | (2006.01) |
| C07D 277/30 | (2006.01) |
| C07D 209/08 | (2006.01) |
| C07D 277/62 | (2006.01) |
| C07D 209/42 | (2006.01) |
| C07D 513/04 | (2006.01) |
| C07D 209/46 | (2006.01) |
| C07D 209/48 | (2006.01) |
| C07D 285/06 | (2006.01) |
| C07D 211/56 | (2006.01) |
| C07D 211/58 | (2006.01) |
| C07D 211/76 | (2006.01) |
| C07D 213/04 | (2006.01) |
| C07D 213/38 | (2006.01) |
| C07D 213/56 | (2006.01) |
| C07D 335/02 | (2006.01) |

(52) U.S. Cl.
CPC .............. *A61K 31/55* (2013.01); *C07C 233/80* (2013.01); *C07C 235/56* (2013.01); *C07C 237/40* (2013.01); *C07C 271/22* (2013.01); *C07D 207/06* (2013.01); *C07D 207/337* (2013.01); *C07D 209/08* (2013.01); *C07D 209/42* (2013.01); *C07D 209/46* (2013.01); *C07D 209/48* (2013.01); *C07D 211/56* (2013.01); *C07D 211/58* (2013.01); *C07D 211/76* (2013.01); *C07D 213/04* (2013.01); *C07D 213/38* (2013.01); *C07D 213/56* (2013.01); *C07D 223/16* (2013.01); *C07D 231/14* (2013.01); *C07D 231/20* (2013.01); *C07D 231/22* (2013.01); *C07D 231/56* (2013.01); *C07D 233/61* (2013.01); *C07D 233/64* (2013.01); *C07D 239/36* (2013.01); *C07D 261/08* (2013.01); *C07D 261/10* (2013.01); *C07D 263/32* (2013.01); *C07D 263/34* (2013.01); *C07D 277/20* (2013.01); *C07D 277/28* (2013.01); *C07D 277/30* (2013.01); *C07D 277/62* (2013.01); *C07D 285/06* (2013.01); *C07D 295/14* (2013.01); *C07D 309/14* (2013.01); *C07D 317/58* (2013.01); *C07D 333/20* (2013.01); *C07D 335/02* (2013.01); *C07D 405/04* (2013.01); *C07D 409/04* (2013.01); *C07D 471/04* (2013.01); *C07D 495/04* (2013.01); *C07D 513/04* (2013.01); *C07C 2101/02* (2013.01)

(56) References Cited

FOREIGN PATENT DOCUMENTS

| | | | |
|---|---|---|---|
| WO | 2010/084160 | 7/2010 | |
| WO | 2010/143582 | 12/2010 | |
| WO | 2011/035941 | 3/2011 | |
| WO | 2011/042217 | 4/2011 | |
| WO | 2011/131576 | 10/2011 | |
| WO | WO 2012/135113 | * 10/2012 | .................... 546/200 |

OTHER PUBLICATIONS

Binda, et al., "Biochemical, Structural, and Biological Evaluation of Tranylcypromine Derivatives as Inhibitors of Histone Demethylases LSD1 and LSD2", J. Am. Chem. Soc. 2010, vol. 132, pp. 6827-6833.

Yang, et al., "Structurual Basis for the Inhibition of the LSD1 Histone Demethylase by the Antidepressant trans-2-Phenylcyclopropylamine", Biochemistry, vol. 46, 2007, pp. 8058-8065.

Extended European Search Report issued in corresponding European Patent Application No. 12821416.0, Apr. 15, 2015—10 pages.

* cited by examiner

CYCLOPROPANEAMINE COMPOUND

TECHNICAL FIELD

The present invention relates to a cyclopropanamine compound having a lysine specific demethylase 1 (sometimes abbreviated as LSD1 in the present specification) inhibitory action and useful as a medicament such as a prophylactic or therapeutic agent for cancer, schizophrenia, Alzheimer's disease, Parkinson's disease and Huntington's chorea, and the like.

BACKGROUND OF THE INVENTION

LSD1 is a demethylation enzyme of histone, catalyzes a demethylation reaction of a monomethylated product and a dimethylated product of the 4th lysine residue of histone H3 (H3K4me1/2), and forms formaldehyde as a by-product. In addition, LSD1 forms a complex with flavin adenine dinucleotide (FAD) which is a kind of coenzyme, and FAD promotes oxidation of lysine residue by enzymes as a redox mediator.

WO 2010/084160 (patent document 1) discloses a compound of the following formula or a pharmaceutically acceptable salt thereof as an LSD1 inhibitor:

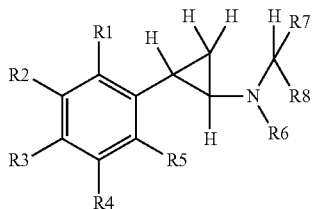

FORMULA I wherein R1-R5 are H, halo and the like; R6 is H or alkyl; R7 is H, alkyl or cycloalkyl; R8 is -L-heterocyclyl or -L-aryl wherein L is —(CH$_2$)$_n$—(CH$_2$)$_n$—, —(CH$_2$)$_n$NH(CH$_2$)$_n$—, —(CH$_2$)$_n$O(CH$_2$)$_n$— or —(CH$_2$)$_n$S(CH$_2$)$_n$—, and n is 0, 1, 2 or 3.

WO 2010/043721 (patent document 2) discloses a compound of the following formula or a pharmaceutically acceptable salt thereof as an LSD1 inhibitor:

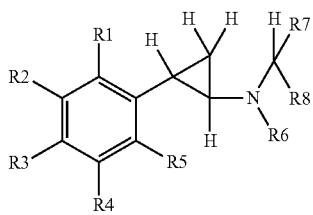

FORMULA I wherein R1-R5 are H, halo and the like; R6 is H or alkyl; R7 is H, alkyl or cycloalkyl; R8 is —C(═O)NRxRy or —C(═O)Rz wherein Rx and Ry are each independently H, alkyl and the like, and Rz is H, alkoxy and the like.

WO 2011/035941 (patent document 3) discloses a compound of the following formula or a pharmaceutically acceptable salt thereof as an LSD1 inhibitor:

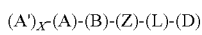

(A')$_{X'}$-(A)-(B)-(Z)-(L)-(D)    I wherein (A') is aryl, arylalkoxy, heterocyclyl and the like; (A) is heteroaryl or aryl; X is 0, 1, 2 or 3; (B) is a cyclopropyl ring; (Z) is —NH—; (L) is —CH$_2$CH$_2$— and the like; (D) is —N(~R1)-R2, —O—R3 or —S—R3 wherein R1 and R2 are each independently H, alkyl and the like; and R3 is H, alkyl and the like.

WO 2011/042217 (patent document 4) discloses a compound of the following formula or a pharmaceutically acceptable salt thereof as an LSD1 inhibitor:

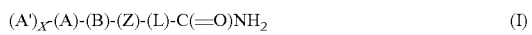

(A')$_{X'}$-(A)-(B)-(Z)-(L)-C(═O)NH$_2$    (I)

wherein (A') is aryl, arylalkoxy, arylalkyl, heterocyclyl and the like; (A) is heteroaryl or aryl; X is 0, 1, 2 or 3; (B) is a cyclopropyl ring; (Z) is —NH—; (L) is —(CH$_2$)$_m$CR1R2- wherein m is 0, 1, 2, 3, 4, 5 or 6; and R1 and R2 are each independently H or C1-6 alkyl.

US2010/0324147 (patent document 5) discloses a compound of the following formula or a salt thereof as an LSD1 inhibitor:

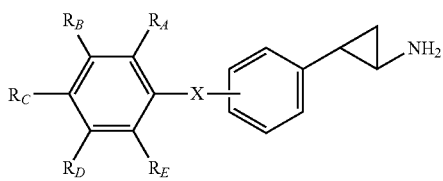

wherein X is a bond, O, S or NH; and R$_A$, R$_B$, R$_C$, R$_D$ and R$_E$ are each independently H, C1-7 alkyl and the like.

WO 2010/143582 (patent document 6) discloses a compound of the following formula or a pharmaceutically acceptable salt thereof as an LSD1 inhibitor:

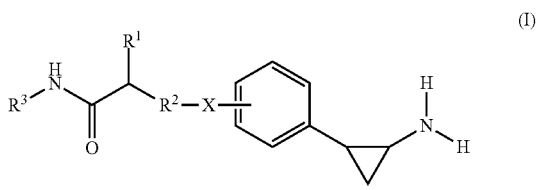

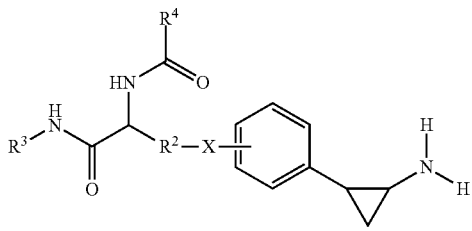

wherein R$^1$ is H, an alkyl group optionally having a substituent attached thereto and the like; R$^2$ is an alkylene group optionally having a substituent attached thereto; R$^3$ is an alkyl group optionally having a substituent attached thereto, a phenyl group optionally having a substituent attached thereto and the like; R$^4$ is an alkyl group optionally having a substituent attached thereto, a phenyl group optionally having a substituent attached thereto and the like; and X is O, NH$_2$, NHCO, CONH, S or CH$_2$.

J. Am. Chem. Soc. 2010, 132, 6827-6833 (non-patent document 1) discloses compounds of the following formulas as an LSD 1/2 inhibitor:

(13b)

[Structure: H2N-cyclopropyl(R,S)-C6H4-NH-C(=O)-Ph · HCl]

(15e)

[Structure: H2N-cyclopropyl(S,S)-C6H4-NH-C(=O)-CH(CH2Ph)-NH-C(=O)-O-CH2-Ph]

(14e)

[Structure: H2N-cyclopropyl(R,S)-C6H4-NH-C(=O)-CH(S)(CH2Ph)-NH-C(=O)-O-CH2-Ph · HCl]

The Journal of Neuroscience, Oct. 17, 2007, 27(42): 11254-11262 (non-patent document 2) discloses that a decrease in histone H3K4 methylation and a decrease in Gad1 mRNA expression are observed in the brain of schizophrenia patients.

DOCUMENT LIST

Patent Documents patent document 1: WO2010/084160
patent document 2: WO2010/043721
patent document 3: WO2011/035941
patent document 4: WO2011/042217
patent document 5: US2010/0324147
patent document 6: WO2010/143582

Non-Patent Documents non-patent document 1: J. Am. Chem. Soc. 2010, 132, 6827-6833
non-patent document 2: The Journal of Neuroscience, Oct. 17, 2007, 27(42):11254-11262

SUMMARY OF THE INVENTION

Problems to be Solved by the Invention

An object of the present invention is to provide a cyclopropanamine compound having a superior LSD1 inhibitory action and high LSD1 selectivity, and useful as a medicament such as a prophylactic or therapeutic agent for cancer, schizophrenia, Alzheimer's disease, Parkinson's disease and Huntington's chorea.

Means of Solving the Problems

The present inventors have conducted intensive studies in an attempt to solve the aforementioned problems and found that a compound represented by the following formula (I) has a superior LSD1 inhibitory action and high LSD1 selectivity, which resulted in the completion of the present invention.

Accordingly, the present invention relates to the following.

[1] A compound represented by the formula (I)

[Chemical structure of formula (I) showing A-C(=O)-N(R)-phenyl ring with substituents $Q^1, Q^2, Q^3, Q^4$ connected to cyclopropyl ring with $Z^1, Z^2, Z^3, H$ and N(X)-C($Y^1$)($Y^2$)($Y^3$)]

wherein A is a hydrocarbon group optionally having substituent(s), or a heterocyclic group optionally having substituent(s);

R is a hydrogen atom, a hydrocarbon group optionally having substituent(s), or a heterocyclic group optionally having substituent(s); or A and R are optionally bonded to each other to form a ring optionally having substituent(s);

$Q^1, Q^2, Q^3$ and $Q^4$ are each independently a hydrogen atom or a substituent; $Q^1$ and $Q^2$, and $Q^3$ and $Q^4$, are each optionally bonded to each other to form a ring optionally having substituent(s);

X is a hydrogen atom, an acyclic hydrocarbon group optionally having substituent(s), or a saturated cyclic group optionally having substituent(s);

$Y^1, Y^2$ and $Y^3$ are each independently a hydrogen atom, a hydrocarbon group optionally having substituent(s), or a heterocyclic group optionally having substituent(s);

X and $Y^1$, and $Y^1$ and $Y^2$, are each optionally bonded to each other to form a ring optionally having substituent(s); and $Z^1, Z^2$ and $Z^3$ are each independently a hydrogen atom or a substituent, or a salt thereof (hereinafter sometimes to be abbreviated as compound (I)).

[2] The compound of [1], wherein

A is (1) a $C_{3-8}$ cycloalkyl group optionally having substituent(s),
(2) a $C_{6-14}$ aryl group optionally having substituent(s),
(3) a $C_{6-14}$ aryl $C_{1-6}$ alkyl group optionally having substituent(s),
(4) a $C_{6-14}$ aryl $C_{1-6}$ alkyl $C_{6-14}$ aryl group optionally having substituent(s),
(5) a 4- to 11-membered heterocyclic group containing, as a ring-constituting atom besides carbon atom, 1 to 3 hetero atoms selected from a nitrogen atom, a sulfur atom and an oxygen atom, and optionally having substituent(s), or
(6) a $C_{10-14}$ cyclic hydrocarbon group optionally having substituent(s);

R is a hydrogen atom or a $C_{1-6}$ alkyl group optionally having substituent(s); or A and R are optionally bonded to each other to form a 4- to 10 membered heterocycle optionally having substituent(s), or a salt thereof.

[2A] The compound of [1] or [2], wherein
A is
(1) a $C_{6-14}$ aryl group optionally having 1 to 3 substituents selected from
  (a) a halogen atom,
  (b) a $C_{1-6}$ alkyl group optionally having 1 to 5 halogen atoms,
  (c) a $C_{6-14}$ aryloxy group,
  (d) a $C_{6-14}$ aryl $C_{1-6}$ alkyloxy group,
  (e) a $C_{6-14}$ aryl-carbonylamino group,
  (f) a $C_{6-14}$ aryl $C_{1-6}$ alkylamino group,
  (g) a 4- to 7-membered heterocyclic group containing, as a ring-constituting atom besides carbon atom, 1 to 4 hetero atoms selected from a nitrogen atom, a sulfur atom and an oxygen atom, and optionally having an oxo group and optionally having 1 or 2 $C_{1-6}$ alkyl groups, and
  (h) a $C_{1-6}$ alkyl group optionally having a 5-membered heterocyclic group containing, as a ring-constituting atom besides carbon atom, 2 or 3 nitrogen atoms,
(2) a $C_{6-14}$ aryl $C_{1-6}$ alkyl group optionally having a $C_{6-14}$ aryl $C_{1-6}$ alkyloxy-carbonylamino group,
(3) a $C_{6-14}$ aryl $C_{1-6}$ alkyl $C_{6-14}$ aryl group,
(4) a $C_{3-8}$ cycloalkyl group,
(5) a 5-membered heterocyclic group containing, as a ring-constituting atom besides carbon atom, 1 to 3 hetero atoms selected from a nitrogen atom, a sulfur atom and an oxygen atom, and optionally having 1 to 3 substituents selected from 1 or 2 $C_{1-6}$ alkyl groups optionally having 1 to 5 halogen atoms and a phenyl group,
(6) a $C_{10-14}$ cyclic hydrocarbon group, or
(7) a 9- to 11-membered heterocyclic group containing, as a ring-constituting atom besides carbon atom, 1 to 3 hetero atoms selected from a nitrogen atom, a sulfur atom and an oxygen atom, and optionally having 1 to 3 substituents selected from a $C_{1-6}$ alkyl-carbonyl group, a furyl group and a thienyl group;
R is a hydrogen atom or a $C_{1-6}$ alkyl group optionally having substituent(s); or
A and R are optionally bonded to each other to form a 4- to 10-membered heterocycle having 1 or 2 oxo groups,
or a salt thereof.

[2B] The compound of [1], [2] or [2A], wherein
A is
a phenyl-$C_{1-6}$ alkyl group,
a $C_{3-6}$ cycloalkyl group,
a tetrahydronaphthyl group,
a phenyl group,
a biphenylyl group,
a furyl group,
a thienyl group,
an oxazolyl group,
an isoxazolyl group,
a thiazolyl group,
a pyrazolyl group,
an indazolyl group,
a benzofuryl group,
a benzimidazolyl group,
a benzothiazolyl group,
an indolyl group, or
a tetrahydrobenzazepinyl group, each of which optionally has substituent(s);
R is a hydrogen atom or a $C_{1-6}$ alkyl group; or
A and R are optionally bonded to each other to form a dihydroisoindole ring having 1 or 2 oxo groups,
or a salt thereof.

[2C] The compound of [1], [2], [2A] or [2B], wherein
A is
a phenyl-$C_{1-6}$ alkyl group,
a $C_{3-6}$ cycloalkyl group,
a tetrahydronaphthyl group,
a phenyl group,
a biphenylyl group,
a furyl group,
a thienyl group,
an oxazolyl group,
an isoxazolyl group,
a thiazolyl group,
a pyrazolyl group,
an indazolyl group,
a benzofuryl group,
a benzimidazolyl group,
a benzothiazolyl group,
an indolyl group, or
a tetrahydrobenzazepinyl group, each of which optionally has 1 to 3 substituents selected from
(1) a halogen atom,
(2) a $C_{1-6}$ alkyl group optionally having 1 to 3 substituents selected from a halogen atom, a phenyl group, an imidazolyl group and a triazolyl group,
(3) a $C_{1-6}$ alkoxy group optionally having 1 to 3 substituents selected from a halogen atom and a phenyl group,
(4) a $C_{1-6}$ alkyl-carbonyl group,
(5) a di-$C_{1-6}$ alkylamino group,
(6) a $C_{1-5}$ alkylsulfonyl group,
(7) a sulfamoyl group,
(8) a $C_{1-6}$ alkylsulfonylamino group,
(9) an oxo group,
(10) a $C_{3-6}$ cycloalkyl group,
(11) a phenyl group optionally having 1 to 3 substituents selected from a halogen atom and a $C_{1-6}$ alkyl group,
(12) a phenoxy group,
(13) a phenylcarbonylamino group,
(14) a benzyloxycarbonylamino group,
(15) a benzoyl group,
(16) a benzylamino group,
(17) a pyrazolyl group,
(18) a dihydropyrazolyl group optionally having 1 to 3 substituents selected from a $C_{1-6}$ alkyl group and an oxo group,
(19) an oxazolyl group,
(20) a thiazolyl group having 1 or 2 $C_{1-6}$ alkyl groups,
(21) a tetrazolyl group,
(22) a pyrrolyl group,
(23) a piperazinyl group having 1 to 3 $C_{1-6}$ alkyl groups,
(24) an imidazolyl group,
(25) a pyridyl group,
(26) a pyrimidinyl group,
(27) a piperidyl group optionally having one oxo group,
(28) a thienyl group,
(29) a furyl group, and
(30) a thiadiazolyl group;
R is a hydrogen atom or a $C_{1-6}$ alkyl group; or
A and R are optionally bonded to each other to form a dihydroisoindole ring having 1 or 2 oxo groups,
or a salt thereof.

[2D] The compound of [1], [2], [2A], [2B] or [2C], wherein
A is
a phenyl-$C_{1-6}$ alkyl group,
a phenyl group,
a biphenylyl group or
a pyrazolyl group, each of which optionally has 1 to 3 substituents selected from (1) a halogen atom,
(2) a $C_{1-6}$ alkyl group optionally having 1 to 3 substituents selected from a halogen atom and a phenyl group,
(3) a phenylcarbonylamino group,
(4) a benzyloxycarbonylamino group, and
(5) a piperidyl group optionally having one oxo group;
R is a hydrogen atom; or
A and R are optionally bonded to each other to form a dihydroisoindole ring having 1 or 2 oxo groups,
or a salt thereof.
[2E] The compound of [1], [2], [2A], [2B], [2C] or [2D], wherein
R is a hydrogen atom or a $C_{1-6}$ alkyl group, or a salt thereof.
[3] The compound of [1], [2], [2A], [2B], [20], [2D] or [2E], wherein
$Q^1$ is a hydrogen atom or a $C_{1-6}$ alkyl group, and
$Q^2$, $Q^3$ and $Q^4$ are each a hydrogen atom,
or a salt thereof.
[3A] The compound of [1], [2], [2A], [2B], [2C], [2D], [2E] or
[3], wherein
$Q^1$, $Q^2$, $Q^3$ and $Q^4$ are each a hydrogen atom,
or a salt thereof.
[4] The compound of [1], [2], [2A], [2B], [2C], [2D], [2E], [3] or [3A], wherein
X is a hydrogen atom or an optionally substituted $C_{1-6}$ alkyl group;
$Y^1$, $Y^2$ and $Y^3$ are each independently
(1) a hydrogen atom,
(2) a $C_{1-20}$ alkyl group optionally having substituent(s),
(3) a $C_{3-8}$ cycloalkyl group optionally having substituent(s),
(4) a $C_{6-14}$ aryl group optionally having substituent(s),
(5) a $C_{6-14}$ aryl $C_{1-6}$ alkyl group optionally having substituent(s),
(6) a 5- to 7-membered monocyclic aromatic heterocyclic group containing, as a ring-constituting atom besides carbon atom, 1 to 4 hetero atoms selected from a nitrogen atom, a sulfur atom and an oxygen atom, and optionally having substituent(s), or
(7) a bicyclic or tricyclic aromatic heterocyclic group containing, as a ring-constituting atom besides carbon atom, 1 to 4 hetero atoms selected from a nitrogen atom, a sulfur atom and an oxygen atom, and optionally having substituent(s);
X and $Y^1$ are optionally bonded to each other to form, together with the adjacent nitrogen atom and carbon atom,
a 5- to 7-membered monocyclic nitrogen-containing nonaromatic heterocycle containing, as a ring-constituting atom besides carbon atom, one nitrogen atom, and optionally further containing one hetero atom selected from a nitrogen atom, a sulfur atom and an oxygen atom, and optionally having substituent(s);
$Y^1$ and $Y^2$ are optionally bonded to each other to form, together with the adjacent carbon atom,
(1) a 5- to 7-membered monocyclic nonaromatic heterocycle containing, as a ring-constituting atom besides carbon atom, one or two hetero atoms selected from a nitrogen atom, a sulfur atom and an oxygen atom, and optionally having substituent(s), or
(2) a 7- to 10-membered bridged heterocycle containing, as a ring-constituting atom besides carbon atom, one or two hetero atoms selected from a nitrogen atom, a sulfur atom and an oxygen atom, and optionally having substituent(s),
or a salt thereof.
[4A] The compound of [1], [2], [2A], [23], [2C], [2D], [2E], [3], [3A] or [4], wherein
X is a hydrogen atom or an optionally substituted $C_{1-6}$ alkyl group;
$Y^1$, $Y^2$ and $Y^3$ are each independently
(1) a hydrogen atom,
(2) a $C_{1-20}$ alkyl group optionally having 1 to 3 substituents selected from
  (a) an amino group,
  (b) a $C_{1-8}$ alkoxy group,
  (c) a $C_{8-14}$ aryloxy group, and
  (d) a $C_{6-14}$ aryl $C_{1-8}$ alkyloxy group,
(3) a $C_{3-8}$ cycloalkyl group,
(4) a $C_{8-14}$ aryl group optionally having 1 to 3 substituents selected from
  (a) a halogen atom,
  (b) a $C_{1-6}$ alkoxy group,
  (c) a $C_{1-3}$ alkylenedioxy group, and
  (d) a di-$C_{1-6}$ alkylamino group,
(5) a $C_{6-14}$ aryl $C_{1-8}$ alkyl group,
(6) a 5- to 7-membered monocyclic aromatic heterocyclic group containing, as a ring-constituting atom besides carbon atom, 1 to 4 hetero atoms selected from a nitrogen atom, a sulfur atom and an oxygen atom, and optionally having substituent(s), or
(7) a bicyclic or tricyclic aromatic heterocyclic group containing, as a ring-constituting atom besides carbon atom, 1 to 4 hetero atoms selected from a nitrogen atom, a sulfur atom and an oxygen atom, and optionally having substituent(s);
X and $Y^1$ are optionally bonded to each other to form, together with the adjacent nitrogen atom and carbon atom,
an optionally substituted 5- to 7-membered monocyclic nitrogen-containing nonaromatic heterocycle containing, as a ring-constituting atom besides carbon atom, one nitrogen atom and optionally further containing one hetero atom selected from a nitrogen atom, a sulfur atom and an oxygen atom; and
$Y^1$ and $Y^2$ are optionally bonded to each other to form, together with the adjacent carbon atom,
(1) a $C_{3-8}$ cycloalkane ring optionally having substituent(s),
(2) a 2,3-dihydroindene ring,
(3) a fluorene ring,
(4) a 5- to 7-membered monocyclic nonaromatic heterocycle containing, as a ring-constituting atom besides carbon atom, one or two hetero atoms selected from a nitrogen atom, a sulfur atom and an oxygen atom, and optionally having 1 to 3 substituents selected from
  (a) a $C_{1-6}$ alkyl group optionally having substituent(s),
  (b) a $C_{6-14}$ aryl $C_{1-6}$ alkyl group,
  (c) a $C_{2-6}$ alkenyloxy-carbonyl group,
  (d) a $C_{3-8}$ cycloalkyl group, and
  (e) a $C_{6-14}$ aryl group, or
(5) a 7- to 10-membered bridged heterocycle containing, as a ring-constituting atom besides carbon atom, one or two hetero atoms selected from a nitrogen atom, a sulfur atom and an oxygen atom, and optionally having substituent(s),
or a salt thereof.
[4B] The compound of [1], [2], [2A], [2B], [2C], [2D], [2E], [3], [³A], [4] or [4A], wherein
X is a hydrogen atom or a $C_{1-6}$ alkyl group optionally substituted by one $C_{3-6}$ cycloalkyl group;
$Y^1$, $Y^2$ and $Y^3$ are each independently
(1) a hydrogen atom,
(2) a $C_{1-20}$ alkyl group optionally having 1 to 3 substituents selected from an amino group, a $C_{1-6}$ alkoxy group, a phenyl group, a phenyloxy group and a benzyloxy group,
(3) a $C_{3-8}$ cycloalkyl group, (4) a phenyl group optionally having 1 to 3 substituents selected from a halogen atom, a $C_{1-6}$ alkoxy group, a $C_{1-3}$ alkylenedioxy group and a di-$C_{1-6}$ alkylamino group,
(5) a pyridyl group optionally having 1 to 3 $C_{1-6}$ alkoxy groups,
(6) a naphthyl group,
(7) a biphenylyl group,
(8) a thienyl group,
(9) an imidazolyl group,
(10) a thiazolyl group,
(11) a piperidyl group optionally having 1 to 3 $C_{1-6}$ alkyl groups,
(12) an imidazopyridyl group,
(13) an imidazothiazolyl group,
(14) a thienopyridyl group, or
(15) a 1,8-naphthyridinyl group;
$Y^1$ and $Y^2$ are optionally bonded to each other to form, together with the adjacent carbon atom,
a $C_{3-8}$ cycloalkane ring,
a pyrrolidine ring,
a piperidine ring,
a tetrahydropyran ring,
a 2,3-dihydroindene ring,
a fluorene ring,
a 8-azabicyclo[3.2.1]octane ring, or
a tetrahydrothiopyran ring, each of which optionally has 1 to 3 substituents selected from
(1) a halogen atom,
(2) a $C_{1-6}$ alkyl group optionally having 1 to 3 substituents selected from a halogen atom and a phenyl group,
(3) a $C_{3-6}$ cycloalkyl group,
(4) an oxo group,
(5) a phenyl group,
(6) a $C_{2-6}$ alkenyloxy-carbonyl group, and
(7) a $C_{1-6}$ alkyl-carbonyl group; and
X and $Y^1$ are optionally bonded to each other to form a pyrrolidine ring together with the adjacent nitrogen atom and carbon atom,
or a salt thereof.
[5] The compound of [1], [2], [2A], [2B], [2C], [2D], [2E], [$^3$], [3A], [4], [4A] or [4B], wherein
$Z^1$, $Z^2$ and $Z^3$ are each a hydrogen atom, or a salt thereof.
[6] The compound of [1], [2], [2A], [2B], [2C], [2D], [2E], [$^3$], [3A], [4], [4A], [4B] or [5], wherein
A is
a phenyl-$C_{1-6}$ alkyl group,
a $C_{3-6}$ cycloalkyl group,
a tetrahydronaphthyl group,
a phenyl group,
a biphenylyl group,
a furyl group,
a thienyl group,
an oxazolyl group,
an isoxazolyl group,
a thiazolyl group,
a pyrazolyl group,
an indazolyl group,
a benzofuryl group,
a benzimidazolyl group,
a benzothiazolyl group,
an indolyl group, or
a tetrahydrobenzazepinyl group, each of which optionally has 1 to 3 substituents selected from
(1) a halogen atom,
(2) a $C_{1-6}$ alkyl group optionally having 1 to 3 substituents selected from a halogen atom, a phenyl group, an imidazolyl group and a triazolyl group,
(3) a $C_{1-6}$ alkoxy group optionally having 1 to 3 substituents selected from a halogen atom and a phenyl group,
(4) a $C_{1-6}$ alkyl-carbonyl group,
(5) a di-$C_{1-6}$ alkylamino group,
(6) a $C_{1-6}$ alkylsulfonyl group,
(7) a sulfamoyl group,
(8) a $C_{1-6}$ alkylsulfonylamino group,
(9) an oxo group,
(10) a $C_{3-6}$ cycloalkyl group,
(11) a phenyl group optionally having 1 to 3 substituents selected from a halogen atom and a $C_{1-6}$ alkyl group,
(12) a phenoxy group,
(13) a phenylcarbonylamino group,
(14) a benzyloxycarbonylamino group,
(15) a benzoyl group,
(16) a benzylamino group,
(17) a pyrazolyl group,
(18) a dihydropyrazolyl group optionally having 1 to 3 substituents selected from a $C_{1-6}$ alkyl group and an oxo group,
(19) an oxazolyl group,
(20) a thiazolyl group having 1 or 2 $C_{1-6}$ alkyl groups,
(21) a tetrazolyl group,
(22) a pyrrolyl group,
(23) a piperazinyl group having 1 to 3 $C_{1-6}$ alkyl groups,
(24) an imidazolyl group,
(25) a pyridyl group,
(26) a pyrimidinyl group,
(27) a piperidyl group optionally having one oxo group,
(28) a thienyl group,
(29) a furyl group, and
(30) a thiadiazolyl group;
R is a hydrogen atom or a $C_{1-6}$ alkyl group; or
A and R are optionally bonded to each other to form a dihydroisoindole ring having 1 or 2 oxo groups;
$Q^1$ is a hydrogen atom or a $C_{1-6}$ alkyl group;
$Q^2$, $Q^3$ and $Q^4$ are each a hydrogen atom;
X is a hydrogen atom or a $C_{1-6}$ alkyl group optionally substituted by one $C_{3-6}$ cycloalkyl group;
$Y^1$, $Y^2$ and $Y^3$ are each independently
(1) a hydrogen atom,
(2) a $C_{1-20}$ alkyl group optionally having 1 to 3 substituents selected from an amino group, a $C_{1-6}$ alkoxy group, a phenyl group, a phenyloxy group and a benzyloxy group,
(3) a $C_{3-8}$ cycloalkyl group,
(4) a phenyl group optionally having 1 to 3 substituents selected from a halogen atom, a $C_{1-6}$ alkoxy group, a $C_{1-3}$ alkylenedioxy group and a di-$C_{1-6}$ alkylamino group,
(5) a pyridyl group optionally having 1 to 3 $C_{1-6}$ alkoxy groups,
(6) a naphthyl group,
(7) a biphenylyl group,
(8) a thienyl group,
(9) an imidazolyl group,
(10) a thiazolyl group,
(11) a piperidyl group optionally having 1 to 3 $C_{1-6}$ alkyl groups,
(12) an imidazopyridyl group,
(13) an imidazothiazolyl group,
(14) a thienopyridyl group, or
(15) a 1,8-naphthyridinyl group;
$Y^1$ and $Y^2$ are optionally bonded to each other to form, together with the adjacent carbon atom,
a $C_{3-8}$ cycloalkane ring,
a pyrrolidine ring,
a piperidine ring,
a tetrahydropyran ring,
a 2,3-dihydroindene ring, a fluorene ring,
a 8-azabicyclo[3.2.1]octane ring, or
a tetrahydrothiopyran ring, each of which optionally has 1 to 3 substituents selected from
(1) a halogen atom,
(2) a $C_{1-6}$ alkyl group optionally having 1 to 3 substituents selected from a halogen atom and a phenyl group,
(3) a $C_{3-6}$ cycloalkyl group,
(4) an oxo group,
(5) a phenyl group,
(6) a $C_{2-6}$ alkenyloxy-carbonyl group, and
(7) a $C_{1-6}$ alkyl-carbonyl group;
X and $Y^1$ are optionally bonded to each other to form a pyrrolidine ring, together with the adjacent nitrogen atom and carbon atom; and
$Z^1$, $Z^2$ and $Z^3$ are each a hydrogen atom,
or a salt thereof.
[6A] The compound of [1], [2], [2A], [2B], [2C], [2D], [2E], [3], [3A], [4], [4A], [4B], [5] or [6], wherein
A is
a phenyl-$C_{1-5}$ alkyl group,
a phenyl group,
a biphenylyl group, or
a pyrazolyl group, each of which optionally has 1 to 3 substituents selected from
(1) a halogen atom,
(2) a $C_{1-6}$ alkyl group optionally having 1 to 3 substituents selected from a halogen atom and a phenyl group,
(3) a phenylcarbonylamino group,
(4) a benzyloxycarbonylamino group, and
(5) a piperidyl group optionally having one oxo group;
R is a hydrogen atom; or
A and R are optionally bonded to each other to form a dihydroisoindole ring having 1 or 2 oxo groups;
$Q^1$ is a hydrogen atom or a $C_{1-6}$ alkyl group;
$Q^2$, $Q^3$ and $Q^4$ are each a hydrogen atom;
X is a hydrogen atom;
$Y^1$, $Y^2$ and $Y^3$ are each independently
(1) a hydrogen atom,
(2) a $C_{1-20}$ alkyl group,
(3) a $C_{3-8}$ cycloalkyl group, or
(4) a phenyl group optionally having 1 to 3 $C_{1-6}$ alkoxy groups;
$Y^1$ and $Y^2$ are optionally bonded to each other to form, together with the adjacent carbon atom,
piperidine ring optionally having 1 to 3 $C_{1-6}$ alkyl groups;
X and $Y^1$ are optionally bonded to each other to form a pyrrolidine ring together with the adjacent nitrogen atom and carbon atom; and
$Z^1$, $Z^2$ and $Z^3$ are each a hydrogen atom,
or a salt thereof.
[7] The compound of [1], [2], [2A], [2B], [2C], [2D], [2E], [3], [3A], [4], [4A], [4B], [5], [6] or [6A], wherein
A is
a phenyl group optionally having 1 to 3 $C_{1-6}$ alkyl groups substituted by 1 to 3 halogen atoms,
a biphenylyl group, or
a pyrazolyl group;
R is a hydrogen atom; or
A and R are optionally bonded to each other to form a dihydroisoindole ring having 1 or 2 oxo groups;
$Q^1$ is a hydrogen atom or a $C_{1-6}$ alkyl group;
$Q^2$, $Q^3$ and $Q^4$ are each a hydrogen atom;
X is a hydrogen atom;
$Y^1$, $Y^2$ and $Y^3$ are each independently a hydrogen atom or a $C_{3-8}$ cycloalkyl group;

$Y^1$ and $Y^2$ are optionally bonded to each other to form, together with the adjacent carbon atom,
a piperidine ring optionally having 1 to 3 $C_{1-6}$ alkyl groups; and
$Z^1$, $Z^2$ and $Z^3$ are each a hydrogen atom,
or a salt thereof.
[7A] N-(4-{trans-2-[(cyclopropylmethyl)amino]cyclopropyl}phenyl)biphenyl-4-carboxamide,
N-(4-{trans-2-[(1-methylpiperidin-4-yl)amino]cyclopropyl}phenyl)-3-(trifluoromethyl)benzamide,
N-(4-{(1R,2S)-2-[(1-methylpiperidin-4-yl)amino]cyclopropyl}phenyl)-3-(trifluoromethyl)benzamide,
N-(4-{(1S,2R)-2-[(1-methylpiperidin-4-yl)amino]cyclopropyl}phenyl)-3-(trifluoromethyl)benzamide or
N-(4-{trans-2-[(cyclopropylmethyl)amino]cyclopropyl}phenyl)-1H-pyrazole-4-carboxamide,
or a salt thereof.
[8] N-(4-{trans-2-[(cyclopropylmethyl)amino]cyclopropyl}phenyl)biphenyl-4-carboxamide or a salt thereof.
[8A] The compound of [8], wherein N-(4-{trans-2-[(cyclopropylmethyl)amino]cyclopropyl}phenyl)biphenyl-4-carboxamide is
N-(4-{(1R,2S)-2-[(cyclopropylmethyl)amino]cyclopropyl}phenyl)biphenyl-4-carboxamide, or
N-(4-{(1S,2R)-2-[(cyclopropylmethyl)amino]cyclopropyl}phenyl)biphenyl-4-carboxamide,
or a salt thereof.
[9] N-(4-{trans-2-[(1-methylpiperidin-4-yl)amino]cyclopropyl}phenyl)-3-(trifluoromethyl)benzamide or a salt thereof.
[9A] The compound of [9], wherein N-(4-{trans-2-[(1-methylpiperidin-4-yl)amino]cyclopropyl}phenyl)-3-(trifluoromethyl)benzamide is
N-(4-{(1R,2S)-2-[(1-methylpiperidin-4-yl)amino]cyclopropyl}phenyl)-3-(trifluoromethyl)benzamide, or
N-(4-{(1S,2R)-2-[(1-methylpiperidin-4-yl)amino]cyclopropyl}phenyl)-3-(trifluoromethyl)benzamide,
or a salt thereof.
[10] N-(4-{trans-2-[(cyclopropylmethyl)amino]cyclopropyl}phenyl)-1H-pyrazole-4-carboxamide or a salt thereof.
[11] A medicament containing the compound of [1] or a salt thereof.
[12] The medicament of [11], which is a prophylactic or therapeutic agent for cancer.
[13] The medicament of [11], which is an LSD1 inhibitor.
[14] The medicament of [11], which is a prophylactic or therapeutic agent for schizophrenia, Alzheimer's disease, Parkinson's disease or Huntington's chorea.
[15] A method for the prophylaxis or treatment of schizophrenia, Alzheimer's disease, Parkinson's disease or Huntington's chorea, comprising administering an effective amount of the compound of [1] or a salt thereof to a mammal.
[15A] A method for the prophylaxis or treatment of cancer, comprising administering an effective amount of the compound of [1] or a salt thereof to a mammal.
[16] Use of the compound of [1] or a salt thereof for the production of a prophylactic or therapeutic agent for schizophrenia, Alzheimer's disease, Parkinson's disease or
Huntington's chorea.
[16A] Use of the compound of [1] or a salt thereof for the production of a prophylactic or therapeutic agent for cancer.

[17] The compound of [1] or a salt thereof for use in the prophylaxis or treatment of schizophrenia, Alzheimer's disease, Parkinson's disease or Huntington's chorea.

[17A] The compound of [1] or a salt thereof for use in the prophylaxis or treatment of cancer.

[18] A method of inhibiting LSD1, comprising administering an effective amount of the compound of [1] or a salt thereof to a mammal.

[18A] A prophylactic or therapeutic agent for schizophrenia, Alzheimer's disease, Parkinson's disease or Huntington's chorea, comprising the compound of [1] or a salt thereof.

[18B] A prophylactic or therapeutic agent for cancer, comprising the compound of [1] or a salt thereof.

[18C] Use of the compound of [1] or a salt thereof for the production of an LSD1 inhibitor.

The definition of each symbol used in the present specification is described in detail in the following.

Examples of the "substituent" for $Q_1$, $Q_2$, $Q_3$, $Q_4$, $Z_1$, $Z_2$ or $Z^3$ include a halogen atom, a cyano group, a nitro group, a hydrocarbon group optionally having substituent(s), a heterocyclic group optionally having substituent(s), an acyl group optionally having substituent(s), an amino group optionally having substituent(s), a carbamoyl group optionally having substituent(s), a sulfamoyl group optionally having substituent(s), a hydroxy group optionally having a substituent, a sulfanyl (SH) group optionally having a substituent and the like.

Examples of the "halogen atom" include fluorine, chlorine, bromine and iodine.

Examples of the "hydrocarbon group" in the "hydrocarbon group optionally having substituent(s)" for A, R, $Y^1$, $Y^2$ or $Y^3$, and in the "hydrocarbon group optionally having substituent(s)" exemplified as the substituent for $Q^1$, $Q^2$, $Q^3$, $Q^4$, $Z^1$, $Z^2$ or $Z^3$ include (1) a $C_{1-20}$ alkyl group (e.g., methyl, ethyl, propyl, isopropyl, butyl, isobutyl, sec-butyl, tert-butyl, pentyl, hexyl, heptyl, octyl, nonyl, decyl, undecyl, dodecyl), preferably, a $C_{1-6}$ alkyl group (e.g., methyl, ethyl, propyl, isopropyl, butyl, isobutyl, sec-butyl, tert-butyl, pentyl, hexyl),
(2) a $C_{2-6}$ alkenyl group (e.g., vinyl, allyl, isopropenyl, 2-butenyl),
(3) a $C_{2-6}$ alkynyl group (e.g., ethynyl, propargyl, 2-butynyl),
(4) a $C_{3-8}$ cycloalkyl group (e.g., cyclopropyl, cyclobutyl, cyclopentyl, cyclohexyl, cycloheptyl, cyclooctyl),
(5) a $C_{3-6}$ cycloalkenyl group (e.g., cyclopropenyl, cyclobutenyl, cyclopentenyl, cyclohexenyl, cycloheptenyl, cyclooctenyl),
(6) a $C_{6-14}$ aryl group (e.g., phenyl, 1-naphthyl, 2-naphthyl, 2-anthryl, biphenylyl),
(7) a $C_{6-14}$ aryl $C_{1-6}$ alkyl group (e.g., benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl),
(8) a $C_{6-14}$ aryl $C_{1-6}$ alkyl $C_{6-14}$ aryl group (e.g., benzylphenyl, phenethylphenyl), and
(9) a $C_{10-14}$ cyclic hydrocarbon group (e.g., tetrahydronaphthyl).

Examples of the substituent of the aforementioned "hydrocarbon group optionally having substituent(s)" include substituents selected from the following substituent group A and the like.

[Substituent Group A]
(1) a halogen atom (e.g., fluorine, chlorine, bromine, iodine),
(2) a nitro group,
(3) a cyano group,
(4) a hydroxy group,
(5) an optionally halogenated $C_{1-6}$ alkoxy group,
(6) an optionally halogenated $C_{1-6}$ alkylthio group,
(7) a $C_{6-14}$ aryloxy group (e.g., phenoxy, naphthoxy),
(8) a $C_{6-14}$ aryl $C_{1-6}$ alkyloxy group (e.g., benzyloxy),
(9) a 5- to 7-membered heterocyclyloxy group,
(10) an amino group,
(11) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(12) a 4- to 7-membered (preferably, 5- to 7-membered) heterocyclic group optionally having substituent(s),
(13) a formyl group,
(14) a carboxy group,
(15) a carbamoyl group,
(16) a thiocarbamoyl group,
(17) an optionally halogenated $C_{1-6}$ alkyl-carbonyl group,
(18) a $C_{1-6}$ alkoxy-carbonyl group,
(19) a $C_{6-14}$ aryl-carbonyl group (e.g., benzoyl, 1-naphthoyl, 2-naphthoyl),
(20) a heterocyclylcarbonyl group optionally having substituent(s),
(21) a $C_{6-14}$ aryloxy-carbonyl group (e.g., phenyloxycarbonyl, 1-naphthyloxycarbonyl, 2-naphthyloxycarbonyl),
(22) a $C_{6-14}$ aryl $C_{1-6}$ alkyloxy-carbonyl group (e.g., benzyloxycarbonyl, phenethyloxycarbonyl),
(23) a mono- or di-$C_{1-6}$ alkyl-carbamoyl group (e.g., methylcarbamoyl, ethylcarbamoyl, dimethylcarbamoyl, diethylcarbamoyl, N-ethyl-N-methylcarbamoyl),
(24) a carbamoyl-$C_{1-6}$ alkyl-carbamoyl group (e.g., carbamoylmethylcarbamoyl, carbamoylethylcarbamoyl),
(25) a $C_{6-14}$ aryl-carbamoyl group (e.g., phenylcarbamoyl),
(26) a heterocyclylcarbamoyl group optionally having substituent(s),
(27) an optionally halogenated $C_{1-6}$ alkylsulfonyl group,
(28) a $C_{6-14}$ arylsulfonyl group (e.g., phenylsulfonyl, 1-naphthylsulfonyl, 2-naphthylsulfonyl),
(29) a formylamino group,
(30) an optionally halogenated $C_{1-6}$ alkyl-carbonylamino group,
(31) a $C_{6-14}$ aryl $C_{1-6}$ alkylamino group (e.g., benzylamino),
(32) a $C_{6-14}$ aryl-carbonylamino group (e.g., phenylcarbonylamino, naphthylcarbonylamino),
(33) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(34) a $C_{6-14}$ aryl $C_{1-6}$ alkyloxy-carbonylamino group (e.g., benzyloxycarbonylamino),
(35) a $C_{1-6}$ alkylsulfonylamino group (e.g., methylsulfonylamino, ethylsulfonylamino),
(36) a $C_{1-6}$ alkyl-carbonyloxy group (e.g., acetoxy, propanoyloxy),
(37) a $C_{6-14}$ aryl-carbonyloxy group (e.g., benzoyloxy, 1-naphthoyloxy, 2-naphthoyloxy),
(38) a $C_{1-6}$ alkoxy-carbonyloxy group (e.g., methoxycarbonyloxy, ethoxycarbonyloxy, propoxycarbonyloxy, butoxycarbonyloxy),
(39) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(40) a $C_{6-14}$ aryl-carbamoyloxy group (e.g., phenylcarbamoyloxy, naphthylcarbamoyloxy),
(41) a 5- or 6-membered heterocyclylcarbonyloxy group (e.g., nicotinoyloxy),
(42) a sulfamoyl group,
(43) an oxo group,
(44) a $C_{3-6}$ cycloalkyl group, and
(45) a phenyl group optionally having 1 to 3 substituents selected from a halogen atom and a $C_{1-6}$ alkyl group.

The number of the substituents is, for example, 1 to 5, preferably 1 to 3. When the number of the substituents is two or more, the respective substituents may be the same or different.

When the "hydrocarbon group" of the aforementioned "hydrocarbon group optionally having substituent(s)" is a $C_{3-8}$ cycloalkyl group, a $C_{3-8}$ cycloalkenyl group, a $C_{6-14}$ aryl group, a $C_{6-14}$ aryl $C_{1-6}$ alkyl group or a $C_{6-14}$ aryl $C_{1-6}$ alkyl $C_{6-14}$ aryl group, examples of the substituent of the "hydrocarbon group optionally having substituent(s)" include a substituent selected from
(1) the aforementioned substituent group A,
(2) a $C_{1-3}$ alkylenedioxy group (e.g., methylenedioxy, ethylenedioxy),
(3) a $C_{1-6}$ alkyl group optionally having 1 to 5 halogen atoms, and
(4) a $C_{1-6}$ alkyl group optionally having a 5-membered heterocyclic group (e.g., imidazolyl, triazolyl) containing 2 or 3 nitrogen atoms as a ring-constituting atom besides carbon atom,
and the like.

The number of the substituents is, for example, 1 to 5, preferably 1 to 3. When the number of the substituents is two or more, the respective substituents may be the same or different.

Examples of the aforementioned "optionally halogenated $C_{1-6}$ alkoxy group" include a $C_{1-6}$ alkoxy group (e.g., methoxy, ethoxy, propoxy, butoxy, pentyloxy) optionally having 1 to 5, preferably 1 to 3, halogen atoms (e.g., fluorine, chlorine, bromine, iodine) and the like. Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like.

Examples of the aforementioned "optionally halogenated $C_{1-6}$ alkylthio group" include a $C_{1-6}$ alkylthio group (e.g., methylthio, ethylthio, propylthio, isopropylthio, butylthio, sec-butylthio, tert-butylthio) optionally having 1 to 5, preferably 1 to 3, halogen atoms (e.g., fluorine, chlorine, bromine, iodine) and the like. Specific examples include methylthio, difluoromethylthio, trifluoromethylthio, ethylthio, propylthio, isopropylthio, butylthio, 4,4,4-trifluorobutylthio, pentylthio, hexylthio and the like.

Examples of the "4- to 7-membered heterocyclic group" of the aforementioned "4- to 7-membered heterocyclic group optionally having substituent(s)" include a 4- to 7-membered (preferably, 5- to 7-membered) heterocyclic group containing, as a ring-constituting atom besides carbon atom, 1 to 4 hetero atoms selected from a nitrogen atom, a sulfur atom and an oxygen atom and the like. Preferable examples of the 4- to 7-membered heterocyclic group include a 4- to 7-membered (preferably, 5- to 7-membered) nonaromatic heterocyclic group such as pyrrolidinyl (e.g., 1-, 2- or 3-pyrrolidinyl); imidazolidinyl (e.g., 1-, 2-, 4- or 5-imidazolidinyl); imidazolinyl (e.g., 2- or 4-imidazolinyl); pyrazolidinyl (e.g., 2-, 3- or 4-pyrazolidinyl); piperidinyl (e.g., 1-, 2-, 3- or 4-piperidinyl); piperazinyl (e.g., 1- or 2-piperazinyl); tetrahydropyranyl; morpholinyl; thiomorpholinyl; dihydropyrazolyl and the like; and
a 5- to 7-membered aromatic heterocyclic group such as thienyl (e.g., 2- or 3-thienyl); furyl (e.g., 2- or 3-furyl); pyrrolyl (e.g., 1-, 2- or 3-pyrrolyl); imidazolyl (e.g., 1-, 2- or 4-imidazolyl); thiazolyl (e.g., 2-, 4- or 5-thiazolyl); oxazolyl (e.g., 2-, 4- or 5-oxazolyl); isothiazolyl (e.g., 3-isothiazolyl); isoxazolyl (e.g., 3-isoxazolyl); pyridyl (e.g., 2-, 3- or 4-pyridyl); pyrazolyl (e.g., 1-, 3- or 4-pyrazolyl); pyrazinyl (e.g., 2-pyrazinyl); pyrimidinyl (e.g., 2-, 4- or 5-pyrimidinyl); pyridazinyl (e.g., 3- or 4-pyridazinyl); oxadiazolyl (e.g., 1,2,4-oxadiazol-5-yl; 1,2,4-oxadiazol-3-yl); thiadiazolyl (e.g., 1,2,4-thiadiazol-5-yl; 1,2,4-thiadiazol-3-yl); triazolyl (e.g., 1,2,3-triazol-1-yl; 1,2,3-triazol-4-yl; 1,2,4-triazol-1-yl; 1,2,4-triazol-3-yl); tetrazolyl (e.g., 1- or 5-tetrazolyl); pyranyl (e.g., 2-, 3- or 4-pyranyl) and the like.

Examples of the aforementioned "optionally halogenated $C_{1-6}$ alkyl-carbonyl group" include a $C_{1-6}$ alkyl-carbonyl group (e.g., acetyl, propanoyl, butanoyl, pentanoyl, hexanoyl) optionally having 1 to 5, preferably 1 to 3, halogen atoms (e.g., fluorine, chlorine, bromine, iodine) and the like. Specific examples include acetyl, monochloroacetyl, trifluoroacetyl, trichloroacetyl, propanoyl, butanoyl, pentanoyl, hexanoyl and the like.

Examples of the aforementioned "$C_{1-6}$ alkoxy-carbonyl group" include methoxycarbonyl, ethoxycarbonyl, propoxycarbonyl, tert-butoxycarbonyl and the like.

Examples of the "heterocyclylcarbonyl group" of the aforementioned "heterocyclylcarbonyl group optionally having substituent(s)" include nicotinoyl, isonicotinoyl, thenoyl (e.g., 2-thenoyl, 3-thenoyl), furoyl (e.g., 2-furoyl, 3-furoyl), morpholinocarbonyl, piperidinocarbonyl, pyrrolidin-1-ylcarbonyl, indolylcarbonyl and the like.

Examples of the "heterocyclylcarbamoyl group" of the aforementioned "heterocyclylcarbamoyl group optionally having substituent(s)" include morpholinocarbamoyl, piperidinocarbamoyl, pyridylcarbamoyl (e.g., 2-pyridylcarbamoyl, 3-pyridylcarbamoyl, 4-pyridylcarbamoyl), thienylcarbamoyl (e.g., 2-thienylcarbamoyl, 3-thienylcarbamoyl), indolylcarbamoyl and the like.

Examples of the aforementioned "optionally halogenated $C_{1-6}$ alkylsulfonyl group" include a $C_{1-6}$ alkylsulfonyl group (e.g., methylsulfonyl, ethylsulfonyl, propylsulfonyl, isopropylsulfonyl, butylsulfonyl, sec-butylsulfonyl, tert-butylsulfonyl) optionally having 1 to 5, preferably 1 to 3, halogen atoms (e.g., fluorine, chlorine, bromine, iodine) and the like. Specific examples include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl and the like.

Examples of the aforementioned "optionally halogenated $C_{1-6}$ alkyl-carbonylamino group" include a $C_{1-6}$ alkyl-carbonylamino group (e.g., acetylamino, propanoylamino, butanoylamino) optionally having 1 to 5, preferably 1 to 3, halogen atoms (e.g., fluorine, chlorine, bromine, iodine) and the like. Specific examples include acetylamino, trifluoroacetylamino, propanoylamino, butanoylamino and the like.

Examples of the substituent of the aforementioned "5- to 7-membered heterocyclic group optionally having substituent(s)", "heterocyclylcarbonyl group optionally having substituent(s)" and "heterocyclylcarbamoyl group optionally having substituent(s)" include a substituent selected from the following substituent group B and the like.

[Substituent Group B]
(1) a halogen atom (e.g., fluorine, chlorine, bromine, iodine),
(2) a $C_{1-3}$ alkylenedioxy group (e.g., methylenedioxy, ethylenedioxy),
(3) a nitro group,
(4) a cyano group,
(5) an oxo group,
(6) an optionally halogenated $C_{1-5}$ alkyl group,
(7) a carbamoyl-$C_{1-6}$ alkyl group (e.g., carbamoylmethyl),
(8) an optionally halogenated $C_{3-6}$ cycloalkyl group,
(9) a $C_{6-14}$ aryl group (e.g., phenyl, naphthyl),
(10) a $C_{6-14}$ aryl $C_{1-6}$ alkyl group (e.g., benzyl, phenethyl),
(11) an optionally halogenated $C_{1-6}$ alkoxy group,

(12) an optionally halogenated $C_{1-6}$ alkylthio group,
(13) a hydroxy group,
(14) an amino group,
(15) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(16) a formyl group,
(17) a carboxy group,
(18) a carbamoyl group,
(19) a thiocarbamoyl group,
(20) an optionally halogenated $C_{1-6}$ alkyl-carbonyl group,
(21) a $C_{1-6}$ alkoxy-carbonyl group,
(22) a $C_{2-6}$ alkenyloxy-carbonyl group (e.g., allyloxycarbonyl),
(23) a $C_{6-14}$ aryl-carbonyl group (e.g., benzoyl, 1-naphthoyl, 2-naphthoyl),
(24) a mono- or di-$C_{1-6}$ alkyl-carbamoyl group (e.g., methylcarbamoyl, ethylcarbamoyl, dimethylcarbamoyl, diethylcarbamoyl, N-ethyl-N-methylcarbamoyl),
(25) a mono- or di-$C_{6-14}$ aryl $C_{1-6}$ alkyl-carbamoyl group (e.g., benzylcarbamoyl),
(26) an optionally halogenated $C_{1-6}$ alkylsulfonyl group,
(27) a $C_{6-14}$ arylsulfonyl group (e.g., phenylsulfonyl),
(28) a sulfamoyl group,
(29) a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl),
(30) a formylamino group,
(31) an optionally halogenated $C_{1-6}$ alkyl-carbonylamino group,
(32) a $C_{1-6}$ alkoxy-carbonylamino group (e.g., methoxycarbonylamino, ethoxycarbonylamino, propoxycarbonylamino, butoxycarbonylamino),
(33) a $C_{1-6}$ alkylsulfonylamino group (e.g., methylsulfonylamino, ethylsulfonylamino),
(34) a $C_{1-6}$ alkyl-carbonyloxy group (e.g., acetoxy, propanoyloxy),
(35) a $C_{1-6}$ alkoxy-carbonyloxy group (e.g., methoxycarbonyloxy, ethoxycarbonyloxy, propoxycarbonyloxy, butoxycarbonyloxy),
(36) a 5- or 6-membered aromatic heterocyclic group (e.g., tetrazolyl, thiazolyl, oxazolyl, furyl, thienyl, pyrazolyl, pyrrolyl, imidazolyl, pyridyl, pyrimidinyl, thiadiazolyl) optionally having 1 to 3 $C_{1-6}$ alkyl groups,
(37) a dihydropyrazolyl group optionally having 1 to 3 substituents selected from a $C_{1-6}$ alkyl group and an oxo group,
(38) a piperazinyl group having 1 to 3 $C_{1-6}$ alkyl groups,
(39) a piperidyl group optionally having one oxo group,
(40) a $C_{1-6}$ alkyl group optionally having 1 to 3 substituents selected from a halogen atom, a phenyl group, an imidazolyl group and a triazolyl group,
(41) a $C_{1-6}$ alkoxy group optionally having 1 to 3 substituents selected from a halogen atom and a phenyl group,
(42) a $C_{1-6}$ alkylsulfonylamino group,
(43) a phenyl group optionally having 1 to 3 substituents selected from a halogen atom and a $C_{1-6}$ alkyl group,
(44) a phenoxy group,
(45) a phenylcarbonylamino group,
(46) a benzyloxycarbonylamino group, and
(47) a benzylamino group.

The number of the substituents is, for example, 1 to 3. When the number of the substituents is two or more, the respective substituents may be the same or different.

Examples of the aforementioned "optionally halogenated $C_{1-6}$ alkyl group" include a $C_{1-6}$ alkyl group (e.g., methyl, ethyl, propyl, isopropyl, butyl, isobutyl, sec-butyl, tert-butyl, pentyl, hexyl) optionally having 1 to 5, preferably 1 to 3, halogen atoms (e.g., fluorine, chlorine, bromine, iodine). Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

Examples of the aforementioned "optionally halogenated $C_{3-6}$ cycloalkyl group" include a $C_{3-6}$ cycloalkyl group (e.g., cyclopropyl, cyclobutyl, cyclopentyl, cyclohexyl) optionally having 1 to 5, preferably 1 to 3, halogen atoms (e.g., fluorine, chlorine, bromine, iodine) and the like. Specific examples include cyclopropyl, cyclobutyl, cyclopentyl, cyclohexyl, 4,4-dichlorocyclohexyl, 2,2,3,3-tetrafluorocyclopentyl, 4-chlorocyclohexyl and the like.

Examples of each of the aforementioned "optionally halogenated $C_{1-6}$ alkoxy group", "optionally halogenated $C_{1-6}$ alkylthio group", "optionally halogenated $C_{1-6}$ alkyl-carbonyl group", "$C_{1-5}$ alkoxy-carbonyl group", "optionally halogenated $C_{1-6}$ alkylsulfonyl group" and "optionally halogenated $C_{1-6}$ alkyl-carbonylamino group" include those exemplified as the "substituent" of the aforementioned "hydrocarbon group optionally having substituent(s)".

Examples of the "heterocyclic group" of the "heterocyclic group optionally having substituent(s)" for A, R, $Y^1$, $Y^2$ or $Y^3$, and the "heterocyclic group optionally having substituent(s)" exemplified as the substituent for $Q^1$, $Q^2$, $Q^3$, $Q^4$, $Z^1$, $Z^2$ or $Z^3$ include (i) an aromatic heterocyclic group, (ii) a nonaromatic heterocyclic group and (iii) a 7- to 10-membered bridged heterocyclic group, each of which contains, as a ring-constituting atom besides carbon atom, 1 to 4 hetero atoms selected from a nitrogen atom, a sulfur atom and an oxygen atom.

Here, examples of the "aromatic heterocyclic group" include a 4- to 14-membered (preferably 4- to 10-membered) aromatic heterocyclic group containing, as a ring-constituting atom besides carbon atom, 1 to 4 hetero atoms selected from a nitrogen atom, a sulfur atom and an oxygen atom, and the like. Preferable examples of the "aromatic heterocyclic group" include a monocyclic aromatic heterocyclic group such as thienyl, furyl, pyrrolyl, imidazolyl, pyrazolyl, triazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, furazanyl, pyranyl and the like;

a fused polycyclic (preferably bicyclic or tricyclic) aromatic heterocyclic group such as benzothiophenyl, benzofuranyl, benzimidazolyl, benzoxazolyl, benzothiazolyl, benzisothiazolyl, naphtho[2,3-b]thiophenyl, phenoxathiinyl, indolyl, isoindolyl, 1H-indazolyl, purinyl, 4H-quinolizinyl, isoquinolyl, quinolyl, phthalazinyl, naphthyridinyl (e.g., 1,8-naphthyridinyl), quinoxalinyl, quinazolinyl, cinnolinyl, carbazolyl, β-carbolinyl, phenanthridinyl, acridinyl, phenazinyl, phenothiazinyl, phenoxazinyl, phthalimido, imidazopyridyl, imidazothiazolyl, thienopyridyl etc., and the like.

Examples of the "nonaromatic heterocyclic group" include a 4- to 14-membered (preferably 4- to 10-membered) nonaromatic heterocyclic group containing, as a ring-constituting atom besides carbon atom, 1 to 4 hetero atoms selected from a nitrogen atom, a sulfur atom and an oxygen atom and the like. Preferable examples of the "nonaromatic heterocyclic group" include a monocyclic nonaromatic heterocyclic group such as azetidinyl, tetrahydrothiophenyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydrothiazolyl, tetrahydroisothiazolyl, tetrahydrooxazolyl, tetrahydroisoxazolyl, piperidinyl, piperazinyl, tetrahydropyridinyl, dihydropyridinyl, tetrahydropyrimidinyl, tetrahydropyridazinyl, tetrahydropyranyl, azepanyl, morpholinyl, thiomorpholinyl, diazepanyl, azepinyl, azocanyl, diazocanyl and the like;

a fused polycyclic (preferably bicyclic or tricyclic) nonaromatic heterocyclic group such as dihydrobenzofuranyl, dihydrobenzimidazolyl, dihydrobenzoxazolyl, dihydrobenzothiazolyl, dihydrobenzisothiazolyl, dihydronaphtho[2,3-b]thiophenyl, tetrahydroisoquinolyl, tetrahydroquinolyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, octahydroisoquinolyl and the like.

Preferable examples of the "7- to 10-membered bridged heterocyclic group" include quinuclidinyl, 7-azabicyclo[2.2.1]heptanyl and the like.

Examples of the substituent of the "heterocyclic group optionally having substituent(s)" include substituents selected from the aforementioned substituent group B and the like.

The number of the substituents is, for example, 1 to 3. When the number of the substituents is two or more, the respective substituents may be the same or different.

Examples of the acyl group of the "acyl group optionally having substituent(s)" exemplified as the substituent for $Q^1$, $Q^2$, $Q^3$, $Q^4$, $Z^1$, $Z^2$ or $Z^3$ include —$COR^{1A}$, —CO—$OR^{1A}$, —$SO_2R^{1A}$, —$SOR^{1A}$, —$PO(OR^{1A})(OR^{2A})$ wherein $R^{1A}$ and $R^{2A}$ are each independently a hydrogen atom, a hydrocarbon group or a heterocyclic group, and the like.

Examples of the "hydrocarbon group" for $R^{1A}$ or $R^{2A}$ include the "hydrocarbon groups" exemplified for the "hydrocarbon group optionally having substituent(s)" exemplified as the substituent for $Q^1$, $Q^2$, $Q^3$, $Q^4$, $Z^1$, $Z^2$ or $Z^3$. The hydrocarbon group is preferably a $C_{1-6}$ alkyl group, a $C_{2-6}$ alkenyl group, a $C_{3-8}$ cycloalkyl group, a $C_{3-8}$ cycloalkenyl group, a $C_{6-14}$ aryl group, a $C_{6-14}$ aryl $C_{1-6}$ alkyl group and the like.

Examples of the "heterocyclic group" for $R^{1A}$ or $R^{2A}$ include the "heterocyclic groups" exemplified for the "heterocyclic group optionally having substituent(s)" $Q^1$, $Q^2$, $Q^3$, $Q^4$, $Z^1$, exemplified as the substituent for Q or $Z^3$. The heterocyclic group is preferably thiazolyl, oxazolyl, isothiazolyl, isoxazolyl, pyrazolyl, pyridyl, pyrazinyl, benzoxazolyl, benzothiazolyl, quinolyl, isoquinolyl, pyrrolidinyl, piperidinyl, piperazinyl and the like.

The acyl group optionally has 1 to 3 substituents at substitutable position(s). Examples of such substituent include an optionally halogenated $C_{1-6}$ alkyl group (e.g., methyl, ethyl); an optionally halogenated $C_{1-6}$ alkoxy group (e.g., methoxy, ethoxy); a halogen atom (e.g., fluorine, chlorine, bromine, iodine); a nitro group; a hydroxy group; an amino group (e.g., methylamino, dimethylamino) optionally mono- or di-substituted by a $C_{1-6}$ alkyl group (e.g., methyl, ethyl); a $C_{1-6}$ alkoxycarbonylamino group (e.g., tert-butoxycarbonylamino) and the like.

Preferable examples of the acyl group include a formyl group, a carboxyl group, a $C_{1-6}$ alkyl-carbonyl group (e.g., acetyl, propionyl, butyryl, isobutyryl, valeryl, isovaleryl, pivaloyl, hexanoyl), a $C_{2-6}$ alkenyl-carbonyl group (e.g., crotonoyl), a $C_{3-8}$ cycloalkyl-carbonyl group (e.g., cyclobutanecarbonyl, cyclopentanecarbonyl, cyclohexanecarbonyl, cycloheptanecarbonyl), a $C_{3-8}$ cycloalkenyl-carbonyl group (e.g., 2-cyclohexenecarbonyl), a $C_{6-14}$ aryl-carbonyl group (e.g., benzoyl, 1-naphthoyl, 2-naphthoyl), a $C_{6-14}$ aryl $C_{1-6}$ alkyl-carbonyl group (e.g., benzylcarbonyl, phenethylcarbonyl), an aromatic heterocyclylcarbonyl group (e.g., nicotinoyl, isonicotinoyl), a nonaromatic heterocyclylcarbonyl group (e.g., pyrrolidinylcarbonyl, piperidinylcarbonyl), a $C_{1-6}$ alkoxy-carbonyl group (e.g., methoxycarbonyl, ethoxycarbonyl, propoxycarbonyl, butoxycarbonyl, tert-butoxycarbonyl), a $C_{6-14}$ aryloxy-carbonyl group (e.g., phenyloxycarbonyl, naphthyloxycarbonyl), a $C_{6-14}$ aryl $C_{1-6}$ alkyloxy-carbonyl group (e.g., benzyloxycarbonyl, phenethyloxycarbonyl), a $C_{1-6}$ alkylsulfinyl group (e.g., methylsulfinyl, ethylsulfinyl), a alkylsulfonyl group (e.g., methylsulfonyl, ethylsulfonyl), a $C_{6-14}$ arylsulfonyl group (e.g., phenylsulfonyl), a phosphono group, a mono- or di-$C_{1-6}$ alkylphosphono group (e.g., dimethylphosphono, diethylphosphono, diisopropylphosphono, dibutylphosphono) and the like.

Examples of the "amino group optionally having substituent(s)", "carbamoyl group optionally having substituent(s)" and "sulfamoyl group optionally having substituent(s)" exemplified as the substituent for $Q^1$, $Q^2$, $Q^3$, $Q^4$, $Z^1$, $Z^2$, or $Z^3$ include an amino group, a carbamoyl group and a sulfamoyl group, each of which optionally has 1 or 2 substituents selected from (1) the "hydrocarbon group optionally having substituent(s)", "acyl group optionally having substituent(s)" and "heterocyclic group optionally having substituent(s)", each exemplified as the substituent for $Q^1$, $Q^2$, $Q^3$, $Q^4$, $Z^1$, $Z^2$ or $Z^3$; and (2) a carbamoyl group optionally having 1 or 2 substituents selected from a $C_{1-6}$ alkyl group (e.g., methyl, ethyl), a $C_{3-8}$ cycloalkyl group (e.g., cyclopropyl, cyclohexyl), a $C_{6-14}$ aryl group (e.g., phenyl) and a $C_{6-14}$ aryl $C_{1-6}$ alkyl group (e.g., benzyl). When the nitrogen atom constituting the amino group, carbamoyl group and sulfamoyl group is substituted by two substituents, the substituents may form, together with the adjacent nitrogen atom, a nitrogen-containing heterocycle. Examples of the "nitrogen-containing heterocycle" include a 5- to 7-membered nitrogen-containing heterocycle containing one nitrogen atom as a ring-constituting atom besides carbon atom, and optionally further containing 1 or 2 hetero atoms selected from a nitrogen atom, a sulfur atom and an oxygen atom. Preferable examples of the nitrogen-containing heterocycle include pyrrolidine, imidazolidine, pyrazolidine, piperidine, piperazine, morpholine, thiomorpholine and the like.

The "amino group optionally having substituent(s)", "carbamoyl group optionally having substituent(s)" and "sulfamoyl group optionally having substituent(s)" are preferably an amino group, a carbamoyl group and a sulfamoyl group, respectively, each of which optionally has "1 or 2 substituents selected from a $C_{1-6}$ alkyl group, a $C_{2-6}$ alkenyl group, a $C_{3-8}$ cycloalkyl group, a $C_{6-14}$ aryl group, a $C_{6-14}$ aryl $C_{1-6}$ alkyl group, a $C_{1-6}$ alkyl-carbonyl group, a $C_{6-14}$ aryl-carbonyl group, a $C_{6-14}$ aryl $C_{1-6}$ alkyl-carbonyl group, an aromatic heterocyclylcarbonyl group, a nonaromatic heterocyclylcarbonyl group, a $C_{1-6}$ alkoxy-carbonyl group, an aromatic heterocyclic group, a carbamoyl group, a mono- or di-$C_{1-6}$ alkyl-carbamoyl group and a mono- or di-$C_{6-14}$ aryl $C_{1-6}$ alkyl-carbamoyl group, each of which optionally has 1 to 3 substituents selected from a halogen atom (e.g., fluorine, chlorine, bromine, iodine), an optionally halogenated $C_{1-6}$ alkoxy group, a hydroxy group, a nitro group, an amino group and a carbamoyl group".

Preferable examples of the amino group optionally having substituent(s) include an amino group, a mono- or di-$C_{1-6}$ alkylamino group (e.g., methylamino, dimethylamino, ethylamino, diethylamino, propylamino, dibutylamino), a mono- or di-$C_{2-6}$ alkenylamino group (e.g., diallylamino), a mono- or di-$C_{3-8}$ cycloalkylamino group (e.g., cyclopropylamino, cyclohexylamino), a mono- or di-$C_{6-14}$ arylamino group (e.g., phenylamino), a mono- or di-$C_{6-14}$ aryl $C_{1-6}$ alkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{6-14}$ aryl $C_{1-6}$ alkyl-carbonylamino group (e.g., benzylcarbonylamino), a mono- or di-aromatic heterocyclylcarbonylamino group (e.g., nicotinoylamino, isonicotinoylamino), a mono- or di-nonaromatic heterocyclylcarbonylamino group (e.g., piperidinylcarbonylamino), a mono- or di-$C_{1-6}$ alkoxy-carbonylamino group (e.g., tert-butoxycarbonylamino), an aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{6-14}$ aryl $C_{1-6}$ alkyl-carbamoyl)amino group (e.g., benzylcarbamoylamino) and the like.

Preferable examples of the carbamoyl group optionally having substituent(s) include a carbamoyl group, a mono- or di-$C_{1-6}$ alkyl-carbamoyl group (e.g., methylcarbamoyl, ethylcarbamoyl, dimethylcarbamoyl, diethylcarbamoyl, N-ethyl-N-methylcarbamoyl), a mono- or di-$C_{2-6}$ alkenyl-carbamoyl group (e.g., diallylcarbamoyl), a mono- or di-$C_{3-8}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{6-14}$ aryl $C_{1-6}$ alkyl-carbamoyl group (e.g., benzylcarbamoyl, phenethylcarbamoyl), a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl), an aromatic heterocyclylcarbamoyl group (e.g., pyridylcarbamoyl), and a nitrogen-containing heterocyclylcarbonyl group (e.g., morpholinocarbonyl).

Preferable examples of the sulfamoyl group optionally having substituent(s) include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-8}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{6-14}$ aryl $C_{1-6}$ alkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl), an aromatic heterocyclylsulfamoyl group (e.g., pyridylsulfamoyl) and the like.

Examples of the "hydroxy group optionally having a substituent" and "sulfanyl group optionally having a substituent" exemplified as the substituent for $Q^1$, $Q^2$, $Q^3$, $Q^4$, $Z^1$, $Z^2$ or $Z^3$ include a hydroxy group and a sulfanyl group, each optionally having a substituent selected from the "hydrocarbon group optionally having substituent(s)", "acyl group optionally having substituent(s)" and "heterocyclic group optionally having substituent(s)" each exemplified as the substituent for $Q^1$, $Q^2$, $Q^3$, $Q^4$, $Z^1$, $Z^2$, or $Z^3$.

The "hydroxy group optionally having substituent(s)" and "sulfanyl group optionally having substituent(s)" are preferably a hydroxy group and a sulfanyl group, each optionally having the "substituent selected from a $C_{1-6}$ alkyl group, a $C_{2-6}$ alkenyl group, a $C_{3-8}$ cycloalkyl group, a $C_{6-14}$ aryl group, a $C_{6-14}$ aryl $C_{1-6}$ alkyl group, a $C_{1-6}$ alkyl-carbonyl group, a $C_{6-14}$ aryl-carbonyl group and an aromatic heterocyclic group, each of which optionally has 1 to 3 substituents selected from a halogen atom (e.g., fluorine, chlorine, bromine, iodine), an optionally halogenated $C_{1-6}$ alkoxy group, a hydroxy group, a nitro group, an amino group and a carbamoyl group".

Preferable examples of the hydroxy group optionally having substituent(s) include a hydroxy group, a $C_{1-6}$ alkoxy group (e.g., methoxy, ethoxy, propoxy, isopropoxy, butoxy, isobutoxy, sec-butoxy, tert-butoxy, pentyloxy, isopentyloxy, neopentyloxy, hexyloxy), a $C_{2-6}$ alkenyloxy group (e.g., alkyloxy, 2-butenyloxy, 2-pentenyloxy, 3-hexenyloxy), a $C_{3-8}$ cycloalkyloxy group (e.g., cyclohexyloxy), a $C_{6-14}$ aryloxy group (e.g., phenoxy, naphthyloxy), a $C_{6-14}$ aryl $C_{1-6}$ alkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), an aromatic heterocyclyloxy group (e.g., pyridyloxy) and the like.

Preferable examples of the sulfanyl group optionally having substituent(s) include a sulfanyl group, a $C_{1-6}$ alkylthio group (e.g., methylthio, ethylthio, propylthio, isopropylthio, butylthio, isobutylthio, sec-butylthio, tert-butylthio, pentylthio, isopentylthio, neopentylthio, hexylthio), a $C_{2-6}$ alkenylthio group (e.g., allylthio, 2-butenylthio, 2-pentenylthio, 3-hexenylthio), a $C_{3-8}$ cycloalkylthio group (e.g., cyclohexylthio), a $C_{6-14}$ arylthio group (e.g., phenylthio, naphthylthio), a $C_{6-14}$ aryl $C_{1-6}$ alkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), an aromatic heterocyclylthio group (e.g., pyridylthio) and the like.

Examples of the "hydrocarbon group" of the "acyclic hydrocarbon group optionally having substituent(s)" for X include (1) a $C_{1-6}$ alkyl group (e.g., methyl, ethyl, propyl, isopropyl, butyl, isobutyl, sec-butyl, tert-butyl, pentyl, hexyl), (2) a $C_{2-6}$ alkenyl group (e.g., vinyl, allyl, isopropenyl, 2-butenyl), (3) a $C_{2-6}$ alkynyl group (e.g., ethynyl, propargyl, 2-butynyl) and the like.

Examples of the substituent of the "acyclic hydrocarbon group optionally having substituent(s)" for X include the substituents selected from the aforementioned substituent group A and the like.

The number of the substituents is, for example, 1 to 5, preferably 1 to 3. When the number of the substituents is two or more, the respective substituents may be the same or different.

Examples of the "saturated cyclic group" of the "saturated cyclic group optionally having substituent(s)" for X include (1) a $C_{3-8}$ cycloalkyl group (e.g., cyclopropyl, cyclobutyl, cyclopentyl, cyclohexyl, cycloheptyl, cyclooctyl), (2) a 4- to 14-membered (preferably 4- to 8-membered, more preferably 5- or 6-membered) saturated heterocyclic group (e.g., azetidinyl, tetrahydrothiophenyl, tetrahydrofuranyl, pyrrolidinyl, imidazolidinyl, oxazolidinyl, pyrazolidinyl, thiazolidinyl, oxazolidinyl, isothiazolidinyl, isoxazolidinyl, piperidinyl, piperazinyl, morpholinyl, thiomorpholinyl, azepanyl, diazepanyl, oxazepanyl, thiazepanyl, azocanyl, diazocanyl) containing, as a ring-constituting atom besides carbon atom, 1 to 4 hetero atoms selected from a nitrogen atom, a sulfur atom and an oxygen atom, and the like.

Examples of the substituent of the "saturated cyclic group optionally having substituent(s)" for X include the substituents selected from the aforementioned substituent group B and the like.

The number of the substituents is, for example, 1 to 3. When the number of the substituents is two or more, the respective substituents may be the same or different.

Examples of the "ring" of the "ring optionally having substituent(s)" optionally formed by A and R, bonded to each other, together with the adjacent carbonyl and nitrogen atom include a 5- to 7-membered monocyclic nitrogen-containing nonaromatic heterocycle (e.g., 2-oxopyrrolidine, 2-oxopiperidine, 2-oxopiperazine, 3-oxomorpholine, 3-oxothiomorpholine), and a 4- to 10-membered heterocycle (e.g., dihydroisoindole), each containing one nitrogen atom as a ring-constituting atom besides carbon atom, and optionally further containing one hetero atom selected from a nitrogen atom, a sulfur atom and an oxygen atom, and having 1 or 2 oxo groups, and the like.

Examples of the substituent of the "ring optionally having substituent(s)" optionally formed by A and R bonded to each other include the substituents selected from the aforementioned substituent group B and the like.

The number of the substituents is, for example, 1 to 3. When the number of the substituents is two or more, the respective substituents may be the same or different.

Examples of the "ring" of the "ring optionally having substituent(s)" optionally formed by $Q^1$ and $Q^2$, and $Q^3$ and $Q^4$, each bonded to each other, together with the adjacent carbon atoms include a 5- or 6-membered aromatic ring or nonaromatic ring each optionally containing, as a ring-constituting atom besides carbon atom, 1 to 3 hetero atoms selected from a nitrogen atom, a sulfur atom and an oxygen atom and the like. Examples of the "aromatic ring" include benzene, thiophene, furan, pyrrole, pyrazole, imidazole, thiazole, oxazole, isothiazole, isoxazole, oxadiazole, thiadiazole, triazole, pyridine, pyrazine, pyrimidine, pyridazine, pyran and the like. Examples of the "nonaromatic ring" include cyclopentene, cyclohexene, cyclohexadiene, dihydrothiophene, dihydrofuran, pyrroline, pyrazoline, imidazoline, thiazoline, oxazoline, isothiazoline, isoxazoline, tetrahydropyridine, dihydropyridine, tetrahydropyrazine, dihydropyrazine, tetrahydropyrimidine, dihydropyrimidine, tetrahydropyridazine, dihydropyridazine, dihydropyran and the like.

Examples of the substituent of the "ring optionally having substituent(s)" optionally formed by $Q^1$ and $Q^2$, and $Q^3$ and $Q^4$, each bonded to each other, include the substituents selected from the aforementioned substituent group B and the like.

The number of the substituents is, for example, 1 to 3. When the number of the substituents is two or more, the respective substituents may be the same or different.

Examples of the "ring" of the "ring optionally having substituent(s)" optionally formed by X and $Y^1$, bonded to each other, together with the adjacent nitrogen atom and carbon atom include a 5- to 7-membered nitrogen-containing nonaromatic heterocycle containing one nitrogen atom as a ring-constituting atom besides carbon atom, and optionally further containing one hetero atom selected from a nitrogen atom, a sulfur atom and an oxygen atom and the like. Examples of the "nitrogen-containing nonaromatic ring" include pyrrolidine, pyrroline, pyrazoline, imidazoline, thiazolidine, oxazolidine, isothiazolidine, isoxazolidine, thiazoline, oxazoline, isothiazoline, isoxazoline, piperidine, piperazine, morpholine, thiomorpholine, azepane, diazepane, oxazepane, thiazepane and the like.

Examples of the substituent of the "ring optionally having substituent(s)" optionally formed by X and $Y^1$ bonded to each other include the substituents selected from the aforementioned substituent group B and the like.

The number of the substituents is, for example, 1 to 3. When the number of the substituents is two or more, the respective substituents may be the same or different.

Examples of the "ring" of the "ring optionally having substituent(s)" optionally formed by $Y^1$ and $Y^2$, bonded to each other, together with the adjacent carbon atom include
(1) a $C_{3-8}$ cycloalkane ring (e.g., cyclopropane, cyclobutane, cyclopentane, cyclohexane, cycloheptane, cyclooctane),
(2) a 2,3-dihydroindene ring,
(3) a fluorene ring,
(4) a 4- to 14-membered (preferably 4- to 10-membered) nonaromatic heterocycle containing, as a ring-constituting atom besides carbon atom, 1 to 4 hetero atoms selected from a nitrogen atom, a sulfur atom and an oxygen atom and the like.

Preferable examples of the "nonaromatic heterocycle" include a monocyclic nonaromatic heterocycle such as azetidine, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydrothiazoline, tetrahydroisothiazoline, tetrahydrooxazoline, tetrahydroisoxazoline, piperidine, piperazine, tetrahydropyridine, dihydropyridine, tetrahydropyrimidine, tetrahydropyridazine, tetrahydropyran, azepane, morpholine, thiomorpholine, diazepane, azepine, azocane, diazocane, tetrahydrothiopyran and the like;
a fused polycyclic (preferably bicyclic or tricyclic) nonaromatic heterocycle such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline, 8-azabicyclo[3.2.1]octane and the like.

Examples of the substituent of the "ring optionally having substituent(s)" optionally formed by $Y^1$ and $Y^2$ bonded to each other include the substituents selected from the aforementioned substituent group B and the like.

The number of the substituents is, for example, 1 to 3. When the number of the substituents is two or more, the respective substituents may be the same or different.

Preferably, $Q^1$ is a hydrogen atom or a $C_{1-6}$ alkyl group, and $Q^2$, $Q^3$ and $Q^4$ are each a hydrogen atom.

$Q^1$, $Q^2$, $Q^3$ and $Q^4$ are each more preferably a hydrogen atom.

$Z^1$, $Z^2$ and $Z^3$ are each preferably a hydrogen atom.

A is preferably a hydrocarbon group optionally having substituent(s), more preferably,
(1) a $C_{6-14}$ aryl group (e.g., phenyl, biphenylyl) optionally having 1 to 3 substituents selected from
    (a) a halogen atom,
    (b) a $C_{1-6}$ alkyl group optionally having 1 to 5 halogen atoms,
    (c) a $C_{6-14}$ aryloxy group,
    (d) a $C_{6-14}$ aryl $C_{1-6}$ alkyloxy group,
    (e) a $C_{6-14}$ aryl-carbonylamino group,
    (f) a $C_{6-14}$ aryl $C_{1-6}$ alkylamino group, and
    (g) a 5- to 7-membered nonaromatic heterocyclic group (e.g., piperidyl) containing, as a ring-constituting atom besides carbon atom, one or two hetero atoms selected from a nitrogen atom, a sulfur atom and an oxygen atom, and optionally having an oxo group, (2) a $C_{6-14}$ aryl $C_{1-6}$ alkyl group optionally having a $C_{6-14}$ aryl $C_{1-6}$ alkyloxy-carbonylamino group, or (3) a $C_{6-14}$ aryl $C_{1-6}$ alkyl $C_{6-14}$ aryl group.

R is preferably a hydrogen atom or a $C_{1-6}$ alkyl group, more preferably, a hydrogen atom.

X is preferably a hydrogen atom or a $C_{1-6}$ alkyl group optionally substituted by one $C_{3-6}$ cycloalkyl group, more preferably, a hydrogen atom or a $C_{1-6}$ alkyl group, further preferably, a hydrogen atom.

Preferably, $Y^1$, $Y^2$ and $Y^3$ are each independently (1) a hydrogen atom, (2) a $C_{1-20}$ alkyl group optionally having 1 to 3 substituents selected from an amino group, a $C_{1-6}$ alkoxy group, a phenyl group, a phenyloxy group and a benzyloxy group, (3) a $C_{3-8}$ cycloalkyl group, (4) a phenyl group optionally having 1 to 3 substituents selected from a halogen atom, a $C_{1-6}$ alkoxy group, a $C_{1-3}$ alkylenedioxy group and a di-$C_{1-6}$ alkylamino group, 5) a pyridyl group optionally having 1 to 3 $C_{1-6}$ alkoxy groups, (6) a naphthyl group, (7) a biphenylyl group, (8) a thienyl group, (9) an imidazolyl group,

(10) a thiazolyl group,

(11) a piperidyl group optionally having 1 to 3 $C_{1-6}$ alkyl groups,

(12) an imidazopyridyl group,

(13) an imidazothiazolyl group,

(14) a thienopyridyl group, or

(15) an 1,8-naphthyridinyl group.

In another preferable embodiment, $Y^1$, $Y^2$ and $Y^3$ are each independently (1) a hydrogen atom, (2) a $C_{1-20}$ alkyl group optionally having 1 to 3 substituents selected from
  (a) an amino group,
  (b) a $C_{1-6}$ alkoxy group,
  (c) a $C_{6-14}$ aryloxy group, and
  (d) a $C_{6-14}$ aryl $C_{1-6}$ alkyloxy group, (3) a $C_{3-8}$ cycloalkyl group, (4) a $C_{6-14}$ aryl group (e.g., phenyl, naphthyl, biphenylyl) optionally having 1 to 3 substituents selected from
  (a) a halogen atom,
  (b) a $C_{1-6}$ alkoxy group, and
  (c) a $C_{1-3}$ alkylenedioxy group, (5) a $C_{6-14}$ aryl $C_{1-6}$ alkyl group, or (6) a 5- to 7-membered monocyclic aromatic heterocyclic group (e.g., pyridyl, thienyl) containing, as a ring-constituting atom besides carbon atom, 1 to 4 hetero atoms selected from a nitrogen atom, a sulfur atom and an oxygen atom, and optionally having 1 to 3 $C_{1-6}$ alkoxy groups.

An embodiment wherein X and $Y^1$ are bonded to each other to form, together with the adjacent nitrogen atom and carbon atom, a 5- to 7-membered monocyclic nitrogen-containing nonaromatic heterocycle (e.g., pyrrolidine) containing one nitrogen atom as a ring-constituting atom besides carbon atom, and optionally further containing one hetero atom selected from a nitrogen atom, a sulfur atom and an oxygen atom is also preferable.

When X and $Y^1$ are bonded to each other to form, together with the adjacent nitrogen atom and carbon atom, a ring optionally having substituent(s), $Y^2$ and $Y^3$ are each preferably a hydrogen atom.

An embodiment wherein $Y^1$ and $Y^2$ are bonded to each other to form, together with the adjacent carbon atom, a $C_{3-8}$ cycloalkane ring,
a pyrrolidine ring,
a piperidine ring,
a tetrahydropyran ring,
a 2,3-dihydroindene ring,
a fluorene ring,
a 8-azabicyclo[3.2.1]octane ring, or
a tetrahydrothiopyran ring, each of which optionally has 1 to 3 substituents selected from (1) a halogen atom, (2) a $C_{1-6}$ alkyl group optionally having 1 to 3 substituents selected from a halogen atom and a phenyl group, (3) a $C_{3-6}$ cycloalkyl group, (4) an oxo group, (5) a phenyl group, (6) a $C_{2-6}$ alkenyloxy-carbonyl group, and (7) a $C_{1-6}$ alkyl-carbonyl group, is also preferable.

An embodiment wherein $Y^1$ and $Y^2$ are bonded to each other to form, together with the adjacent carbon atom, (1) $C_{3-8}$ cycloalkane (e.g., cycloheptane, cyclooctane), (2) 2,3-dihydroindene, (3) fluorene, or (4) a 5- to 7-membered monocyclic nonaromatic heterocycle (e.g., piperidine) containing, as a ring-constituting atom besides carbon atom, one or two hetero atoms selected from a nitrogen atom, a sulfur atom and an oxygen atom, and optionally having 1 to 3 substituents selected from
  (a) a $C_{1-6}$ alkyl group,
  (b) a $C_{6-14}$ aryl $C_{1-6}$ alkyl group, and
  (c) a $C_{2-6}$ alkenyloxy-carbonyl group, is also preferable.

When $Y^1$ and $Y^2$ are optionally bonded to each other to form, together with the adjacent carbon atom, a ring optionally having substituent(s), X and $Y^3$ are each preferably a hydrogen atom.

In the formula (I), the configuration of a substituent represented by the formula

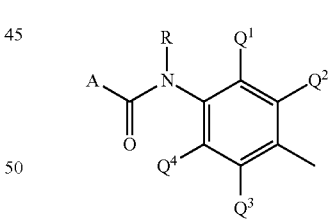

and a substituent represented by the formula —N(X)—C($Y^1$)($Y^2$)($Y^3$) on a cyclopropane ring is preferably a trans form rather than a cis form.

Specific preferable examples of compound (I) include the following compound.

[Compound A]

Compound (I) wherein

A is (1) a $C_{6-14}$ aryl group (e.g., phenyl, biphenylyl) optionally having 1 to 3 substituents selected from
  (a) a halogen atom,
  (b) a $C_{1-6}$ alkyl group optionally having 1 to 5 halogen atoms,
  (c) a $C_{6-14}$ aryloxy group, (d) a $C_{6-14}$ aryl $C_{1-6}$ alkyloxy group,
(e) a $C_{6-14}$ aryl-carbonylamino group,
(f) a $C_{6-14}$ aryl $C_{1-6}$ alkylamino group, and
(g) a 5- to 7-membered nonaromatic heterocyclic group (e.g., piperidinyl) containing, as a ring-constituting atom besides carbon atom, one or two hetero atoms selected from a nitrogen atom, a sulfur atom and an oxygen atom, and optionally having an oxo group, (2) a $C_{6-14}$ aryl $C_{1-6}$ alkyl group optionally having a $C_{6-14}$ aryl $C_{1-6}$ alkyloxy-carbonylamino group, or
(3) a $C_{6-14}$ aryl $C_{1-6}$ alkyl $C_{6-14}$ aryl group;
R is a hydrogen atom;
$Q^1$, $Q^2$, $Q^3$ and $Q^4$ are each a hydrogen atom;
X is a hydrogen atom or a $C_{1-6}$ alkyl group;
$Y^1$, $Y^2$ and $Y^3$ are each independently
(1) a hydrogen atom,
(2) a $C_{1-20}$ alkyl group optionally having 1 to 3 substituents selected from
  (a) an amino group,
  (b) a $C_{1-6}$ alkoxy group,
  (c) a $C_{6-14}$ aryloxy group, and
  (d) a $C_{6-14}$ aryl $C_{1-6}$ alkyloxy group,
(3) a $C_{3-6}$ cycloalkyl group,
(4) a $C_{6-14}$ aryl group (e.g., phenyl, naphthyl, biphenylyl) optionally having 1 to 3 substituents selected from
  (a) a halogen atom,
  (b) a $C_{1-6}$ alkoxy group, and
  (c) a $C_{1-3}$ alkylenedioxy group,
(5) a $C_{6-14}$ aryl $C_{1-6}$ alkyl group, or
(6) a 5- to 7-membered monocyclic aromatic heterocyclic group (e.g., pyridyl, thienyl) containing, as a ring-constituting atom besides carbon atom, 1 to 4 hetero atoms selected from a nitrogen atom, a sulfur atom and an oxygen atom, and optionally having 1 to 3 $C_{1-6}$ alkoxy groups;
X and $Y^1$ are optionally bonded to each other to form, together with the adjacent nitrogen atom and carbon atom, a 5- to 7-membered monocyclic nitrogen-containing nonaromatic heterocycle (e.g., pyrrolidine) containing one nitrogen atom as a ring-constituting atom besides carbon atom, and optionally further containing one hetero atom selected from a nitrogen atom, a sulfur atom and an oxygen atom;
$Y^1$ and $Y^2$ are optionally bonded to each other to form, together with the adjacent carbon atom,
(1) $C_{3-8}$ cycloalkane (e.g., cycloheptane, cyclooctane),
(2) 2,3-dihydroindene,
(3) fluorene, or
(4) a 5- to 7-membered monocyclic nonaromatic heterocycle (e.g., piperidine) containing, as a ring-constituting atom besides carbon atom, one or two hetero atoms selected from a nitrogen atom, a sulfur atom and an oxygen atom, and optionally having 1 to 3 substituents selected from
  (a) a $C_{1-6}$ alkyl group,
  (b) a $C_{6-14}$ aryl $C_{1-6}$ alkyl group, and
  (c) a $C_{2-6}$ alkenyloxy-carbonyl group; and
$Z^1$, $Z^2$ and $Z^3$ are each a hydrogen atom.

The salt of compound (I) is preferably a pharmacologically acceptable salt. Examples of such salt include salts with inorganic bases, salts with organic bases, salts with inorganic acids, salts with organic acids, and salts with basic or acidic amino acids.

Preferable examples of salts with inorganic bases include alkali metal salts such as sodium salts, potassium salts and the like; alkali earth metal salts such as calcium salts, magnesium salts and the like; aluminum salts; and ammonium salts.

Preferable examples of salts with organic bases include salts with trimethylamine, triethylamine, pyridine, picoline, ethanolamine, diethanolamine, triethanolamine, dicyclohexylamine, N,N-dibenzylethylenediamine and the like.

Preferable examples of salts with inorganic acids include salts with hydrochloric acid, hydrobromic acid, nitric acid, sulfuric acid, phosphoric acid and the like.

Preferable examples of salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of salts with basic amino acids include salts with arginine, lysine, ornithine and the like.

Preferable examples of salts with acidic amino acids include salts with aspartic acid, glutamic acid and the like.

The salt of compound (I) is preferably a salt with an inorganic acid (preferably, hydrochloric acid) or an organic acid (preferably, trifluoroacetic acid).

Compound (I) may also be used as a prodrug. A prodrug of compound (I) means a compound which is converted to compound (I) due to a reaction due to an enzyme, gastric acid, etc. under the physiological condition in the living body, that is, a compound which is converted to compound (I) with oxidation, reduction, hydrolysis, and the like according to an enzyme; a compound which is converted to compound (I) by hydrolysis etc. due to gastric acid, and the like. A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation and dimethylaminomethylcarbonylation); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation) and the like. Any of these compounds can be produced from compound (I) by a method known per se.

The prodrug of compound (I) may be a compound that converts to compound (I) under physiological conditions as described in Development of Pharmaceutical Products, vol. 7, Molecular Design, 163-198, Hirokawa Shoten (1990).

Compound (I) may be labeled with an isotope (e.g., $^2$H, $^3$H, $^{14}$C, $^{35}$S, $^{125}$I, $^{11}$C, $^{18}$F) and the like.

Compound (I) labeled with or substituted by an isotope can be used, for example, as a tracer used for Positron Emission Tomography (PET) (PET tracer), and is useful in the field of medical diagnosis and the like.

Compound (I) may be an anhydrate or a hydrate. Compound (I) may be a solvate or a non-solvate. Furthermore, compound (I) may be a deuterated compound.

Compound (I) may be a crystal, and both a single crystal and crystal mixtures are encompassed in compound (I). Crystals can be produced by crystallization according to crystallization methods known per se.

In addition, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, and stability). The cocrystal and cocrystal salt can be produced by cocrystallization method known per se.

When compound (I) includes isomers such as optical isomers, stereoisomers, regioisomers, rotational isomers, geometrical isomers, and the like, one of the isomers and mixture are also encompassed in compound (I).

Compound (I) or a prodrug thereof (hereinafter sometimes to be simply abbreviated as the compound of the present invention) has low toxicity (e.g., acute toxicity, chronic toxicity, genetic toxicity, reproductive toxicity, cardiotoxicity, carcinogenicity), and can be used as it is or in the form of a pharmaceutical composition (in the present specification, sometimes to be abbreviated as "medicament of the present invention") after mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As a pharmaceutical acceptable carrier here, common organic or inorganic carrier substances are used as formulation raw materials. Carriers are added as vehicles, lubricants, binders and disintegrants in the solid formulations; and as solvents, solubilizing agents, suspending agents, isotonization agents, buffering agents, soothing agents etc. in the liquid formulations. If desired, formulation additives such as preservatives, antioxidants, colorants, sweeteners, etc. can be used.

Preferable examples of the vehicles are as follows: lactose, sucrose, D-mannitol, D-sorbitol, starch, α-starch, dextrin, crystalline cellulose, low-substituted hydroxypropyl cellulose, sodium carboxymethylcellulose, gum Arabic, pullulan, light anhydrous silicic acid, synthetic aluminum silicate, and magnesium metasilicic aluminate.

Preferable examples of the lubricant include magnesium stearate, calcium stearate, talc, colloidal silica, and the like.

Preferable examples of the binders are as follows: α-starch, sucrose, gelatin, gum Arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropyl methylcellulose, and polyvinylpyrrolidone.

Preferable examples of the disintegrants are as follows: lactose, sucrose, starch, carboxymethylcellulose, calcium carboxymethylcellulose, croscarmellose sodium, sodium carboxymethyl starch, light anhydrous silicic acid, and low-substituted hydroxypropylcellulose.

Preferable examples of the solvents are as follows: water for injection, physiological saline, Linger solution, alcohol, propylene glycol, polyethylene glycol, sesame oil, corn oil, olive oil, and cottonseed oil.

Preferable examples of the solubilizing agents are as follows: polyethylene glycol, propylene glycol, D-mannitol, trehalose, benzyl benzoate, ethanol, tris-aminomethane, cholesterol, triethanolamine, sodium carbonate, sodium citrate, sodium salicylate, and sodium acetate.

Preferable examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, and polyoxyethylene hydrogenated castor oil.

Preferable examples of the isotonization agents include sodium chloride, glycerin, D-mannitol, D-sorbitol, and glucose.

Preferable examples of the buffering agent include buffer solutions such as phosphates, acetates, carbonates, and citrates.

Preferable examples of the soothing agent include benzyl alcohol.

Preferable examples of the preservative include p-hydroxybenzoates, chlorobutanol, benzyl alcohol, phenethyl alcohol, dehydroacetic acid, and sorbic acid.

Preferable examples of antioxidants include sulfites and ascorbates.

Preferable examples of the colorants include water soluble edible tar dyes (e.g., edible dyes such as Food Red No. 2 and No. 3, Food Yellow No. 4 and No. 5, Food Blue No. 1 and 2, etc.); water insoluble lake dyes (e.g., aluminum salts of the aforementioned water soluble edible tar dyes), and natural dyes (e.g., β-carotene, chlorophyll, ferric oxide red).

Preferable examples of the sweeteners include sodium saccharin, dipotassium glycyrrhizinate, aspartame and stevia.

Examples of the dosage form of the medicament of the present invention include oral preparations such as tablet (including sublingual tablet, orally disintegrating tablet), capsule (including soft capsule, microcapsule), granule, powder, troche, syrup, emulsion, suspension and the like; and parenteral agents such as injection (e.g., subcutaneous injection, intravenous injection, intramuscular injection, intraperitoneal injection, drip infusion), external preparation (e.g., dermal preparation, ointment), suppository (e.g., rectal suppository, vaginal suppository), pellet, nasal preparation, pulmonary preparation (inhalant), eye drop and the like, which can be respectively safely administered orally or parenterally.

These preparations may be a release control preparation (e.g., sustained-release microcapsule) such as an immediate-release preparation, a sustained-release preparation and the like.

The medicament of the present invention can be manufactured by the common methods in the field of formulation technology, for example, methods listed in the Japanese Pharmacopoeia, and the like.

The content of the compound of the present invention in the medicament of the present invention varies based on the dosage forms, dosages of the compound of the present invention, and the like. For example, it is approximately about 0.1 to 100 wt %.

The compound of the present invention has a superior LSD1 inhibitory action and can be used as a prophylactic or therapeutic agent for various diseases in mammals (e.g., human, mouse, rat, rabbit, dog, cat, bovine, horse, swine, monkey). Moreover, since the compound of the present invention shows low monoamine oxidase A (MAO-A) and monoamine oxidase B (MAO-B) inhibitory activity and high LSD1 selectivity, it causes fewer side effects.

In addition, the compound of the present invention is expected to show, after transfer into the brain, suppression of a decrease in histone H3K4 methylation and suppression of a decrease in Gad1 mRNA expression, which are derived from the inhibition of LSD1. As a result, it is also useful as a medicament based on superior actions of nerve activation, enhancement of neural plasticity, promotion of neurogenesis, and promotion of BDNF production.

The compound of the present invention can be used as a prophylactic or therapeutic agent for cancer. Examples of the cancer include breast cancer, prostate cancer, pancreatic cancer, gastric cancer, lung cancer, colon cancer, rectal cancer, esophagus cancer, duodenal cancer, tongue cancer, pharyngeal cancer, brain tumor, neurinoma, non-small cell lung cancer, small cell lung cancer, liver cancer, kidney cancer, bile duct cancer, uterine body cancer, cervical cancer, ovarian cancer, urinary bladder cancer, skin cancer, hemangioma, malignant lymphoma, malignant melanoma, thyroid cancer, bone tumor, vascular fibroma, retinoblastoma, penile cancer, pediatric solid cancer, Kaposi's sarcoma, Kaposi's sarcoma derived from AIDS, maxillary tumor, fibrous histiocytoma, leiomyosarcoma, rhabdomyosarcoma, and leukemia. Among these, the compound can be preferably used for prostate cancer, leukemia, and malignant lymphoma.

It is known that the level of H3K4me2, which is a substrate of LSD1, and memory improvement are correlated (Nature 2007, Vol. 447, page 175), and the compound of the present invention having a superior LSD1 inhibitory action can also be used as a prophylactic or therapeutic agent for neurodegenerative diseases.

The compound of the present invention can be used as a prophylactic or therapeutic agent for central nervous system diseases. It is useful as a prophylactic or therapeutic agent for diseases such as (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia, chronic fatigue syndrome, anxiety neurosis, compulsive neurosis, panic disorder, epilepsy, anxiety symptom, anxious mental state, emotional abnormality, cyclothymia, nervous erethism, faint, addiction, low sex drive, attention deficit hyperactivity disorder (ADHD), psychotic major depression, refractory major depression, treatment-resistant depression], (2) neurodegenerative diseases [e.g., Alzheimer's disease, Alzheimer-type senile dementia, Parkinson's disease, Huntington's chorea, multi-infarct dementia, frontotemporal dementia, frontotemporal dementia with Parkinsonism, progressive supranuclear palsy, Pick's syndrome, Niemann-Pick syndrome, corticobasal degeneration, Down's disease, vascular dementia, postencephalitic parkinsonism, dementia with Lewy body, HIV dementia, amyotrophic lateral sclerosis (ALS), motor neurogenesis disease (MND), Creutzfeldt-Jakob disease or prion disease, cerebral palsy, progressive supranuclear palsy, multiple sclerosis], (3) age-related cognition and memory disorders [e.g., age-related memory disorders, senile dementia]

(4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary disease, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol intoxication, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hearing loss, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, stress ulcer, diarrhea, constipation, postoperative ileus, and the like.

The compound of the present invention is particularly useful as a prophylactic or therapeutic agent for diseases such as schizophrenia, Alzheimer's disease, Parkinson's disease, Huntington's chorea and the like.

Since the compound of the present invention has a superior LSD1 inhibitory activity and action, it is expected to show a superior treatment effect for the above-mentioned diseases.

The dosage of the compound of the present invention varies depending on the administration subjects, administration routes, target diseases, symptoms, and the like. For example, for oral administration to adult patients with cancer, generally a single dose is about 0.01 to 100 mg/kg body weight, preferably 0.1 to 50 mg/kg body weight, further preferably 0.5 to 20 mg/kg body weight, and this dosage is preferably administered 1 to 3 times daily.

The compound of the present invention can be used in combination with a medicament such as chemotherapeutic agent, immunotherapeutic agent, medicament inhibiting actions of cell growth factor and receptor thereof (hereinafter to be abbreviated as a concomitant drug).

By combining the compound of the present invention and a concomitant drug, a superior effect such as (1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

Examples of the chemotherapeutic agent include alkylating agents (e.g., nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin), metabolic antagonists (e.g., mercaptopurine, 6-mercaptopurine riboside, thioinosine, methotrexate, pemetrexed, enocitabine, cytarabine, cytarabine ocfosfate, ancitabine hydrochloride, 5-FU drug (e.g., fluorouracil, tegafur, UFT, doxifluridine, carmofur, gallocitabine, emitefur, capecitabine), aminopterine, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, bendamustine), antitumor antibiotics (e.g., actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride) and plant-derived antitumor agents (e.g., etoposide, etoposide phosphate, vinblastine sulfate, vincristine sulfate, vindesine sulfate, teniposide, paclitaxel, docetaxel, vinorelbine).

Examples of the immunotherapeutic agent include picibanil, krestin, schizophyllan, lentinan, ubenimex, interferon, interleukin, macrophage colony stimulating factor, granulocyte colony stimulating factor, erythropoietin, lymphotoxin, BCG vaccine, *corynebacterium parvum*, levamisole, polysaccharide K, procodazole and anti-CTLA4 antibody.

Examples of the "medicament inhibiting actions of cell growth factor and receptor thereof" include anti-VEGF antibody (e.g., Bevacizumab), anti-HER2 antibody (e.g., Trastuzumab, Pertuzumab), anti-EGFR antibody (e.g., Cetuximab, Panitumumab, Matuzumab, Nimotuzumab), anti-VEGFR antibody, anti-HGF antibody, Imatinib mesylate, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), 2-[N-[3-[4-[5-[N-(3-fluorophenyl)carbamoylmethyl]-1H-pyrazol-3-ylamino]quinazolin-7-yloxy]propyl]-N-ethylamino]ethyl phosphate (AZD-1152), 4-[9-chloro-7-(2,6-difluorophenyl)-5H-primido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethyl ester (AZD-6244), N-[2(R),3-dihydroxypropoxy]-3,4-difluoro-2-(2-fluoro-4-iodophenylamino)benzamide (PD-0325901) and everolimus (RAD001).

Examples of the concomitant drug for the central nervous system diseases include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, 5-$HT_{1A}$ agonist, (buspirone hydrochloride, tandospirone citrate, osemozotan hydrochloride etc.), 5-$HT_3$ antagonist (cyamemazine etc.), non-cardioselective β blocker (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine site agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine etc.), therapeutic drug for Parkinson's disease, therapeutic drug for ALS (riluzole etc., neurotrophic factor etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin, indomethacin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug, and the like.

The above-mentioned concomitant drug may be used in a combination of two or more kinds at an appropriate ratio.

When the compound of the present invention is used in combination with a concomitant drug, the respective dosages can be reduced within a safe range in consideration of the opposite effects of the respective drugs. As a result, the opposite effect caused by these agents can be prevented safely.

The compound of the present invention can also be used in combination with a non-medication therapy. Specific examples of the non-medication therapy include (1) operation; (2) hypertensive chemical therapy using angiotensin II and the like; (3) gene therapy; (4) hyperthermic therapy; (5) cryotherapy; (6) laser ablation method; (7) radiation therapy; and (8) immunotherapy.

The production method of compound (I) of the present invention is explained in the following.

Compound (I) of the present invention can be produced, for example, according to the method shown in the following reaction scheme or a method analogous thereto and the like.

The compounds in the schemes may form a salt, and examples of such salt include those similar to the aforementioned salts of compound (I).

While the compounds obtained in each step can be directly used for the next reaction in the form of a reaction mixture or as a crude product, they can be isolated and purified from a reaction mixture according to a conventionally known method such as concentration, extraction, recrystallization, distillation, chromatography and the like.

In addition, the compound obtained in each step may be used after optical resolution by a known means such as chiral column chromatography, optical fractional crystallization, diastereomer derivatization and the like.

The outline of each reaction scheme is shown below, wherein each symbol in the compounds is as defined above.

[Production Method 1]

Compound (I) can be produced by the following production method or a method analogous thereto.

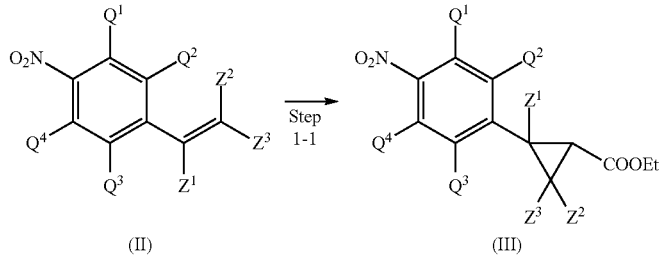
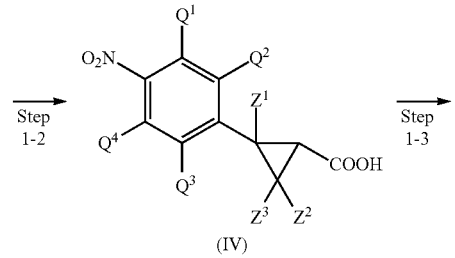

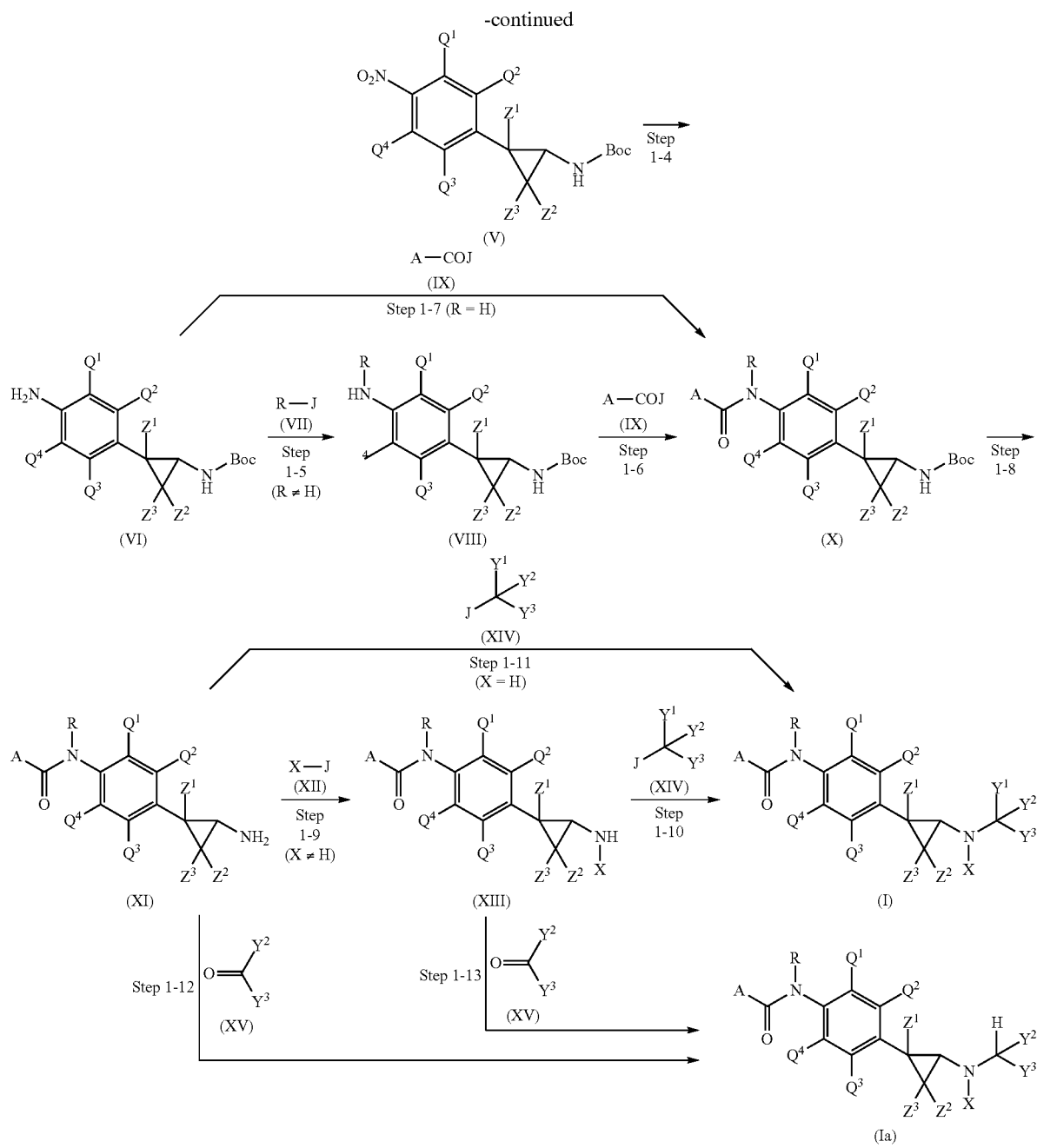

wherein each symbol is as defined above, and J is a halogen atom (e.g., F, Cl, Br, I), p-toluenesulfonyloxy (OTs), methanesulfonyloxy (OMs) or OH.

[Step 1-1]

In this Step, compound (II) is reacted with ethyl diazoacetate in the presence of a metal catalyst to produce compound (III).

The starting material compound (II) may be a commercially available product, or can be produced by a method known per se [for example, the method described in Synlett 2002, 1137; Journal of Organic Chemistry 2003, 68, 6354; Bioorganic and Medicinal Chemistry 2008, 16, 5452 and the like] or a method analogous thereto.

This reaction is generally performed in an inert solvent.

The amount of ethyl diazoacetate to be used is generally 1-10 molar equivalents relative to compound (II).

Examples of the inert solvent include chloroform, dichloromethane, 1,2-dichloroethane, carbon tetrachloride, tetrahydrofuran, diethyl ether, 1,2-dimethoxyethane, 1,4-dioxane, toluene, benzene, chlorobenzene, cyclohexane, N,N-dimethylformamide, N,N-dimethylacetamide, acetonitrile and the like. Two or more kinds of these solvents may be used in an appropriate ratio.

Examples of the metal catalyst include copper(I) chloride, copper(II) acetylacetonate, copper(II) trifluoromethanesulfonate, copper(II) sulfate, palladium(II) acetate, palladium (II) chloride, dirhodium(II) tetraacetate, and the like. Two or more kinds of these metal catalysts may be used in an appropriate ratio.

The amount of the metal catalyst to be used is generally 0.01-1 molar equivalent, preferably 0.1-0.5 molar equivalent, relative to compound (II).

The reaction temperature is generally about 0-150° C.

While the reaction time is not particularly limited, it is generally 0.1-100 hr, preferably 0.5-72 hr.

[Step 1-2]

In this Step, compound (IV) is produced by subjecting compound (III) to hydrolysis.

This reaction is generally performed in the presence of a base, in water or a water-containing solvent.

Examples of the base include sodium ethoxide, sodium methoxide, sodium hydroxide, lithium hydroxide, potassium hydroxide, barium hydroxide, sodium hydroperoxide and the like.

The amount of the base to be used is generally 1-1000 molar equivalents relative to compound (III).

Examples of the solvent to be used as the water-containing solvent include tetrahydrofuran, methanol, ethanol, isopropanol, 1,4-dioxane, N,N-dimethylformamide, N,N-dimethylacetamide, acetonitrile, dimethyl sulfoxide, acetone and the like. Two or more kinds of these solvents may be used in an appropriate ratio.

The reaction temperature is generally about 0-100° C.

While the reaction time is not particularly limited, it is generally 0.1-100 hr, preferably 0.5-72 hr.

[Step 1-3]

In this Step, compound (IV) is reacted with diphenylphosphoryl azide and tert-butyl alcohol to produce compound (V).

This reaction is generally performed in the presence of a base in an inert solvent or an excess amount of tert-butyl alcohol.

Examples of the base include triethylamine, diisopropylethylamine, 1,8-diazabicyclo[5.4.0]undec-7-ene, potassium carbonate, cesium carbonate, potassium tert-butoxide and the like. Among these, triethylamine and diisopropylethylamine are preferable.

The amount of the base to be used is generally 1-10 molar equivalents relative to compound (IV).

Examples of the inert solvent include toluene, benzene, xylene, tetrahydrofuran, 1,4-dioxane, N,N-dimethylformamide, N,N-dimethylacetamide, acetonitrile and the like. Two or more kinds of these solvents may be used in an appropriate ratio.

The reaction temperature is generally about 0-150° C.

While the reaction time is not particularly limited, it is generally 0.1-100 hr, preferably 0.5-72 hr.

[Step 1-4]

In this Step, compound (V) is subjected to a reduction reaction to produce compound (VI).

This reaction is generally performed in the presence of a metal reagent in a water-containing solvent.

Examples of the metal reagent include iron, zinc, nickel, tin, tin(II) chloride and the like.

The amount of the metal reagent to be used is generally 1-1000 molar equivalents relative to compound (V).

The progress of this reaction can be accelerated by adding an additive such as calcium chloride, ammonium chloride, sodium acetate, acetic acid, hydrochloric acid, hydrazine and the like to the reaction system. The amount of such additive to be used is generally not less than 1 molar equivalent relative to compound (V).

Examples of the solvent to be used as a water-containing solvent include methanol, ethanol, isopropanol, tetrahydrofuran, 1,4-dioxane, N,N-dimethylformamide, N,N-dimethylacetamide, acetonitrile and the like. Two or more kinds of these solvents may be used in an appropriate ratio.

The reaction temperature is generally about 0-100° C.

While the reaction time is not particularly limited, it is generally 0.1-100 hr, preferably 0.5-72 hr.

[Step 1-5]

In this Step, compound (VI) is reacted with compound (VII) under basic conditions to produce compound (VIII) (R≠H).

Compound (VII) may be a commercially available product, or can be produced by a method known per se [for example, the method described in "Advanced Organic Chemistry, 4th Ed." (by Jerry March), "Comprehensive Organic Transformations, 2nd Ed." (by Richard C. Larock) and the like] or a method analogous thereto.

The amount of compound (VII) to be used is generally 0.1-10 molar equivalents relative to compound (VI).

This reaction is generally performed in the presence of a base in an inert solvent.

Examples of the base include triethylamine, diisopropylethylamine, 1,8-diazabicyclo[5.4.0]undec-7-ene, potassium carbonate, sodium carbonate, cesium carbonate, potassium tert-butoxide, sodium hydroxide and the like. Among these, triethylamine, diisopropylethylamine and potassium carbonate are preferable.

The amount of such base to be used is generally not less than 1 molar equivalent relative to compound (VI).

Examples of the inert solvent include tetrahydrofuran, 1,4-dioxane, N,N-dimethylformamide, N,N-dimethylacetamide, acetonitrile, dimethyl sulfoxide, acetone, methylene chloride and the like. Two or more kinds of these solvents may be used in an appropriate ratio.

The reaction temperature is generally about 0-150° C.

While the reaction time is not particularly limited, it is generally 0.1-100 hr, preferably 0.5-72 hr.

[Step 1-6]

In this Step, compound (VIII) is reacted with compound (IX) to produce compound (X).

Compound (IX) may be a commercially available product, or can be produced by a method known per se [for example, the method described in "Advanced Organic Chemistry, 4th Ed." (by Jerry March), "Comprehensive Organic Transformations, 2nd Ed." (by Richard C. Larock) and the like] or a method analogous thereto.

The amount of compound (IX) to be used is generally 0.1-molar equivalents relative to compound (VIII).

This reaction is generally performed in the presence of a base in an inert solvent.

Examples of the base include triethylamine, diisopropylethylamine, pyridine, N,N-dimethylaniline, 1,8-diazabicyclo [5.4.0]undec-7-ene, potassium carbonate, sodium carbonate, cesium carbonate, potassium tert-butoxide, sodium hydroxide and the like. Among these, triethylamine and diisopropylethylamine are preferable.

The amount of the base to be used is generally not less than 1 molar equivalent relative to compound (VIII).

Examples of the inert solvent include tetrahydrofuran, diethyl ether, 1,2-dimethoxyethane, 1,4-dioxane, toluene, benzene, xylene, N,N-dimethylformamide, N,N-dimethylacetamide, acetonitrile, ethyl acetate, methylene chloride and the like can be mentioned. Two or more kinds of these solvents may be used in an appropriate ratio.

When a carboxylic acid is used as compound (IX), the reaction can be accelerated by adding a condensing agent in the reaction system.

Examples of the condensing agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N',N'-tetramethyluronium hexafluorophosphate and the like.

The amount of the condensing agent to be used is generally 1-10 molar equivalents relative to compound (VIII).

In this reaction, a suitable condensation accelerator (e.g., 1-hydroxybenzotriazole, N-hydroxysuccinimide, N,N-dimethyl-4-aminopyridine etc.) can be used as necessary.

The amount of the condensation accelerator to be used is generally 0.1-10 molar equivalents relative to compound (VIII).

The reaction temperature is generally about 0-150° C.

While the reaction time is not particularly limited, it is generally 0.1-100 hr, preferably 0.5-72 hr.

[Step 1-7]

In this Step, compound (VI) is reacted with compound (IX) to produce compound (X) (R=H).

This reaction can be carried out in the same manner as in the aforementioned Step 1-6.

[Step 1-8]

In this Step, compound (X) is subjected to a reaction for removal of a tert-butoxycarbonyl group to produce compound (XI).

This reaction is generally performed in the presence of an acid in an inert solvent or an excess amount of an acid.

Examples of the acid include trifluoroacetic acid, hydrochloric acid, hydrobromic acid, sulfuric acid, hydrofluoric acid and the like. Among these, hydrochloric acid and trifluoroacetic acid are preferable.

The amount of the acid to be used is generally 1-1000 molar equivalents relative to compound (X).

Examples of the inert solvent include methanol, ethanol, isopropanol, water, methylene chloride, toluene, benzene, xylene, tetrahydrofuran, 1,4-dioxane, N,N-dimethylformamide, N,N-dimethylacetamide, acetonitrile and the like. Two or more kinds of these solvents may be used in an appropriate ratio.

The reaction temperature is generally about 0-150° C.

While the reaction time is not particularly limited, it is generally 0.1-100 hr, preferably 0.5-72 hr.

[Step 1-9]

In this Step, compound (XI) is reacted with compound (XII) under basic conditions to produce compound (XIII) (X≠H).

Compound (XII) may be a commercially available product, or can be produced by a method known per se [for example, the method described in "Advanced Organic Chemistry, 4th Ed." (by Jerry March), "Comprehensive Organic Transformations, 2nd Ed." (by Richard C. Larock) and the like] or a method analogous thereto.

The amount of compound (XII) to be used is generally 0.1-10 molar equivalents relative to compound (XI).

This reaction is generally performed in the presence of a base in an inert solvent.

Examples of the base include triethylamine, diisopropylethylamine, 1,8-diazabicyclo[5.4.0]undec-7-ene, potassium carbonate, sodium carbonate, cesium carbonate, potassium tert-butoxide, sodium hydroxide and the like. Among these, triethylamine, diisopropylethylamine and potassium carbonate are preferable.

The amount of the base to be used is generally not less than 1 molar equivalent relative to compound (XI).

Examples of the inert solvent include tetrahydrofuran, 1,4-dioxane, N,N-dimethylformamide, N,N-dimethylacetamide, acetonitrile, dimethyl sulfoxide, acetone, methylene chloride and the like. Two or more kinds of these solvents may be used in an appropriate ratio.

The reaction temperature is generally about 0-150° C.

While the reaction time is not particularly limited, it is generally 0.1-100 hr, preferably 0.5-72 hr.

[Step 1-10]

In this Step, compound (XIII) is reacted with compound (XIV) under basic conditions to produce compound (I).

Compound (XIV) may be a commercially available product, or can be produced by a method known per se [for example, the method described in "Advanced Organic Chemistry, 4th Ed." (by Jerry March), "Comprehensive Organic Transformations, 2nd Ed." (by Richard C. Larock) and the like] or a method analogous thereto.

The amount of compound (XIV) to be used is generally 0.1-10 molar equivalents relative to compound (XIII).

This reaction is generally performed in the presence of a base in an inert solvent.

Examples of the base include triethylamine, diisopropylethylamine, 1,8-diazabicyclo[5.4.0]undec-7-ene, potassium carbonate, sodium carbonate, cesium carbonate, potassium tert-butoxide, sodium hydroxide and the like. Among these, triethylamine, diisopropylethylamine and potassium carbonate are preferable.

The amount of the base to be used is generally not less than 1 molar equivalent relative to compound (XIII).

Examples of the inert solvent include tetrahydrofuran, 1,4-dioxane, N,N-dimethylformamide, N,N-dimethylacetamide, acetonitrile, dimethyl sulfoxide, acetone, methylene chloride and the like. Two or more kinds of these solvents may be used in an appropriate ratio.

The reaction temperature is generally about 0-15.0° C.

While the reaction time is not particularly limited, it is generally 0.1-100 hr, preferably 0.5-72 hr.

Compound (I) can also be produced by one step from compound (XI) without via compound (XIII).

[Step 1-11]

In this Step, compound (XI) is reacted with compound (XIV) under basic conditions to produce compound (I) (X=H).

This reaction can be carried out in the same manner as in the aforementioned Step 1-10.

[Step 1-12]

In this Step, compound (XI) is reacted with compound (XV) in the presence of a reducing agent to produce compound (Ia). Compound (Ia) is compound (I) wherein $Y^1$=H. Compound (Ia) is encompassed in compound (I).

Compound (XV) may be a commercially available product, or can be produced by a method known per se [for example, the method described in "Advanced Organic Chemistry, 4th Ed." (by Jerry March), "Comprehensive Organic Transformations, 2nd Ed." (by Richard C. Larock) and the like] or a method analogous thereto.

The amount of compound (XV) to be used is generally 0.1-molar equivalents relative to compound (XI).

This reaction is generally performed in the presence of a reducing agent in an inert solvent.

Examples of the reducing agent include sodium triacetoxyborohydride, sodium cyanoborohydride, sodium borohydride, 2-picoline borane complex and the like.

The amount of the reducing agent to be used is generally 1-10 molar equivalents relative to compound (XI).

Examples of the inert solvent include tetrahydrofuran, methanol, ethanol, isopropanol, 1,4-dioxane, N,N-dimethylformamide, N,N-dimethylacetamide, acetonitrile, methylene chloride, acetic acid, water and the like. Two or more kinds of these solvents may be used in an appropriate ratio.

The reaction temperature is generally about 0-150° C.

While the reaction time is not particularly limited, it is generally 0.1-100 hr, preferably 0.5-72 hr.

Compound (XI) is reacted in advance with compound (XV) in the presence of a dehydrating agent (titanium(IV) isopropoxide, sodium hydrogen carbonate, sodium sulfate, magnesium sulfate, molecular sieve etc.) to produce enamine, which is reacted with a reducing agent to produce the object compound (Ia).

[Step 1-13]

In this Step, compound (XIII) is reacted with compound (XV) in the presence of a reducing agent to produce compound (Ia).

This reaction can be carried out in the same manner as in the aforementioned Step 1-12.

Compound (Ia) can also be produced by one step from compound (XI) without via compound (XIII).

[Production Method 2]

Compound (XI) can also be produced by the following production method or a method analogous thereto.

wherein each symbol is as defined above, J is a halogen atom (e.g., F, Cl, Br, I), OTs, OMs or OH, and $L^1$ and $L^2$ are each independently H, Cl, Br, I, trifluoromethanesulfonyloxy (OTf), $B(OH)_2$, $BF_3K$, $B(-OCMe_2CMe_2O-)$) or a 9-BBN group.

[Step 2-1]

In this Step, compound (XVI) is reacted with compound (VII) under basic conditions to produce compound (XVII) (R≠H). This reaction can be carried out in the same manner as in the aforementioned Step 1-5.

[Step 2-2]

In this Step, compound (XVII) is reacted with compound (IX) to produce compound (XVIII).

This reaction can be carried out in the same manner as in the aforementioned Step 1-6.

[Step 2-3]

In this Step, compound (XVI) is reacted with compound (IX) to produce compound (XVIII) (R=H).

This reaction can be carried out in the same manner as in the aforementioned Step 1-6.

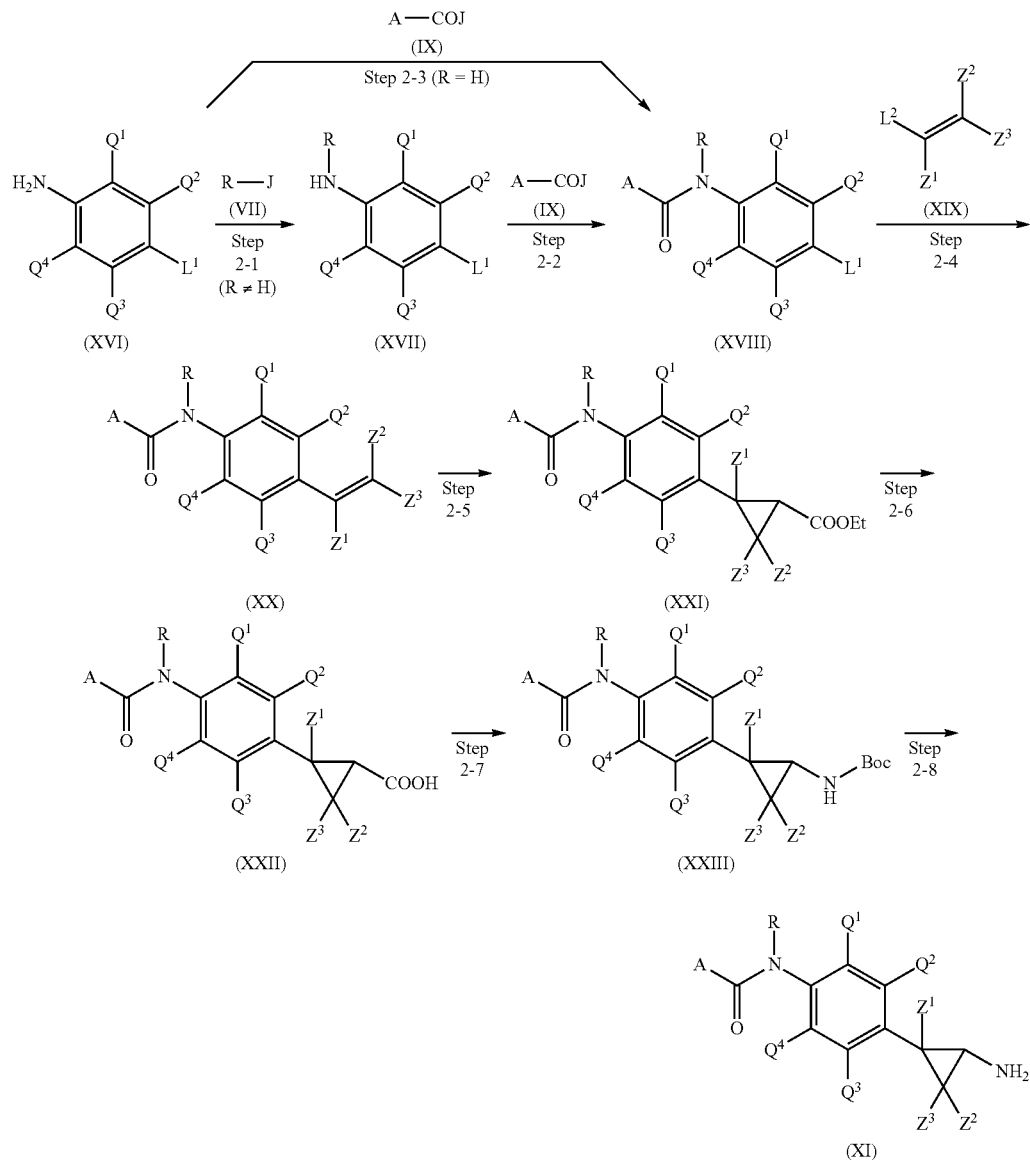

[Step 2-4]

In this Step, compound (XVIII) is coupled with vinyl compound (XIX) in the presence of a metal catalyst to produce compound (XX).

Vinyl compound (XIX) may be a commercially available product, or can be produced by a method known per se [for example, the method described in Synlett 2002, 1137; Journal of Organic Chemistry 2003, 68, 6354; Bioorganic and Medicinal Chemistry 2008, 16, 5452 and the like] or a method analogous thereto.

This reaction is generally performed in an inert solvent.

This reaction is performed under microwave irradiation where necessary.

The amount of compound (XIX) to be used is generally 0.1-10 molar equivalents relative to compound (XVIII).

Examples of the inert solvent include water, methanol, ethanol, chloroform, dichloromethane, 1,2-dichloroethane, carbon tetrachloride, tetrahydrofuran, diethyl ether, 1,2-dimethoxyethane, 1,4-dioxane, toluene, xylene, benzene, chlorobenzene, N,N-dimethylformamide, N,N-dimethylacetamide, 1-methylpiperidone, acetonitrile, dimethyl sulfoxide and the like.

Two or more kinds of these solvents may be used in an appropriately ratio.

Examples of the metal catalyst include palladium(II) acetate, palladium(II) chloride, tris(dibenzylideneacetone)dipalladium(0), bis(acetylacetonato)palladium(II), nickel(II) chloride, copper(I) chloride, copper(I) acetate and the like. Two or more kinds of these metal catalysts may be used in an appropriately ratio.

The amount of the metal catalyst to be used is generally 0.001-1 molar equivalent, preferably 0.01-0.5 molar equivalent, relative to compound (XVIII).

The reaction can be accelerated by adding an appropriate ligand to the metal catalyst.

Examples of the ligand include triphenylphosphine, tri(o-tolyl)phosphine, tri(tert-butyl)phosphine, 1,1'-bis(diphenylphosphino)ferrocene, 2,2'-bis(diphenylphosphino)-1,1'-binaphthyl and the like. A complex of the ligand with the aforementioned metal catalyst may be prepared in advance and used, or a commercially available complex already prepared may also be used.

The amount of the ligand to be used is generally 0.001-2 molar equivalents, preferably 0.01-1 molar equivalent, relative to compound (XVIII).

The reaction temperature is generally about 0-200° C. While the reaction time is not particularly limited, it is generally 0.01-100 hr, preferably 0.1-72 hr.

[Step 2-5]

In this Step, compound (XX) is reacted with ethyl diazoacetate in the presence of a metal catalyst to produce compound (XXI).

This reaction can be carried out in the same manner as in the aforementioned Step 1-1.

[Step 2-6]

In this Step, compound (XXI) is subjected to hydrolysis to produce compound (XXII).

This reaction can be carried out in the same manner as in the aforementioned Step 1-2.

[Step 2-7]

In this Step, compound (XXII) is reacted with diphenylphosphoryl azide and tert-butyl alcohol to produce compound (XXIII).

This reaction can be carried out in the same manner as in the aforementioned Step 1-3.

[Step 2-8]

In this Step, compound (XXIII) is subjected to a reaction for removal of a tert-butoxycarbonyl group to produce compound (XI).

This reaction can be carried out in the same manner as in the aforementioned Step 1-8.

[Production Method 3]

Compound (Ic) which is compound (I) wherein X is a group represented by

wherein $Y^4$ and $Y^5$ are each independently a hydrogen atom, a hydrocarbon group optionally having substituent(s), or a heterocyclic group optionally having substituent(s), and $Y^4$ and $Y^5$ are optionally bonded to each other to form a ring optionally having substituent(s), can be produced by the following production method or a method analogous thereto. Compound (Ib) is compound (I) wherein X=H. Compounds (Ib) and (Ic) are encompassed in compound (I).

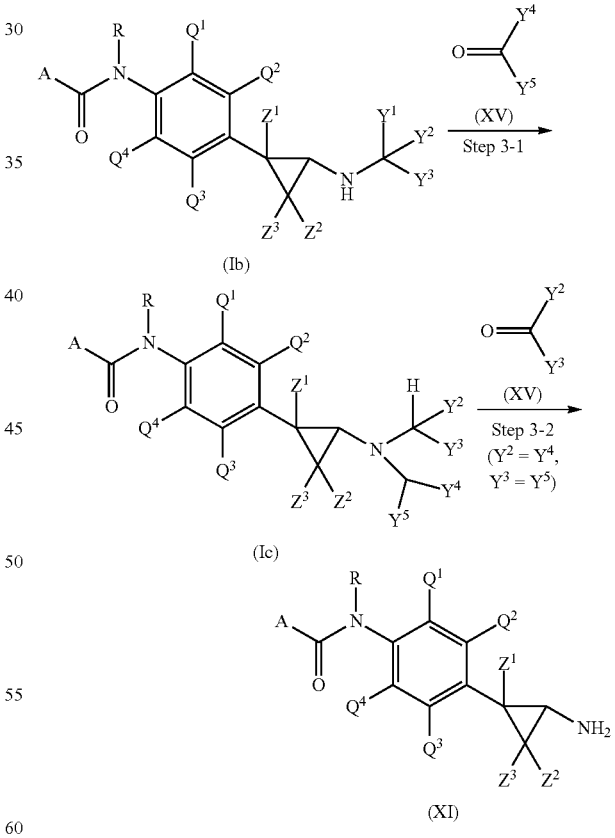

wherein each symbol is as defined above, and J is a halogen atom (e.g., F, Cl, Br, I), OTs, OMs or OH.

[Step 3-1]

In this Step, compound (Ib) is reacted with compound (XV) in the presence of a reducing agent to produce compound (Ic).

Compound (XV) may be a commercially available product, or can be produced by a method known per se [for example, the method described in "Advanced Organic Chemistry, 4th Ed." (by Jerry March), "Comprehensive Organic Transformations, 2nd Ed." (by Richard C. Larock) and the like] or a method analogous thereto.

This reaction can be carried out in the same manner as in the aforementioned Step 1-12.

[Step 3-2]

In this Step, compound (XI) is reacted with compound (XV) in the presence of a reducing agent to produce compound (Ic).

Compound (XV) may be a commercially available product, or can be produced by a method known per se [for example, the method described in "Advanced Organic Chemistry, 4th Ed." (by Jerry March), "Comprehensive Organic Transformations, 2nd Ed." (by Richard C. Larock) and the like] or a method analogous thereto.

This reaction can be carried out in the same manner as in the aforementioned Step 1-12.

[Production Method 4]

Compound (Ib) which is compound (I) wherein X=H can also be produced by the following production method or a method analogous thereto. Compound (Id) is compound (I) wherein R=H, X=H. Compounds (Ib) and (Id) are encompassed in compound (I).

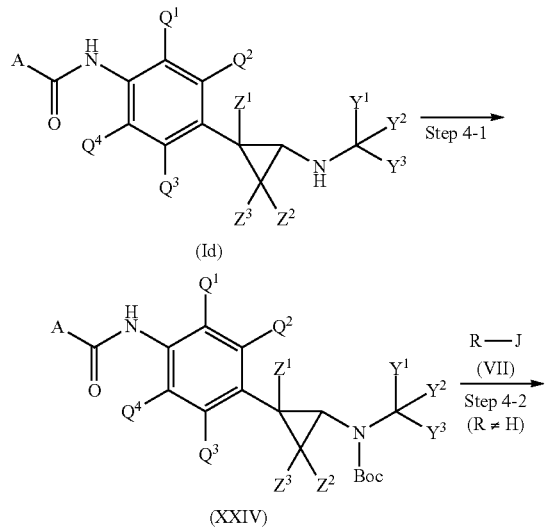

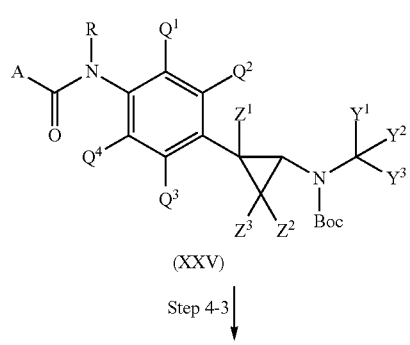

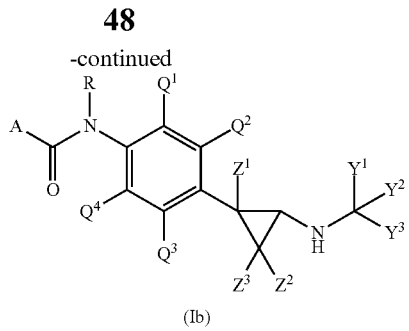

wherein each symbol is as defined above, and J is a halogen atom (e.g., F, Cl, Br, I), OTs, OMs or OH.

[Step 4-1]

In this Step, compound (Id) is reacted with di-tert-butyl dicarbonate under basic conditions to produce compound (XXIV).

The amount of the di-tert-butyl dicarbonate to be used is generally 0.1-10 molar equivalents relative to compound (Id).

This reaction is generally performed in the presence of a base in an inert solvent.

Examples of the base include triethylamine, diisopropylethylamine, 1,8-diazabicyclo[5.4.0]undec-7-ene, potassium carbonate, sodium carbonate, cesium carbonate, potassium tert-butoxide, sodium hydroxide and the like. Among these, triethylamine, diisopropylethylamine and sodium hydroxide are preferable.

The amount of the base to be used is generally not less than 1 molar equivalent relative to compound (Id).

Examples of the inert solvent include tetrahydrofuran, 1,4-dioxane, N,N-dimethylformamide, N,N-dimethylacetamide, acetonitrile, dimethyl sulfoxide, acetone, methylene chloride, water and the like. Two or more kinds of these solvents may be used in an appropriate ratio.

The reaction temperature is generally about 0-100° C.

While the reaction time is not particularly limited, it is generally 0.1-100 hr, preferably 0.5-72 hr.

[Step 4-2]

In this Step, compound (XXIV) is reacted with compound (VII) under basic conditions to produce compound (XXV) (R≠H).

This reaction can be carried out in the same manner as in the aforementioned Step 1-5.

[Step 4-3]

In this Step, compound (XXV) is subjected to a reaction for removal of a tert-butoxycarbonyl group to produce compound (Ib).

This reaction can be carried out in the same manner as in the aforementioned Step 1-8.

[Production Method 5]

Compound (Ie) which is compound (I) wherein R=H, X=H, $Y^1$=H can also be produced by the following production method or a method analogous thereto. Compound (Ie) is encompassed in compound (I).

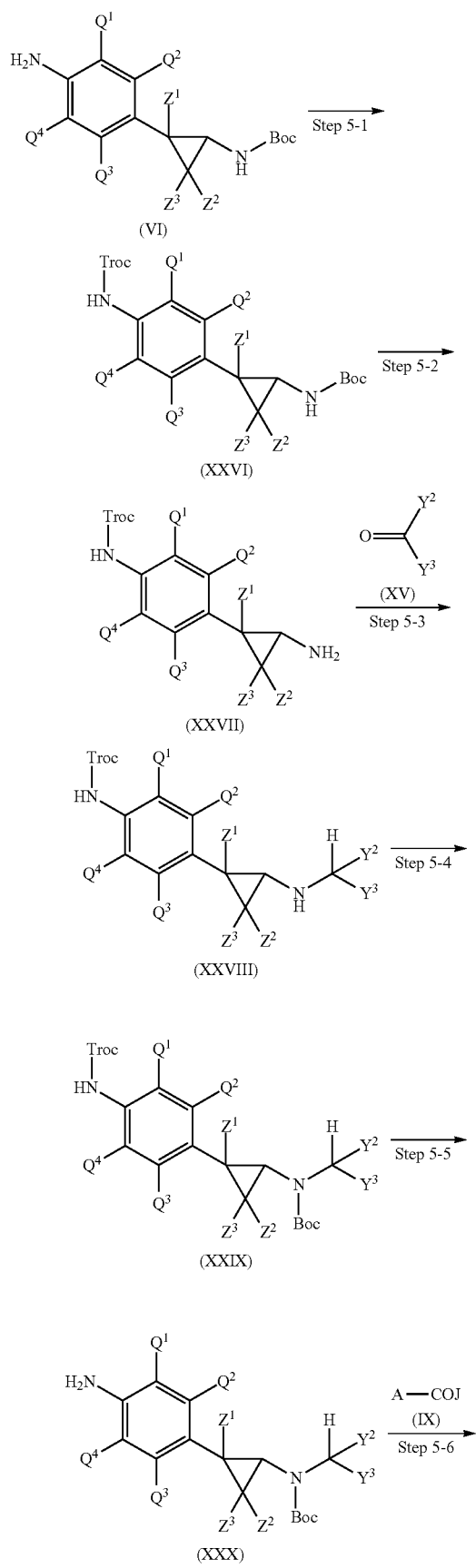

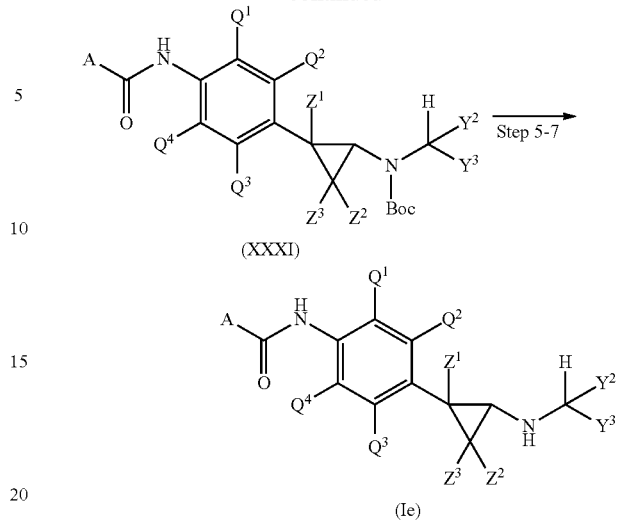

wherein each symbol is as defined above, J is a halogen atom (e.g., F, Cl, Br, I), OTs, OMs or OH, and Troc is 2,2,2-trichloroethoxycarbonyl.

[Step 5-1]

In this Step, compound (VI) is reacted with 2,2,2-trichloroethyl chloroformate under basic conditions to produce compound (XXVI).

The amount of the 2,2,2-trichloroethyl chloroformate to be used is generally 0.1-10 molar equivalents relative to compound (VI).

This reaction is generally performed in the presence of a base in an inert solvent.

Examples of the base include triethylamine, diisopropylethylamine, 1,8-diazabicyclo[5.4.0]undec-7-ene, potassium carbonate, sodium carbonate, cesium carbonate, potassium tert-butoxide, sodium hydroxide and the like. Among these, triethylamine, diisopropylethylamine and potassium carbonate are preferable.

The amount of the base to be used is generally not less than 1 molar equivalent relative to compound (VI).

Examples of the inert solvent include tetrahydrofuran, 1,4-dioxane, N,N-dimethylformamide, N,N-dimethylacetamide, acetonitrile, dimethyl sulfoxide, acetone, methylene chloride and the like. Two or more kinds of these solvents may be used in an appropriate ratio.

The reaction temperature is generally about 0-150° C.

While the reaction time is not particularly limited, it is generally 0.1-100 hr, preferably 0.5-72 hr.

[Step 5-2]

In this Step, compound (XXVI) is subjected to a reaction for removal of a tert-butoxycarbonyl group to produce compound (XXVII).

This reaction can be carried out in the same manner as in the aforementioned Step 1-8.

[Step 5-3]

In this Step, compound (XXVII) is reacted with compound (XV) in the presence of a reducing agent to produce compound (XXVIII).

This reaction can be carried out in the same manner as in the aforementioned Step 1-12.

[Step 5-4]

In this Step, compound (XXVIII) is reacted with di-tert-butyl dicarbonate under basic conditions to produce compound (XXIX).

This reaction can be carried out in the same manner as in the aforementioned Step 4-1.

[Step 5-5]

In this Step, compound (XXIX) is subjected to a reaction for removal of a 2,2,2-trichloroethoxycarbonyl group to produce compound (XXX).

This reaction is generally performed in the presence of an acid and a metal reagent in a polar solvent.

Examples of the acid include acetic acid, citric acid, trifluoroacetic acid, hydrochloric acid, hydrobromic acid and the like. Among these, acetic acid is preferable.

The amount of the acid to be used is generally 1-1000 molar equivalents relative to compound (XXIX).

Examples of the metal reagent include zinc, iron, tin, cadmium and the like. Among these, zinc is preferable.

The amount of the metal reagent to be used is generally 1-1000 molar equivalents relative to compound (XXIX).

Examples of the polar solvent include water, methanol, ethanol, isopropanol, tetrahydrofuran, 1,4-dioxane, N,N-dimethylformamide, N,N-dimethylacetamide, acetonitrile, dimethyl sulfoxide, acetic acid, trifluoroacetic acid and the like. Two or more kinds of these solvents may be used in an appropriate ratio.

The reaction temperature is generally about 0-150° C.

While the reaction time is not particularly limited, it is generally 0.1-100 hr, preferably 0.5-72 hr.

[Step 5-6]

In this Step, compound (XXX) is reacted with compound (IX) to produce compound (XXXI).

This reaction can be carried out in the same manner as in the aforementioned Step 1-6.

[Step 5-7]

In this Step, compound (XXXI) is subjected to a reaction is for removal of a tert-butoxycarbonyl group to produce compound (Ie).

This reaction can be carried out in the same manner as in the aforementioned Step 1-8.

[Production Method 6]

Compound (If) which is compound (I) wherein A-CON(R)— is a group represented by

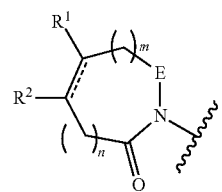

wherein $R^1$ and $R^2$ are each independently an optionally fused hydrocarbon group optionally having substituent(s), E is a methylene group optionally having substituent(s) or a carbonyl group, and m and n are each independently an integer of 0 to 3, and $Y^1$=H can also be produced by the following production method or a method analogous thereto. Compound (If) is encompassed in compound (I).

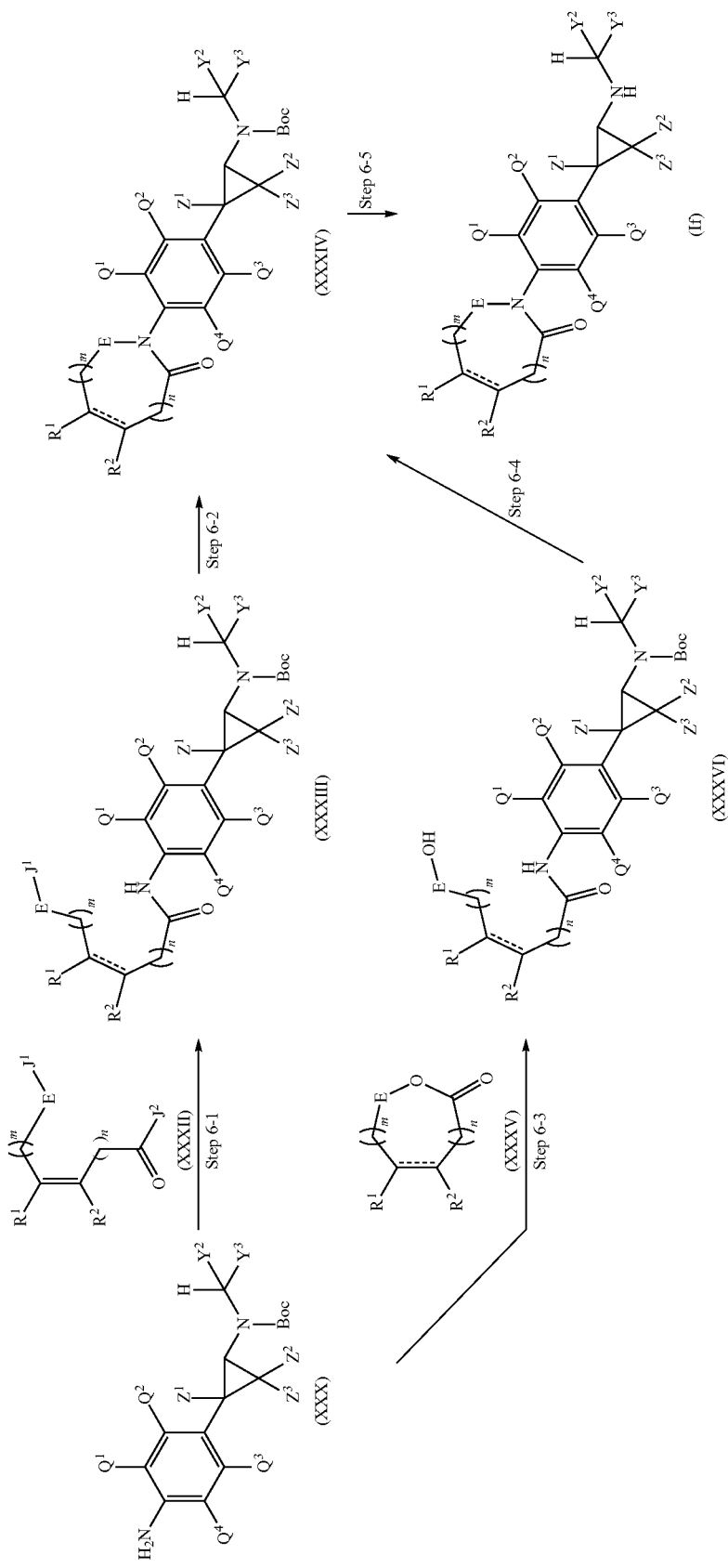

wherein each symbol is as defined above, and $J^1$ and $J^2$ are each independently a halogen atom (e.g., F, Cl, Br, I), OTs, OMs or OH.

[Step 6-1]

In this Step, compound (XXX) is reacted with compound (XXXII) to produce compound (XXXIII).

Compound (XXXII) may be a commercially available product, or can be produced by a method known per se [for example, the method described in "Advanced Organic Chemistry, 4th Ed." (by Jerry March), "Comprehensive Organic Transformations, 2nd Ed." (by Richard C. Larock) and the like] or a method analogous thereto.

This reaction can be carried out in the same manner as in the aforementioned Step 1-6.

[Step 6-2]

In this Step, compound (XXXIII) is cyclized to produce compound (XXXIV).

This reaction is generally performed in the presence of a base in an inert solvent.

Examples of the base include triethylamine, diisopropylethylamine, 1,8-diazabicyclo[5.4.0]undec-7-ene, potassium carbonate, sodium carbonate, cesium carbonate, potassium tert-butoxide, sodium hydroxide and the like. Among these, triethylamine, diisopropylethylamine, and potassium carbonate are preferable.

The amount of the base to be used is generally not less than 1 molar equivalent relative to compound (XXXIII).

Examples of the inert solvent include tetrahydrofuran, 1,4-dioxane, N,N-dimethylformamide, N,N-dimethylacetamide, acetonitrile, dimethyl sulfoxide, acetone, methylene chloride and the like. Two or more kinds of these solvents may be used in an appropriate ratio.

When carboxylic acid (E=CO, $J^1$=OH) is used as compound (XXXIII), the reaction can be accelerated by adding a condensing agent to the reaction system.

Examples of the condensing agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N',N'-tetramethyluronium hexafluorophosphate and the like.

The amount of the condensing agent to be used is generally 1-10 molar equivalents relative to compound (XXXIII).

In this reaction, a suitable condensation accelerator (e.g., 1-hydroxybenzotriazole, N-hydroxysuccinimide, N,N-dimethyl-4-aminopyridine etc.) can be used as necessary.

The amount of the condensation accelerator to be used is generally 0.1-10 molar equivalents relative to compound (XXXIII).

The reaction temperature is generally about 0-150° C.

While the reaction time is not particularly limited, it is generally 0.1-100 hr, preferably 0.5-72 hr.

Compound (XXXIV) can also be produced by one step from compound (XXX) without via compound (XXXIII).

[Step 6-3]

In this Step, compound (XXX) is reacted with compound (XXXV) to produce compound (XXXVI).

Compound (XXXV) may be a commercially available product, or can be produced by a method known per se [for example, the method described in "Advanced Organic Chemistry, 4th Ed." (by Jerry March), "Comprehensive Organic Transformations, 2nd Ed." (by Richard C. Larock) and the like] or a method analogous thereto.

This reaction can be carried out in the same manner as in is the aforementioned Step 1-5.

[Step 6-4]

In this Step, compound (XXXVI) is cyclized to produce compound (XXXIV).

This reaction is generally performed in the presence of an acid or condensing agent in an inert solvent.

Examples of the acid include hydrochloric acid, hydrobromic acid, acetic acid, p-toluenesulfonic acid, sulfuric acid, pyrophosphoric acid and the like. Among these, hydrochloric acid and p-toluenesulfonic acid are preferable.

The amount of the acid to be used is generally 0.01-10 molar equivalents relative to compound (XXXVI).

Examples of the inert solvent include tetrahydrofuran, 1,4-dioxane, N,N-dimethylformamide, N,N-dimethylacetamide, acetonitrile, dimethyl sulfoxide, acetone, methylene chloride and the like. Two or more kinds of these solvents may be used in an appropriate ratio.

Examples of the condensing agent include acetic anhydride, trifluoroacetic anhydride, p-toluenesulfonyl chloride, Mitsunobu reagent (mixture of dialkyl azodicarboxylate and trialkylphosphine or triarylphosphine), 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N', N'-tetramethyluronium hexafluorophosphate and the like.

The amount of the condensing agent to be used is generally 1-10 molar equivalents relative to compound (XXXVI).

In this reaction, a suitable condensation accelerator (e.g., 1-hydroxybenzotriazole, N-hydroxysuccinimide, N,N-dimethyl-4-aminopyridine etc.) can be used as necessary.

The amount of the condensation accelerator to be used is generally 0.1-10 molar equivalents relative to compound (XXXVI).

The reaction temperature is generally about 0-200° C.

While the reaction time is not particularly limited, it is generally 0.1-100 hr, preferably 0.5-72 hr.

Compound (XXXIV) can also be produced by one step from compound (XXX) without via compound (XXXVI).

[Step 6-5]

In this Step, compound (XXXIV) is subjected to a reaction for removal of a tert-butoxycarbonyl group to produce compound (If).

This reaction can be carried out in the same manner as in the aforementioned Step 1-8.

It is also possible to produce a compound encompassed in the present invention by further applying substituent introduction or functional group conversion to compound (I) according to a means known per se. Substituent introduction and functional group conversion are performed according to known conventional methods such as conversion to carboxy group by ester hydrolysis, conversion to carbamoyl group by amidation of carboxy group, conversion to hydroxymethyl group by reduction of carboxy group, conversion to alcohol compound by reduction or alkylation of carbonyl group, reductive amination of carbonyl group, oximation of carbonyl group, acylation, ureation, sulfonylation or alkylation of amino group, amination of activated halogen with amine, conversion to amino group by reduction of nitro group, and acylation, carbamation, sulfonylation or alkylation of hydroxy group. When a reactive substituent causing an unintended reaction during substituent introduction and functional group conversion is present, a protecting group may be introduced in advance into the reactive substituent as necessary according to a means known per se, the object reaction is performed and the protecting group is removed according to a means known per se, whereby compounds encompassed in the present invention can be produced.

In each of the above-mentioned reactions, when the starting compounds have an amino group, a carboxyl group, a hydroxy group or a carbonyl group as a substituent, such groups may be protected with the protecting groups generally used in peptide chemistry, etc. In such case, if necessary, such protecting groups can be removed after the reactions to obtain the objective compounds.

Examples of the amino-protecting group include formyl, and $C_{1-6}$ alkylcarbonyl (e.g., acetyl, ethylcarbonyl etc.), phenylcarbonyl, $C_{1-6}$ alkoxy-carbonyl (e.g., methoxycarbonyl, ethoxycarbonyl, tert-butoxycarbonyl etc.), phenyloxycarbonyl, $C_{7-10}$ aralkyl-carbonyl (e.g., benzylcarbonyl etc.), trityl, phthaloyl, N,N-dimethylaminomethylene and the like, each of which optionally has substituent(s). Examples of the substituent of the "amino-protecting group" include a halogen atom (e.g., fluorine, chlorine, bromine, iodine), $C_{1-6}$ alkyl-carbonyl (e.g., methylcarbonyl, ethylcarbonyl, butylcarbonyl etc.), a nitro group and the like, wherein the number of the substituents is 1 to several (e.g., 3).

Examples of the carboxyl-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 halogen atoms, a $C_{1-6}$ alkoxy group, a nitro group etc.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 halogen atoms, a $C_{1-6}$ alkyl group, a $C_{1-6}$ alkoxy group, a nitro group etc.

Examples of the carbonyl-protecting group include cyclic acetal (e.g., 1,3-dioxane), non-cyclic acetal (e.g., di-$C_{1-5}$ alkyl acetal) and the like.

Removal of the above-mentioned protecting group can be performed according to a known method, for example, the method described in Protective Groups in Organic Synthesis, John Wiley and Sons (1980) and the like. For example, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like can be used.

EXAMPLES

The present invention is explained in detail in the following by referring to Examples, Experimental Examples and Formulation Examples. However, the examples do not limit the present invention and the present invention can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

In silica gel column chromatography, the indication of NH means use of aminopropylsilane-bonded silica gel. In HPLC (high performance liquid chromatography), the indication of C18 means use of octadecyl-bonded silica gel. The ratio of elution solvents is, unless otherwise specified, a volume mixing ratio.

$^1$H NMR (proton nuclear magnetic resonance spectrum) was measured by Fourier-transform NMR. For the analysis, ACD/SpecManager (trade name) and the like were used. Very mild peaks showing protons of hydroxyl group, amino group and the like are not described.

MS (mass spectrum) was measured by LC/MS (liquid chromatography mass spectrometer). As the ionization method, ESI (ElectroSpray Ionization) method or APCI (Atmospheric Pressure Chemical Ionization) method was used as API (Atmospheric Pressure Ionization), and the measurement was performed in a positive mode (API+) or negative mode (API−). The data indicates measured values (found). Generally, a molecular ion peak is observed, but an ion peak added with a solvent such as acetonitrile ($CH_3CN$) and the like or sodium ion (Na+) is sometimes observed. When a compound having a tert-butoxycarbonyl group (-Boc) is used, a peak free of a tert-butoxycarbonyl group or tert-butyl group may be observed as a fragment ion. In addition, when a compound having a hydroxyl group (—OH) is used, a peak free of $H_2O$ may be observed as a fragment ion. In the case of a salt, generally, a molecular ion peak of a free form or a fragment ion peak is observed.

In the following Examples, the following abbreviations are used.

TFA: trifluoroacetic acid, DMSO: dimethyl sulfoxide, DMF: N,N-dimethylformamide, THF: tetrahydrofuran.

Example 1

N-{4-[trans-2-(benzylamino)cyclopropyl]phenyl}benzamide

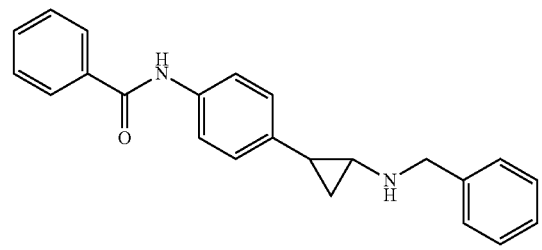 [SMILES: O=C(Nc1ccc(C2CC2NCc2ccccc2)cc1)c1ccccc1]

A) tert-butyl(trans-2-{4-[(phenylcarbonyl)amino]phenyl}cyclopropyl)carbamate

To a solution of tert-butyl [trans-2-(4-aminophenyl)cyclopropyl]carbamate (150 mg) described in a document (J. Am. Chem. Soc., 2010, 132, 6827.) in acetonitrile (6 mL) were added benzoyl chloride (84 μL) and triethylamine (101 μL). The mixture was stirred at room temperature overnight and water was added. The mixture was extracted with ethyl acetate, and the extract was washed with saturated brine, dried over anhydrous sodium sulfate, and concentrated under reduced pressure. The residue was purified by silica gel column chromatography (hexane/ethyl acetate) to give the title compound (212 mg).

$^1$H NMR (400 MHz, DMSO-$d_6$) δ 1.07 (2H, brs), 1.38 (9H, s), 1.88 (1H, brs), 2.56-2.65 (1H, m), 7.07 (2H, d, J=8.6 Hz), 7.24 (1H, brs), 7.48-7.62 (3H, m), 7.66 (2H, d, J=7.6 Hz), 7.94 (2H, d, J=7.6 Hz), 10.18 (1H, s).

B)
N-[4-(trans-2-aminocyclopropyl)phenyl]benzamide hydrochloride tert-Butyl(trans-2-{4-[(phenylcarbonyl)amino]phenyl}cyclopropyl)carbamate (212 mg) was dissolved in 4N hydrochloric acid/ethyl acetate solution (2 mL), and the mixture was stirred at room temperature for 2 hr and the solvent was evaporated under reduced pressure to give the title compound (148 mg).

$^1$H NMR (400 MHz, DMSO-$d_6$) δ 1.13-1.25 (1H, m), 1.32-1.44 (1H, m), 2.24-2.35 (1H, m), 2.79 (1H, brs), 7.14 (2H, d, J=8.1 Hz), 7.47-7.65 (3H, m), 7.72 (2H, d, J=7.8 Hz), 7.95 (2H, d, J=7.3 Hz), 8.38 (3H, brs), 10.25 (1H, s).

C) N-{4-[trans-2-(benzylamino)cyclopropyl]phenyl}benzamide

To a solution of N-[4-(trans-2-aminocyclopropyl)phenyl]benzamide hydrochloride (70 mg) in methanol (2 mL) were added benzaldehyde (25 μL) and sodium hydrogen carbonate (30.5 mg). The reaction mixture was stirred at 70° C. for 1 hr, and ice-cooled to 0° C. and sodium borohydride (13.8 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was recrystallized (hexane/ethyl acetate) to give the title compound (49.1 mg).

MS (API+): [M+H]$^+$ 343.3.

$^1$H NMR (400 MHz, CDCl$_3$) δ 0.96 (1H, brs), 1.11 (1H, brs), 1.92 (1H, brs), 2.37 (1H, brs), 3.89 (2H, brs), 7.00 (2H, d, J=7.8 Hz), 7.21-7.36 (4H, m), 7.45-7.60 (5H, m), 7.73 (1H, brs), 7.82-7.91 (2H, m).

Example 2

N-{4-[trans-2-(octylamino)cyclopropyl]phenyl}benzamide

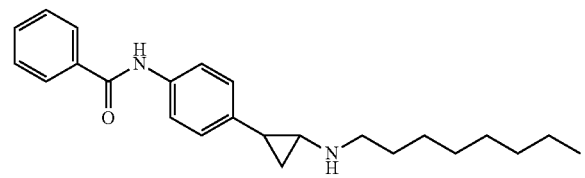 [SMILES: CCCCCCCCNC1CC1c1ccc(NC(=O)c2ccccc2)cc1]

By a method similar to Example 1, Step C, the title compound (59.4 mg) was obtained from N-[4-(trans-2-aminocyclopropyl)phenyl]benzamide hydrochloride (100 mg) and octylaldehyde (44.4 mg).

$^1$H NMR (400 MHz, DMSO-$d_6$) δ 0.81-0.97 (5H, m), 1.24 (10H, brs), 1.39 (2H, brs), 1.70-1.79 (1H, m), 2.12-2.31 (2H, m), 2.54-2.62 (2H, m), 7.02 (2H, s), 7.48-7.55 (2H, m), 7.55-7.59 (1H, m), 7.60-7.66 (2H, m), 7.93 (2H, d, J=7.3 Hz), 10.15 (1H, s).

Example 3

N-{4-[trans-2-(benzylamino)cyclopropyl]phenyl}-3-bromobenzamide

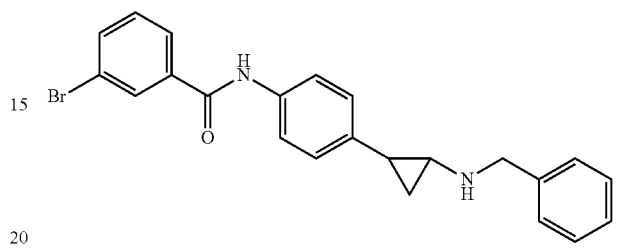

A) tert-butyl [trans-2-(4-{[(3-bromophenyl)carbonyl]amino}phenyl)cyclopropyl]carbamate To a solution of tert-butyl [trans-2-(4-aminophenyl)cyclopropyl]carbamate (300 mg) described in a document (J. Am. Chem. Soc., 2010, 132, 6827.) in acetonitrile (12 mL) were added 3-bromobenzoyl chloride (191 μL) and triethylamine (202 μL). The mixture was stirred at room temperature overnight and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) to give the title compound (407 mg).

$^1$H NMR (400 MHz, CDCl$_3$) δ 1.15 (2H, t, J=5.6 Hz), 1.46 (9H, s), 2.04 (1H, s), 2.70 (1H, brs), 4.86 (1H, brs), 7.15 (2H, d, J=7.6 Hz), 7.36 (1H, t, J=7.9 Hz), 7.52 (2H, d, J=7.6 Hz), 7.67 (1H, d, J=8.1 Hz), 7.71-7.81 (2H, m), 8.00 (1H, s).

B) N-[4-(trans-2-aminocyclopropyl)phenyl]-3-bromobenzamide hydrochloride tert-Butyl [trans-2-(4-{[(3-bromophenyl)carbonyl]amino}phenyl)cyclopropyl]carbamate (407 mg) was dissolved in 4N hydrochloric acid/ethyl acetate solution (2 mL), and the mixture was stirred at room temperature for 2 hr. The solvent was evaporated under reduced pressure to give the title compound (320 mg).

$^1$H NMR (400 MHz, DMSO-$d_6$) δ 1.15-1.24 (1H, m), 1.32-1.40 (1H, m), 2.29 (1H, brs), 2.76-2.84 (1H, m), 7.15 (2H, d, J=8.1 Hz), 7.50 (1H, t, J=7.9 Hz), 7.70 (2H, d, J=8.1 Hz), 7.80 (1H, d, J=7.8 Hz), 7.95 (1H, d, J=8.1 Hz), 8.13 (1H, s), 8.33 (3H, brs), 10.35 (1H, s).

C) N-{4-[trans-2-(benzylamino)cyclopropyl]phenyl}-3-bromobenzamide

To a solution of N-[4-(trans-2-aminocyclopropyl)phenyl]-3-bromobenzamide hydrochloride (80 mg) in methanol (2 mL) were added benzaldehyde (22 μL) and sodium hydrogen carbonate (27.4 mg). The mixture was stirred at 70° C. for 1 hr, and ice-cooled to 0° C. and sodium borohydride (12.4 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) and recrystallized (hexane/ethyl acetate) to give the title compound (21.0 mg).

MS (API+): [M+H]+ 421.2.

$^1$H NMR (400 MHz, CDCl$_3$) δ 0.96 (1H, dt, J=6.9, 5.6 Hz), 1.11 (1H, dt, J=9.1, 4.9 Hz), 1.88-1.95 (2H, m), 2.33-2.40 (1H, m), 3.89 (2H, d, J=2.4 Hz), 6.98 (2H, d, J=8.6 Hz), 7.22-7.38 (6H, m), 7.48 (2H, d, J=8.6 Hz), 7.66 (1H, ddd, J=7.9, 1.9, 1.0 Hz), 7.77 (2H, d, J=6.4 Hz), 7.98 (1H, t, J=1.7 Hz).

Example 4

3-bromo-N-{4-[trans-2-(octylamino)cyclopropyl]phenyl}benzamide

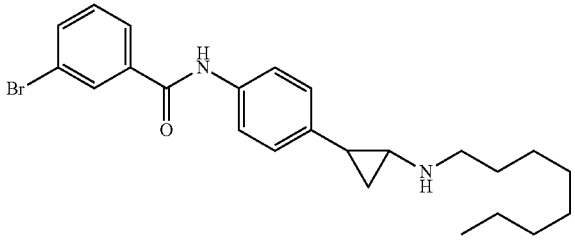 [SMILES: CCCCCCCCNC1CC1c1ccc(NC(=O)c2cccc(Br)c2)cc1]

To a solution of N-[4-(trans-2-aminocyclopropyl)phenyl]-3-bromobenzamide hydrochloride (80 mg) in methanol (2 mL) were added octylaldehyde (34 μL) and sodium hydrogen carbonate (27.4 mg). The reaction mixture was stirred at 70° C. for 1 hr, and ice-cooled to 0° C. and sodium borohydride (12.4 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) and recrystallized (hexane/ethyl acetate) to give the title compound (48.3 mg).

MS (API+): [M+H]+ 443.3.

$^1$H NMR (400 MHz, DMSO-d$_6$) δ 0.80-0.96 (5H, m), 1.24 (10H, s), 1.38 (2H, d, J=7.1 Hz), 1.70-1.80 (1H, m), 2.13-2.22 (1H, m), 2.22-2.30 (1H, m), 2.57 (2H, t, J=6.8 Hz), 7.02 (2H, d, J=8.6 Hz), 7.49 (1H, t, J=7.9 Hz), 7.61 (2H, d, J=8.6 Hz), 7.79 (1H, d, J=8.1 Hz), 7.94 (1H, d, J=8.1 Hz), 8.08-8.15 (1H, m), 10.25 (1H, s).

Example 5

3-bromo-N-(4-{trans-2-[(1-methylpiperidin-4-yl)amino]cyclopropyl}phenyl)benzamide

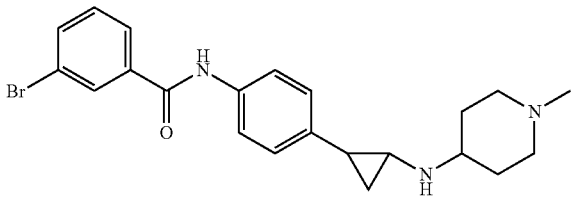 [SMILES: CN1CCC(NC2CC2c2ccc(NC(=O)c3cccc(Br)c3)cc2)CC1]

To a solution of N-[4-(trans-2-aminocyclopropyl)phenyl]-3-bromobenzamide hydrochloride (80 mg) in methanol (2 mL) were added 1-methylpiperidin-4-one (24.6 mg) and sodium hydrogen carbonate (27.4 mg). The mixture was stirred at 70° C. for 1 hr, and ice-cooled to 0° C. and sodium borohydride (12.4 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (ethyl acetate) and recrystallized (ethyl acetate) to give the title compound (10.0 mg).

MS (API+): [M+H]+ 428.3.

$^1$H NMR (400 MHz, DMSO-d$_6$) δ 0.89-0.96 (2H, m), 1.20-1.35 (2H, m), 1.68-1.79 (3H, m), 1.86 (2H, t, J=10.5 Hz), 2.11 (3H, s), 2.14-2.21 (1H, m), 2.47 (2H, brs), 2.62-2.70 (2H, m), 7.01 (2H, d, J=8.6 Hz), 7.50 (1H, t, J=7.9 Hz), 7.61 (2H, d, J=8.6 Hz), 7.79 (1H, d, J=7.1 Hz), 7.94 (1H, d, J=8.1 Hz), 8.12 (1H, s), 10.25 (1H, s).

Example 6

3-bromo-N-(4-{trans-2-[(3,4-dimethoxybenzyl)amino]cyclopropyl}phenyl)benzamide

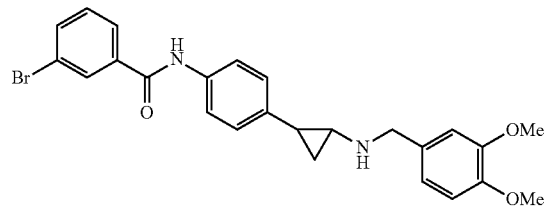 [SMILES: COc1ccc(CNC2CC2c2ccc(NC(=O)c3cccc(Br)c3)cc2)cc1OC]

To a solution of N-[4-(trans-2-aminocyclopropyl)phenyl]-3-bromobenzamide hydrochloride (80 mg) in methanol (2 mL) were added 3,4-dimethoxybenzaldehyde (36.2 mg) and sodium hydrogen carbonate (27.4 mg). The mixture was stirred at 70° C. for 1 hr, and ice-cooled to 0° C. and sodium borohydride (12.4 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (ethyl acetate) and recrystallized (ethyl acetate) to give the title compound (44.2 mg).

MS (API+): [M+H]+ 481.3.

$^1$H NMR (400 MHz, DMSO-d$_6$) δ 0.86-1.06 (2H, m), 1.80 (1H, brs), 2.15 (1H, brs), 2.79 (1H, brs), 3.62-3.75 (8H, m), 6.74-6.91 (3H, m), 6.97 (2H, d, J=8.3 Hz), 7.49 (1H, t, J=7.8 Hz), 7.60 (2H, d, J=8.1 Hz), 7.79 (1H, d, J=7.8 Hz), 7.94 (1H, d, J=7.3 Hz), 8.12 (1H, s), 10.25 (1H, s).

Example 7

N-{4-[trans-2-(benzylamino)cyclopropyl]phenyl}-3-methylbenzamide

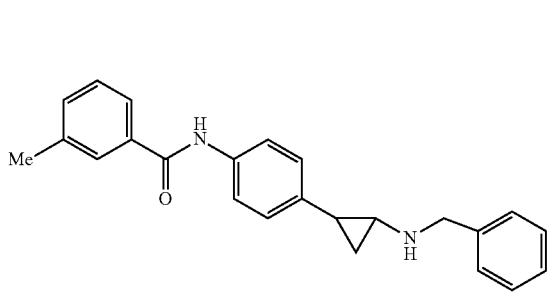 [SMILES: Cc1cccc(C(=O)Nc2ccc(C3CC3NCc3ccccc3)cc2)c1]

A) tert-butyl [trans-2-(4-{[(3-methylphenyl)carbonyl]amino}phenyl)cyclopropyl]carbamate To a solution of tert-butyl [trans-2-(4-aminophenyl)cyclopropyl]carbamate (100 mg) described in a document (J. Am. Chem. Soc., 2010, 132, 6827.) in acetonitrile (4 mL) were added 3-methylbenzoyl chloride (62.3 mg) and triethylamine (56 μL). The mixture was stirred at room temperature for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) to give the title compound (141 mg).

$^1$H NMR (400 MHz, CDCl$_3$) δ 1.10-1.20 (2H, m), 1.46 (9H, s), 2.05 (1H, s), 2.43 (3H, s), 2.71 (1H, brs), 4.85 (1H, brs), 7.15 (2H, d, J=7.8 Hz), 7.34-7.39 (2H, m), 7.54 (2H, d, J=8.1 Hz), 7.64 (1H, d, J=4.4 Hz), 7.68 (1H, s), 7.76 (1H, brs).

B) N-[4-(trans-2-aminocyclopropyl)phenyl]-3-methylbenzamide hydrochloride tert-Butyl [trans-2-(4-{[(3-methylphenyl)carbonyl]amino}phenyl)cyclopropyl]carbamate (141 mg) was dissolved in 4N hydrochloric acid/ethyl acetate solution (2 mL). The mixture was stirred at room temperature for 2 hr and the solvent was evaporated under reduced pressure to give the title compound (51.6 mg).

$^1$H NMR (400 MHz, DMSO-d$_6$) δ 1.15-1.24 (1H, m), 1.35 (1H, brs), 2.28 (1H, brs), 2.40 (3H, s), 2.79 (1H, d, J=3.7 Hz), 7.14 (2H, d, J=8.6 Hz), 7.38-7.43 (2H, m), 7.66-7.78 (4H, m), 8.33 (3H, brs), 10.19 (1H, s).

C) N-{4-[trans-2-(benzylamino)cyclopropyl]phenyl}-3-methylbenzamide

To a solution of N-[4-(trans-2-aminocyclopropyl)phenyl]-3-methylbenzamide hydrochloride (113 mg) in methanol (3 mL) were added benzaldehyde (38 μL) and sodium hydrogen carbonate (47.0 mg). The mixture was stirred at 70° C. for 1 hr, and ice-cooled to 0° C. and sodium borohydride (21.2 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) and recrystallized (hexane/ethyl acetate) to give the title compound (85.6 mg).

MS (API+): [M+H]$^+$ 357.1.

$^1$H NMR (400 MHz, DMSO-d$_6$) δ 0.87-0.94 (1H, m), 0.94-1.02 (1H, m), 1.76-1.85 (1H, m), 2.14-2.21 (1H, m), 2.39 (3H, s), 2.81-2.92 (1H, m), 3.76 (2H, s), 6.95 (2H, d, J=8.6 Hz), 7.18-7.25 (1H, m), 7.26-7.34 (4H, m), 7.37-7.43 (2H, m), 7.60 (2H, d, J=8.6 Hz), 7.69-7.77 (2H, m), 10.10 (1H, s).

Example 8

N-{4-[trans-2-(benzylamino)cyclopropyl]phenyl}-3-(trifluoromethyl)benzamide

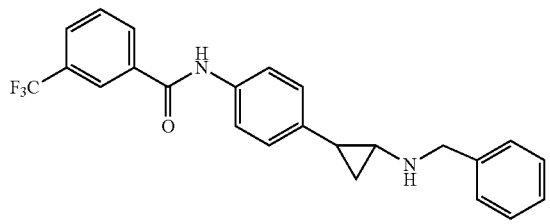 [SMILES: O=C(Nc1ccc(C2CC2NCc2ccccc2)cc1)c1cccc(C(F)(F)F)c1]

A) tert-butyl {trans-2-[4-({[3-(trifluoromethyl)phenyl]carbonyl}amino)phenyl]cyclopropyl}-carbamate To a solution of tert-butyl [trans-2-(4-aminophenyl)cyclopropyl]carbamate (100 mg) described in a document (J. Am. Chem. Soc., 2010, 132, 6827.) in acetonitrile (4 mL) were added 3-(trifluoromethyl)benzoyl chloride (126 mg) and triethylamine (84 μL). The mixture was stirred at room temperature for 30 min and water was added. The mixture was extracted with ethyl acetate, and the extract was washed with saturated brine and dried over anhydrous sodium sulfate. The solvent was evaporated under reduced pressure. The residue was crystallized (hexane/ethyl acetate) to give the title compound (161 mg).

$^1$H NMR (400 MHz, CDCl$_3$) δ 1.17 (2H, brs), 1.46 (9H, s), 2.00-2.11 (1H, m), 2.66-2.76 (1H, m), 4.78-4.94 (1H, m), 7.17 (2H, d, J=7.3 Hz), 7.54 (2H, d, J=7.6 Hz), 7.64 (1H, s), 7.79 (2H, d, J=14.4 Hz), 8.03-8.09 (1H, m), 8.12 (1H, s).

B) N-[4-(trans-2-aminocyclopropyl)phenyl]-3-(trifluoromethyl)benzamide hydrochloride tert-Butyl {trans-2-[4-({[3-(trifluoromethyl)phenyl]carbonyl}amino)phenyl]cyclopropyl}-carbamate (161 mg) was dissolved in 4N hydrochloric acid/ethyl acetate solution (2 mL), and the mixture was stirred at room temperature for 2 hr. The solvent was evaporated under reduced pressure to give the title compound (130 mg).

$^1$H NMR (400 MHz, DMSO-d$_6$) δ 1.16-1.26 (1H, m), 1.36 (1H, d, J=3.9 Hz), 2.29 (1H, brs), 2.80 (1H, brs), 7.17 (2H, d, J=8.1 Hz), 7.71 (2H, d, J=8.3 Hz), 7.79 (1H, t, J=7.2 Hz), 7.97 (1H, d, J=7.6 Hz), 8.21-8.38 (5H, m), 10.48 (1H, s).

C) N-{4-[trans-2-(benzylamino)cyclopropyl]phenyl}-3-(trifluoromethyl)benzamide To a solution of N-[4-(trans-2-aminocyclopropyl)phenyl]-3-(trifluoromethyl)benzamide hydrochloride (107 mg) in methanol (2 mL) were added benzaldehyde (30 μL) and sodium hydrogen carbonate (37.8 mg). The mixture was stirred at 70° C. for 1 hr, and ice-cooled to 0° C. and sodium borohydride (17.0 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) and recrystallized (hexane/ethyl acetate) to give the title compound (66.0 mg).

MS (API+): [M+H]$^+$ 411.3.

$^1$H NMR (400 MHz, DMSO-d$_6$) δ 0.93 (1H, d, J=6.1 Hz), 0.96-1.03 (1H, m), 1.81 (1H, brs), 2.20 (1H, d, J=3.4 Hz), 3.77 (2H, s), 6.98 (2H, d, J=8.6 Hz), 7.18-7.25 (1H, m), 7.26-7.34 (4H, m), 7.61 (2H, d, J=8.3 Hz), 7.75-7.82 (1H, m), 7.96 (1H, d, J=7.6 Hz), 8.22-8.29 (2H, m), 10.37 (1H, s).

Example 9

N-{4-[trans-2-(benzylamino)cyclopropyl]phenyl}-3-tert-butylbenzamide

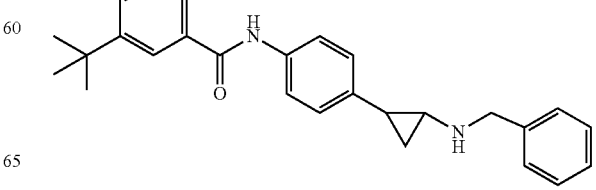

A) tert-butyl [trans-2-(4-{[(3-tert-butylphenyl)carbonyl]-amino}phenyl)cyclopropyl]carbamate By a method similar to Example 28, Step A, the title compound (100 mg) was obtained from tert-butyl [trans-2-(4-aminophenyl)cyclopropyl]carbamate (100 mg) and 3-tert-butylbenzoic acid (86 mg).

$^1$H NMR (400 MHz, CDCl$_3$) δ 1.08-1.20 (2H, m), 1.35 (9H, s), 1.46 (9H, s), 2.05 (1H, br. s), 2.71 (1H, brs), 4.86 (1H, brs), 7.15 (2H, d, J=7.8 Hz), 7.36-7.46 (1H, m), 7.50-7.65 (4H, m), 7.72 (1H, s), 7.92 (1H, s).

B) N-[4-(trans-2-aminocyclopropyl)phenyl]-3-tert-butylbenzamide hydrochloride By a method similar to Example 1, Step B, the title compound (64.3 mg) was obtained from tert-butyl [trans-2-(4-{[(3-tert-butylphenyl)carbonyl]amino}phenyl)cyclopropyl]-carbamate (99 mg).

$^1$H NMR (400 MHz, DMSO-d$_6$) δ 1.16-1.24 (1H, m), 1.32-1.40 (10H, m), 2.29 (1H, ddd, J=9.9, 6.5, 3.4 Hz), 2.79 (1H, dt, J=7.6, 4.1 Hz), 7.15 (2H, d, J=8.6 Hz), 7.42-7.48 (1H, m), 7.60-7.65 (1H, m), 7.70 (2H, d, J=8.6 Hz), 7.76 (1H, d, J=7.8 Hz), 7.92 (1H, t, J=1.8 Hz), 8.34 (3H, brs), 10.21 (1H, s).

C) N-{4-[trans-2-(benzylamino)cyclopropyl]phenyl}-3-tert-butylbenzamide

By a method similar to Example 1, Step C, the title compound (15.0 mg) was obtained from N-[4-(trans-2-aminocyclopropyl)phenyl]-3-tert-butylbenzamide hydrochloride (62.6 mg).

$^1$H NMR (400 MHz, CDCl$_3$) δ 0.97 (1H, dt, J=7.0, 5.5 Hz), 1.07-1.15 (1H, m), 1.36 (9H, s), 1.92 (2H, ddd, J=9.2, 5.9, 3.2 Hz), 2.37 (1H, ddd, J=7.2, 4.1, 3.2 Hz), 3.85-3.94 (2H, m), 6.96-7.01 (2H, m), 7.22-7.35 (4H, m), 7.37-7.43 (1H, m), 7.51 (2H, d, J=8.3 Hz), 7.55-7.63 (2H, m), 7.75 (1H, brs), 7.92 (1H, t, J=1.7 Hz).

Example 10

N-{4-[trans-2-(benzylamino)cyclopropyl]phenyl}-3-phenoxybenzamide

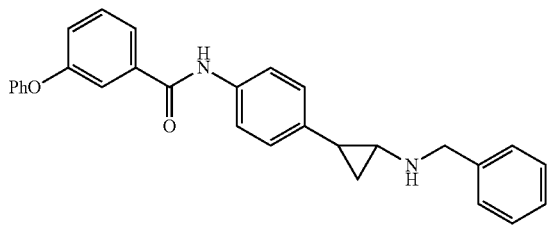 [SMILES: O=C(Nc1ccc(C2CC2NCc2ccccc2)cc1)c1cccc(Oc2ccccc2)c1]

A) tert-butyl [trans-2-(4-{[(3-phenoxyphenyl)carbonyl]amino}phenyl)cyclopropyl]carbamate By a method similar to Example 28, Step A, the title compound (93.8 mg) was obtained from tert-butyl [trans-2-(4-aminophenyl)cyclopropyl]carbamate (100 mg) and 3-phenoxybenzoic acid (104 mg).

$^1$H NMR (400 MHz, CDCl$_3$) δ 1.10-1.19 (2H, m), 1.46 (9H, s), 2.04 (1H, brs), 2.70 (1H, brs), 4.85 (1H, brs), 7.02-7.07 (2H, m), 7.11-7.20 (4H, m), 7.34-7.40 (2H, m), 7.44 (1H, t, J=7.9 Hz), 7.48-7.54 (3H, m), 7.56 (1H, d, J=7.8 Hz), 7.71 (1H, s).

B) N-[4-(trans-2-aminocyclopropyl)phenyl]-3-phenoxybenzamide hydrochloride

By a method similar to Example 1, Step B, the title compound (51.9 mg) was obtained from tert-butyl [trans-2-(4-{[(3-phenoxyphenyl)carbonyl]amino}phenyl)cyclopropyl]carbamate (92 mg).

$^1$H NMR (400 MHz, DMSO-d$_6$) δ 1.15-1.23 (1H, m), 1.32-1.40 (1H, m), 2.29 (1H, ddd, J=10.1, 6.4, 3.5 Hz), 2.79 (1H, brs), 7.07 (2H, dd, J=8.6, 1.0 Hz), 7.14 (2H, d, J=8.8 Hz), 7.16-7.26 (2H, m), 7.40-7.47 (2H, m), 7.51-7.59 (2H, m), 7.69 (2H, d, J=8.6 Hz), 7.75 (1H, d, J=8.1 Hz), 8.38 (3H, brs), 10.27 (1H, s).

C) N-{4-[trans-2-(benzylamino)cyclopropyl]phenyl}-3-phenoxybenzamide

By a method similar to Example 1, Step C, the title compound (8.3 mg) was obtained from N-[4-(trans-2-aminocyclopropyl)phenyl]-3-phenoxybenzamide hydrochloride (27.1 mg).

$^1$H NMR (400 MHz, DMSO-d$_6$) δ 0.87-0.94 (1H, m), 0.98 (1H, dt, J=9.2, 4.5 Hz), 1.75-1.83 (1H, m), 2.14-2.21 (1H, m), 2.86 (1H, brs), 3.76 (2H, s), 6.94 (2H, d, J=8.6 Hz), 7.04-7.09 (2H, m), 7.16-7.24 (3H, m), 7.25-7.33 (4H, m), 7.40-7.47 (2H, m), 7.50-7.61 (4H, m), 7.73 (1H, d, J=8.1 Hz), 10.16 (1H, s).

Example 11

N-{4-[trans-2-(benzylamino)cyclopropyl]phenyl}-3-(benzyloxy)benzamide hydrochloride

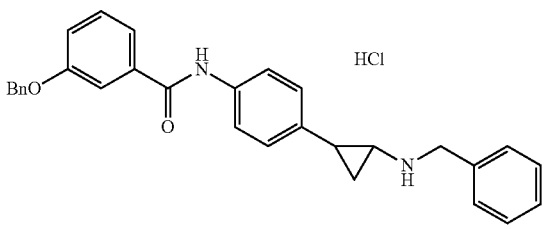 [SMILES: O=C(Nc1ccc(C2CC2NCc2ccccc2)cc1)c1cccc(OCc2ccccc2)c1 ; Cl]

A) tert-butyl {trans-2-[4-({[3-(benzyloxy)phenyl]carbonyl}amino)phenyl]cyclopropyl}carbamate By a method similar to Example 28, Step A, the title compound (164 mg) was obtained from tert-butyl [trans-2-(4-aminophenyl)cyclopropyl]carbamate (100 mg) and 3-(benzyloxy)benzoic acid (110 mg).

$^1$H NMR (400 MHz, DMSO-d$_6$) δ 0.99-1.13 (2H, m), 1.38 (9H, s), 1.83-1.92 (1H, m), 2.59 (1H, brs), 5.19 (2H, s), 7.07 (2H, d, J=8.6 Hz), 7.20-7.27 (2H, m), 7.32-7.38 (1H, m), 7.38-7.45 (3H, m), 7.45-7.51 (2H, m), 7.54 (1H, d, J=7.6 Hz), 7.58 (1H, d, J=1.7 Hz), 7.65 (2H, d, J=8.6 Hz), 10.14 (1H, s).

B) N-[4-(trans-2-aminocyclopropyl)phenyl]-3-(benzyloxy)benzamide hydrochloride By a method similar to Example 1, Step B, the title compound (115 mg) was obtained from tert-butyl {trans-2-[4-({[3-(benzyloxy)phenyl]carbonyl}amino)phenyl]cyclopropyl}-carbamate (164 mg).

$^1$H NMR (400 MHz, DMSO-$d_5$) δ 1.19 (1H, d, J=6.8 Hz), 1.30-1.38 (1H, m), 2.28 (1H, brs), 2.76-2.83 (1H, m), 5.19 (2H, s), 7.14 (2H, d, J=8.6 Hz), 7.24 (1H, dd, J=7.9, 2.1 Hz), 7.36 (1H, d, J=7.1 Hz), 7.38-7.51 (5H, m), 7.54 (1H, d, J=7.8 Hz), 7.58 (1H, d, J=2.0 Hz), 7.71 (2H, d, J=8.6 Hz), 8.30 (3H, brs), 10.21 (1H, s).

C) N-{4-[trans-2-(benzylamino)cyclopropyl]phenyl}-3-(benzyloxy)benzamide hydrochloride By a method similar to Example 1, Step C, 4N hydrochloric acid/ethyl acetate solution was added to N-{4-[trans-2-(benzylamino)cyclopropyl]phenyl}-3-(benzyloxy)benzamide obtained from N-[4-(trans-2-aminocyclopropyl)phenyl]-3-(benzyloxy)benzamide hydrochloride (109 mg) and benzaldehyde (29.3 µL), and the resulting solid was collected by filtration to give the title compound (96.1 mg).

$^1$H NMR (400 MHz, DMSO-$d_6$) δ 1.22-1.34 (1H, m), 1.46 (1H, brs), 2.41 (1H, brs), 2.89 (1H, brs), 4.29 (2H, brs), 5.19 (2H, s), 7.11 (2H, d, J=8.6 Hz), 7.24 (1H, dd, J=8.3, 2.0 Hz), 7.30-7.63 (13H, m), 7.70 (2H, d, J=8.3 Hz), 9.44 (2H, br. s), 10.20 (1H, s).

Example 12

N-(4-{trans-2-[(pyridin-3-ylmethyl)amino]cyclopropyl}phenyl)-benzamide bis(trifluoroacetate)

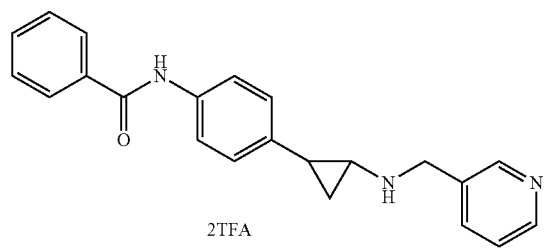 [SMILES: O=C(Nc1ccc(C2CC2NCc2cccnc2)cc1)c1ccccc1]

2TFA

To a solution of N-[4-(trans-2-aminocyclopropyl)phenyl]benzamide hydrochloride (23 mg) and 3-pyridinecarboxyaldehyde (17 mg) in methanol (0.5 mL) were added acetic acid (0.1 mL) and a solution of 2-picoline borane (23 mg) in methanol (0.4 mL). The reaction mixture was stirred at 60° C. overnight, and the solvent was evaporated by an air blowing apparatus. The residue was purified by HPLC (C18, mobile phase: water/acetonitrile (with 0.1% TFA)) to give the title compound (2.8 mg).

MS (API+): [M+H]$^+$ 344.2.

The compounds produced by the method described in the above-mentioned Example 12 or a method analogous thereto are shown in the following Tables. In the Tables, MS shows measured values.

TABLE 1-1

| Ex. No. | IUPAC name | structure | salt | MS |
|---|---|---|---|---|
| 13 | N-(4-{trans-2-[(thiophen-2-ylmethyl)amino]-cyclopropyl}-phenyl)benzamide | 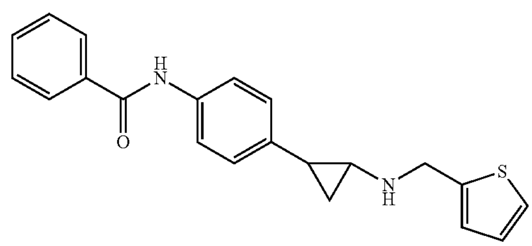 [SMILES: O=C(Nc1ccc(C2CC2NCc2cccs2)cc1)c1ccccc1] | CF3COOH | 349.1 |
| 14 | N-(4-{trans-2-[(3-phenyl-propyl)amino]-cyclopropyl}-phenyl)benzamide | 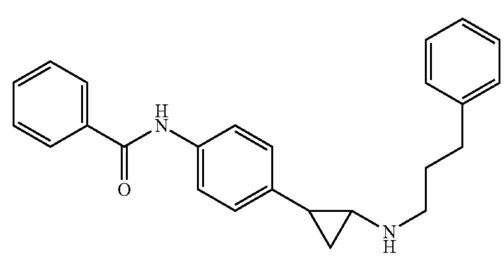 [SMILES: O=C(Nc1ccc(C2CC2NCCCc2ccccc2)cc1)c1ccccc1] | CF3COOH | 371.3 |
| 15 | N-(4-{trans-2-[(2-fluoro-benzyl)amino]-cyclopropyl}-phenyl)benzamide | 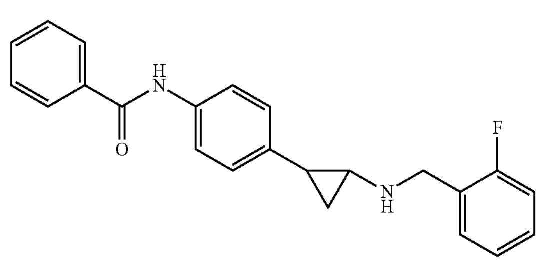 [SMILES: O=C(Nc1ccc(C2CC2NCc2ccccc2F)cc1)c1ccccc1] | CF3COOH | 361.2 |

TABLE 1-1-continued

| Ex. No. | IUPAC name | structure | salt | MS |
|---|---|---|---|---|
| 16 | N-(4-{trans-2-[(biphenyl-4-ylmethyl)amino]-cyclopropyl}-phenyl)benzamide | 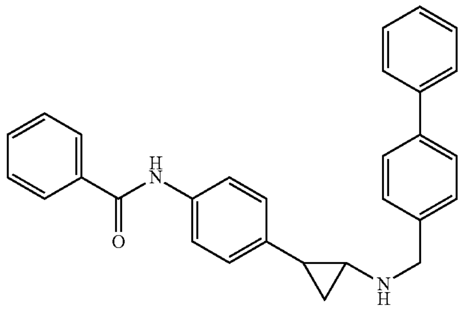 [SMILES: O=C(Nc1ccc(C2CC2NCc2ccc(-c3ccccc3)cc2)cc1)c1ccccc1] | CF3COOH | 419.3 |
| 17 | N-(4-{trans-2-[(2,2-dimethyl-propyl)amino]-cyclopropyl}-phenyl)benzamide | 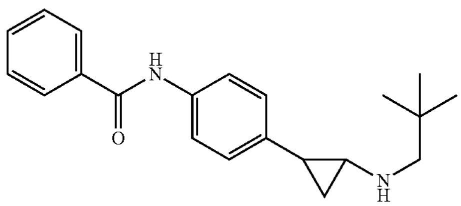 [SMILES: CC(C)(C)CNC1CC1c1ccc(NC(=O)c2ccccc2)cc1] | CF3COOH | 323.3 |
| 18 | N-(4-{trans-2-[(naphthalen-2-ylmethyl)amino]-cyclopropyl}-phenyl)benzamide | 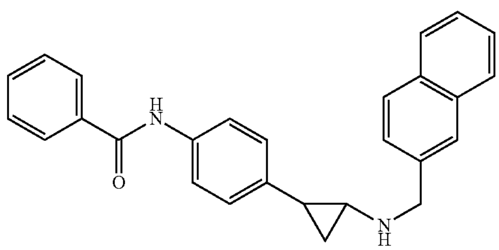 [SMILES: O=C(Nc1ccc(C2CC2NCc2ccc3ccccc3c2)cc1)c1ccccc1] | CF3COOH | 393.3 |
| 19 | N-(4-{trans-2-[(1-phenyl-ethyl)amino]-cyclopropyl}-phenyl)benzamide | 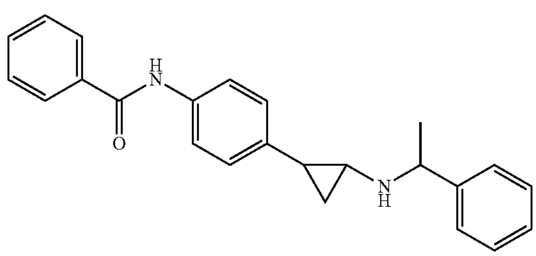 [SMILES: CC(NC1CC1c1ccc(NC(=O)c2ccccc2)cc1)c1ccccc1] | CF3COOH | 357.2 |
| 20 | N-{4-[trans-2-(2,3-dihydro-1H-inden-1-ylamino)cyclo-propyl]phenyl}-benzamide | 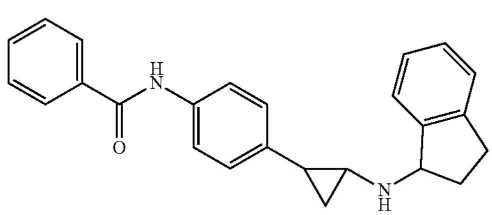 [SMILES: O=C(Nc1ccc(C2CC2NC2CCc3ccccc32)cc1)c1ccccc1] | CF3COOH | 369.3 |

TABLE 1-2

| Ex. No. | IUPAC name | structure | salt | MS |
|---|---|---|---|---|
| 21 | N-{4-[trans-2-(9H-fluoren-9-yl amino)cyclopropyl]phenyl}-benzamide | 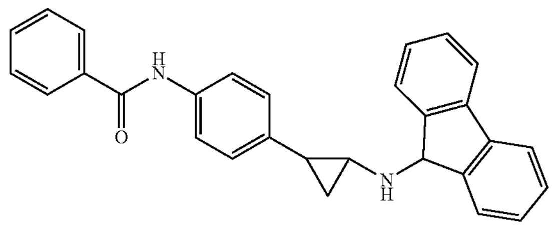 [SMILES: O=C(Nc1ccc(C2CC2NC2c3ccccc3-c3ccccc32)cc1)c1ccccc1] | CF3COOH | 417.3 |
| 22 | N-{4-[trans-2-(dodecylamino)-cyclopropyl]-phenyl}benzamide | 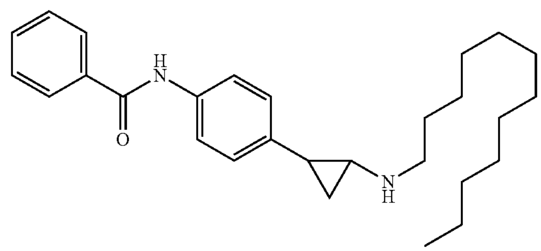 [SMILES: CCCCCCCCCCCCNC1CC1c1ccc(NC(=O)c2ccccc2)cc1] | CF3COOH | 421.4 |
| 23 | N-{4-[trans-2-(cycloheptyl-amino)cyclopropyl]phenyl}-benzamide | 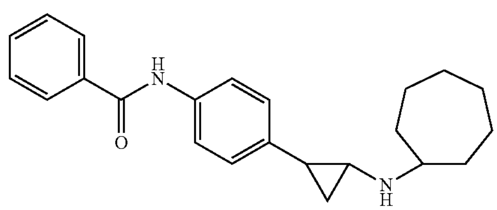 [SMILES: O=C(Nc1ccc(C2CC2NC2CCCCCC2)cc1)c1ccccc1] | CF3COOH | 349.3 |
| 24 | N-{4-[trans-2-(cyclooctyl-amino)cyclopropyl]phenyl}-benzamide | 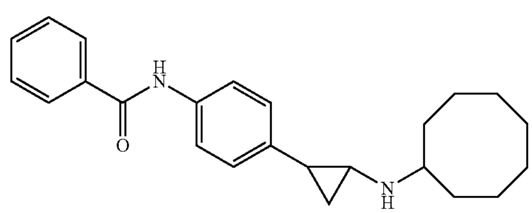 [SMILES: O=C(Nc1ccc(C2CC2NC2CCCCCCC2)cc1)c1ccccc1] | CF3COOH | 363.3 |
| 25 | N-(4-{trans-2-[(1-benzyl-piperidin-4-yl)amino]cyclopropyl}phenyl)-benzamide | 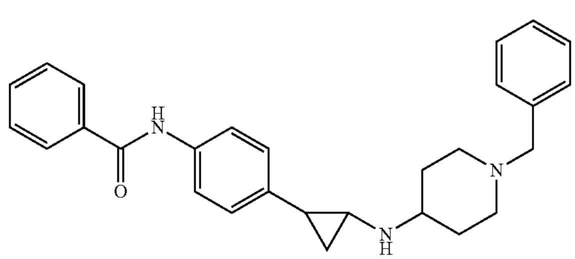 [SMILES: O=C(Nc1ccc(C2CC2NC2CCN(Cc3ccccc3)CC2)cc1)c1ccccc1] | 2CF3COOH | 426.3 |
| 26 | N-[4-(trans-2-{[2-(benzyloxy)-ethyl]amino}-cyclopropyl)-phenyl]benzamide | 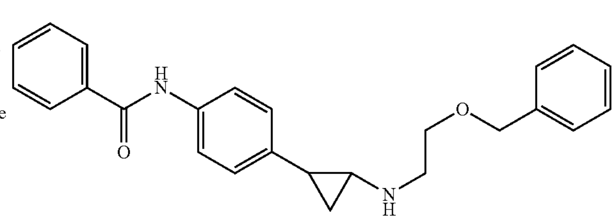 | CF3COOH | 387.3 |

| Ex. No. | IUPAC name | structure | salt | MS |
|---|---|---|---|---|
| 27 | N-{4-[trans-2-(dimethylamino)-cyclopropyl]-phenyl}benzamide | 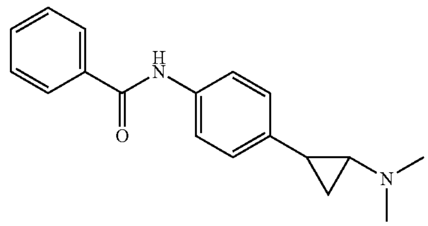 [SMILES: CN(C)C1CC1c1ccc(NC(=O)c2ccccc2)cc1] | CF3COOH | 281.1 |

Example 28

3-benzyl-N-{4-[trans-2-(benzylamino)cyclopropyl]phenyl}benzamide

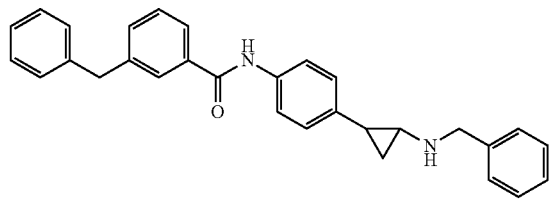 [SMILES: O=C(Nc1ccc(C2CC2NCc2ccccc2)cc1)c1cccc(Cc2ccccc2)c1]

A) tert-butyl [trans-2-(4-{[(3-benzylphenyl)carbonyl]amino}phenyl)cyclopropyl]carbamate To a solution of tert-butyl [trans-2-(4-aminophenyl)cyclopropyl]carbamate (100 mg) described in a document (J. Am. Chem. Soc., 2010, 132, 6827.) in acetonitrile (4 mL) were added 3-benzylbenzoic acid (103 mg) described in a document (J. Org. Chem. 2001, 66, 2874.), N-ethyl-N'-(3-dimethylaminopropyl)carbodiimide hydrochloride (93 mg), 1-hydroxybenzotriazole (65.3 mg) and triethylamine (140 µL). The mixture was stirred at room temperature overnight and water was added. The mixture was extracted with ethyl acetate, and the extract was washed with saturated brine and dried over anhydrous sodium sulfate. The solvent was evaporated under reduced pressure. The residue was recrystallized (hexane/ethyl acetate) to give the title compound (126 mg).

$^1$H NMR (400 MHz, CDCl$_3$) δ 1.13 (2H, t, J=6.6 Hz), 1.45 (9H, s), 1.97-2.03 (1H, m), 2.68 (1H, brs), 4.03 (2H, s), 4.89 (1H, brs), 7.11 (2H, d, J=8.6 Hz), 7.15-7.24 (3H, m), 7.25-7.32 (2H, m), 7.35 (2H, s), 7.51 (2H, d, J=8.3 Hz), 7.65-7.69 (1H, m), 7.71 (1H, s), 7.88 (1H, brs).

B) N-[4-(trans-2-aminocyclopropyl)phenyl]-3-benzylbenzamide hydrochloride tert-Butyl [trans-2-(4-{[(3-benzylphenyl)carbonyl]amino}phenyl)cyclopropyl]carbamate (125 mg) was dissolved in 4N hydrochloric acid/ethyl acetate solution (2 mL), and the mixture was stirred at room temperature overnight. The solvent was evaporated under reduced pressure to give the title compound (54.7 mg).

MS (API+): [M+H]$^+$ 343.1.

C) 3-benzyl-N-{4-[trans-2-(benzylamino)cyclopropyl]phenyl}benzamide

To a solution of N-[4-(trans-2-aminocyclopropyl)phenyl]-3-benzylbenzamide hydrochloride (69.6 mg) in methanol (1.5 mL) were added benzaldehyde (19 µL) and sodium hydrogen carbonate (23.2 mg). The mixture was stirred at 70° C. for 1 hr, and ice-cooled to 0° C. and sodium borohydride (10.4 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) and crystallized (hexane/ethyl acetate) to give the title compound (29.7 mg).

MS (API+): [M+H]$^+$ 433.3.

$^1$H NMR (400 MHz, DMSO-d$_6$) δ 0.88-0.94 (1H, m), 0.98 (1H, dt, J=9.0, 4.5 Hz), 1.75-1.83 (1H, m), 2.14-2.20 (1H, m), 2.86 (1H, brs), 3.76 (2H, s), 4.03 (2H, s), 6.95 (2H, d, J=8.6 Hz), 7.16-7.24 (2H, m), 7.24-7.33 (8H, m), 7.43 (2H, d, J=4.6 Hz), 7.58 (2H, d, J=8.3 Hz), 7.76 (1H, t, J=4.0 Hz), 7.80 (1H, s), 10.11 (1H, s).

Example 29

3-(benzylamino)-N-{4-[trans-2-(benzylamino)cyclopropyl]phenyl}benzamide

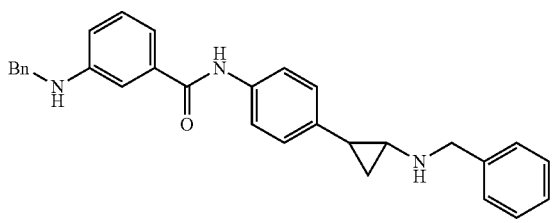 [SMILES: O=C(Nc1ccc(C2CC2NCc2ccccc2)cc1)c1cccc(NCc2ccccc2)c1]

A) methyl 3-[benzyl(tert-butoxycarbonyl)amino]benzoate

To a solution of methyl 3-(tert-butoxycarbonylamino)benzoate (1.08 g) described in a document (Bioorg. Med. Chem. 2010, 18, 3175.) in DMF (40 mL) was added sodium hydride (258 mg). The reaction mixture was stirred at room temperature for 15 min, and benzyl bromide (613 µL) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) to give the title compound (125 mg).

$^1$H NMR (400 MHz, CDCl$_3$) δ 1.42 (9H, s), 3.89 (3H, s), 4.86 (2H, s), 7.19-7.34 (7H, m), 7.80-7.85 (1H, m), 7.88 (1H, s).

B) 3-[benzyl(tert-butoxycarbonyl)amino]benzoic acid

By a method similar to Example 33, Step A, the title compound (121 mg) was obtained from methyl 3-[benzyl(tert-butoxycarbonyl)amino]benzoate (125 mg).

$^1$H NMR (400 MHz, CDCl$_3$) δ1.46 (9H, s), 4.90 (2H, s), 7.22-7.27 (3H, m), 7.30-7.43 (4H, m), 7.91 (1H, dd, J=8.7, 1.6 Hz), 7.96 (1H, s).

C) tert-butyl benzyl{3-[(4-{trans-2-[(tert-butoxycarbonyl)amino]cyclopropyl}phenyl)carbamoyl]phenyl}-carbamate By a method similar to Example 28, Step A, the title compound (81.6 mg) was obtained from tert-butyl [trans-2-(4-aminophenyl)cyclopropyl]carbamate (110 mg) and 3-[benzyl(tert-butoxycarbonyl)amino]benzoic acid (121 mg).

$^1$H NMR (400 MHz, CDCl$_3$) δ 1.08-1.18 (2H, m), 1.41-1.48 (18H, m), 1.86-1.97 (1H, m), 2.63-2.76 (1H, m), 4.85 (2H, s), 6.52-6.65 (1H, m), 6.89-6.99 (1H, m), 7.11 (2H, d, J=8.6 Hz), 7.18-7.40 (4H, m), 7.44-7.55 (2H, m), 7.64 (2H, s), 7.75-7.83 (1H, m), 7.87-8.00 (1H, m).

D) N-[4-(trans-2-aminocyclopropyl)phenyl]-3-(benzylamino)benzamide dihydrochloride By a method similar to Example 1, Step B, the title compound (35.7 mg) was obtained from tert-butyl benzyl{3-[(4-{trans-2-[(tert-butoxycarbonyl)amino]cyclopropyl}-phenyl)carbamoyl]phenyl}carbamate (82 mg).

$^1$H NMR (400 MHz, DMSO-d$_6$) δ 1.18 (1H, d, J=7.8 Hz), 1.36 (1H, t, J=4.3 Hz), 2.24-2.34 (1H, m), 2.78 (1H, dd, J=8.2, 4.0 Hz), 4.34 (2H, s), 6.79 (1H, d, J=8.1 Hz), 7.07-7.27 (6H, m), 7.29-7.41 (4H, m), 7.68 (2H, d, J=8.6 Hz), 8.41 (3H, d, J=4.4 Hz), 10.07 (1H, s).

E) 3-(benzylamino)-N-{4-[trans-2-(benzylamino)cyclopropyl]phenyl}benzamide

By a method similar to Example 1, Step C, the title compound (5.0 mg) was obtained from N-[4-(trans-2-aminocyclopropyl)phenyl]-3-(benzylamino)benzamide hydrochloride (40 mg).

$^1$H NMR (400 MHz, DMSO-d$_5$) δ 1.22-1.31 (1H, m), 1.45-1.53 (1H, m), 2.41-2.48 (1H, m), 2.85-2.93 (1H, m), 4.27-4.32 (2H, m), 4.34 (2H, s), 6.76-6.81 (1H, m), 7.09 (4H, s), 7.16-7.26 (2H, m), 7.33 (2H, s), 7.36-7.40 (2H, m), 7.40-7.45 (3H, m), 7.50-7.58 (2H, m), 7.67 (2H, d, J=8.6 Hz), 9.53-9.67 (2H, m), 10.03-10.10 (1H, m).

Example 30

N-{4-[trans-2-(pyrrolidin-1-yl)cyclopropyl]phenyl}benzamide hydrochloride

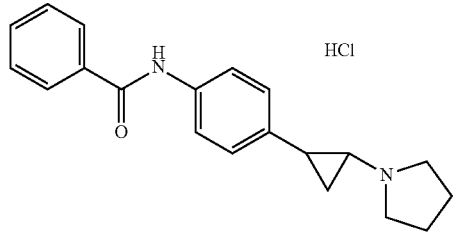 [SMILES: O=C(Nc1ccc(C2CC2N2CCCC2)cc1)c1ccccc1 ; Cl]

To a mixture of N-[4-(trans-2-aminocyclopropyl)phenyl]benzamide hydrochloride (100 mg), triethylamine (0.145 mL), and N,N-dimethylformamide (2.0 mL) was added 1,4-dibromobutane (0.050 mL), and the mixture was stirred at 60° C. for 2 hr. To the reaction mixture was added saturated aqueous sodium hydrogen carbonate solution, and the mixture was extracted twice with ethyl acetate. The organic layers were combined, washed with saturated brine, dried over anhydrous magnesium sulfate and concentrated under reduced pressure. The residue was purified by silica gel column chromatography (ethyl acetate/methanol), and the fractions containing the object product were collected and concentrated.

The residue was dissolved in methanol (5.0 mL), 10% hydrochloric acid methanol solution (1.0 mL) was added, and the mixture was concentrated under reduced pressure to give the title compound (9.8 mg).

MS (API+): [M+H]$^+$ 307.3.

$^1$H NMR (300 MHz, CD$_3$OD) δ 1.36-1.48 (1H, m), 1.63 (1H, ddd, J=10.7, 6.7, 4.3 Hz), 2.00-2.14 (2H, m), 2.14-2.32 (2H, m), 2.64 (1H, ddd, J=10.4, 6.7, 3.5 Hz), 3.05-3.20 (1H, m), 3.26-3.41 (2H, m), 3.64-3.88 (2H, m), 7.16-7.23 (2H, m), 7.49-7.59 (3H, m), 7.62-7.70 (2H, m), 7.88-7.95 (2H, m).

Example 31

N-{4-[trans-2-(benzylamino)cyclopropyl]phenyl}-3-[(phenylcarbonyl)amino]benzamide

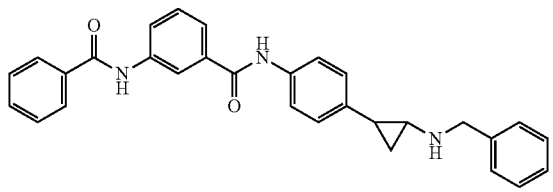 [SMILES: O=C(Nc1cccc(C(=O)Nc2ccc(C3CC3NCc3ccccc3)cc2)c1)c1ccccc1]

A) tert-butyl(trans-2-{4-[({3-[(phenylcarbonyl)amino]phenyl}carbonyl)amino]phenyl}-cyclopropyl)carbamate To a solution of tert-butyl [trans-2-(4-aminophenyl)cyclopropyl]carbamate (124 mg) described in a document (J. Am. Chem. Soc., 2010, 132, 6827.) in acetonitrile (4 mL) were added 3-[(phenylcarbonyl)amino]benzoic acid (100 mg), N-ethyl-N'-(3-dimethylaminopropyl)carbodiimide hydrochloride (95 mg), 1-hydroxybenzotriazole (67.2 mg) and triethylamine (69 μL). The mixture was stirred at room temperature overnight and water was added. Ethyl acetate was added to the mixture, and the resulting solid was collected by filtration to give the title compound (188 mg).

$^1$H NMR (400 MHz, DMSO-d$_6$) δ 1.00-1.13 (2H, m), 1.39 (9H, s), 1.83-1.92 (1H, m), 2.60 (1H, brs), 7.08 (2H, d, J=8.6 Hz), 7.24 (1H, brs), 7.47-7.71 (7H, m), 7.98-8.05 (3H, m), 8.30 (1H, s), 10.22 (1H, s), 10.45 (1H, s).

B) N-[4-(trans-2-aminocyclopropyl)phenyl]-3-[(phenylcarbonyl)amino]benzamide hydrochloride tert-Butyl(trans-2-{4-[({3-[(phenylcarbonyl)amino]phenyl}carbonyl)amino]phenyl}-cyclopropyl)carbamate (188 mg) was dissolved in 4N hydrochloric acid/ethyl acetate solution (2 mL), and the mixture was stirred at room temperature for 2 hr. The solvent was evaporated under reduced pressure to give the title compound (107 mg).

¹H NMR (400 MHz, DMSO-d₆) δ 1.16-1.24 (1H, m), 1.31-1.40 (1H, m), 2.23-2.33 (1H, m), 2.77-2.84 (1H, m), 7.15 (2H, d, J=8.6 Hz), 7.48-7.65 (4H, m), 7.65-7.75 (3H, m), 7.96-8.03 (3H, m), 8.21-8.37 (4H, m), 10.28 (1H, s), 10.47 (1H, s).

C) N-{4-[trans-2-(benzylamino)cyclopropyl]phenyl}-3-[(phenylcarbonyl)amino]benzamide To a solution of N-[4-(trans-2-aminocyclopropyl)phenyl]-3-[(phenylcarbonyl)amino]benzamide hydrochloride (85.5 mg) in methanol (2 mL) were added benzaldehyde (21 μL) and sodium hydrogen carbonate (26.4 mg). The mixture was stirred at 70° C. for 1 hr, and ice-cooled to 0° C. and sodium borohydride (11.9 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) and crystallized (hexane/ethyl acetate) to give the title compound (6.2 mg).

MS (API+): [M+H]⁺ 462.2.
¹H NMR (400 MHz, CDCl₃) δ 0.92-0.99 (1H, m), 1.10 (1H, dt, J=9.2, 4.8 Hz), 1.91 (1H, ddd, J=9.2, 5.9, 3.2 Hz), 2.33-2.39 (1H, m), 3.84-3.94 (2H, m), 6.98 (2H, d, J=8.6 Hz), 7.22-7.35 (5H, m), 7.43-7.54 (5H, m), 7.54-7.60 (1H, m), 7.63 (1H, d, J=7.8 Hz), 7.82-7.91 (3H, m), 8.01 (1H, s), 8.07 (1H, s), 8.15 (1H, s).

Example 32

N-{4-[trans-2-(benzylamino)cyclopropyl]phenyl}-3-piperidin-1-ylbenzamide

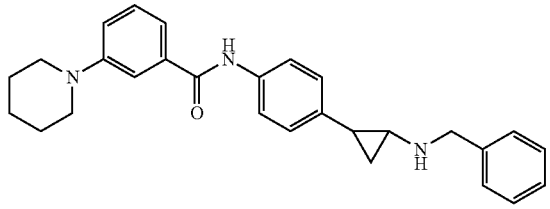 [SMILES: O=C(Nc1ccc(C2CC2NCc2ccccc2)cc1)c1cccc(N2CCCCC2)c1]

A) tert-butyl {trans-2-[4-({[3-(piperidin-1-yl)phenyl]carbonyl}amino)phenyl]cyclopropyl}carbamate To a solution of tert-butyl [trans-2-(4-aminophenyl)cyclopropyl]carbamate (105 mg) described in a document (J. Am. Chem. Soc., 2010, 132, 6827.) in acetonitrile (3 mL) were added 3-(piperidin-1-yl)benzoic acid (105 mg) described in a document (J. Med. Chem. 1997, 40, 331.), N-ethyl-N'-(3-dimethylaminopropyl)carbodiimide hydrochloride (81 mg), 1-hydroxybenzotriazole (57.2 mg) and triethylamine (59 μL). The mixture was stirred at room temperature overnight and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) to give the title compound (142 mg).

¹H NMR (400 MHz, DMSO-d₆) δ 0.99-1.11 (2H, m), 1.35-1.41 (9H, m), 1.51-1.60 (2H, m), 1.63 (4H, d, J=4.9 Hz), 1.87 (1H, brs), 2.55-2.63 (1H, m), 3.18-3.24 (4H, m), 4.83 (1H, s), 7.06 (2H, d, J=8.6 Hz), 7.09-7.15 (1H, m), 7.28-7.35 (2H, m), 7.42 (1H, s), 7.63 (2H, d, J=8.6 Hz), 10.06 (1H, s).

B) N-{4-[trans-2-aminocyclopropyl]phenyl}-3-(piperidin-1-yl)benzamide dihydrochloride tert-Butyl{trans-2-[4-({[3-(piperidin-1-yl)phenyl]carbonyl}amino)phenyl]cyclopropyl}carbamate (142 mg) was dissolved in 4N hydrochloric acid/ethyl acetate solution (2 mL), and the mixture was stirred at room temperature for 3 hr. The solvent was evaporated under reduced pressure to give the title compound (121 mg).

¹H NMR (400 MHz, DMSO-d₆) δ 1.14-1.27 (1H, m), 1.31-1.45 (1H, m), 1.63 (2H, brs), 1.81 (4H, brs), 2.25-2.36 (1H, m), 2.79 (1H, brs), 3.29-3.48 (4H, m), 7.15 (2H, d, J=8.8 Hz), 7.26 (1H, s), 7.52 (2H, brs), 7.71 (2H, d, J=8.6 Hz), 8.38-8.53 (3H, m), 10.31 (1H, brs).

C) N-{4-[trans-2-(benzylamino)cyclopropyl]phenyl}-3-(piperidin-1-yl)benzamide

To a solution of N-{4-[trans-2-aminocyclopropyl]phenyl}-3-(piperidin-1-yl)benzamide dihydrochloride (64.2 mg) in methanol (2 mL) were added benzaldehyde (16 μL) and sodium hydrogen carbonate (19.8 mg). The reaction mixture was stirred at 70° C. for 1 hr, and ice-cooled to 0° C. and sodium borohydride (8.9 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) to give the title compound (51.0 mg).

MS (API+): [M+H]⁺ 426.3.
¹H NMR (400 MHz, CDCl₃) δ 0.92-0.99 (1H, m), 1.10 (1H, dt, J=9.4, 4.7 Hz), 1.55-1.63 (2H, m), 1.71 (4H, quin, J=5.6 Hz), 1.88-1.94 (1H, m), 2.36 (1H, dt, J=7.2, 3.6 Hz), 3.19-3.25 (4H, m), 3.84-3.93 (2H, m), 6.97 (2H, d, J=8.6 Hz), 7.07 (1H, dd, J=8.2, 2.6 Hz), 7.17 (1H, d, J=7.6 Hz), 7.22-7.35 (6H, m), 7.45 (1H, t, J=2.0 Hz), 7.50 (2H, d, J=8.6 Hz), 7.79 (1H, brs).

Example 33

N-{4-[trans-2-(benzylamino)cyclopropyl]phenyl}-3-(2-oxopiperidin-1-yl)benzamide

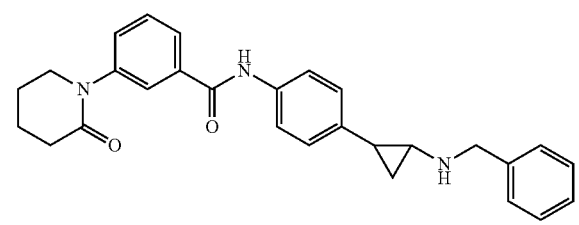 [SMILES: O=C(Nc1ccc(C2CC2NCc2ccccc2)cc1)c1cccc(N2CCCCC2=O)c1]

A) 3-(2-oxopiperidin-1-yl)benzoic acid

To a solution of methyl 3-(2-oxopiperidin-1-yl)benzoate (114 mg) described in a document (J. Med. Chem. 1997, 40, 331.) in THF (3.0 mL)-water (0.5 mL) was added lithium hydroxide monohydrate (61.5 mg). The mixture was stirred at room temperature overnight, and 10% citric acid solution was added. The mixture was extracted with ethyl acetate, and the extract was washed with saturated brine and dried over anhydrous sodium sulfate. The solvent was evaporated under reduced pressure to give the title compound (34.7 mg).

$^1$H NMR (400 MHz, DMSO-d$_6$) δ 1.67-1.98 (4H, m), 2.40 (2H, t, J=6.5 Hz), 3.63 (2H, t, J=5.5 Hz), 7.39-7.60 (2H, m), 7.73-7.90 (2H, m), 12.39 (1H, brs).

B) tert-butyl{trans-2-[4-({[3-(2-oxopiperidin-1-yl)phenyl]carbonyl}amino)phenyl]cyclopropyl}carbamate To a solution of tert-butyl [trans-2-(4-aminophenyl)cyclopropyl]carbamate (230 mg) described in a document (J. Am. Chem. Soc., 2010, 132, 6827.) in acetonitrile (7 mL) were added 3-(2-oxopiperidin-1-yl)benzoic acid (169 mg), N-ethyl-N'-(3-dimethylaminopropyl)carbodiimide hydrochloride (177 mg), 1-hydroxybenzotriazole (125 mg) and triethylamine (128 μL). The mixture was stirred at room temperature overnight and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) to give the title compound (53.4 mg).

$^1$H NMR (400 MHz, CDCl$_3$) δ 1.09-1.18 (2H, m), 1.46 (9H, s), 1.81-1.91 (2H, m), 1.91-2.07 (3H, m), 2.58 (2H, t, J=5.5 Hz), 2.69 (1H, brs), 3.65 (2H, brs), 4.90 (1H, brs), 7.11 (2H, d, J=8.6 Hz), 7.32-7.38 (1H, m), 7.38-7.46 (1H, m), 7.53 (2H, =8.6 Hz), 7.68-7.75 (2H, m), 8.40 (1H, brs).

C) N-{4-[trans-2-aminocyclopropyl]phenyl}-3-(2-oxopiperidin-1-yl)benzamide hydrochloride A mixed solution of tert-butyl{trans-2-[4-({[3-(2-oxopiperidin-1-yl)phenyl]carbonyl}amino)phenyl]cyclopropyl}-carbamate (53.4 mg) in 4N hydrochloric acid/ethyl acetate solution (2 mL) was stirred at room temperature for 2 hr. The solvent was evaporated under reduced pressure to give the title compound (38.5 mg).

$^1$H NMR (400 MHz, CD$_3$OD) δ 1.31-1.48 (2H, m), 1.96-2.08 (4H, m), 2.39 (1H, brs), 2.58 (2H, t, J=6.2 Hz), 2.82-2.90 (1H, m), 3.76 (2H, t, J=5.6 Hz), 7.21 (2H, d, J=8.6 Hz), 7.49-7.55 (1H, m), 7.56-7.63 (1H, m), 7.67 (2H, d, J=8.6 Hz), 7.81-7.92 (2H, m).

D) N-{4-[trans-2-(benzylamino)cyclopropyl]phenyl}-3-(2-oxopiperidin-1-yl)benzamide To a solution of N-{4-[trans-2-aminocyclopropyl]phenyl}-3-(2-oxopiperidin-1-yl)benzamide hydrochloride (27.1 mg) in methanol (1 mL) were added benzaldehyde (7.14 μL) and sodium hydrogen carbonate (8.9 mg). The mixture was stirred at 70° C. for 1 hr, and ice-cooled to 0° C. and sodium borohydride (4.0 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) to give the title compound (10.9 mg).

MS (API+): [M+H]$^+$ 440.3.

$^1$H NMR (400 MHz, CDCl$_3$) δ 0.92-0.99 (1H, m), 1.10 (1H, dt, J=9.2, 4.8 Hz), 1.88-2.01 (6H, m), 2.33-2.39 (1H, m), 2.58 (2H, t, J=5.7 Hz), 3.61-3.69 (2H, m), 3.89 (2H, d, J=1.7 Hz), 6.97 (2H, d, J=8.6 Hz), 7.22-7.37 (6H, m), 7.39-7.45 (1H, m), 7.51 (2H, d, J=8.6 Hz), 7.68-7.73 (2H, m), 8.35 (1H, brs).

Example 34

N-{4-[trans-2-(benzylamino)cyclopropyl]phenyl}-3-(2-phenylethyl)benzamide

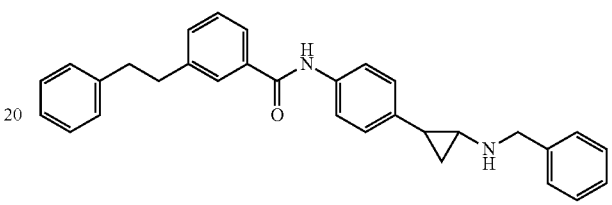

A) tert-butyl {trans-2-[4-({[3-(2-phenylethyl)phenyl]carbonyl}amino)phenyl]cyclopropyl}carbamate By a method similar to Example 28, Step A, the title compound (232 mg) was obtained from tert-butyl [trans-2-(4-aminophenyl)cyclopropyl]carbamate (191 mg) and 3-(2-phenylethyl)benzoic acid (145 mg).

$^1$H NMR (300 MHz, DMSO-d$_6$) δ 0.98-1.13 (2H, m), 1.38 (9H, s), 1.82-1.93 (1H, m), 2.58 (1H, brs), 2.87-3.02 (4H, m), 7.06 (2H, d, J=8.3 Hz), 7.14-7.32 (6H, m), 7.36 (2H, d, J=8.3 Hz), 7.65 (2H, d, J=8.7 Hz), 7.86 (2H, d, J=8.3 Hz), 10.08 (1H, s).

B) N-[4-(trans-2-aminocyclopropyl)phenyl]-3-(2-phenylethyl)benzamide hydrochloride By a method similar to Example 1, Step B, the title compound (154 mg) was obtained from tert-butyl{trans-2-[4-({[3-(2-phenylethyl)phenyl]carbonyl}amino)phenyl]cyclopropyl}-carbamate (232 mg).

$^1$H NMR (300 MHz, DMSO-d$_6$) δ 1.11-1.25 (1H, m), 1.30-1.41 (1H, m), 2.21-2.36 (1H, m), 2.73-2.83 (1H, m), 2.86-3.02 (4H, m), 7.07-7.40 (9H, m), 7.70 (2H, d, J=8.7 Hz), 7.85 (2H, d, J=8.3 Hz), 8.34 (3H, brs) 10.14 (1H, s).

C) N-{4-[trans-2-(benzylamino)cyclopropyl]phenyl}-3-(2-phenylethyl)benzamide

By a method similar to Example 1, Step C, the title compound (85.4 mg) was obtained from N-[4-(trans-2-aminocyclopropyl)phenyl]-3-(2-phenylethyl)benzamide hydrochloride (100 mg).

$^1$H NMR (300 MHz, DMSO-d$_6$) δ 0.83-1.03 (2H, m), 1.80 (1H, ddd, =9.0, 5.8, 3.0 Hz), 2.18 (1H, dt, J=6.7, 3.6 Hz), 2.83-3.03 (4H, m), 3.77 (2H, s), 6.94 (2H, d, J=8.3 Hz), 7.13-7.40 (12H, m), 7.60 (2H, d, J=8.7 Hz), 7.85 (2H, d, J=8.3 Hz), 10.04 (1H, s).

Example 35

N-{4-[trans-2-(benzylamino)cyclopropyl]phenyl}biphenyl-4-carboxamide

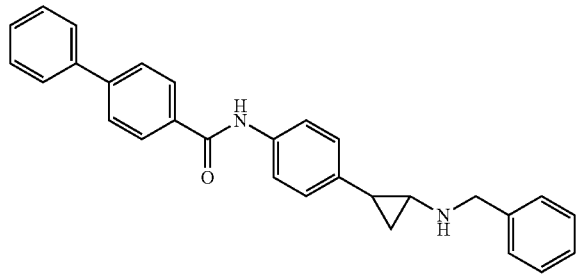 [SMILES: O=C(Nc1ccc(C2CC2NCc2ccccc2)cc1)c1ccc(-c2ccccc2)cc1]

A) tert-butyl(trans-2-{4-[(biphenyl-4-ylcarbonyl)amino]phenyl}cyclopropyl)carbamate To a solution of tert-butyl [trans-2-(4-aminophenyl)cyclopropyl]carbamate (150 mg) described in a document (J. Am. Chem. Soc., 2010, 132, 6827.) in acetonitrile (6 mL) were added biphenyl-4-carboxylic acid (100 mg), N-ethyl-N'-(3-dimethylaminopropyl)carbodiimide hydrochloride (116 mg), 1-hydroxybenzotriazole (82 mg) and triethylamine (84 μL). The mixture was stirred at room temperature overnight and water was added. The mixture was extracted with ethyl acetate, and the extract was washed with saturated brine and dried over anhydrous sodium sulfate. The solvent was evaporated under reduced pressure. The residue was recrystallized (methanol/ethyl acetate) to give the title compound (131 mg).
MS (API+): [M−tBu+2H]$^+$ 373.2.

B) N-[4-(trans-2-aminocyclopropyl)phenyl]biphenyl-4-carboxamide hydrochloride tert-Butyl(trans-2-{4-[(biphenyl-4-ylcarbonyl)amino]phenyl}cyclopropyl)carbamate (154 mg) was dissolved in 4N hydrochloric acid/ethyl acetate solution (2 mL), and the mixture was stirred at room temperature for 2 hr. The solvent was evaporated under reduced pressure to give the title compound (81.9 mg).
MS (API+): [M+H]$^+$ 329.2.

C) N-{4-[trans-2-(benzylamino)cyclopropyl]phenyl}biphenyl-4-carboxamide

To a solution of N-[4-(trans-2-aminocyclopropyl)phenyl]biphenyl-4-carboxamide hydrochloride (82 mg) in methanol (2 mL) were added benzaldehyde (25 μL) and sodium hydrogen carbonate (31.5 mg). The reaction mixture was stirred at 70° C. for 1 hr, and ice-cooled to 0° C. and sodium borohydride (14.2 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate) to give the title compound (6.4 mg).

MS (API+): [M+H]$^+$ 419.2.
$^1$H NMR (400 MHz, DMSO-d$_6$) δ 0.88-1.03 (2H, m), 1.81 (1H, s), 2.16-2.24 (1H, m), 3.77 (2H, s), 6.97 (2H, d, J=8.6 Hz), 7.22 (1H, d, J=6.9 Hz), 7.27-7.34 (4H, m), 7.44 (1H, d, J=7.3 Hz), 7.48-7.55 (2H, m), 7.64 (2H, d, J=8.6 Hz), 7.74-7.79 (2H, m), 7.83 (2H, d, J=8.6 Hz), 8.04 (2H, d, J=8.6 Hz), 10.19 (1H, s).

Example 36

N-{4-[trans-2-(benzylamino)cyclopropyl]phenyl}biphenyl-3-carboxamide

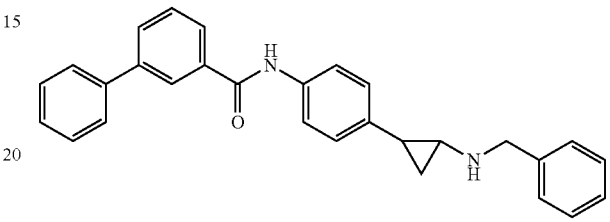

A) tert-butyl(trans-2-{4-[(biphenyl-3-ylcarbonyl)amino]phenyl}cyclopropyl)carbamate To a solution of tert-butyl[trans-2-(4-aminophenyl)cyclopropyl]carbamate (100 mg) described in a document (J. Am. Chem. Soc., 2010, 132, 6827.) in acetonitrile (4 mL) were added biphenyl-3-carbonyl chloride (131 mg) and triethylamine (61.1 mg). The mixture was stirred at room temperature overnight and water was added. To the reaction mixture was added ethyl acetate, and the resulting solid was collected by filtration to give the title compound (154 mg).
MS (API+): [M−$^t$Bu+2H]$^+$ 373.2.

B) N-[4-(trans-2-aminocyclopropyl)phenyl]biphenyl-3-carboxamide hydrochloride tert-Butyl(trans-2-{4-[(biphenyl-3-ylcarbonyl)amino]phenyl}cyclopropyl)carbamate (154 mg) was dissolved in 4N hydrochloric acid/ethyl acetate solution (2 mL), and the mixture was stirred at room temperature for 2 hr. The solvent was evaporated under reduced pressure to give the title compound (130 mg).
MS (API+): [M+H]$^+$ 329.2.

C) N-{4-[trans-2-(benzylamino)cyclopropyl]phenyl}biphenyl-3-carboxamide

To a solution of N-[4-(trans-2-aminocyclopropyl)phenyl]biphenyl-3-carboxamide hydrochloride (130 mg) in methanol (4 mL) were added benzaldehyde (40 μL) and sodium hydrogen carbonate (49.9 mg). The mixture was stirred at 70° C. for 1 hr, and ice-cooled to 0° C. and sodium borohydride (22.5 mg) was added. The mixture was stirred for 1 hr and water was added. The mixture was extracted with ethyl acetate, and the extract was washed with saturated brine and dried over anhydrous sodium sulfate. The solvent was evaporated under reduced pressure. The residue was recrystallized (hexane/ethyl acetate) to give the title compound (60.4 mg).
MS (API+): [M+CH$_3$CN+H]$^+$460.4.
$^1$H NMR (400 MHz, DMSO-d$_6$) δ 0.85-1.06 (2H, m), 1.76-1.86 (1H, m), 2.16-2.23 (1H, m), 2.81-2.96 (1H, m), 3.77 (2H, s), 6.97 (2H, d, J=8.6 Hz), 7.18-7.26 (1H, m), 7.26-7.35 (4H, m), 7.43 (1H, d, J=7.3 Hz), 7.49-7.56 (2H, m), 7.63 (3H, d, J=8.3 Hz), 7.77 (2H, d, J=7.3 Hz), 7.90 (2H, dd, J=18.3, 7.8 Hz), 8.20 (1H, s), 10.24 (1H, s).

Example 37

N-{4-[trans-2-(benzylamino)cyclopropyl]phenyl}biphenyl-4-carboxamide trifluoroacetate

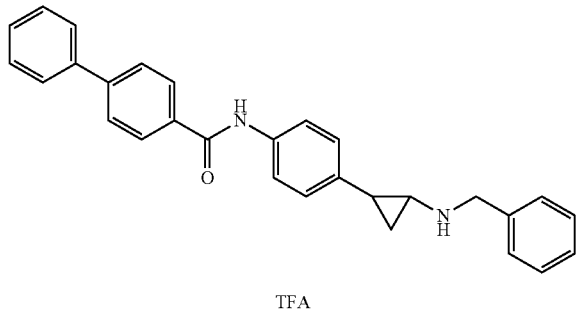 [SMILES: O=C(Nc1ccc(C2CC2NCc2ccccc2)cc1)c1ccc(-c2ccccc2)cc1]

TFA

To a solution of N-[4-(trans-2-aminocyclopropyl)phenyl]biphenyl-4-carboxamide hydrochloride (26 mg) and benzaldehyde (10 mg) in methanol (1 mL) was added acetic acid (0.1 mL), and the mixture was stirred at 45° C. for 1 hr and 2-picoline borane (17 mg) was added. The mixture was stirred at 60° C. overnight, and the solvent was evaporated by an air blowing apparatus. The residue was purified by HPLC (C18, mobile phase: water/acetonitrile (with 0.1% TFA)) to give the title compound (3.3 mg).

MS (API+): [M+H]$^+$ 419.3

The compounds produced by the method described in the above-mentioned Example 37 or a method analogous thereto are shown in the following Tables. In the Tables, MS shows measured values.

TABLE 1-3

| Ex. No. | IUPAC name | structure | salt | MS |
|---|---|---|---|---|
| 38 | N-(4-{trans-2-[(pyridin-3-ylmethyl)amino]cyclopropyl}phenyl)biphenyl-4-carboxamide | 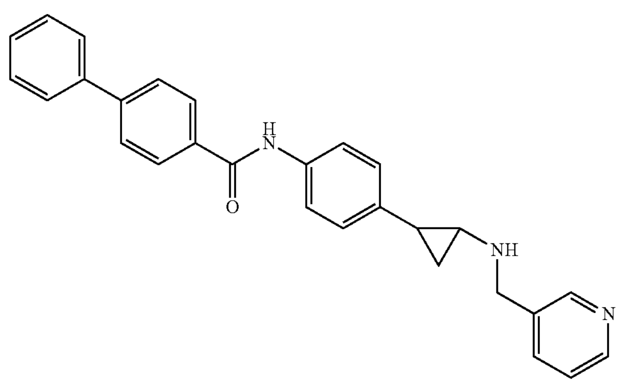 [SMILES: O=C(Nc1ccc(C2CC2NCc2cccnc2)cc1)c1ccc(-c2ccccc2)cc1] | 2CF3COOH | 420.3 |
| 39 | N-(4-{trans-2-[(pyridin-4-ylmethyl)amino]cyclopropyl}phenyl)biphenyl-4-carboxamide | 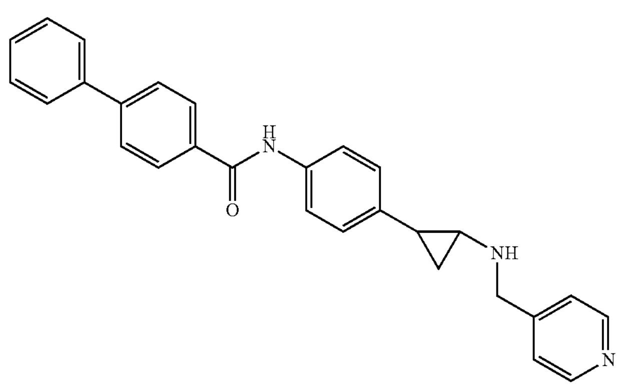 [SMILES: O=C(Nc1ccc(C2CC2NCc2ccncc2)cc1)c1ccc(-c2ccccc2)cc1] | 2CF3COOH | 420.3 |

| Ex. No. | IUPAC name | structure | salt | MS |
|---|---|---|---|---|
| 40 | N-(4-{trans-2-[(cyclopropyl-methyl)amino]-cyclopropyl}-phenyl)biphenyl-4-carboxamide | 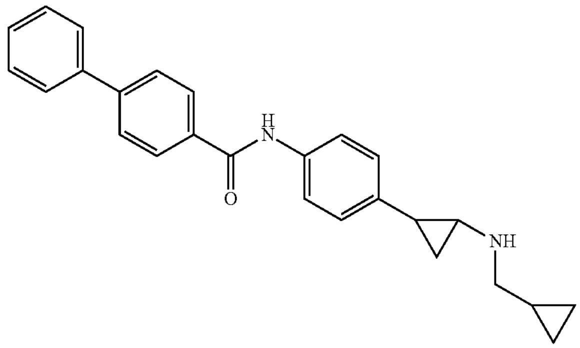 [SMILES: O=C(Nc1ccc(C2CC2NCC2CC2)cc1)c1ccc(-c2ccccc2)cc1] | CF3COOH | 383.3 |
| 41 | N-(4-{trans-2-[(3-methoxybenzyl)-amino]cyclo-propyl}phenyl)-biphenyl-4-carboxamide | 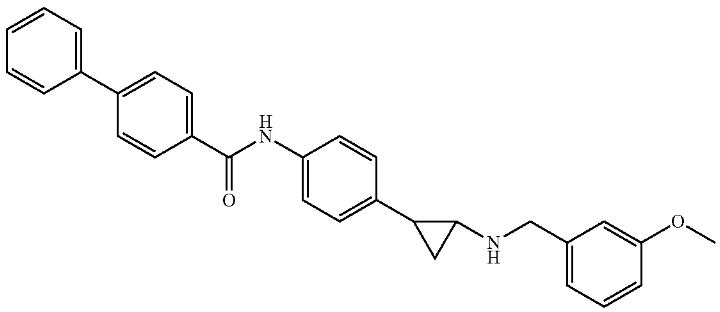 [SMILES: COc1cccc(CNC2CC2c2ccc(NC(=O)c3ccc(-c4ccccc4)cc3)cc2)c1] | CF3COOH | 449.3 |
| 42 | N-(4-{trans-2-[(1,3-benzodioxol-5-ylmethyl)amino]-cyclopropyl}-phenyl)biphenyl-4-carboxamide | 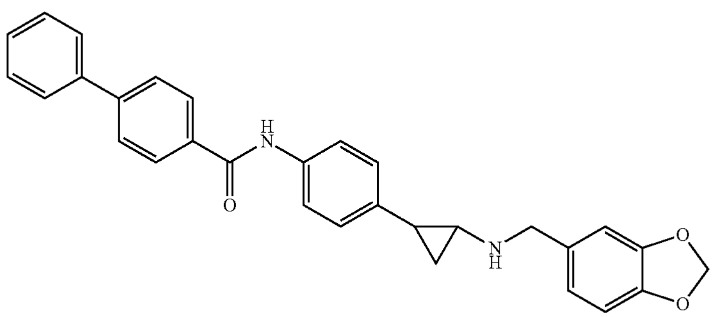 [SMILES: O=C(Nc1ccc(C2CC2NCc2ccc3c(c2)OCO3)cc1)c1ccc(-c2ccccc2)cc1] | CF3COOH | 463.3 |
| 43 | N-(4-{trans-2-[(4-methoxybenzyl)-amino]cyclo-propyl}phenyl)-biphenyl-4-carboxamide | 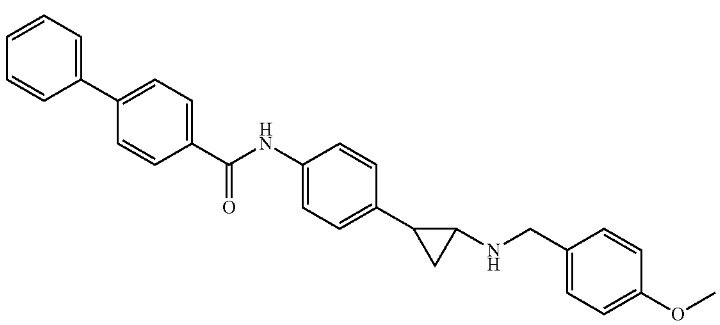 [SMILES: COc1ccc(CNC2CC2c2ccc(NC(=O)c3ccc(-c4ccccc4)cc3)cc2)cc1] | CF3COOH | 449.3 |
| 44 | N-(4-{trans-2-[(2-aminoethyl)-amino]cyclo-propyl}phenyl)-biphenyl-4-carboxamide | 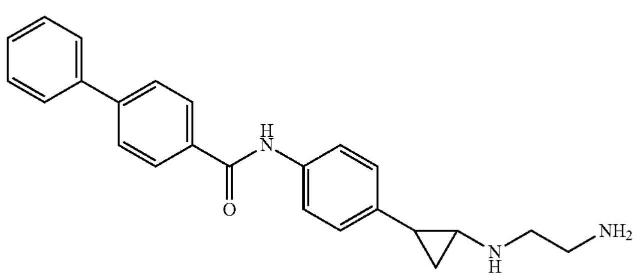 [SMILES: NCCNC1CC1c1ccc(NC(=O)c2ccc(-c3ccccc3)cc2)cc1] | 2CF3COOH | 372.3 |

TABLE 1-3-continued

| Ex. No. | IUPAC name | structure | salt | MS |
|---|---|---|---|---|
| 45 | N-{4-[trans-2-(cyclooctyl-amino)cyclo-propyl]phenyl}-biphenyl-4-carboxamide | 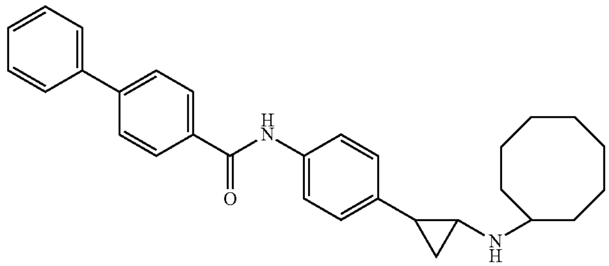 [SMILES: O=C(Nc1ccc(C2CC2NC2CCCCCCC2)cc1)c1ccc(-c2ccccc2)cc1] | CF3COOH | 439.3 |

TABLE 1-4

| Ex. No. | IUPAC name | structure | salt | MS |
|---|---|---|---|---|
| 46 | N-(4-{trans-2-[(3,4-dimethoxy-benzyl) amino]cyclo-propyl}phenyl) -biphenyl-4-carboxamide | 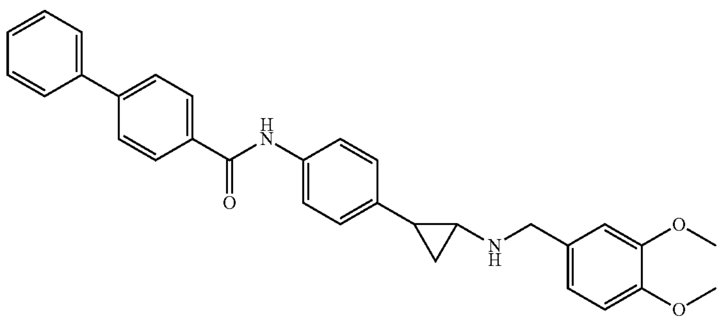 [SMILES: COc1ccc(CNC2CC2c2ccc(NC(=O)c3ccc(-c4ccccc4)cc3)cc2)cc1OC] | CF3COOH | 479.3 |
| 47 | N-(4-{trans-2-[(1-phenylethyl)amino]-cyclopropyl}phenyl)-biphenyl-4-carboxamide | 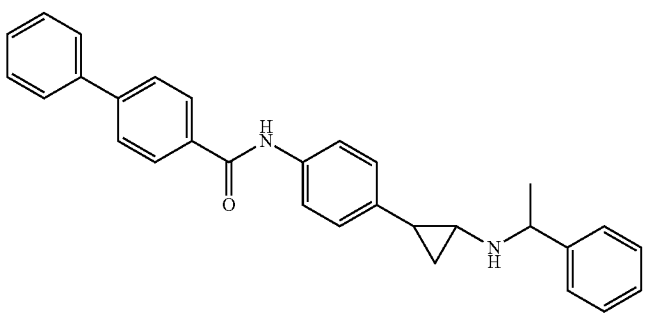 [SMILES: CC(NC1CC1c1ccc(NC(=O)c2ccc(-c3ccccc3)cc2)cc1)c1ccccc1] | CF3COOH | 433.3 |
| 48 | N-(4-{trans-2-[(2-methoxy-1-methyl-ethyl)amino]cyclo-propyl}phenyl)-biphenyl-4-carboxamide | 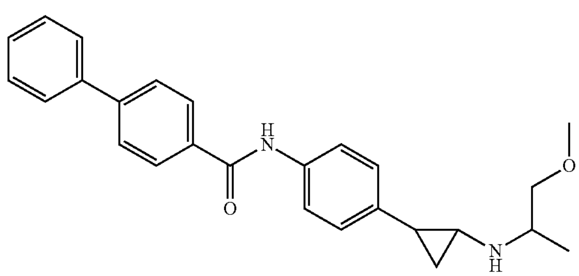 [SMILES: COCC(C)NC1CC1c1ccc(NC(=O)c2ccc(-c3ccccc3)cc2)cc1] | CF3COOH | 401.3 |

TABLE 1-4-continued

| Ex. No. | IUPAC name | structure | salt | MS |
|---|---|---|---|---|
| 49 | N-(4-{trans-2-[(1-ethylpropyl)amino]-cyclopropyl}phenyl)-biphenyl-4-carboxamide | 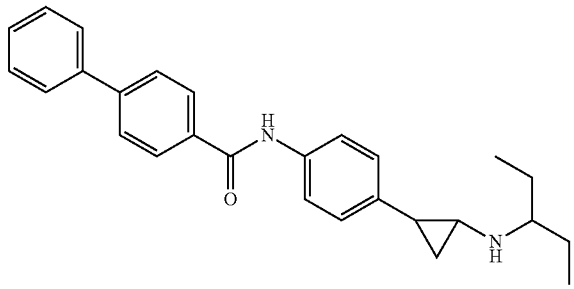 [SMILES: CCC(CC)NC1CC1c1ccc(NC(=O)c2ccc(-c3ccccc3)cc2)cc1] | CF3COOH | 399.3 |
| 50 | N-(4-{trans-2-[(1-methylpiperidin-4-yl)amino]cyclo-propyl}phenyl)-biphenyl-4-carboxamide | 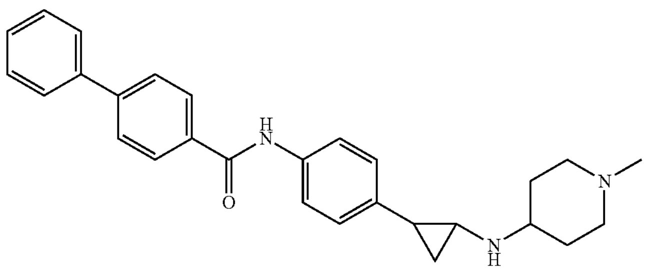 [SMILES: CN1CCC(NC2CC2c2ccc(NC(=O)c3ccc(-c4ccccc4)cc3)cc2)CC1] | 2CF3COOH | 426.4 |
| 51 | N-(4-{trans-2-[(1-benzylpiperidin-4-yl)amino]cyclo-propyl}phenyl)-biphenyl-4-carboxamide | 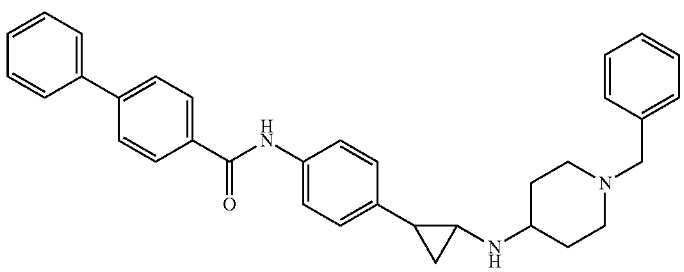 [SMILES: O=C(Nc1ccc(C2CC2NC2CCN(Cc3ccccc3)CC2)cc1)c1ccc(-c2ccccc2)cc1] | 2CF3COOH | 502.4 |
| 52 | N-{4-[trans-2-{[2-(benzyloxy)ethyl]-amino}cyclopropyl]-phenyl}biphenyl-4-carboxamide | 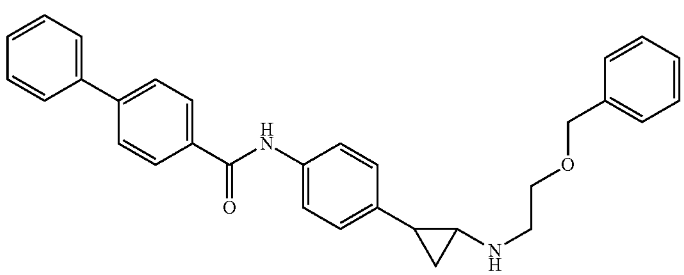 [SMILES: O=C(Nc1ccc(C2CC2NCCOCc2ccccc2)cc1)c1ccc(-c2ccccc2)cc1] | CF3COOH | 463.3 |
| 53 | N-(4-{trans-2-[(3,4-dichloro-benzyl)amino]-cyclopropyl}phenyl)-biphenyl-4-carboxamide | 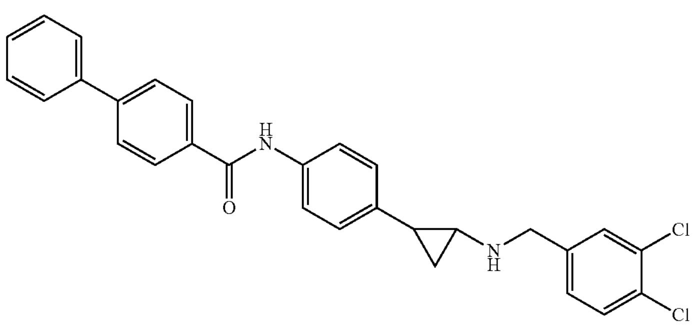 [SMILES: O=C(Nc1ccc(C2CC2NCc2ccc(Cl)c(Cl)c2)cc1)c1ccc(-c2ccccc2)cc1] | CF3COOH | 487.3 |

TABLE 1-5

| Ex. No. | IUPAC name | structure | salt | MS |
|---|---|---|---|---|
| 54 | N-{4-[trans-2-{[(6-methoxypyridin-3-yl)methyl]amino}-cyclopropyl]-phenyl}biphenyl-4-carboxamide | 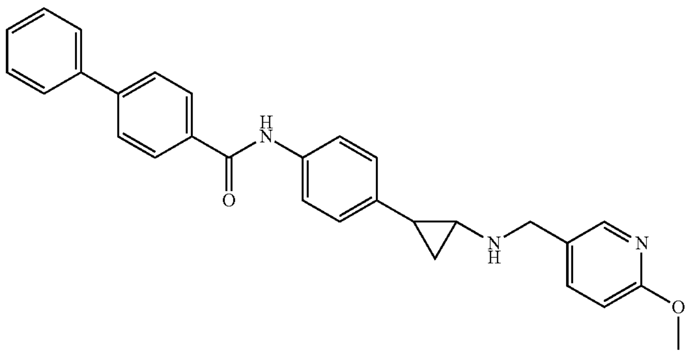 [SMILES: COc1ccc(CNC2CC2c2ccc(NC(=O)c3ccc(-c4ccccc4)cc3)cc2)cn1] | 2CF3COOH | 450.3 |
| 55 | allyl 4-{[trans-2-{4-[(biphenyl-4-yl-carbonyl) amino]-phenyl}cyclo-propyl]amino}-piperidine-1-carboxylate | 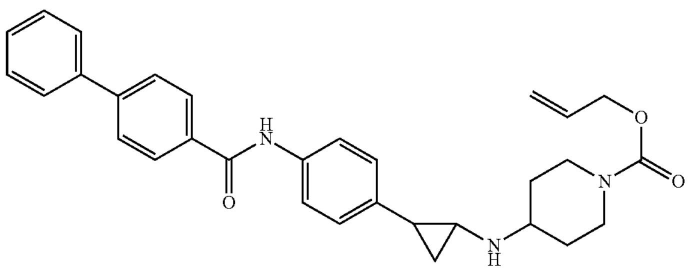 [SMILES: C=CCOC(=O)N1CCC(NC2CC2c2ccc(NC(=O)c3ccc(-c4ccccc4)cc3)cc2)CC1] | CF3COOH | 496.4 |
| 56 | N-(4-{trans-2-[(1-methyl-2-phenoxyethyl)-amino]cyclo-propyl}phenyl)-biphenyl-4-carboxamide | 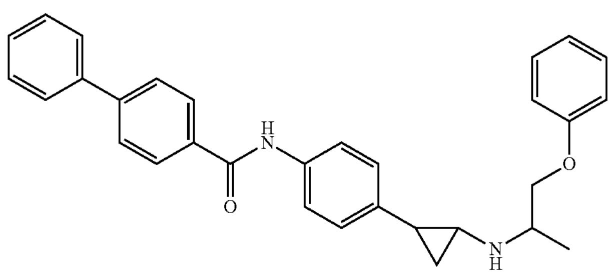 [SMILES: CC(COc1ccccc1)NC1CC1c1ccc(NC(=O)c2ccc(-c3ccccc3)cc2)cc1] | CF3COOH | 463.3 |

Example 57

N-{4-[trans-2-(benzylamino)cyclopropyl]phenyl}-Nα-[(benzyloxy) carbonyl]-L-phenylalaninamide hydrochloride

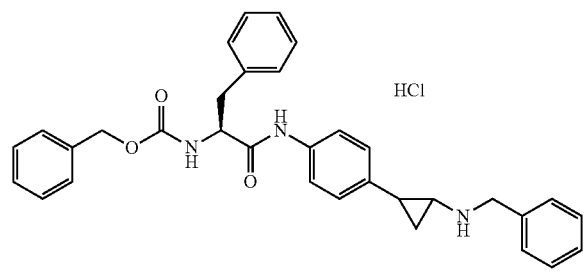 [SMILES: O=C(N[C@@H](Cc1ccccc1)C(=O)Nc1ccc(C2CC2NCc2ccccc2)cc1)OCc1ccccc1 ; Cl]

To a mixture of N-[4-(trans-2-aminocyclopropyl)phenyl]-Nα-[(benzyloxy)carbonyl]-L-phenylalaninamide hydrochloride (100 mg) described in a document (J. Am. Chem. Soc. 2010, 132, 6827.), sodium hydrogen carbonate (27.0 mg), and methanol (2.00 mL) was added benzaldehyde (0.022 mL), and the mixture was stirred at 70° C. for 1 hr. The reaction mixture was cooled in an ice bath, sodium borohydride (12.2 mg) was added and the mixture was stirred at 0° C. for 1.5 hr. The reaction mixture was diluted with dehydrated THF (4.00 mL), and cooled in an ice bath, and sodium borohydride (8.12 mg) was added. The ice bath was removed, and the mixture was stirred at room temperature overnight. The reaction mixture was diluted with methanol (2.00 mL) and dehydrated THF (2.00 mL), and cooled in an ice bath, sodium borohydride (8.12 mg) was added, and the mixture was stirred at 0° C. for 3 hr. To the reaction mixture was added saturated aqueous sodium hydrogen carbonate, and the mixture was concentrated under reduced pressure. To the residue was added water, and the mixture was extracted twice with ethyl acetate. The organic layers were combined, washed with saturated brine, dried over anhydrous magnesium sulfate and concentrated under reduced pressure. The residue was purified by silica gel column chromatography (hexane/ethyl acetate), and the fractions containing the object product were combined and concentrated. The residue was dissolved in methanol (5.00 mL), 10% hydrochloric acid methanol solution (1.00 mL) was added, and the mixture was concentrated under reduced pressure to give the title compound (82.3 mg).

MS (API+): [M+H]$^+$ 520.4.

$^1$H NMR (300 MHz, CD$_3$OD) δ 1.25-1.41 (1H, m), 1.49 (1H, ddd, J=10.5, 6.6, 4.4 Hz), 2.42 (1H, ddd, J=10.2, 6.6, 3.5 Hz), 2.89-3.03 (2H, m), 3.03-3.19 (1H, m), 4.37 (2H, s), 4.48 (1H, t, J=7.5 Hz), 4.97-5.12 (2H, m), 7.05 (2H, d, J=8.5 Hz), 7.14-7.35 (10H, m), 7.35-7.54 (7H, m).

Example 58

N-{4-[trans-2-(benzylamino)cyclopropyl]phenyl}-Nα-[(benzyloxy)carbonyl]-D-phenylalaninamide hydrochloride

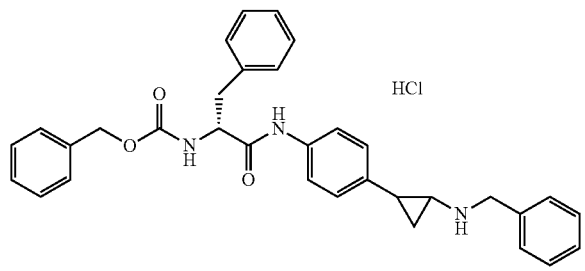 [SMILES: O=C(N[C@H](Cc1ccccc1)C(=O)Nc1ccc(C2CC2NCc2ccccc2)cc1)OCc1ccccc1 ; Cl]

To a mixture of N-[4-(trans-2-aminocyclopropyl)phenyl]-Nα-[(benzyloxy)carbonyl]-D-phenylalaninamide hydrochloride (100 mg) described in a document (J. Am. Chem. Soc. 2010, 132, 6827.), sodium hydrogen carbonate (27.0 mg), and methanol (4.00 mL) was added benzaldehyde (0.022 mL), and the mixture was stirred at 70° C. for 1 hr. The reaction mixture was diluted with dehydrated THF (6.00 mL), and cooled in an ice bath. Sodium borohydride (24.4 mg) was added and the mixture was stirred at 0° C. for 2 hr. To the reaction mixture was added saturated aqueous sodium hydrogen carbonate, and the mixture was concentrated under reduced pressure. Water was added to the residue, and the mixture was extracted twice with ethyl is acetate. The organic layers were combined, washed with saturated brine, dried over anhydrous magnesium sulfate and concentrated under reduced pressure. The residue was purified by silica gel column chromatography (hexane/ethyl acetate), and the fractions containing the object product were combined and concentrated. The residue was dissolved in methanol (5.00 mL), 10% hydrochloric acid methanol solution (1.00 mL) was added, and the mixture was concentrated under reduced pressure to give the title compound (84.6 mg).

MS (API+): [M+H]$^+$ 520.4.

$^1$H NMR (300 MHz, CD$_3$OD) δ 1.25-1.41 (1H, m), 1.42-1.55 (1H, m), 2.35-2.48 (1H, m), 2.88-3.03 (2H, m), 3.03-3.20 (1H, m), 4.37 (2H, s), 4.47 (1H, t, J=7.4 Hz), 4.96-5.13 (2H, m), 7.05 (2H, d, J=8.5 Hz), 7.15-7.36 (10H, m), 7.36-7.53 (7H, m).

In the following Examples, description of salts (e.g., HCl, 2HCl, TFA, 2TFA) in the structural formulas is omitted.

Example 59

N-(4-{trans-2-[(cyclopropylmethyl)amino]cyclopropyl}phenyl)biphenyl-4-carboxamide hydrochloride

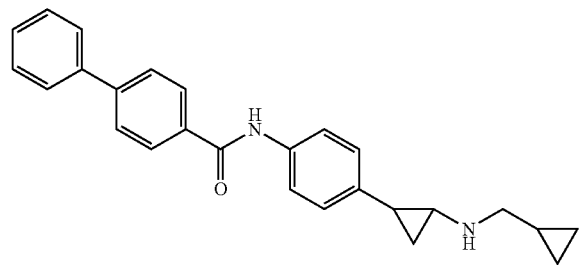 [SMILES: O=C(Nc1ccc(C2CC2NCC2CC2)cc1)c1ccc(-c2ccccc2)cc1]

A solution of N-[4-(trans-2-aminocyclopropyl)phenyl]biphenyl-4-carboxamide hydrochloride (2.2 g) in methanol (75 mL)/THF (75 mL) was ice-cooled, and cyclopropanecarbaldehyde (549 mg) and sodium hydrogen carbonate (1.01 g) were added. The mixture was stirred at 60° C. for 1 hr, and ice-cooled to 0° C. and sodium borohydride (456 mg) was added. The mixture was stirred for 1 hr, and saturated aqueous sodium hydrogen carbonate solution was added. The mixture was extracted with ethyl acetate, and the extract was washed with saturated brine and dried over anhydrous sodium sulfate. The solvent was evaporated under reduced pressure. The residue was purified by silica gel column chromatography (hexane/ethyl acetate, ethyl acetate/methanol). 10% Hydrochloric acid methanol solution was added and the solvent was evaporated under reduced pressure. The residue was recrystallized from methanol/diisopropyl ether to give the title compound (1.62 g).

MS (API+): [M+H]$^+$ 383.1.

$^1$H NMR (300 MHz, CD$_3$OD) δ 0.38-0.48 (2H, m), 0.69-0.78 (2H, m), 1.06-1.21 (1H, m), 1.35-1.55 (2H, m), 2.47 (1H, ddd, J=10.1, 6.5, 3.5 Hz), 2.96-3.04 (1H, m), 3.09 (2H, dd, J=7.5, 2.1 Hz), 7.21 (2H, d, J=8.7 Hz), 7.36-7.44 (1H, m), 7.45-7.53 (2H, m), 7.65-7.73 (4H, m), 7.78 (2H, d, J=8.5 Hz), 8.02 (2H, d, J 8.7 Hz).

Example 60

N-(4-{trans-2-[bis(cyclopropylmethyl)amino]cyclopropyl}phenyl)biphenyl-4-carboxamide hydrochloride

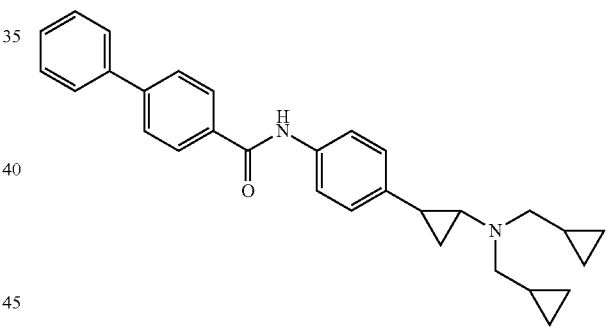

To a solution of N-[4-(trans-2-aminocyclopropyl)phenyl]biphenyl-4-carboxamide hydrochloride (100 mg) in methanol (5.4 mL) were added acetic acid (0.6 mL), cyclopropanecarbaldehyde (0.023 mL) and 2-picoline-borane complex (44 mg). The mixture was stirred at room temperature for 21 hr, and DMF (4 mL) and 2-picoline-borane complex (29.3 mg) were added. The mixture was stirred at room temperature for 2 hr, and cyclopropanecarbaldehyde (0.010 mL) was added. The mixture was stirred at room temperature for 3 hr, and cyclopropanecarbaldehyde (0.008 mL) was added. The mixture was stirred at room temperature for 1 hr, water and ethyl acetate were added, and the mixture was concentrated under reduced pressure. To the residue was added saturated aqueous sodium hydrogen carbonate solution, and the mixture was extracted twice with ethyl acetate. The extracts were combined, washed with saturated brine, and dried over anhydrous magnesium sulfate. The solvent was evaporated under reduced pressure. The residue was purified by silica gel column chromatography (hexane/ethyl acetate), and 10% hydrochloric acid methanol solution (1.0 mL) was added to the obtained product. The solvent was evaporated under reduced pressure to give the title compound (26.1 mg).

MS (API+): [M+H]$^+$ 437.3.

$^1$H NMR (300 MHz, CD$_3$OD) δ 0.27-0.61 (4H, m), 0.61-0.96 (4H, m), 1.03-1.39 (2H, m), 1.52 (1H, brs), 1.77 (1H, brs), 2.71 (2H, s), 3.11-3.55 (4H, m), 7.20 (2H, d, J=7.6 Hz), 7.34-7.55 (3H, m), 7.63-7.84 (6H, m), 8.03 (2H, d, J=8.1 Hz).

Example 61

N-{4-[trans-2-(tetrahydro-2H-pyran-4-ylamino)cyclopropyl]phenyl}biphenyl-4-carboxamide hydrochloride

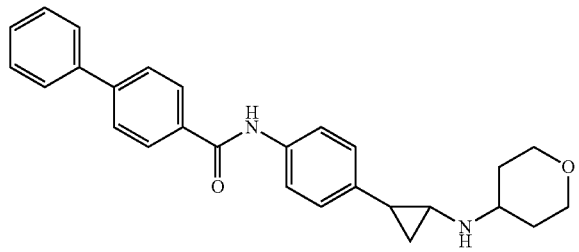 [SMILES: O=C(Nc1ccc(C2CC2NC2CCOCC2)cc1)c1ccc(-c2ccccc2)cc1]

By a method similar to Example 59, the title compound (39 mg) was obtained from N-[4-(trans-2-aminocyclopropyl)phenyl]biphenyl-4-carboxamide hydrochloride (120 mg) and tetrahydro-4H-pyran-4-one (32.9 mg).

MS (API+): [M+H]$^+$ 413.4.

$^1$H NMR (300 MHz, CD$_3$OD) δ 1.37-1.58 (2H, m), 1.64-1.83 (2H, m), 2.10 (2H, d, J=11.6 Hz), 2.42-2.57 (1H, m), 2.93-3.05 (1H, m), 3.41-3.67 (3H, m), 4.04 (2H, d, J=8.1 Hz), 7.21 (2H, d, J=8.0 Hz), 7.34-7.55 (3H, m), 7.65-7.82 (6H, m), 8.01 (2H, d, J=8.1 Hz).

Example 62

N-(4-{trans-2-[(1-acetylpiperidin-4-yl)amino]cyclopropyl}phenyl)biphenyl-4-carboxamide hydrochloride

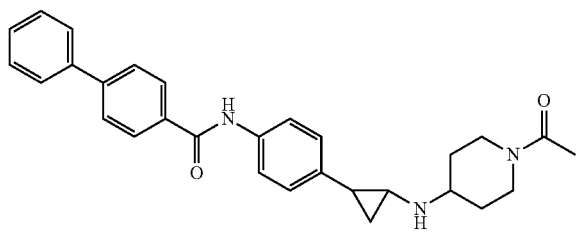 [SMILES: CC(=O)N1CCC(NC2CC2c2ccc(NC(=O)c3ccc(-c4ccccc4)cc3)cc2)CC1]

By a method similar to Example 59, the title compound (31 mg) was obtained from N-[4-(trans-2-aminocyclopropyl)phenyl]biphenyl-4-carboxamide hydrochloride (120 mg) and 1-acetylpiperidin-4-one (46.4 mg).

MS (API+): [M+H]$^+$ 454.3.

$^1$H NMR (300 MHz, CD$_3$OD) δ 1.06-1.88 (5H, m), 2.03-2.43 (5H, m), 2.51-3.16 (3H, m), 3.50-3.87 (1H, m), 3.97-4.25 (1H, m), 4.49-4.78 (1H, m), 7.19-7.53 (5H, m), 7.66-7.81 (6H, m), 8.03 (2H, d, J=7.4 Hz).

Example 63

N-{4-[trans-2-{[1-(2,2,2-trifluoroethyl)piperidin-4-yl]amino}cyclopropyl]phenyl}biphenyl-4-carboxamide hydrochloride

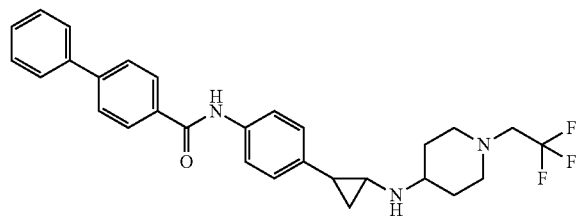 [SMILES: O=C(Nc1ccc(C2CC2NC2CCN(CC(F)(F)F)CC2)cc1)c1ccc(-c2ccccc2)cc1]

By a method similar to Example 59, the title compound (23 mg) was obtained from N-[4-(trans-2-aminocyclopropyl)phenyl]biphenyl-4-carboxamide hydrochloride (164 mg) and 1-(2,2,2-trifluoroethyl)piperidin-4-one (91 mg).

MS (API+): [M+H]$^+$ 494.3

$^1$H NMR (300 MHz, CD$_3$OD) δ 1.43-1.60 (2H, m), 1.82-1.98 (2H, m), 2.20-2.32 (2H, m), 2.45-2.57 (1H, m), 2.69-2.85 (3H, m), 2.98-3.06 (1H, m), 3.36-3.75 (4H, m), 7.23 (2H, d, J=8.6 Hz), 7.39-7.44 (1H, m), 7.47-7.53 (2H, m), 7.68-7.73 (4H, m), 7.79 (2H, d, J=8.7 Hz), 8.01-8.06 (2H, m).

Example 64

N-(4-{trans-2-[(cyclopropylmethyl)amino]cyclopropyl}phenyl)-N-methylbiphenyl-4-carboxamide hydrochloride

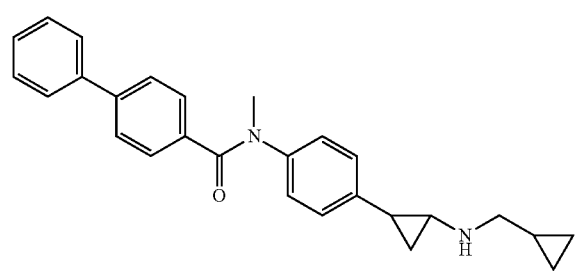 [SMILES: CN(C(=O)c1ccc(-c2ccccc2)cc1)c1ccc(C2CC2NCC2CC2)cc1]

A) tert-butyl(trans-2-{4-[(biphenyl-4-ylcarbonyl)(methyl)amino]phenyl}cyclopropyl)(cyclopropylmethyl) carbamate To a solution of N-(4-{trans-2-[(cyclopropylmethyl)amino]cyclopropyl}phenyl)biphenyl-4-carboxamide hydrochloride (90 mg) and triethylamine (43.5 mg) in THF (2 mL) was added di-tert-butyl dicarbonate (60.9 mg) under ice-cooling. The mixture was stirred at room temperature overnight and water was added. The mixture was extracted with ethyl acetate, and the extract was washed with saturated brine, and dried over anhydrous magnesium sulfate. The solvent was evaporated under reduced pressure. The residue was dissolved in DMF (2.5 mL), sodium hydride (12.9 mg) was added under ice-cooling, and the mixture was stirred for 1 hr.

To the reaction mixture was added methyl iodide (52.9 mg) under ice-cooling, and the mixture was stirred at room temperature overnight, and poured into saturated aqueous sodium hydrogen carbonate solution. The mixture was extracted with ethyl acetate, and the extract was washed with saturated brine, and dried over anhydrous magnesium sulfate. The solvent was evaporated under reduced pressure. The residue was purified by silica gel column chromatography (hexane/ethyl acetate) to give the title
compound (105 mg).
MS (API+): [M−tBu+2H]+ 441.3.

B) N-(4-{trans-2-[(cyclopropylmethyl)amino]cyclopropyl}phenyl)-N-methylbiphenyl-4-carboxamide hydrochloride To a solution of tert-butyl(trans-2-{4-[(biphenyl-4-ylcarbonyl)(methyl)amino]phenyl}cyclopropyl)(cyclopropylmethyl) carbamate (248 mg) in THF (5 mL) was added 10% hydrochloric acid methanol (20 mL) under ice-cooling, and the mixture was stirred at room temperature overnight. The solvent was evaporated under reduced pressure. The residue was recrystallized from methanol/diisopropyl ether to give the title compound (62 mg).
MS (API+): [M+H]+397.3.
1H NMR (300 MHz, CD3OD) δ 0.19-0.29 (2H, m), 0.50-0.61 (2H, m), 0.87-1.02 (1H, m), 1.16-1.30 (1H, m), 1.31-1.43 (1H, m), 2.30 (1H, ddd, J=10.2, 6.5, 3.7 Hz), 2.82 (1H, dt, J=7.8, 4.0 Hz), 2.90 (2H, d, J=7.5 Hz), 3.37 (3H, s), 6.97-7.08 (4H, m), 7.19-7.41 (7H, m), 7.42-7.48 (2H, m).

Example 65

N-(4-{trans-2-[(cyclopropylmethyl)amino]cyclopropyl}phenyl)-3-(trifluoromethyl)benzamide hydrochloride

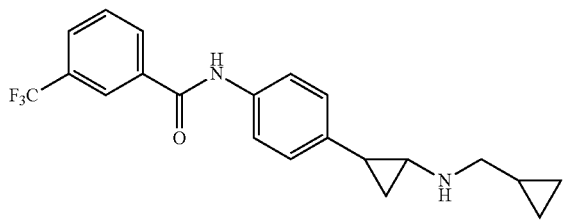 [SMILES: O=C(Nc1ccc(C2CC2NCC2CC2)cc1)c1cccc(C(F)(F)F)c1]

To a solution of N-[4-(trans-2-aminocyclopropyl)phenyl]-3-(trifluoromethyl)benzamide hydrochloride (150 mg) in methanol (10 mL)/THF (10 mL) were added cyclopropanecarbaldehyde (38.3 mg) and sodium hydrogen carbonate (70.6 mg). The mixture was stirred at 60° C. for 1 hr, and ice-cooled to 0° C. and sodium borohydride (31.8 mg) was added. The mixture was stirred at room temperature for 2 hr, and ice-cooled to 0° C., and aqueous sodium hydrogen carbonate solution was added. The mixture was extracted with ethyl acetate, and the extract was washed with water and saturated brine and dried over anhydrous sodium sulfate. The solvent was evaporated under reduced pressure. The residue was purified by silica gel column chromatography (ethyl acetate/methanol). To the obtained product was added 10% hydrochloric acid methanol solution, and the solvent was evaporated under reduced pressure. The residue was recrystallized from methanol/diisopropyl ether to give the title compound (79 mg).
MS (API+): [M+H]+ 375.2.
1H NMR (300 MHz, CD3OD) δ 0.42 (2H, m), 0.68-0.78 (2H, m), 1.05-1.18 (1H, m), 1.34-1.54 (2H, m), 2.46 (1H, ddd, J=10.2, 6.5, 3.3 Hz), 2.98 (1H, m), 3.08 (2H, dd, J=7.5, 2.1 Hz), 7.20 (2H, d, J=8.5 Hz), 7.63-7.77 (3H, m), 7.89 (1H, d, J=7.7 Hz), 8.13-8.28 (2H, m).

Example 66

N-(4-{trans-2-[(1H-imidazol-4-ylmethyl)amino]cyclopropyl}phenyl)biphenyl-4-carboxamide dihydrochloride

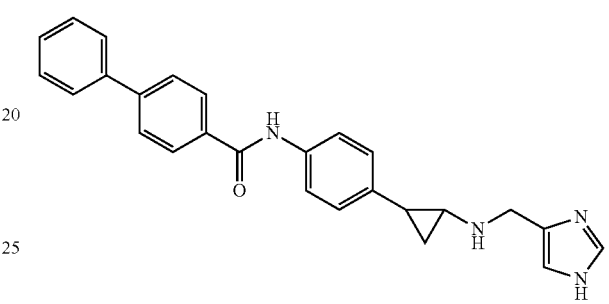

By a method similar to Example 59, the title compound (78 mg) was obtained from N-[4-(trans-2-aminocyclopropyl)phenyl]biphenyl-4-carboxamide hydrochloride (150 mg) and 1H-imidazole-4-carbaldehyde (39.5 mg).
MS (API+): [M+H]+ 409.0.
1H NMR (300 MHz, CD3OD) δ 1.40-1.49 (1H, m), 1.60 (1H, ddd, J=10.6, 6.7, 4.3 Hz), 2.51-2.61 (1H, m), 3.08 (1H, dq, J=4.3, 3.2 Hz), 4.61 (2H, d, J=2.1 Hz), 7.16 (2H, d, J=8.5 Hz), 7.36-7.43 (1H, m), 7.44-7.52 (2H, m), 7.65-7.73 (4H, m), 7.75-7.82 (3H, m), 8.01 (2H, d, J=8.5 Hz), 9.02 (1H, d, J=1.1 Hz).

Example 67

N-(4-{trans-2-[(2-fluorobenzyl)amino]cyclopropyl}phenyl)-3-(trifluoromethyl)benzamide hydrochloride

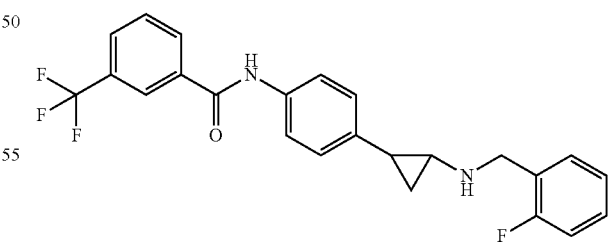

By a method similar to Example 65, the title compound (90 mg) was obtained from N-[4-(trans-2-aminocyclopropyl)phenyl]-3-(trifluoromethyl)benzamide hydrochloride (120 mg) and 2-fluorobenzaldehyde (54.3 mg).
MS (API+): [M+H]+ 429.0.
1H NMR (300 MHz, CD3OD) δ 1.36-1.55 (2H, m), 2.36-2.48 (1H, m), 3.03 (1H, dt, J=7.5, 3.8 Hz), 4.47 (2H, s), 7.15

(2H, d, J=7.9 Hz), 7.20-7.34 (2H, m), 7.47-7.60 (2H, m), 7.63-7.80 (3H, m), 7.91 (1H, d, J=7.9 Hz), 8.16-8.30 (2H, m).

Example 68

N-(4-{trans-2-[(cyclopropylmethyl)amino]cyclopropyl}phenyl)-4-methylbenzamide hydrochloride

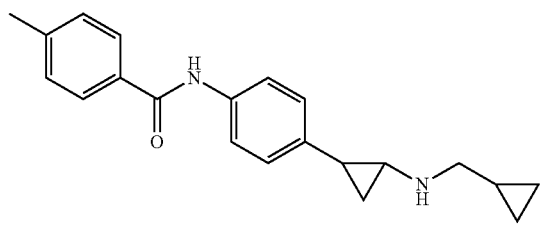 [SMILES: Cc1ccc(C(=O)Nc2ccc(C3CC3NCC3CC3)cc2)cc1]

A) 2,2,2-trichloroethyl(4-{trans-2-[(tert-butoxycarbonyl)amino]cyclopropyl}phenyl)carbamate To a solution of tert-butyl [trans-2-(4-aminophenyl)cyclopropyl]carbamate (16.8 g) described in a document (J. Am. Chem. Soc., 2010, 132, 6827.) and triethylamine (11.32 mL) in THF (338 mL) was added 2,2,2-trichloroethyl chloroformate (11.2 mL). The mixture was stirred at room temperature overnight, and poured into saturated aqueous ammonium chloride solution. The reaction mixture was extracted with ethyl acetate, and the extract was washed with saturated brine, and dried over anhydrous magnesium sulfate. The solvent was evaporated under reduced pressure. The residue was purified by silica gel column chromatography (hexane/ethyl acetate) to give the title compound (19.0 g).
$^1$H NMR (300 MHz, CDCl$_3$) δ 1.07-1.19 (2H, m), 1.45 (9H, s), 1.95-2.08 (1H, m), 2.68 (1H, brs), 4.81 (3H, brs), 6.84 (1H, brs), 7.11 (2H, d, J=7.8 Hz), 7.31 (2H, d, J=7.8 Hz).

B) 2,2,2-trichloroethyl[4-(trans-2-aminocyclopropyl)phenyl]carbamate hydrochloride 2,2,2-Trichloroethyl(4-{trans-2-[(tert-butoxycarbonyl)amino]cyclopropyl}phenyl)carbamate (19.0 g) was dissolved in 4N hydrochloric acid/cyclopentyl methyl ether solution (188 mL), and the mixture was stirred at room temperature for 3 hr. The solvent was evaporated under reduced pressure to give the title compound (16.2 g).
$^1$H NMR (300 MHz, DMSO-d$_6$) δ 1.09-1.22 (1H, m), 1.24-1.37 (1H, m), 2.16-2.30 (1H, m), 2.69-2.81 (1H, m), 4.93 (2H, s), 7.11 (2H, d, J=8.3 Hz), 7.43 (2H, d, J=8.3 Hz), 8.21 (3H, brs), 10.11 (1H, brs).

C) 2,2,2-trichloroethyl(4-{trans-2-[(tert-butoxycarbonyl) (cyclopropylmethyl)amino]cyclopropyl}phenyl)-carbamate To a solution of 2,2,2-trichloroethyl[4-(trans-2-aminocyclopropyl)phenyl]carbamate hydrochloride (16.2 g) and sodium hydrogen carbonate (7.56 g) in THF (112 mL)/methanol (112 mL) was added cyclopropanecarbaldehyde (4.37 mL). The mixture was stirred at 60° C. for 2 hr, and ice-cooled to 0° C. and sodium borohydride (3.4 g) was added. The mixture was stirred at room temperature for 1 hr, and di-tert-butyl dicarbonate (14.7 g) was added. The mixture was stirred at room temperature overnight, and poured into water. The mixture was extracted with ethyl acetate, and the extract was washed with saturated brine, and dried over anhydrous magnesium sulfate. The solvent was evaporated under reduced pressure. The residue was purified by silica gel column chromatography (hexane/ethyl acetate) to give the title compound (15.9 g).
$^1$H NMR (300 MHz, DMSO-d$_6$) δ 0.05-0.15 (1H, m), 0.16-0.27 (1H, m), 0.32-0.51 (2H, m), 0.89-1.04 (1H, m), 1.12-1.25 (2H, m), 1.35 (9H, s), 2.00-2.08 (1H, m), 2.62-2.75 (1H, m), 2.99 (1H, dd, J=14.2, 6.9 Hz), 3.17 (1H, dd, J=14.2, 6.9 Hz), 4.93 (2H, s), 7.08 (2H, d, J=8.7 Hz), 7.40 (2H, d, J=8.1 Hz), 10.06 (1H, brs).

D) tert-butyl [trans-2-(4-aminophenyl)cyclopropyl](cyclopropylmethyl)carbamate

To a solution of 2,2,2-trichloroethyl(4-{trans-2-[(tert-butoxycarbonyl)(cyclopropylmethyl)amino]cyclopropyl}phenyl)-carbamate (15.9 g) in THF (166 mL) were added zinc powder (32.6 g) and acetic acid (5 mL). The reaction mixture was stirred at room temperature for 5 hr, 1N aqueous sodium hydroxide solution (100 mL) and ethyl acetate (500 mL) were added, and the mixture was filtered through celite. The organic layer was separated from the mother liquor, washed successively with water and saturated brine, and dried over anhydrous magnesium sulfate. The solvent was evaporated under reduced pressure. The residue was purified by silica gel column chromatography (NH, hexane/ethyl acetate) to give the title compound (6.83 g).
$^1$H NMR (300 MHz, DMSO-d$_6$) δ 0.06-0.16 (1H, m), 0.16-0.26 (1H, m), 0.33-0.48 (2H, m), 0.89-1.12 (3H, m), 1.36 (9H, s), 1.85-1.95 (1H, m), 2.53-2.60 (1H, m), 2.97 (1H, dd, J=14.2, 6.8 Hz), 3.15 (1H, dd, J=14.2, 6.8 Hz), 4.83 (2H, s), 6.46 (2H, J=7.9 Hz), 6.80 (2H, d, J=7.9 Hz).

E) tert-butyl(cyclopropylmethyl)(trans-2-{4-[(4-methylbenzoyl)amino]phenyl}cyclopropyl)carbamate To a solution of tert-butyl [trans-2-(4-aminophenyl)cyclopropyl](cyclopropylmethyl)carbamate (75.0 mg) and triethylamine (41.5 µL) in THF (1.24 mL) was added 4-toluoyl chloride (39.4 µL). The mixture was stirred at room temperature overnight, and poured into saturated aqueous ammonium chloride solution. The mixture was extracted with ethyl acetate, and the extract was washed with saturated brine, and dried over anhydrous magnesium sulfate. The solvent was evaporated under reduced pressure to give the title compound (104.3 mg).
$^1$H NMR (300 MHz, DMSO-d$_6$) δ 0.06-0.16 (1H, m), 0.18-0.29 (1H, m), 0.34-0.51 (2H, m), 0.91-1.04 (1H, m), 1.11-1.25 (2H, m), 1.36 (9H, s), 2.01-2.11 (1H, m), 2.38 (3H, s), 2.67-2.76 (1H, m), 3.00 (1H, dd, J=14.3, 7.0 Hz), 3.19 (1H, dd, J=14.3, 7.1 Hz), 7.11 (2H, d, J=8.1 Hz), 7.33 (2H, d, J=7.7 Hz), 7.66 (2H, d, J=8.2 Hz), 7.86 (2H, d, J=7.7 Hz), 10.08 (1H, s).

F) N-(4-{trans-2-[(cyclopropylmethyl)amino]cyclopropyl}phenyl)-4-methylbenzamide hydrochloride tert-Butyl(cyclopropylmethyl)(trans-2-{4-[(4-methylbenzoyl)amino]phenyl}cyclopropyl)carbamate (104.3 mg) was dissolved in 4N hydrochloric acid/cyclopentyl methyl ether solution (4 mL), and the mixture was stirred at room temperature overnight. The solvent was evaporated under reduced pressure. The residue was recrystallized from methanol/diisopropyl ether to give the title compound (65.0 mg).

MS (API+): [M+H]$^+$ 321.2.

$^1$H NMR (300 MHz, DMSO-d$_6$) δ 0.32-0.41 (2H, m), 0.52-0.63 (2H, m), 0.99-1.13 (1H, m), 1.21-1.32 (1H, m), 1.42-1.56 (1H, m), 2.38 (3H, s), 2.41-2.47 (1H, m), 2.84-3.04 (3H, m), 7.15 (2H, d, J=7.6 Hz), 7.33 (2H, d, J=7.6 Hz), 7.71 (2H, d, J=7.9 Hz), 7.86 (2H, d, J=7.9 Hz), 9.15 (2H, brs), 10.14 (1H, s).

Example 69

N-(4-{trans-2-[(cyclopropylmethyl)amino]cyclopropyl}phenyl)-4-(trifluoromethyl)benzamide hydrochloride

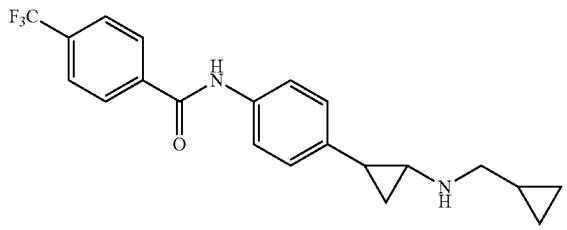 [SMILES: O=C(Nc1ccc(C2CC2NCC2CC2)cc1)c1ccc(C(F)(F)F)cc1]

By a method similar to Example 68, Steps E and F, the title compound (65.9 mg) was obtained from tert-butyl [trans-2-(4-aminophenyl)cyclopropyl](cyclopropylmethyl)carbamate (73.0 mg) and 4-(trifluoromethyl)benzoyl chloride (43.0 μL).

MS (API+): [M+H]$^+$ 375.4.

$^1$H NMR (300 MHz, DMSO-d$_6$) δ 0.31-0.43 (2H, m), 0.50-0.64 (2H, m), 1.01-1.15 (1H, m), 1.23-1.33 (1H, m), 1.43-1.60 (1H, m), 2.43-2.48 (1H, m), 2.83-3.03 (3H, m), 7.18 (2H, d, J=8.2 Hz), 7.72 (2H, d, J=8.2 Hz), 7.92 (2H, d, J=8.2 Hz), 8.15 (2H, d, J=8.2 Hz), 9.27 (2H, brs), 10.48 (1H, s).

Example 70

4-tert-butyl-N-(4-{trans-2-[(cyclopropylmethyl)amino]cyclopropyl}phenyl)benzamide hydrochloride

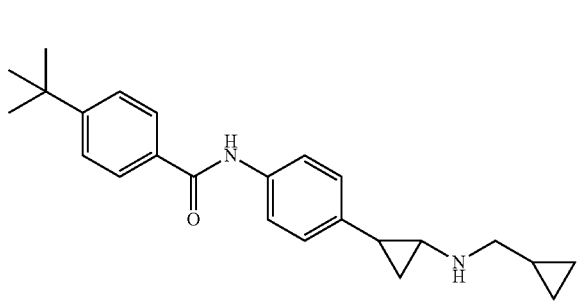

By a method similar to Example 68, Steps E and F, the title compound (67.6 mg) was obtained from tert-butyl [trans-2-(4-aminophenyl)cyclopropyl](cyclopropylmethyl)carbamate (71.3 mg) and 4-tert-butylbenzoyl chloride (55.3 μL).

MS (API+): [M+H]$^+$ 363.4.

$^1$H NMR (300 MHz, DMSO-d$_6$) δ 0.32-0.41 (2H, m), 0.53-0.65 (2H, m), 0.98-1.13 (1H, m), 1.21-1.29 (1H, m), 1.32 (9H, s), 1.41-1.55 (1H, m), 2.39-2.48 (1H, m), 2.81-3.05 (3H, m), 7.15 (2H, d, J=8.1 Hz), 7.54 (2H, d, J=8.1 Hz), 7.71 (2H, d, J=8.1'Hz), 7.88 (2H, d, J=8.1 Hz), 9.16 (2H, brs), 10.16 (1H, s).

Example 71

4-(benzyloxy)-N-(4-{trans-2-[(cyclopropylmethyl)amino]cyclopropyl}phenyl)benzamide hydrochloride

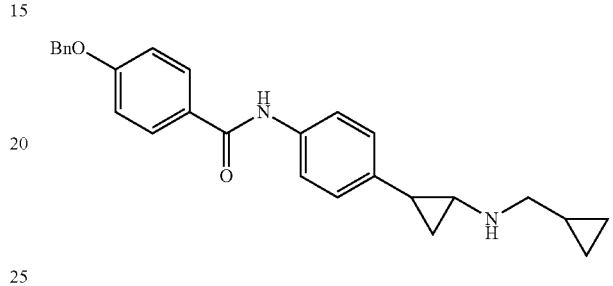

By a method similar to Example 68, Steps E and F, the title compound (50.2 mg) was obtained from tert-butyl [trans-2-(4-aminophenyl)cyclopropyl](cyclopropylmethyl)carbamate (70.9 mg) and 4-(benzyloxy)benzoyl chloride (69.4 mg).

MS (API+): [M+H]$^+$ 413.3.

$^1$H NMR (300 MHz, DMSO-d$_6$) δ 0.30-0.40 (2H, m), 0.51-0.63 (2H, m), 0.96-1.13 (1H, m), 1.21-1.32 (1H, m), 1.39-1.53 (1H, m), 2.42 (1H, m), 2.85-3.04 (3H, m), 5.21 (2H, s), 7.05-7.20 (4H, m), 7.30-7.51 (5H, m), 7.70 (2H, d, J=7.8 Hz), 7.94 (2H, d, J=8.2 Hz), 9.03 (2H, brs), 10.07 (1H, s).

Example 72

N-(4-{trans-2-[(1,3-thiazol-4-ylmethyl)amino]cyclopropyl}phenyl)-3-(trifluoromethyl)benzamide dihydrochloride

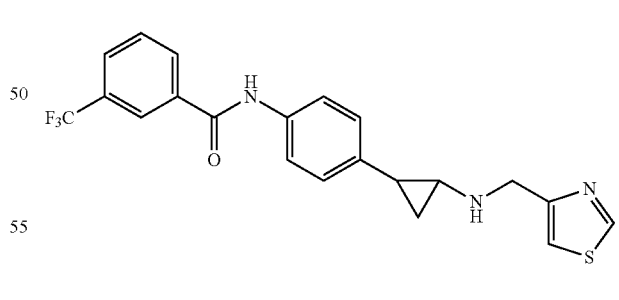

By a method similar to Example 65, the title compound (40 mg) was obtained from N-[4-(trans-2-aminocyclopropyl)phenyl]-3-(trifluoromethyl)benzamide hydrochloride (80 mg) and 1,3-thiazole-4-carbaldehyde (33 mg).

MS (API+): [M+H]$^+$ 417.9.

$^1$H NMR (300 MHz, CD$_3$OD) δ 1.34-1.55 (2H, m), 2.40-2.50 (1H, m), 3.04 (1H, td, J=4.3, 3.4 Hz), 4.58 (2H, s), 7.14

(2H, d, J=8.5 Hz), 7.64-7.79 (4H, m), 7.90 (1H, d, J=7.9 Hz), 8.16-8.29 (2H, m), 9.10 (1H, d, J=1.9 Hz).

Example 73

N-(4-{trans-2-[(cyclopropylmethyl)amino]cyclopropyl}phenyl)-2-fluoro-5-(trifluoromethyl)benzamide hydrochloride

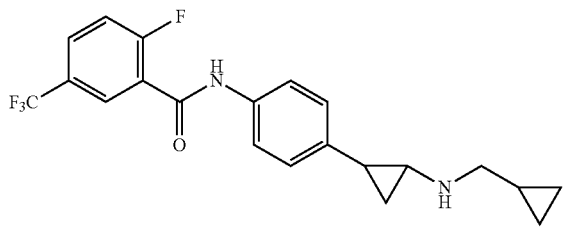 [SMILES: O=C(Nc1ccc(C2CC2NCC2CC2)cc1)c1cc(C(F)(F)F)ccc1F]

A) tert-butyl(cyclopropylmethyl) [trans-2-(4-{[2-fluoro-5-(trifluoromethyl)benzoyl]amino}phenyl)cyclopropyl]carbamate A solution of tert-butyl [trans-2-(4-aminophenyl)cyclopropyl](cyclopropylmethyl)carbamate (80.0 mg) and triethylamine (32.1 mg) in acetonitrile (3 mL) was ice-cooled, and 2-fluoro-5-(trifluoromethyl)benzoyl chloride (71.9 mg) was added. The mixture was stirred at room temperature for 2 hr, and poured into water under ice-cooling. The mixture was extracted with ethyl acetate, and the extract was washed with saturated brine, and dried over anhydrous magnesium sulfate. The solvent was evaporated under reduced pressure. The residue was purified by silica gel column chromatography (hexane/ethyl acetate) to give the title compound (115 mg).

MS (API+): [M−tBu+2H]+ 437.0.

$^1$H NMR (300 MHz, CDCl$_3$) δ 0.12-0.31 (2H, m), 0.37-0.54 (2H, m), 0.93-1.12 (1H, m), 1.22-1.30 (2H, m), 1.45 (9H, s), 2.07-2.16 (1H, m), 2.78-2.88 (1H, m), 2.99-3.13 (1H, m), 3.19-3.35 (1H, m), 7.16 (2H, d, J=8.1 Hz), 7.28-7.38 (1H, m), 7.57 (2H, d, J=8.0 Hz), 7.75-7.84 (1H, m), 8.38 (1H, d, J=14.4 Hz), 8.49 (1H, d, J=6.7 Hz).

B) N-(4-{trans-2-[(cyclopropylmethyl)amino]cyclopropyl}phenyl)-2-fluoro-5-(trifluoromethyl)benzamide hydrochloride A solution of tert-butyl(cyclopropylmethyl)[trans-2-(4-{[2-fluoro-5-(trifluoromethyl)benzoyl]amino}phenyl)-cyclopropyl]carbamate (110 mg) in THF (1 mL) was ice-cooled, and 4N hydrochloric acid/cyclopentyl methyl ether solution (15 mL) was added. The mixture was stirred at room temperature overnight and the solvent was evaporated under reduced pressure. The residue was recrystallized from methanol/diisopropyl ether to give the title compound (72.0 mg).

MS (API+): [M+H]+ 393.0.

$^1$H NMR (300 MHz, CD$_3$OD) δ 0.38-0.48 (2H, m), 0.69-0.79 (2H, m), 1.09-1.18 (1H, m), 1.36-1.58 (2H, m), 2.49 (1H, ddd, J=10.0, 6.5, 3.7 Hz), 2.96-3.04 (1H, m), 3.09 (2H, dd, J=7.5, 2.1 Hz), 7.21 (2H, d, J=8.7 Hz), 7.48 (1H, t, J=9.2 Hz), 7.66 (2H, d, J=8.7 Hz), 7.86-7.97 (1H, m), 8.04 (1H, dd, J=6.2, 2.3 Hz).

Example 74

N-(4-{trans-2-[(1-benzylpiperidin-4-yl)amino]cyclopropyl}phenyl)-3-(trifluoromethyl)benzamide dihydrochloride

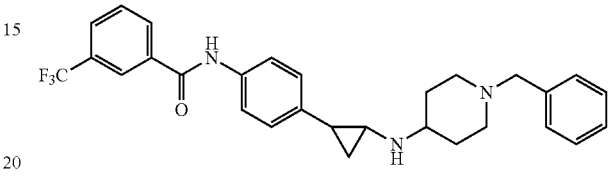

By a method similar to Example 65, the title compound (65 mg) was obtained from N-[4-(trans-2-aminocyclopropyl)phenyl]-3-(trifluoromethyl)benzamide hydrochloride (80 mg) and 1-benzylpiperidin-4-one (55.2 mg).

MS (API+): [M+H]+ 494.2.

$^1$H NMR (300 MHz, CD$_3$OD) δ 1.42-1.63 (2H, m), 2.02-2.21 (2H, m), 2.39-2.59 (3H, m), 3.03 (1H, brs), 3.14-3.25 (2H, m), 3.56-3.74 (3H, m), 4.37 (2H, brs), 7.23 (2H, d, J=8.2 Hz), 7.50-7.61 (5H, m), 7.66-7.80 (3H, m), 7.92 (1H, d, J=7.7 Hz), 8.16-8.29 (2H, m).

Example 75

N-(4-{trans-2-[(1-phenylpiperidin-4-yl)amino]cyclopropyl}phenyl)-3-(trifluoromethyl)benzamide dihydrochloride

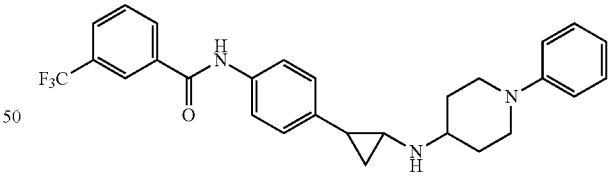

By a method similar to Example 65, the title compound (45 mg) was obtained from N-[4-(trans-2-aminocyclopropyl)phenyl]-3-(trifluoromethyl)benzamide hydrochloride (80 mg) and 1-phenylpiperidin-4-one (51.1 mg).

MS (API+): [M+H]+ 480.1.

$^1$H NMR (300 MHz, CD$_3$OD) δ 1.46-1.69 (2H, m), 2.22-2.44 (2H, m), 2.46-2.66 (3H, m), 3.06-3.16 (1H, m), 3.59-3.97 (5H, m), 7.27 (2H, d, J=8.3 Hz), 7.43-7.51 (1H, m), 7.53-7.61 (2H, m), 7.62-7.68 (2H, m), 7.69-7.79 (3H, m), 7.91 (1H, d, J=7.8 Hz), 8.16-8.30 (2H, m).

Example 76

N-(4-{trans-2-[(1-methylpiperidin-4-yl)amino]cyclopropyl}phenyl)-3-(trifluoromethyl)benzamide dihydrochloride

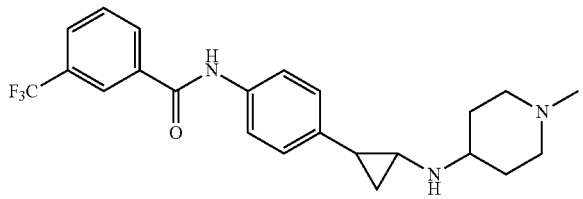 [SMILES: CN1CCC(NC2CC2c2ccc(NC(=O)c3cccc(C(F)(F)F)c3)cc2)CC1]

To a solution of N-[4-(trans-2-aminocyclopropyl)phenyl]-3-(trifluoromethyl)benzamide hydrochloride (80 mg) in methanol (3 mL)/THF (3 mL) were added 1-methylpiperidin-4-one (33.0 mg) and sodium hydrogen carbonate (37.7 mg). The mixture was stirred at 60° C. for 2 hr, and ice-cooled to 0° C. and sodium borohydride (17.0 mg) was added. The mixture was stirred at room temperature for 2 hr, and ice-cooled to 0° C., and saturated aqueous sodium hydrogen carbonate solution was added. The mixture was extracted with ethyl acetate, and the extract was washed with saturated brine, and dried over anhydrous magnesium sulfate. The solvent was evaporated under reduced pressure. The residue was purified by silica gel column chromatography (hexane/ethyl acetate, ethyl acetate/methanol). 10% Hydrochloric acid methanol solution was added and the solvent was evaporated under reduced pressure. The residue was recrystallized from methanol/diisopropyl ether to give the title compound (40 mg).

MS (API+): [M+H]+ 418.0.

$^1$H NMR (300 MHz, CD$_3$OD) δ 1.42-1.65 (2H, m), 2.02-2.22 (2H, m), 2.34-2.63 (3H, m), 2.92 (3H, s), 3.01-3.27 (3H, m), 3.60-3.78 (3H, m), 7.24 (2H, d, J=8.3 Hz), 7.67-7.79 (3H, m), 7.91 (1H, d, J=7.5 Hz), 8.17-8.28 (2H, m).

Example 77

N-(4-{trans-2-[(2-phenylpiperidin-4-yl)amino]cyclopropyl}phenyl)-3-(trifluoromethyl)benzamide dihydrochloride

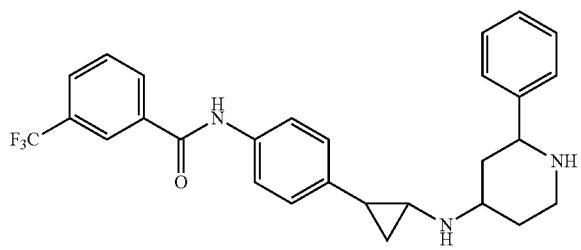 [SMILES: O=C(Nc1ccc(C2CC2NC2CCNC(c3ccccc3)C2)cc1)c1cccc(C(F)(F)F)c1]

A) tert-butyl 2-phenyl-4-{[trans-2-(4-{[3-(trifluoromethyl)benzoyl]amino}phenyl)cyclopropyl]amino}-piperidine-1-carboxylate To a solution of N-[4-(trans-2-aminocyclopropyl)phenyl]-3-(trifluoromethyl)benzamide hydrochloride (60 mg) in methanol (1.5 mL)/THF (1.5 mL) were added tert-butyl 4-oxo-2-phenylpiperidine-1-carboxylate (60.2 mg) and sodium hydrogen carbonate (28.3 mg). The mixture was stirred at 60° C. for 1 hr, and ice-cooled to 0° C. and sodium borohydride (12.7 mg) was added. The mixture was stirred at room temperature for 2 hr, and ice-cooled to 0° C. and saturated aqueous sodium hydrogen carbonate solution was added. The mixture was extracted with ethyl acetate, and the extract was washed with saturated brine, and dried over anhydrous magnesium sulfate. The solvent was evaporated under reduced pressure. The residue was purified by silica gel column chromatography (ethyl acetate/methanol) to give the title compound (62 mg).

MS (API+): [M−Boc+H]+ 480.1.

B) N-(4-{trans-2-[(2-phenylpiperidin-4-yl)amino]cyclopropyl}phenyl)-3-(trifluoromethyl)benzamide dihydrochloride tert-Butyl 2-phenyl-4-{[trans-2-(4-{[3-(trifluoromethyl)benzoyl]amino}phenyl)cyclopropyl]amino}-piperidine-1-carboxylate (62 mg) was dissolved in THF (0.5 mL), and the mixture was ice-cooled to 0° C. 4N Hydrochloric acid/cyclopentyl methyl ether solution (5.0 mL) was added, and the mixture was stirred at room temperature overnight. The solvent was evaporated under reduced pressure. The residue was recrystallized from methanol/diisopropyl ether to give the title compound (24 mg).

MS (API+): [M+H]+ 480.1.

$^1$H NMR (300 MHz, CD$_3$OD) δ 1.43-1.55 (1H, m), 1.56-1.67 (1H, m), 2.05-2.21 (1H, m), 2.31 (1H, d, J=12.1 Hz), 2.47-2.67 (3H, m), 3.07 (1H, d, J=3.4 Hz), 3.35-3.40 (1H, m), 3.62-3.72 (1H, m), 3.83-3.98 (1H, m), 4.49 (1H, d, J=12.6 Hz), 7.22 (2H, t, J=9.8 Hz), 7.48-7.59 (5H, m), 7.64-7.78 (3H, m), 7.90 (1H, d, J=8.1 Hz), 8.15-8.31 (2H, m).

Example 78

2'-chloro-N-(4-{trans-2-[(cyclopropylmethyl)amino]cyclopropyl}phenyl)biphenyl-4-carboxamide hydrochloride

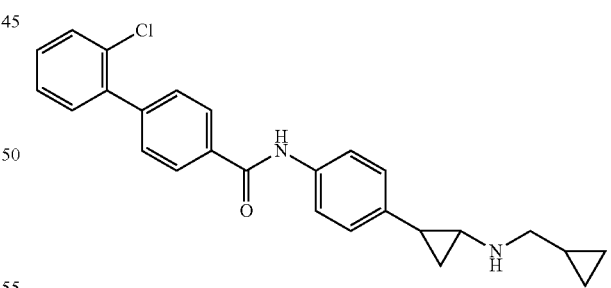

A) tert-butyl [trans-2-(4-{[(2'-chlorobiphenyl-4-yl)carbonyl]amino}phenyl)cyclopropyl](cyclopropylmethyl)-carbamate By a method similar to Example 79, Step A, the title compound (115 mg) was obtained from tert-butyl [trans-2-(4-aminophenyl)cyclopropyl](cyclopropylmethyl)carbamate (75.0 mg) and 2'-chlorobiphenyl-4-carboxylic acid (69.2 mg).

MS (API+): [M−tBu+2H]+ 461.0.

B) 2'-chloro-N-(4-{trans-2-[(cyclopropylmethyl) amino]cyclopropyl}phenyl)biphenyl-4-carboxamide hydrochloride tert-Butyl [trans-2-(4-{[(2'-chlorobiphenyl-4-yl)carbonyl]amino}phenyl)cyclopropyl](cyclopropylmethyl)-carbamate (115 mg) was dissolved in THF (0.5 mL), and the mixture was ice-cooled to 0° C. 4N Hydrochloric acid/cyclopentyl methyl ether solution (5 mL) was added, and the mixture was stirred at room temperature overnight. The solvent was evaporated under reduced pressure. The residue was recrystallized from methanol/diisopropyl ether to give the title compound (65.0 mg).

MS (API+): [M+H]$^+$ 417.0.

$^1$H NMR (300 MHz, CD$_3$OD) δ 0.38-0.52 (2H, m), 0.69-0.80 (2H, m), 1.14 (1H, tt, J=7.8, 4.8 Hz), 1.40 (1H, m), 1.48-1.59 (1H, m), 2.50 (1H, ddd, J=10.2, 6.6, 3.6 Hz), 3.00 (1H, m), 3.06-3.16 (2H, m), 7.21 (2H, d, J=8.7 Hz), 7.34-7.47 (3H, m), 7.49-7.63 (3H, m), 7.70 (2H, d, J=8.7 Hz), 8.00 (2H, d, J=8.5 Hz).

Example 79

N-(4-{trans-2-[(cyclopropylmethyl)amino] cyclopropyl}phenyl)-1H-pyrazole-4-carboxamide hydrochloride

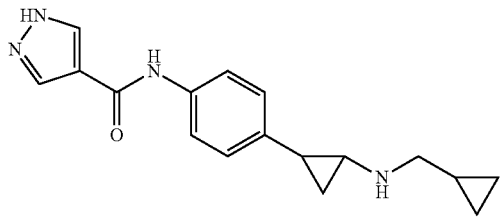 [SMILES: O=C(Nc1ccc(C2CC2NCC2CC2)cc1)c1cn[nH]c1]

A) tert-butyl(cyclopropylmethyl)(trans-2-{4-[(1H-pyrazol-4-ylcarbonyl)amino]phenyl}cyclopropyl) carbamate A solution of tert-butyl [trans-2-(4-aminophenyl)cyclopropyl](cyclopropylmethyl)carbamate (75 mg) in DMF (3 mL) was ice-cooled, and 1H-pyrazole-4-carboxylic acid (33.4 mg), N-ethyl-N'-(3-dimethylaminopropyl)carbodiimide hydrochloride (143 mg), 1-hydroxybenzotriazole (49.4 mg) and diisopropylethylamine (80 mg) were added. The mixture was stirred at room temperature overnight, and saturated aqueous sodium hydrogen carbonate solution was added under ice-cooling. The mixture was extracted with ethyl acetate, and the extract was washed with water and saturated brine, and dried over anhydrous magnesium sulfate. The solvent was evaporated under reduced pressure. The residue was purified by silica gel column chromatography (hexane/ethyl acetate) to give the title compound (72 mg).

MS (API+): [M−tBu+2H]$^+$ 341.0.

B) N-(4-{trans-2-[(cyclopropylmethyl)amino] cyclopropyl}phenyl)-1H-pyrazole-4-carboxamide hydrochloride tert-Butyl(cyclopropylmethyl)(trans-2-{4-[(1H-pyrazol-4-ylcarbonyl)amino]phenyl}cyclopropyl)carbamate (72 mg) was dissolved in THF (0.5 mL), and the mixture was ice-cooled to 0° C. 4N Hydrochloric acid/cyclopentyl methyl ether solution (4.5 mL) was added, and the mixture was stirred at room temperature overnight. The solvent was evaporated under reduced pressure. The residue was recrystallized from methanol/diisopropyl ether to give the title compound (45 mg).

MS (API+): [M+H]$^+$ 297.0.

$^1$H NMR (300 MHz, CD$_3$OD) δ 0.37-0.47 (2H, m), 0.68-0.76 (2H, m), 1.04-1.22 (1H, m), 1.33-1.43 (1H, m), 1.45-1.55 (1H, m), 2.48 (1H, ddd, J=10.1, 6.5, 3.6 Hz), 2.93-3.01 (1H, m), 3.08 (2H, dd, J=7.4, 1.6 Hz), 6.87 (1H, brs), 7.17 (2H, d, J=8.3 Hz), 7.67 (2H, d, J=8.5 Hz), 7.74 (1H, brs).

Example 80

N-(4-{trans-2-[(cyclopropylmethyl)amino] cyclopropyl}phenyl)-4-[(phenylcarbonyl)amino] benzamide hydrochloride

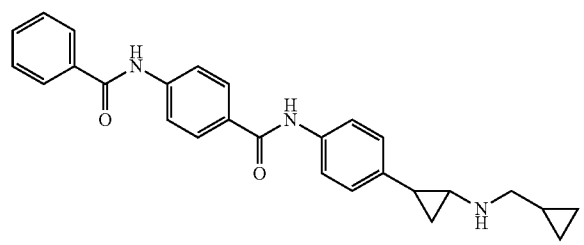 [SMILES: O=C(Nc1ccc(C(=O)Nc2ccc(C3CC3NCC3CC3)cc2)cc1)c1ccccc1]

A) tert-butyl [trans-2-(4-{[4-(benzoylamino)benzoyl] amino}-phenyl)cyclopropyl](cyclopropylmethyl) carbamate To a solution of tert-butyl [trans-2-(4-aminophenyl)cyclopropyl](cyclopropylmethyl)carbamate (90.9 mg), 4-benzamidobenzoic acid (87 mg) and 1-hydroxybenzotriazole (60.9 mg) in DMF (1.5 mL) was added N-ethyl-N'-(3-dimethylaminopropyl)carbodiimide hydrochloride (86 mg). The reaction mixture was stirred at room temperature for 2 hr, and poured into 0.5N hydrochloric acid. The mixture was extracted with ethyl acetate, and the extract was washed successively with water, saturated aqueous sodium hydrogen carbonate solution and saturated brine, and dried over anhydrous magnesium sulfate. The solvent was evaporated under reduced pressure. The residue was washed with ethyl acetate/diisopropyl ether to give the title compound (98.0 mg).

$^1$H NMR (300 MHz, DMSO-d$_6$) δ 0.07-0.17 (1H, m), 0.18-0.29 (1H, m), 0.34-0.52 (2H, m), 0.91-1.02 (1H, m), 1.15-1.28 (2H, m), 1.37 (9H, s), 2.01-2.12 (1H, m), 2.67-2.76 (1H, m), 3.00 (1H, dd, J=14.5, 7.0 Hz), 3.20 (1H, dd, J=14.5, 6.9 Hz), 7.12 (2H, d, J=8.7 Hz), 7.50-7.63 (3H, m), 7.67 (2H, d, J=8.7 Hz), 7.91-8.01 (6H, m), 10.09 (1H, s), 10.51 (1H, s).

B) 4-(benzoylamino)-N-(4-{trans-2-[(cyclopropylmethyl)amino]-cyclopropyl}phenyl)benzamide hydrochloride tert-Butyl [trans-2-(4-{[4-(benzoylamino)benzoyl]amino}phenyl)cyclopropyl]-(cyclopropylmethyl)carbamate (98.0 mg) was dissolved in 4N hydrochloric acid/cyclopentyl methyl ether solution (1 mL), and the mixture was stirred at room temperature for 2 hr. The solvent was evaporated under reduced pressure. The residue was recrystallized from methanol/diisopropyl ether to give the title compound (44.6 mg).

MS (API+): [M+H]$^+$ 426.4.

$^1$H NMR (300 MHz, DMSO-d$_6$) δ 0.32-0.41 (2H, m), 0.54-0.64 (2H, m), 0.98-1.14 (1H, m), 1.23-1.33 (1H, m), 1.43-1.55 (1H, m), 2.39-2.47 (1H, m), 2.85-3.05 (3H, m), 7.16 (2H, d, J=8.4 Hz), 7.51-7.66 (3H, m), 7.73 (2H, d, J=8.3 Hz), 7.89-8.05 (6H, m), 9.13 (2H, brs), 10.15 (1H, s), 10.53 (1H, s).

Example 81

N-(4-{trans-2-[(cyclopropylmethyl)amino]cyclopropyl}-2-methylphenyl)benzamide hydrochloride

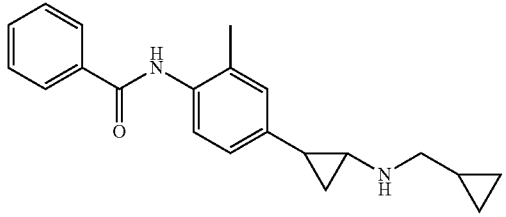 [SMILES: Cc1cc(C2CC2NCC2CC2)ccc1NC(=O)c1ccccc1]

A) N-(4-bromo-2-methylphenyl)benzamide

To a solution of 4-bromo-2-methylaniline (3.55 g) in pyridine (95 mL) was added benzoyl chloride (2.66 mL). The mixture was stirred at room temperature for 1 hr and the solvent was evaporated under reduced pressure. To the residue was added 2N hydrochloric acid. The mixture was extracted with ethyl acetate, and the extract was washed successively with 1N hydrochloric acid, saturated aqueous sodium hydrogen carbonate solution and saturated brine, and dried over anhydrous magnesium sulfate. The solvent was evaporated under reduced pressure. The residue was washed with diisopropyl ether to give the title compound (4.35 g).

$^1$H NMR (300 MHz, DMSO-d$_6$) δ 2.24 (3H, s), 7.33 (1H, d, J=8.5 Hz), 7.41 (1H, dd, J=8.5, 2.5 Hz), 7.49-7.64 (4H, m), 7.94-8.00 (2H, m), 9.90 (1H, brs).

B) ethyl trans-2-[4-(benzoylamino)-3-methylphenyl]cyclopropanecarboxylate

To a solution of N-(4-bromo-2-methylphenyl)benzamide (4.35 g) and 4,4,5,5-tetramethyl-2-vinyl-1,3,2-dioxaborolane (2.54 g) in THF (64.3 mL)/water (10.7 mL) were added 1,1'-bis(diphenylphosphino)ferrocene-palladium(II) dichloride-dichloromethane complex (0.367 g) and triethylamine (4.18 mL). The reaction mixture was stirred at 60° C. overnight, and poured into saturated aqueous ammonium chloride solution. The reaction mixture was extracted with ethyl acetate, and the extract was washed with saturated brine, and dried over anhydrous magnesium sulfate. The solvent was evaporated under reduced pressure. The residue was purified by silica gel column chromatography (hexane/ethyl acetate) to give a mixture (4.42 g) containing N-(2-methyl-4-vinylphenyl)benzamide. To a solution of the mixture (4.42 g) and copper(I) chloride (0.233 g) in toluene (36 mL)/THF (5 mL) was added dropwise a solution of ethyl diazoacetate (9.79 mL) in toluene (25 mL) at 80° C. over 1 hr or longer. The mixture was stirred at 80° C. overnight, cooled to room temperature, and filtered through celite. The mother liquor was concentrated under reduced pressure, and the residue was purified by silica gel column chromatography (hexane/ethyl acetate) to give the title compound (1.29 g).

$^1$H NMR (300 MHz, DMSO-d$_6$) δ 1.21 (3H, t, J=6.7 Hz), 1.34-1.53 (2H, m), 1.87-2.01 (1H, m), 2.20 (3H, s), 2.35-2.46 (1H, m), 4.11 (2H, q, J=6.7 Hz), 7.01 (1H, d, J=8.0 Hz), 7.09 (1H, s), 7.23 (1H, d, J=8.0 Hz), 7.47-7.62 (3H, m), 7.97 (2H, d, J=7.5 Hz), 9.83 (1H, s).

C) trans-2-[4-(benzoylamino)-3-methylphenyl]cyclopropanecarboxylic acid

To a solution of ethyl trans-2-[4-(benzoylamino)-3-methylphenyl]cyclopropanecarboxylate (1.29 g) in ethanol (7.98 mL) was added 1N aqueous sodium hydroxide solution (7.98 mL). The reaction mixture was stirred at 50° C. for 6.5 hr, 1N hydrochloric acid (10 mL) was added under ice-cooling, and the mixture was stirred under ice-cooling for 1 hr. The precipitate was collected by filtration to give the title compound (576.9 mg).

$^1$H NMR (300 MHz, DMSO-d$_6$) δ 1.30-1.47 (2H, m), 1.74-1.85 (1H, m), 2.20 (3H, s), 2.31-2.44 (1H, m), 7.00 (1H, d, J=8.3 Hz), 7.07 (1H, s), 7.19-7.27 (1H, m), 7.46-7.67 (3H, m), 7.97 (2H, d, J=7.6 Hz), 9.82 (1H, s), 12.30 (1H, brs).

D) tert-butyl{trans-2-[4-(benzoylamino)-3-methylphenyl]cyclopropyl}carbamate

To trans-2-[4-(benzoylamino)-3-methylphenyl]cyclopropanecarboxylic acid (576.0 mg) was added toluene (200 mL), and the solvent was evaporated under reduced pressure. The residue was suspended in toluene (10 ml), and triethylamine (0.326 mL), THF (2 mL) and diphenylphosphoryl azide (0.504 mL) were added. The reaction mixture was stirred at room temperature for 1 hr, and tert-butyl alcohol (1.83 mL) was added. The mixture was stirred at 80° C. overnight, and poured into saturated aqueous ammonium chloride solution. The reaction mixture was extracted with ethyl acetate, and the extract was washed successively with saturated aqueous sodium hydrogen carbonate solution and saturated brine, and dried over anhydrous magnesium sulfate. The solvent was evaporated under reduced pressure. The residue was purified by silica gel column chromatography (hexane/ethyl acetate) to give the title compound (125.8 mg).

$^1$H NMR (300 MHz, DMSO-d$_6$) δ 1.01-1.14 (2H, m), 1.39 (9H, s), 1.80-1.94 (1H, m), 2.19 (3H, s), 2.54-2.67 (1H, m), 6.92 (1H, dd, J=8.1, 1.5 Hz), 6.99 (1H, d, J=1.5 Hz), 7.19 (1H, d, J=8.1 Hz), 7.22-7.28 (1H, m), 7.46-7.63 (3H, m), 7.97 (2H, d, J=6.6 Hz), 9.81 (1H, s).

E) N-[4-(trans-2-aminocyclopropyl)-2-methylphenyl]benzamide hydrochloride tert-Butyl {trans-2-[4-(benzoylamino)-3-methylphenyl]cyclopropyl}carbamate (125.8 mg) was dissolved in 4N hydrochloric acid/cyclopentyl methyl ether solution (1.5 mL), and the mixture was stirred at room temperature for 2 hr. The solvent was evaporated under reduced pressure to give the title compound (95.9 mg).

$^1$H NMR (300 MHz, DMSO-d$_6$) δ 1.16-1.29 (1H, m), 1.31-1.42 (1H, m), 2.21 (3H, s), 2.24-2.33 (1H, m), 2.77-2.86 (1H, m), 7.01 (1H, dd, J=8.1, 1.9 Hz), 7.06 (1H, d, J=1.9 Hz), 7.26 (1H, d, J=8.1 Hz), 7.45-7.67 (3H, m), 7.97 (2H, d, J=6.8 Hz), 8.32 (3H, brs), 9.85 (1H, s).

F) N-(4-{trans-2-[(cyclopropylmethyl)amino]cyclopropyl}-2-methylphenyl)benzamide hydrochloride To a solution of N-[4-(trans-2-aminocyclopropyl)-2-methylphenyl]benzamide hydrochloride (90.1 mg) and sodium hydrogen carbonate (50.0 mg) in THF (1.49 mL)/methanol (1.49 mL) was added cyclopropanecarbaldehyde (0.029 mL). The reaction mixture was stirred at 0.60° C. for 1 hr, and ice-cooled to 0° C. and sodium borohydride (22.51 mg) was added. The mixture was stirred at room temperature overnight, and poured into saturated aqueous sodium hydrogen carbonate solution. The reaction mixture was extracted with ethyl acetate, and the extract was washed with saturated brine, and dried over anhydrous magnesium sulfate. The solvent was evaporated under reduced pressure. The residue was purified by silica gel column chromatography (hexane/ethyl acetate) and the solvent was evaporated under reduced pressure. The residue was dissolved in ethyl acetate (5 mL), and 4N hydrochloric acid/ethyl acetate solution (0.5 mL) was added. The solvent was evaporated under reduced pressure, and the residue was recrystallized from methanol/diisopropyl to give the title compound (55.9 mg).

MS (API+): [M+H]$^+$ 321.2.

$^1$H NMR (300 MHz, DMSO-d$_6$) δ 0.33-0.41 (2H, m), 0.54-0.64 (2H, m), 1.00-1.14 (1H, m), 1.23-1.34 (1H, m), 1.47-1.57 (1H, m), 2.21 (3H, s), 2.42-2.48 (1H, m), 2.86-3.05 (3H, m), 7.02 (1H, d, J=8.1 Hz), 7.08 (1H, s), 7.26 (1H, d, J=8.1 Hz), 7.44-7.64 (3H, m), 7.97 (2H, d, J=7.4 Hz), 9.24 (2H, brs), 9.85 (1H, s).

Example 82

N-(4-{trans-2-[(cyclopropylmethyl)amino]cyclopropyl}-3-methylphenyl)benzamide hydrochloride

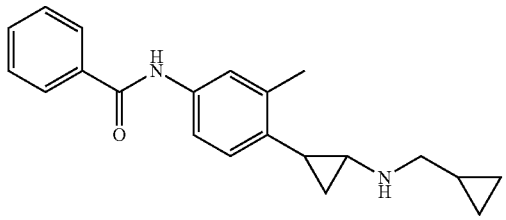 [SMILES: Cc1cc(NC(=O)c2ccccc2)ccc1C1CC1NCC1CC1]

By a method similar to Example 81, the title compound (50.1 mg) was obtained from 4-bromo-3-methylaniline (3.55 g).

MS (API+): [M+H]$^+$ 321.4.

$^1$H NMR (300 MHz, DMSO-d$_6$) δ 0.34-0.43 (2H, m), 0.54-0.67 (2H, m), 0.98-1.27 (2H, m), 1.37-1.51 (1H, m), 2.39 (3H, s), 2.41-2.46 (1H, m), 2.89-3.06 (3H, m), 6.99 (1H, d, J=8.5 Hz), 7.46-7.66 (5H, m), 7.94 (2H, d, J=7.4 Hz), 9.04 (2H, brs), 10.16 (1H, s).

Example 83

N-(4-{trans-2-[(cyclopropylmethyl)amino]cyclopropyl}phenyl)-3-(dimethylamino)benzamide bis(trifluoroacetate)

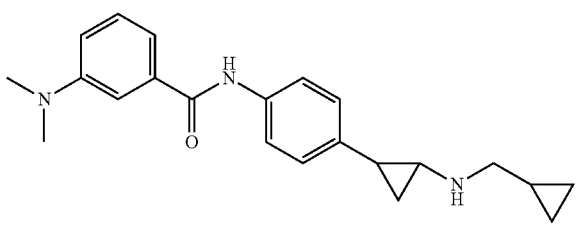 [SMILES: CN(C)c1cccc(C(=O)Nc2ccc(C3CC3NCC3CC3)cc2)c1]

To tert-butyl [trans-2-(4-aminophenyl)cyclopropyl](cyclopropylmethyl)carbamate (30 mg) were added a solution of 3-(dimethylamino)benzoic acid (33 mg) in DMF (1 mL), O-(7-azabenzotriazol-1-yl)-N,N,N',N'-tetramethyluronium hexafluorophosphate (76 mg), and N,N-diisopropylethylamine (26 mg), and the mixture was stirred at room temperature overnight. To the reaction mixture were added water (1 mL) and ethyl acetate (3 mL) and the mixture was stirred. The organic layer was passed through a phase separation filter, and the solvent was evaporated from the separate liquid by an air blowing apparatus. To the residue was added trifluoroacetic acid (200 µL) and the mixture was stirred for 1 hr. The solvent was evaporated by an air blowing apparatus. The residue was purified by HPLC (column: YMC Triart C18, mobile phase: 0.1% trifluoroacetic acid-acetonitrile/0.1% aqueous trifluoroacetic acid solution) to give the title compound (12.6 mg).

MS (API+): [M+H]$^+$ 350.1.

The compounds produced by the method described in the above-mentioned Example 83 or a method analogous thereto are shown in the following Tables. In the Tables, MS shows measured values.

TABLE 1-6

| Ex. No. | IUPAC name | structure | salt | MS |
|---|---|---|---|---|
| 84 | N-(4-{trans-2-[(cyclopropylmethyl)amino]cyclopropyl}-phenyl)-4-(dimethylamino)-benzamide | 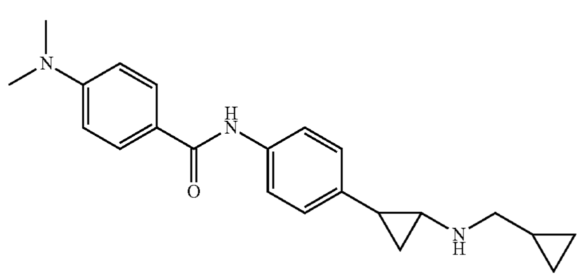 [SMILES: CN(C)c1ccc(C(=O)Nc2ccc(C3CC3NCC3CC3)cc2)cc1] | 2CF3COOH | 350.1 |

TABLE 1-6-continued

| Ex. No. | IUPAC name | structure | salt | MS |
|---|---|---|---|---|
| 85 | N-(4-{trans-2-[(cyclopropylmethyl)amino]cyclopropyl}-phenyl)-5,6,7,8-tetrahydronaphthalene-2-carboxamide | 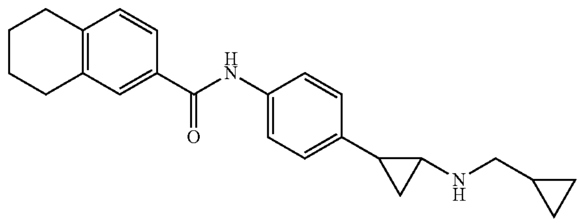 [SMILES: O=C(Nc1ccc(C2CC2NCC2CC2)cc1)c1ccc2c(c1)CCCC2] | CF3COOH | 361.1 |
| 86 | N-(4-{trans-2-[(cyclopropylmethyl)amino]cyclopropyl}-phenyl)-4-(3-methyl-5-oxo-4,5-dihydro-1H-pyrazol-1-yl)benzamide | 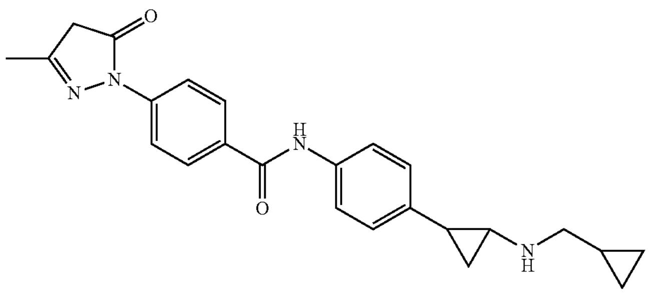 [SMILES: CC1=NN(c2ccc(C(=O)Nc3ccc(C4CC4NCC4CC4)cc3)cc2)C(=O)C1] | CF3COOH | 403.1 |
| 87 | N-{4-{trans-2-[(cyclopropylmethyl)amino]cyclopropyl}-phenyl)-4-(methylsulfonyl)-benzamide | 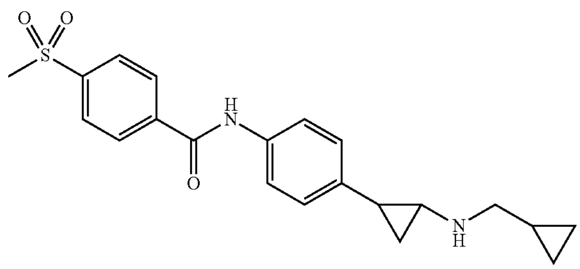 [SMILES: CS(=O)(=O)c1ccc(C(=O)Nc2ccc(C3CC3NCC3CC3)cc2)cc1] | CF3COOH | 385.0 |
| 88 | N-(4-{trans-2-[(cyclopropylmethyl)amino]cyclopropyl}-phenyl)-4-sulfamoylbenzamide | 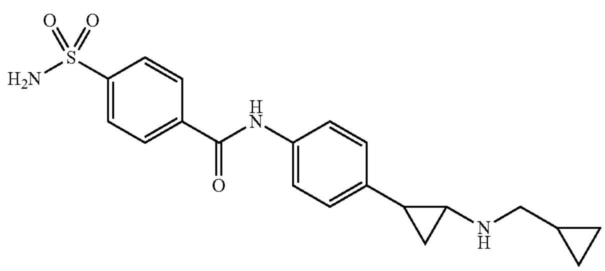 [SMILES: NS(=O)(=O)c1ccc(C(=O)Nc2ccc(C3CC3NCC3CC3)cc2)cc1] | CF3COOH | 386.0 |
| 89 | 4-cyclohexyl-N-(4-{trans-2-[(cyclopropylmethyl)amino]cyclopropyl}-phenyl)benzamide | 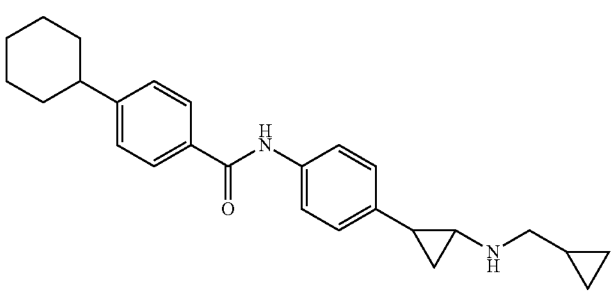 [SMILES: O=C(Nc1ccc(C2CC2NCC2CC2)cc1)c1ccc(C2CCCCC2)cc1] | CF3COOH | 389.1 |
| 90 | N-(4-{trans-2-[(cyclopropylmethyl)amino]cyclopropyl}-phenyl)-1,3-benzothiazole-6-carboxamide | 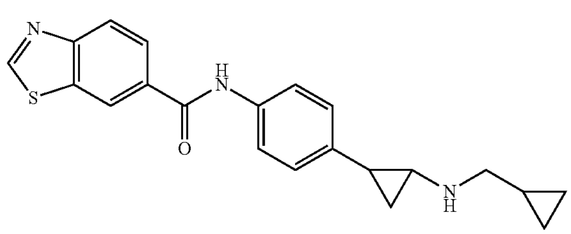 [SMILES: O=C(Nc1ccc(C2CC2NCC2CC2)cc1)c1ccc2ncsc2c1] | CF3COOH | 364.0 |

TABLE 1-6-continued

| Ex. No. | IUPAC name | structure | salt | MS |
|---|---|---|---|---|
| 91 | N-(4-{trans-2-[(cyclopropylmethyl)amino]cyclopropyl}-phenyl)-3-(methylsulfonyl)-benzamide | 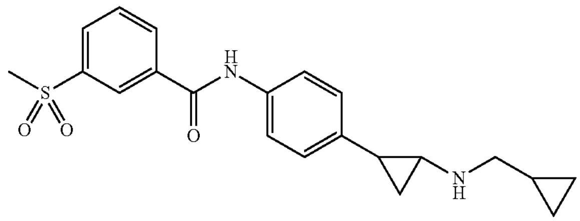 [SMILES: CS(=O)(=O)c1cccc(C(=O)Nc2ccc(C3CC3NCC3CC3)cc2)c1] | CF3COOH | 385.0 |

TABLE 1-7

| Ex. No. | IUPAC name | structure | salt | MS |
|---|---|---|---|---|
| 92 | N-(4-{trans-2-[(cyclopropylmethyl)-amino]cyclopropyl}-phenyl)-4-(1H-imidazol-1-yl)benzamide | 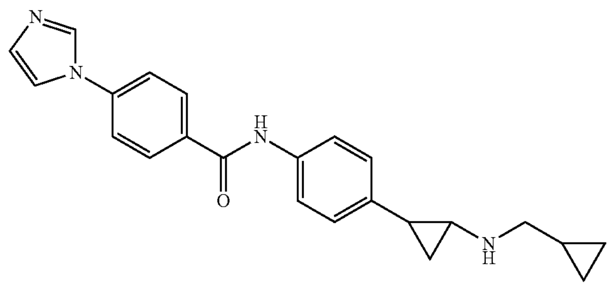 [SMILES: O=C(Nc1ccc(C2CC2NCC2CC2)cc1)c1ccc(-n2ccnc2)cc1] | 2CF3COOH | 373.0 |
| 93 | N-{4-{trans-2-[(cyclopropylmethyl)-amino]cyclopropyl}-phenyl)-5-phenyl-1,2-oxazole-3-carboxamide | 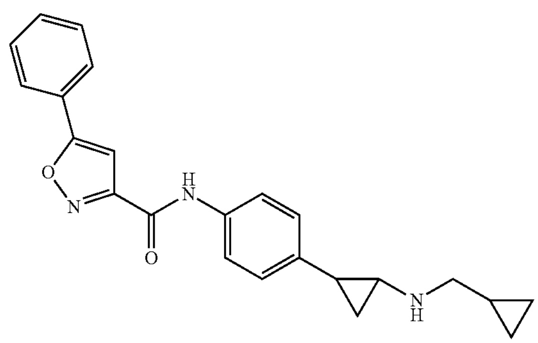 [SMILES: O=C(Nc1ccc(C2CC2NCC2CC2)cc1)c1cc(-c2ccccc2)on1] | CF3COOH | 374.0 |
| 94 | N-(4-{trans-2-[(cyclopropylmethyl)-amino]cyclopropyl}-phenyl)-4-(1H-pyrazol-1-yl)benzamide | 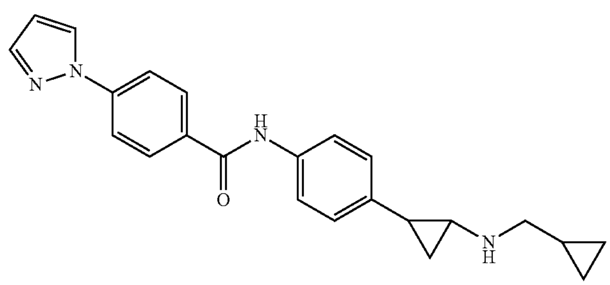 [SMILES: O=C(Nc1ccc(C2CC2NCC2CC2)cc1)c1ccc(-n2cccn2)cc1] | 2CF3COOH | 373.0 |
| 95 | N-(4-{trans-2-[(cyclopropylmethyl)-amino]cyclopropyl}-phenyl)-4-(1,3-oxazol-5-yl)benzamide | 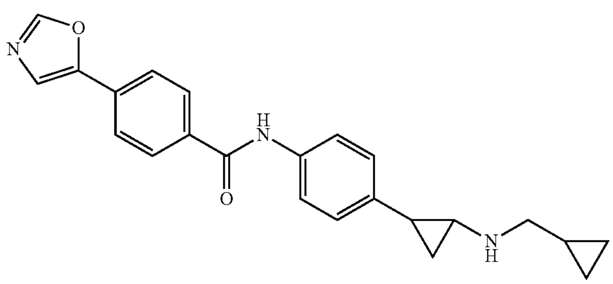 [SMILES: O=C(Nc1ccc(C2CC2NCC2CC2)cc1)c1ccc(-c2cnco2)cc1] | CF3COOH | 374.0 |

TABLE 1-7-continued

| Ex. No. | IUPAC name | structure | salt | MS |
|---|---|---|---|---|
| 96 | N-(4-{trans-2-[(cyclopropylmethyl)-amino]cyclopropyl}-phenyl)-4-(pyridin-4-yl)benzamide | 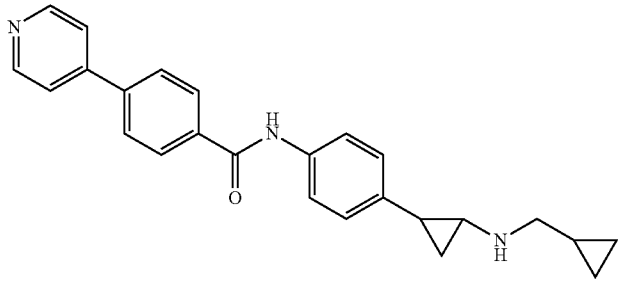 [SMILES: O=C(Nc1ccc(C2CC2NCC2CC2)cc1)c1ccc(-c2ccncc2)cc1] | 2CF3COOH | 384.1 |
| 97 | N-(4-{trans-2-[(cyclopropylmethyl)-amino]cyclopropyl}-phenyl)-2-(3-thienyl)-1H-benzimidazole-6-carboxamide | 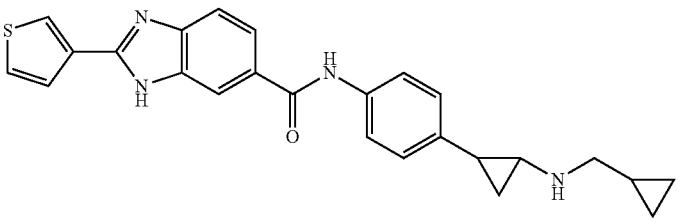 [SMILES: O=C(Nc1ccc(C2CC2NCC2CC2)cc1)c1ccc2nc(-c3ccsc3)[nH]c2c1] | CF3COOH | 429.1 |
| 98 | N-(4-{trans-2-[(cyclopropylmethyl)-amino]cyclopropyl}-phenyl)-2-(2-furyl)-1H-benzimidazole-6-carboxamide | 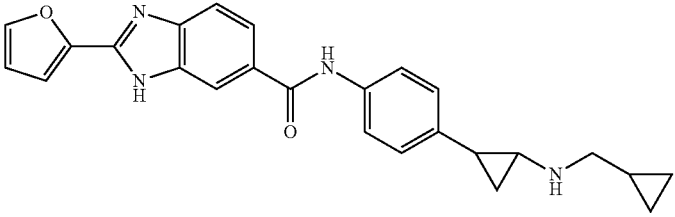 [SMILES: O=C(Nc1ccc(C2CC2NCC2CC2)cc1)c1ccc2nc(-c3ccco3)[nH]c2c1] | CF3COOH | 413.1 |
| 99 | N-(4-{trans-2-[(cyclopropylmethyl)-amino]cyclopropyl}-phenyl)-1H-indazole-5-carboxamide | 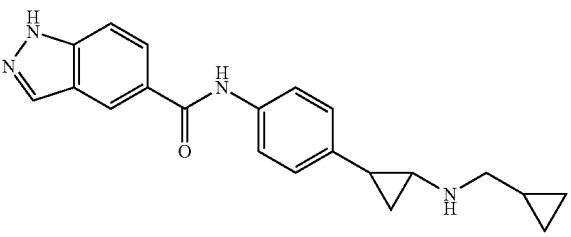 [SMILES: O=C(Nc1ccc(C2CC2NCC2CC2)cc1)c1ccc2[nH]ncc2c1] | 2CF3COOH | 347.0 |

TABLE 1-8

| Ex. No. | IUPAC name | structure | salt | MS |
|---|---|---|---|---|
| 100 | N-(4-{trans-2-[(cyclopropylmethyl)-amino]cyclopropyl}-phenyl)-3-(1H-tetrazol-1-yl)benzamide | 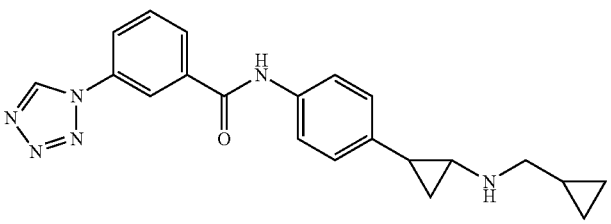 [SMILES: O=C(Nc1ccc(C2CC2NCC2CC2)cc1)c1cccc(-n2cnnn2)c1] | CF3COOH | 375.0 |

TABLE 1-8-continued

| Ex. No. | IUPAC name | structure | salt | MS |
|---|---|---|---|---|
| 101 | N-(4-{trans-2-[(cyclopropylmethyl)-amino]cyclopropyl}-phenyl)-3-(2-methyl-1,3-thiazol-4-yl)benzamide | 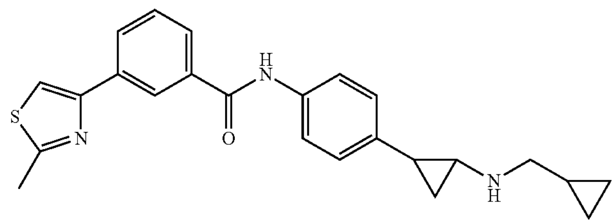 [SMILES: Cc1nc(-c2cccc(C(=O)Nc3ccc(C4CC4NCC4CC4)cc3)c2)cs1] | CF3COOH | 404.1 |
| 102 | N-(4-{trans-2-[(cyclopropylmethyl)-amino]cyclopropyl}-phenyl)-4-(1H-tetrazol-5-yl)benzamide | 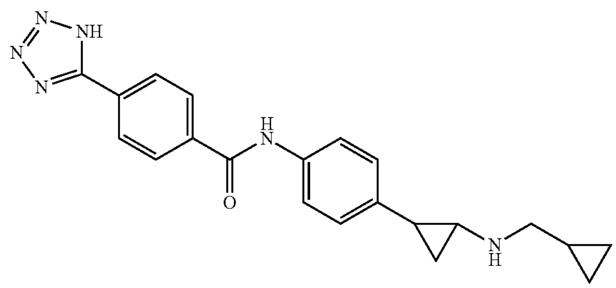 [SMILES: O=C(Nc1ccc(C2CC2NCC2CC2)cc1)c1ccc(-c2nnn[nH]2)cc1] | CF3COOH | 375.0 |
| 103 | N-(4-{trans-2-[(cyclopropylmethyl)-amino]cyclopropyl}-phenyl)-2-phenyl-1,3-oxazole-4-carboxamide | 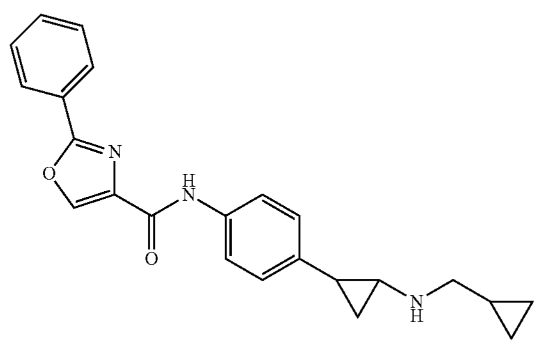 [SMILES: O=C(Nc1ccc(C2CC2NCC2CC2)cc1)c1coc(-c2ccccc2)n1] | CF3COOH | 374.0 |
| 104 | N-(4-{trans-2-[(cyclopropylmethyl)-amino]cyclopropyl}-phenyl)-2-phenyl-1,3-oxazole-5-carboxamide | 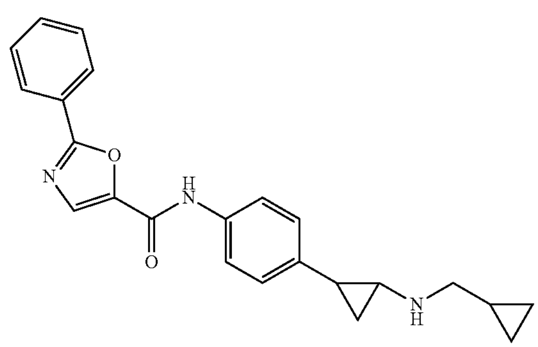 [SMILES: O=C(Nc1ccc(C2CC2NCC2CC2)cc1)c1cnc(-c2ccccc2)o1] | CF3COOH | 374.0 |

Example 105

N-(4-{trans-2-[(cyclopropylmethyl)amino]cyclopropyl}phenyl)-3,4-dimethylbenzamide hydrochloride

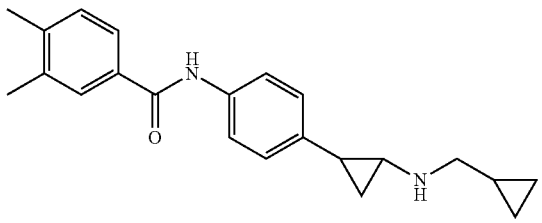 [SMILES: Cc1ccc(C(=O)Nc2ccc(C3CC3NCC3CC3)cc2)cc1C]

By a method similar to Example 80, the title compound (54.7 mg) was obtained from tert-butyl [trans-2-(4-aminophenyl)cyclopropyl](cyclopropylmethyl)carbamate (94.0 mg) and 3,4-dimethylbenzoic acid (56.0 mg).

MS (API+): [M+H]+ 335.3.

$^1$H NMR (300 MHz, DMSO-$d_6$) δ 0.25-0.44 (2H, m), 0.53-0.62 (2H, m), 0.98-1.13 (1H, m), 1.19-1.32 (1H, m), 1.41-1.52 (1H, m), 2.30 (6H, brs), 2.36-2.47 (1H, m), 2.83-2.99 (3H, m), 7.15 (2H, d, J=7.9 Hz), 7.28 (1H, d, J=8.0 Hz), 7.63-7.78 (4H, m), 9.00 (2H, brs), 10.10 (1H, s).

Example 106

N-(4-{trans-2-[(cyclopropylmethyl)amino]cyclopropyl}phenyl)-2,5-dimethylbenzamide hydrochloride

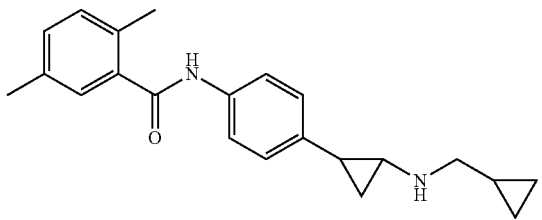 [SMILES: Cc1ccc(C)c(C(=O)Nc2ccc(C3CC3NCC3CC3)cc2)c1]

By a method similar to Example 80, the title compound (50.9 mg) was obtained from tert-butyl [trans-2-(4-aminophenyl)cyclopropyl](cyclopropylmethyl)carbamate (94.6 mg) and 2,5-dimethylbenzoic acid (56.4 mg).

MS (API+): [M+H]+ 335.3.

$^1$H NMR (300 MHz, DMSO-$d_6$) δ 0.33-0.41 (2H, m), 0.53-0.64 (2H, m), 1.00-1.12 (1H, m), 1.19-1.31 (1H, m), 1.42-1.55 (1H, m), 2.31 (6H, s), 2.39-2.47 (1H, m), 2.83-3.05 (3H, m), 7.09-7.27 (5H, m), 7.66 (2H, d, J=7.9 Hz), 9.17 (2H, brs), 10.23 (1H, s).

Example 107

N-(4-{trans-2-[(imidazo[1,2-a]pyridin-6-ylmethyl)amino]cyclopropyl}phenyl)-3-(trifluoromethyl)benzamide dihydrochloride

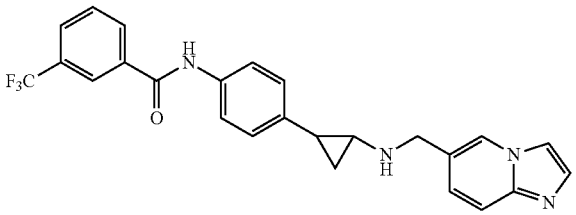 [SMILES: O=C(Nc1ccc(C2CC2NCc2ccc3nccn3c2)cc1)c1cccc(C(F)(F)F)c1]

By a method similar to Example 65, the title compound (33 mg) was obtained from N-[4-(trans-2-aminocyclopropyl)phenyl]-3-(trifluoromethyl)benzamide hydrochloride (80 mg) and imidazo[1,2-a]pyridine-6-carbaldehyde (42.6 mg).

MS (API+): [M+H]+ 451.0.

$^1$H NMR (300 MHz, CD$_3$OD) δ 1.34-1.44 (1H, m), 1.56-1.69 (1H, m), 2.40-2.51 (1H, m), 3.03-3.11 (1H, m), 4.54-4.70 (2H, m), 7.02 (2H, d, J=8.5 Hz), 7.58 (2H, d, J=8.7 Hz), 7.70 (1H, t, J=7.7 Hz), 7.83-7.89 (1H, m), 7.96-8.07 (2H, m), 8.13-8.25 (4H, m), 9.01-9.05 (1H, m).

Example 108

N-(4-{trans-2-[(cyclopropylmethyl)amino]cyclopropyl}phenyl)-4-(trifluoromethoxy)benzamide hydrochloride

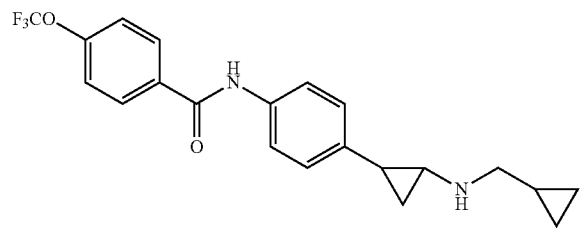 [SMILES: O=C(Nc1ccc(C2CC2NCC2CC2)cc1)c1ccc(OC(F)(F)F)cc1]

By a method similar to Example 80, the title compound (55.7 mg) was obtained from tert-butyl [trans-2-(4-aminophenyl)cyclopropyl](cyclopropylmethyl)carbamate (87.2 mg) and 4-(trifluoromethoxy)benzoic acid (71.3 mg).

MS (API+): [M+H]+ 391.3.

$^1$H NMR (300 MHz, DMSO-$d_6$) δ 0.30-0.41 (2H, m), 0.51-0.65 (2H, m), 0.93-1.13 (1H, m), 1.19-1.36 (1H, m), 1.38-1.55 (1H, m), 2.33-2.46 (1H, m), 2.82-3.04 (3H, m), 7.17 (2H, d, J=8.1 Hz), 7.53 (2H, d, J=8.1 Hz), 7.70 (2H, d, J=8.1 Hz), 8.07 (2H, d, J=8.1 Hz), 8.90 (2H, brs), 10.33 (1H, s).

Example 109

N-(4-{trans-2-[(cyclopropylmethyl)amino]cyclopropyl}phenyl)-3-(trifluoromethoxy)benzamide hydrochloride

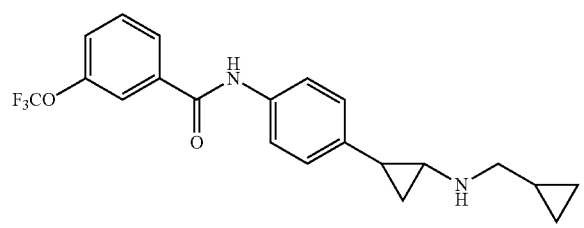 [SMILES: O=C(Nc1ccc(C2CC2NCC2CC2)cc1)c1cccc(OC(F)(F)F)c1]

By a method similar to Example 80, the title compound (82.8 mg) was obtained from tert-butyl [trans-2-(4-aminophenyl)cyclopropyl](cyclopropylmethyl)carbamate (88.4 mg) and 3-(trifluoromethoxy)benzoic acid (72.3 mg).

MS (API+): [M+H]+ 391.3.

$^1$H NMR (300 MHz, DMSO-$d_6$) δ 0.30-0.40 (2H, m), 0.52-0.63 (2H, m), 0.95-1.11 (1H, m), 1.21-1.32 (1H, m), 1.37-1.55 (1H, m), 2.31-2.46 (1H, m), 2.79-3.08 (3H, m), 7.18 (2H, d, J=8.5 Hz), 7.56-7.76 (4H, m), 7.90 (1H, s), 8.01 (1H, d, J=7.8 Hz), 8.96 (2H, brs), 10.37 (1H, s).

Example 110

N-[4-(trans-2-{[4-(dimethylamino)benzyl]amino}cyclopropyl)phenyl]-3-(trifluoromethyl)benzamide dihydrochloride

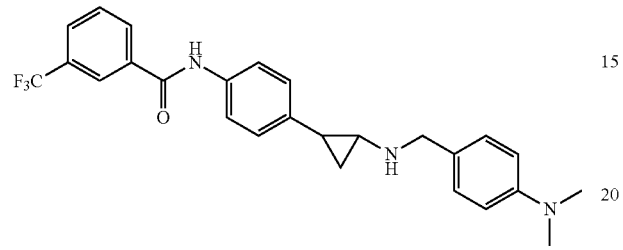

By a method similar to Example 65, the title compound (30 mg) was obtained from N-[4-(trans-2-aminocyclopropyl)phenyl]-3-(trifluoromethyl)benzamide hydrochloride (80 mg) and 4-(dimethylamino)benzaldehyde (43.5 mg).

MS (API+): [M+H]$^+$ 454.0.

$^1$H NMR (300 MHz, CD$_3$OD) δ 1.35-1.45 (1H, m), 1.47-1.58 (1H, m), 2.36-2.47 (1H, m), 2.91-3.03 (1H, m), 3.07-3.24 (6H, m), 4.40 (2H, d, J=2.8 Hz), 7.09-7.16 (2H, m), 7.33 (2H, d, J=8.5 Hz), 7.57 (2H, d, J=8.7 Hz), 7.67 (2H, d, J=8.5 Hz), 7.71-7.77 (1H, m), 7.90 (1H, d, J=7.9 Hz), 8.18-8.26 (2H, m).

Example 111

N-(4-{trans-2-[(1-cyclopropylpiperidin-4-yl)amino]cyclopropyl}phenyl)-3-(trifluoromethyl)benzamide dihydrochloride

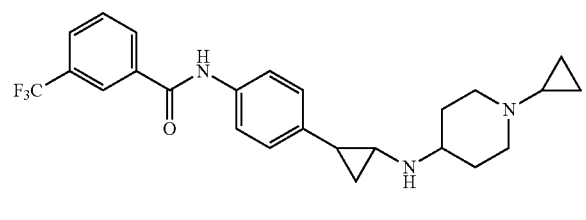 [SMILES: O=C(Nc1ccc(C2CC2NC2CCN(C3CC3)CC2)cc1)c1cccc(C(F)(F)F)c1]

By a method similar to Example 65, the title compound (50 mg) was obtained from N-[4-(trans-2-aminocyclopropyl)phenyl]-3-(trifluoromethyl)benzamide hydrochloride (60 mg) and 1-cyclopropylpiperidin-4-one (30.4 mg).

MS (API+): [M+H]$^+$ 444.3.

$^1$H NMR (300 MHz, CD$_3$OD) δ 0.89-1.00 (2H, m), 1.02-1.10 (2H, m), 1.46 (1H, q, J=6.8 Hz), 1.52-1.62 (1H, m), 2.01-2.16 (2H, m), 2.35-2.47 (2H, m), 2.52 (1H, ddd, J=10.0, 6.5, 3.5 Hz), 2.68-2.82 (1H, m), 3.02 (1H, dt, J=7.6, 3.8 Hz), 3.17-3.29 (2H, m), 3.62-3.81 (3H, m), 7.24 (2H, d, J=8.3 Hz), 7.67-7.78 (3H, m), 7.90 (1H, d, J=7.9 Hz), 8.16-8.27 (2H, m).

Example 112

N-[4-(trans-2-{[1-(1-methylethyl)piperidin-4-yl]amino}cyclopropyl)phenyl]-3-(trifluoromethyl)benzamide dihydrochloride

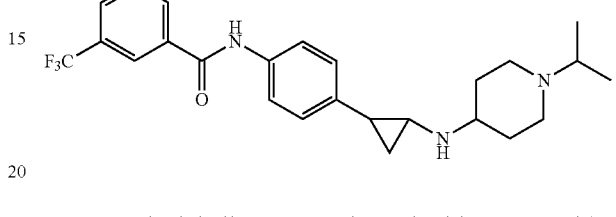

By a method similar to Example 65, the title compound (51 mg) was obtained from N-[4-(trans-2-aminocyclopropyl)phenyl]-3-(trifluoromethyl)benzamide hydrochloride (60 mg) and 1-isopropylpiperidin-4-one (30.9 mg).

MS (API+): [M+H]$^+$ 446.1.

$^1$H NMR (300 MHz, CD$_3$OD) δ 1.36-1.52 (7H, m), 1.56-1.68 (1H, m), 2.09-2.29 (2H, m), 2.43-2.54 (2H, m), 2.55-2.64 (1H, m), 3.01-3.09 (1H, m), 3.14-3.28 (2H, m), 3.50-3.81 (4H, m), 7.24 (2H, d, J=8.7 Hz), 7.63-7.79 (3H, m), 7.90 (1H, d, J=7.9 Hz), 8.16-8.28 (2H, m).

Example 113

N-(4-{trans-2-[(cyclopropylmethyl)amino]cyclopropyl}phenyl)-4-(1H-pyrazol-3-yl)benzamide hydrochloride

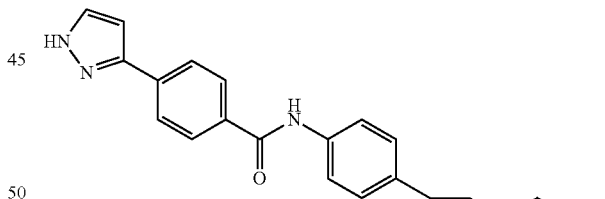

By a method similar to Example 79, the title compound (78 mg) was obtained from tert-butyl [trans-2-(4-aminophenyl)cyclopropyl](cyclopropylmethyl)carbamate (100 mg) and 4-(1H-pyrazol-3-yl)benzoic acid (93 mg).

MS (API+): [M+H]$^+$ 373.0.

$^1$H NMR (300 MHz, CD$_3$OD) δ 0.42 (2H, q, J=4.8 Hz), 0.68-0.77 (2H, m), 1.05-1.19 (1H, m), 1.39 (1H, q, J=6.8 Hz), 1.45-1.55 (1H, m), 2.48 (1H, ddd, J=10.3, 6.6, 3.7 Hz), 2.99 (1H, dt, J=7.8, 4.1 Hz), 3.05-3.13 (2H, m), 6.91-6.96 (1H, m), 7.19 (2H, d, J=8.7 Hz), 7.67 (2H, d, J=8.7 Hz), 7.90-7.98 (3H, m), 8.02 (2H, d, J=7.5 Hz).

Example 114

N-(4-{trans-2-[(cyclopropylmethyl)amino]cyclopropyl}phenyl)-1H-indole-5-carboxamide trifluoroacetate

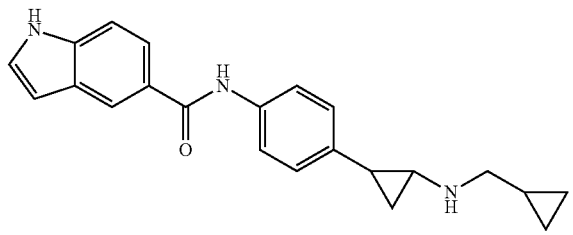 [SMILES: O=C(Nc1ccc(C2CC2NCC2CC2)cc1)c1ccc2[nH]ccc2c1]

To tert-butyl [trans-2-(4-aminophenyl)cyclopropyl](cyclopropylmethyl)carbamate (30 mg) were added a solution of indole-5-carboxylic acid (32 mg) in DMF (1 mL), N-ethyl-N'-(3-dimethylaminopropyl)carbodiimide hydrochloride (28.8 mg) and 1-hydroxybenzotriazole (20 mg), and the mixture was stirred at room temperature overnight. To the reaction solution were added water (1 mL) and ethyl acetate (3 mL) and the mixture was stirred. The organic layer was passed through a phase separation filter, and the solvent was evaporated from the separated liquid by an air blowing apparatus. To the residue was added trifluoroacetic acid (200 μL) and the mixture was stirred for 1 hr. The solvent was evaporated by an air blowing apparatus. The residue was purified by HPLC (column: YMC Triart C18, mobile phase: 0.1% trifluoroacetic acid-acetonitrile/0.1% aqueous trifluoroacetic acid solution) to give the title compound (18.1 mg).

MS (API+): [M+H]$^+$ 345.9.

The compounds produced by the method described in the above-mentioned Example 114 or a method analogous thereto are shown in the following Tables. In the Tables, MS shows measured values.

TABLE 1-9

| Ex. No. | IUPAC name | structure | salt | MS |
|---|---|---|---|---|
| 115 | N-(4-{trans-2-[(cyclopropylmethyl)amino]cyclopropyl}-phenyl)-1H-indole-6-carboxamide | 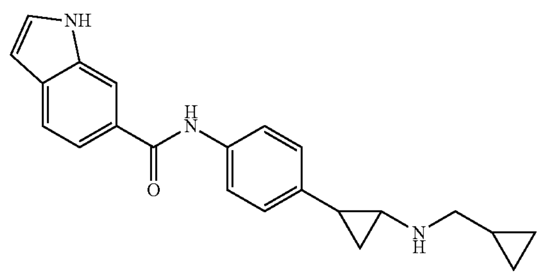 [SMILES: O=C(Nc1ccc(C2CC2NCC2CC2)cc1)c1ccc2cc[nH]c2c1] | CF3COOH | 345.9 |
| 116 | N-(4-{trans-2-[(cyclopropylmethyl)amino]cyclopropyl}-phenyl)-4'-propylbiphenyl-4-carboxamide | 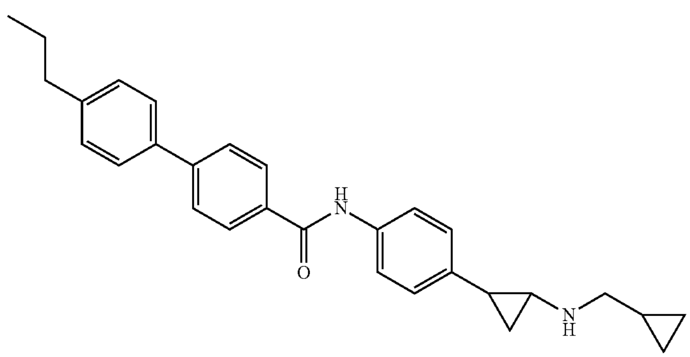 [SMILES: CCCc1ccc(-c2ccc(C(=O)Nc3ccc(C4CC4NCC4CC4)cc3)cc2)cc1] | CF3COOH | 425.1 |
| 117 | N-(4-{trans-2-[(cyclopropylmethyl)amino]cyclopropyl}-phenyl)-4-(1H-pyrrol-1-yl)benzamide | 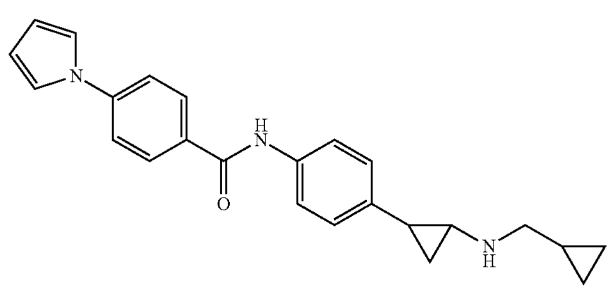 [SMILES: O=C(Nc1ccc(C2CC2NCC2CC2)cc1)c1ccc(-n2cccc2)cc1] | 2CF3COOH | 372.0 |

TABLE 1-9-continued

| Ex. No. | IUPAC name | structure | salt | MS |
|---|---|---|---|---|
| 118 | N-(4-{trans-2-[(cyclopropylmethyl)amino]cyclopropyl}-phenyl)-4'-methylbiphenyl-4-carboxamide | 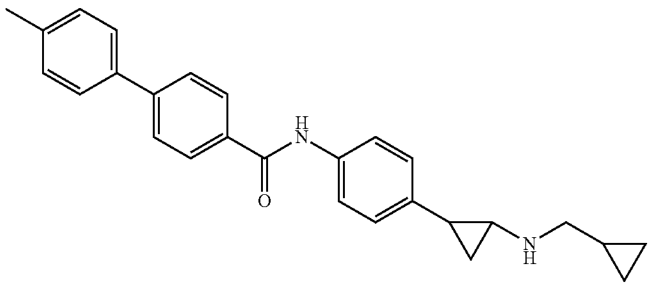 [SMILES: Cc1ccc(-c2ccc(C(=O)Nc3ccc(C4CC4NCC4CC4)cc3)cc2)cc1] | CF3COOH | 397.1 |
| 119 | N-(4-{trans-2-[(cyclopropylmethyl)amino]cyclopropyl}-phenyl)-4-(1,2,3-thiadiazol-4-yl)benzamide | 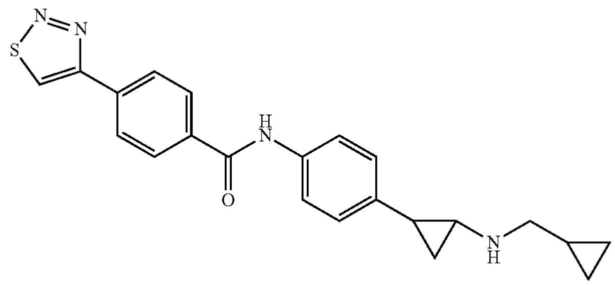 [SMILES: O=C(Nc1ccc(C2CC2NCC2CC2)cc1)c1ccc(-c2csnn2)cc1] | CF3COOH | 390.9 |
| 120 | 4'-tert-butyl-N-(4-{trans-2-[(cyclopropylmethyl)amino]cyclopropyl}-phenyl)biphenyl-4-carboxamide | 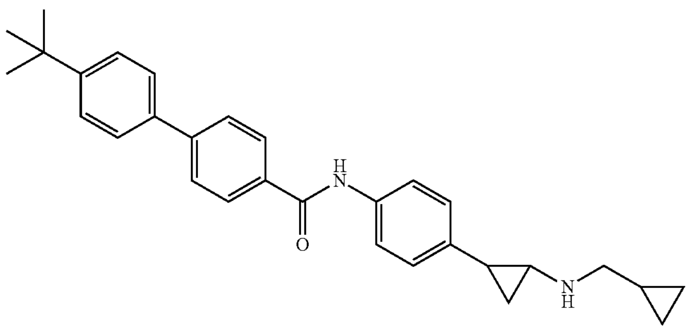 [SMILES: CC(C)(C)c1ccc(-c2ccc(C(=O)Nc3ccc(C4CC4NCC4CC4)cc3)cc2)cc1] | CF3COOH | 439.1 |
| 121 | N-(4-{trans-2-[(cyclopropylmethyl)amino]cyclopropyl}-phenyl)-5-methyl-1-phenyl-1H-pyrazole-4-carboxamide | 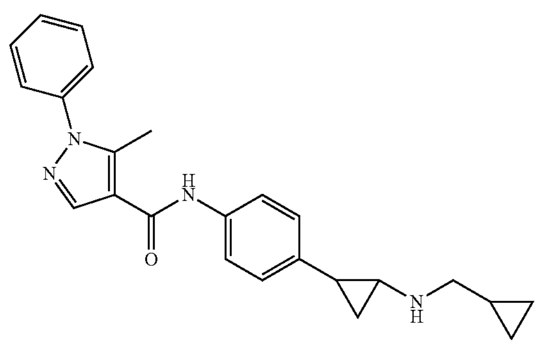 [SMILES: Cc1c(C(=O)Nc2ccc(C3CC3NCC3CC3)cc2)cnn1-c1ccccc1] | 2CF3COOH | 387.0 |
| 122 | N-(4-{trans-2-[(cyclopropylmethyl)amino]cyclopropyl}-phenyl)-5-methyl-2-phenyl-1,3-oxazole-4-carboxamide | 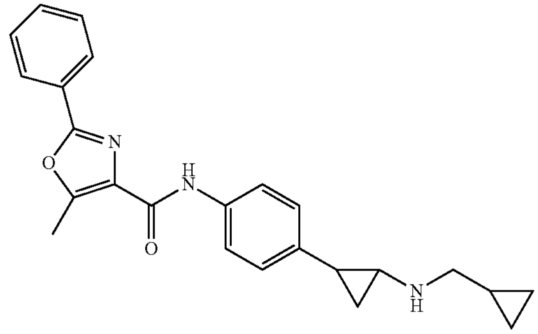 [SMILES: Cc1oc(-c2ccccc2)nc1C(=O)Nc1ccc(C2CC2NCC2CC2)cc1] | CF3COOH | 388.0 |

TABLE 1-10

| Ex. No. | IUPAC name | structure | salt | MS |
|---|---|---|---|---|
| 123 | N-(4-{trans-2-[(cyclopropyl-methyl)amino]cyclo-propyl}phenyl)-5-phenyl-2-furamide | 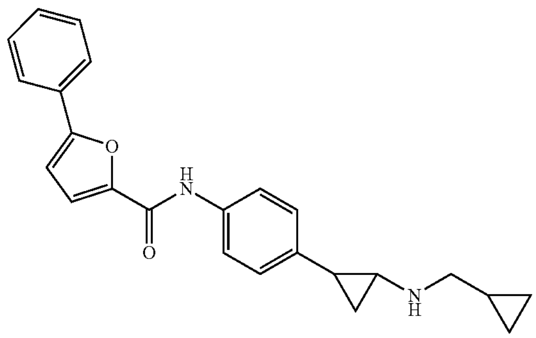 [SMILES: O=C(Nc1ccc(C2CC2NCC2CC2)cc1)c1ccc(-c2ccccc2)o1] | CF3COOH | 372.9 |
| 124 | N~(4-{trans-2-[(cyclopropyl-methyl)amino]cyclo-propyl}phenyl)-1-phenyl-1H-pyrazole-4-carboxamide | 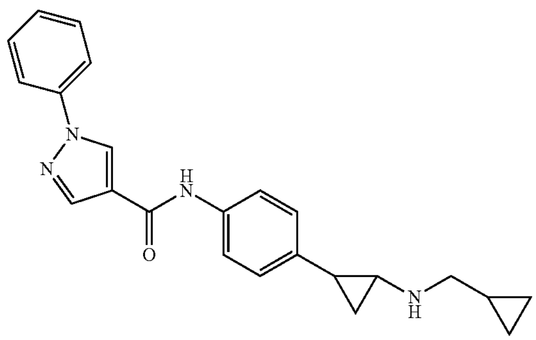 [SMILES: O=C(Nc1ccc(C2CC2NCC2CC2)cc1)c1cnn(-c2ccccc2)c1] | 2CF3COOH | 373.0 |
| 125 | N-(4-{trans-2-[(cyclopropyl-methyl)amino]cyclo-propyl}phenyl)-4-phenyl-1,3-thiazole-2-carboxamide | 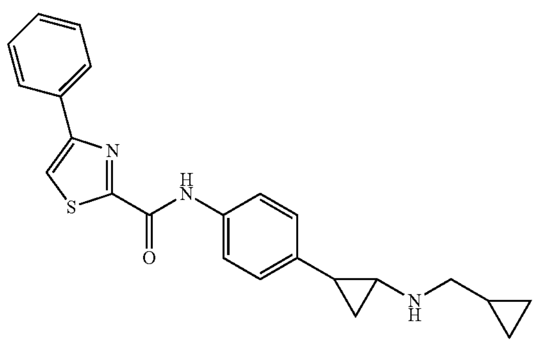 [SMILES: O=C(Nc1ccc(C2CC2NCC2CC2)cc1)c1nc(-c2ccccc2)cs1] | CF3COOH | 389.9 |
| 126 | N- (4-{trans-2-[(cyclopropyl-methyl)amino]cyclo-propyl}phenyl)-5-phenyl-1H-pyrazole-3-carboxamide | 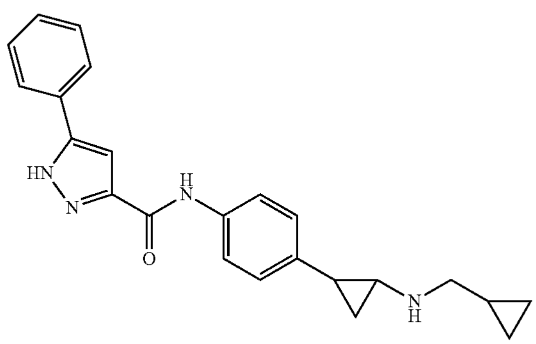 [SMILES: O=C(Nc1ccc(C2CC2NCC2CC2)cc1)c1cc(-c2ccccc2)[nH]n1] | 2CF3COOH | 373.0 |

TABLE 1-10-continued

| Ex. No. | IUPAC name | structure | salt | MS |
|---|---|---|---|---|
| 127 | N-(4-{trans-2-[(cyclopropyl-methyl)amino]cyclo-propyl}phenyl)-1H-indole-3-carboxamide | 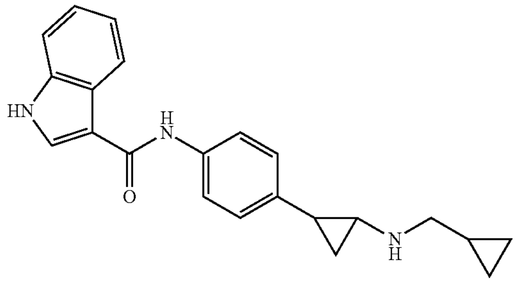 [SMILES: O=C(Nc1ccc(C2CC2NCC2CC2)cc1)c1c[nH]c2ccccc12] | CF3COOH | 345.9 |
| 128 | N-(4-{trans-2-[(cyclopropyl-methyl)amino]cyclo-propyl}phenyl)-1H-indazole-3-carboxamide | 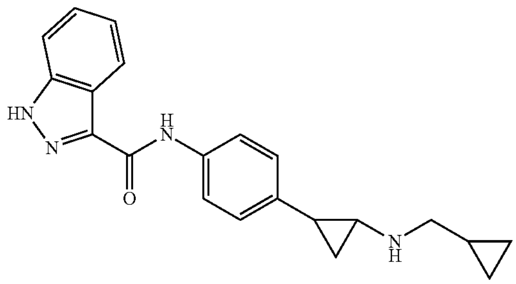 [SMILES: O=C(Nc1ccc(C2CC2NCC2CC2)cc1)c1n[nH]c2ccccc12] | CF3COOH | 346.9 |
| 129 | N-(4-{trans-2-[(cyclopropyl-methyl)amino]cyclo-propyl}phenyl)-1-benzofuran-2-carboxamide | 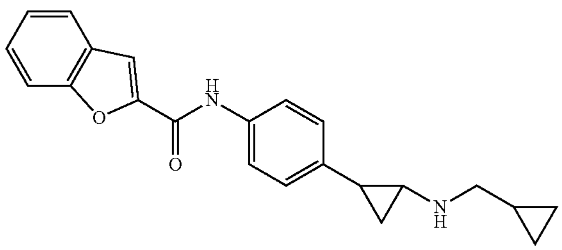 [SMILES: O=C(Nc1ccc(C2CC2NCC2CC2)cc1)c1cc2ccccc2o1] | CF3COOH | 346.9 |
| 130 | N-(4-{trans-2-[(cyclopropyl-methyl)amino]cyclo-propyl}phenyl)-4-(4-methylpiperazin-1-yl)benzamide | 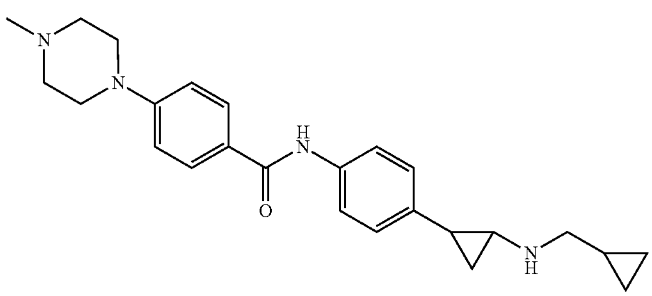 [SMILES: CN1CCN(c2ccc(C(=O)Nc3ccc(C4CC4NCC4CC4)cc3)cc2)CC1] | 3CF3COOH | 405.1 |

TABLE 1-11

| Ex. No. | IUPAC name | structure | salt | MS |
|---|---|---|---|---|
| 131 | N-(4-{trans-2-[(cyclopropyl-methyl)amino]-cyclopropyl}-phenyl)-3-(4-methylpiperazin-1-yl)benzamide | 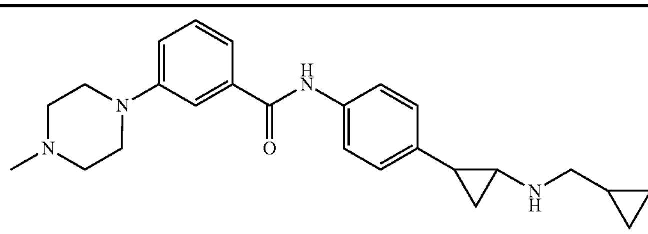 | 3CF3COOH | 405.1 |

TABLE 1-11-continued

| Ex. No. | IUPAC name | structure | salt | MS |
|---|---|---|---|---|
| 132 | N-(4-{trans-2-[(cyclopropyl-methyl)amino]-cyclopropyl}-phenyl)-4-(pyridin-3-yl)benzamide | 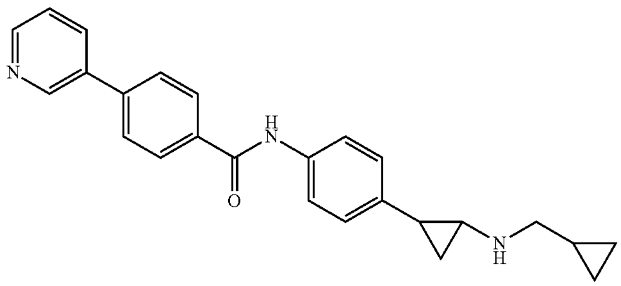 [SMILES: O=C(Nc1ccc(C2CC2NCC2CC2)cc1)c1ccc(-c2cccnc2)cc1] | 2CF3COOH | 384.0 |
| 133 | N-(4-{trans-2-[(cyclopropyl-methyl)amino]-cyclopropyl}-phenyl)-3-phenyl-1,2-oxazole-5-carboxamide | 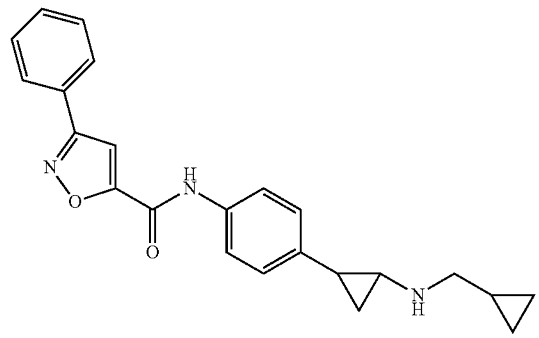 [SMILES: O=C(Nc1ccc(C2CC2NCC2CC2)cc1)c1cc(-c2ccccc2)no1] | CF3COOH | 373.9 |
| 134 | 2-acetyl-N-(4-{trans-2-[(cyclopropyl-methyl)amino]-cyclopropyl}-phenyl)-2,3,4,5-tetrahydro-1H-2-benzazepine-8-carboxamide | 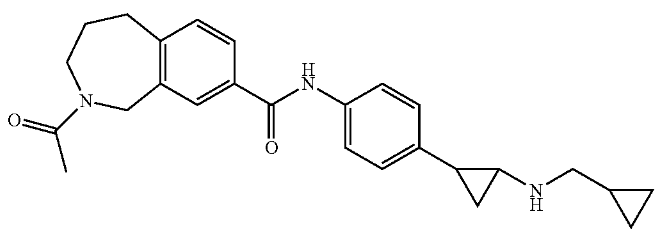 [SMILES: CC(=O)N1CCCc2ccc(C(=O)Nc3ccc(C4CC4NCC4CC4)cc3)cc2C1] | CF3COOH | 418.1 |

Example 135

N-(4-{trans-2-[(cyclopropylmethyl)amino]cyclopropyl}phenyl)-4-[(methylsulfonyl)amino]benzamide hydrochloride

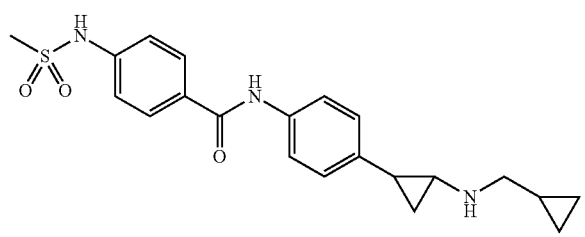 [SMILES: CS(=O)(=O)Nc1ccc(C(=O)Nc2ccc(C3CC3NCC3CC3)cc2)cc1]

By a method similar to Example 80, the title compound (81.1 mg) was obtained from tert-butyl [trans-2-(4-aminophenyl)cyclopropyl](cyclopropylmethyl)carbamate (96.9 mg) and 4-(methanesulfonamido)benzoic acid (83 mg).

MS (API+): [M+H]+ 400.3.

$^1$H NMR (300 MHz, DMSO-$d_6$) δ 0.32-0.40 (2H, m), 0.53-0.62 (2H, m), 0.97-1.12 (1H, m), 1.21-1.33 (1H, m), 1.41-1.53 (1H, m), 2.36-2.46 (1H, m), 2.82-3.01 (3H, m), 3.09 (3H, s), 7.15 (2H, d, J=8.7 Hz), 7.30 (2H, d, J=8.9 Hz), 7.69 (2H, d, J=8.7 Hz), 7.93 (2H, d, J=8.9 Hz), 9.08 (2H, brs), 10.14 (2H, s).

Example 136

N-(4-{trans-2-[(cyclopropylmethyl)amino]cyclopropyl}phenyl)-3-[(methylsulfonyl)amino]benzamide hydrochloride

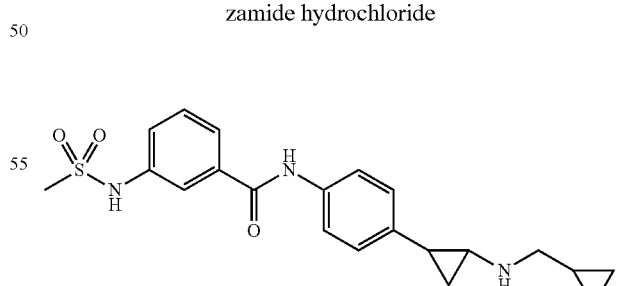

By a method similar to Example 80, the title compound (75.4 mg) was obtained from tert-butyl [trans-2-(4-aminophenyl)cyclopropyl](cyclopropylmethyl)carbamate (95.3 mg) and 3-(methanesulfonamido)benzoic acid (81 mg).

MS (API+): [M+H]+ 400.3.

$^1$H NMR (300 MHz, DMSO-d$_6$) δ 0.26-0.42 (2H, m), 0.51-0.65 (2H, m), 0.93-1.14 (1H, m), 1.18-1.33 (1H, m), 1.37-1.54 (1H, m), 2.32-2.47 (1H, m), 2.83-2.99 (3H, m), 3.04 (3H, s), 7.16 (2H, J=8.5 Hz), 7.37-7.55 (2H, m), 7.63-7.76 (4H, m), 9.03 (2H, brs), 9.98 (1H, brs), 10.27 (1H, s).

Example 137

N-(4-{trans-2-[(cyclopropylmethyl)amino]cyclopropyl}phenyl)-4-phenylthiophene-2-carboxamide hydrochloride

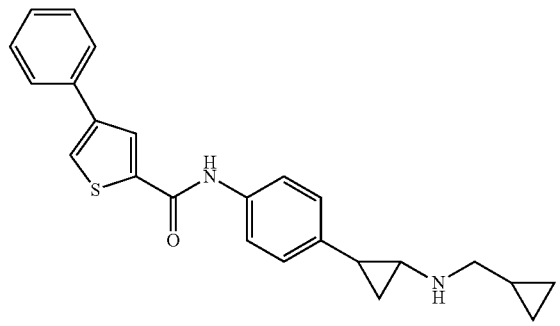 [SMILES: O=C(Nc1ccc(C2CC2NCC2CC2)cc1)c1cc(-c2ccccc2)cs1]

By a method similar to Example 80, the title compound (46.8 mg) was obtained from tert-butyl [trans-2-(4-aminophenyl)cyclopropyl](cyclopropylmethyl)carbamate (83.1 mg) and 4-phenylthiophene-2-carboxylic acid (67.3 mg).

MS (API+): [M+H]$^+$ 389.2.

$^1$H NMR (300 MHz, DMSO-d$_6$) δ 0.27-0.44 (2H, m), 0.53-0.64 (2H, m), 0.95-1.15 (1H, m), 1.21-1.34 (1H, m), 1.40-1.54 (1H, m), 2.35-2.46 (1H, m), 2.84-3.01 (3H, m), 7.19 (2H, d, J=8.5 Hz), 7.35 (1H, t, J=7.4 Hz), 7.48 (2H, dd, J=7.4, 7.3 Hz), 7.69 (2H, d, J=8.5 Hz), 7.75 (2H, d, J=7.3 Hz), 8.18 (1H, d, J=1.4 Hz), 8.52 (1H, brs), 9.01 (1H, brs), 10.32 (1H, brs).

Example 138

N-(4-{trans-2-[(cyclopropylmethyl)amino]cyclopropyl}phenyl)-4-(pyrimidin-2-yl)benzamide hydrochloride

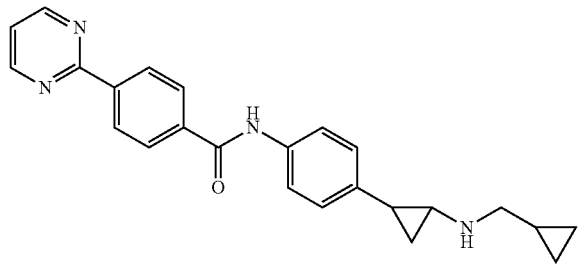 [SMILES: O=C(Nc1ccc(C2CC2NCC2CC2)cc1)c1ccc(-c2ncccn2)cc1]

By a method similar to Example 80, the title compound (34.3 mg) was obtained from tert-butyl [trans-2-(4-aminophenyl)cyclopropyl](cyclopropylmethyl)carbamate (87.7 mg) and 4-(pyrimidin-2-yl)benzoic acid (69.7 mg).

MS (API+): [M+H]$^+$ 385.1.

$^1$H NMR (300 MHz, DMSO-d$_6$) δ 0.30-0.42 (2H, m), 0.53-0.66 (2H, m), 0.98-1.12 (1H, m), 1.24-1.35 (1H, m), 1.43-1.55 (1H, m), 2.39-2.46 (1H, m), 2.86-3.07 (3H, m), 7.19 (2H, d, J=8.6 Hz), 7.53 (1H, t, J=4.9 Hz), 7.75 (2H, d, J=8.7 Hz), 8.11 (2H, d, J=8.6 Hz), 8.53 (2H, d, J=8.6 Hz), 8.97 (2H, d, J=4.9 Hz), 9.06 (2H, brs), 10.37 (1H, s).

Example 139

N-(4-{trans-2-[(cyclopropylmethyl)amino]cyclopropyl}phenyl)-3-(pyrimidin-2-yl)benzamide hydrochloride

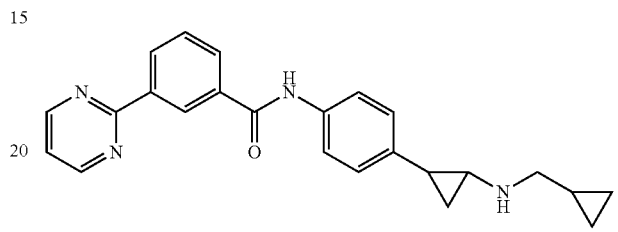

By a method similar to Example 80, the title compound (38.9 mg) was obtained from tert-butyl [trans-2-(4-aminophenyl)cyclopropyl](cyclopropylmethyl)carbamate (93.0 mg) and 3-(pyrimidin-2-yl)benzoic acid (73.9 mg).

MS (API+): [M+H]$^+$ 385.1.

$^1$H NMR (300 MHz, DMSO-d$_6$) δ 0.32-0.42 (2H, m), 0.53-0.65 (2H, m), 0.98-1.11 (1H, m), 1.23-1.35 (1H, m), 1.41-1.55 (1H, m), 2.40-2.47 (1H, m), 2.87-3.08 (3H, m), 7.19 (2H, d, J=8.6 Hz), 7.52 (1H, t, J=4.9 Hz), 7.70 (1H, dd, J=7.8, 7.6 Hz), 7.75 (2H, d, J=8.6 Hz), 8.10 (1H, ddd, J=7.6, 1.7, 1.5 Hz), 8.59 (1H, ddd, J=7.8, 1.6, 1.5 Hz), 8.95 (1H, dd, J=1.7, 1.6 Hz), 8.97 (2H, d, J=4.9 Hz), 9.05 (2H, brs), 10.45 (1H, s).

Example 140

N-(4-{trans-2-[(cyclopropylmethyl)amino]cyclopropyl}phenyl)benzamide hydrochloride

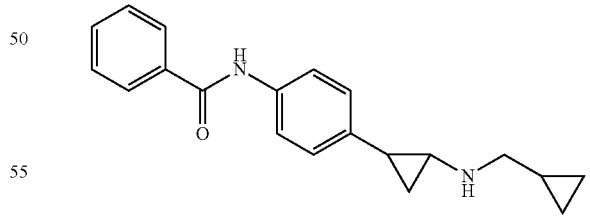

By a method similar to Example 68, Steps E and F, the title compound (79.3 mg) was obtained from tert-butyl [trans-2-(4-aminophenyl)cyclopropyl](cyclopropylmethyl)carbamate (91.8 mg) and benzoyl chloride (42.3 µL).

MS (API+): [M+H]$^+$ 307.3.

$^1$H NMR (300 MHz, DMSO-d$_6$) δ 0.22-0.38 (2H, m), 0.46-0.63 (2H, m), 0.90-1.11 (1H, m), 1.13-1.30 (1H, m), 1.31-1.49 (1H, m), 2.28-2.46 (1H, m), 2.78-2.97 (3H, m), 7.15 (2H, d, J=8.7 Hz), 7.47-7.63 (3H, m), 7.64-7.75 (2H, m), 7.90-7.98 (2H, m), 10.22 (1H, brs).

Example 141

N-(4-{trans-2-[(cyclopropylmethyl)amino]cyclopropyl}phenyl)-cyclohexanecarboxamide hydrochloride

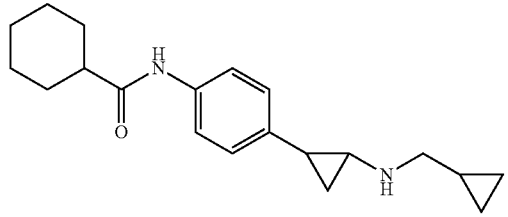 [SMILES: O=C(Nc1ccc(C2CC2NCC2CC2)cc1)C1CCCCC1]

By a method similar to Example 73, the title compound (145 mg) was obtained from tert-butyl [trans-2-(4-aminophenyl)cyclopropyl](cyclopropylmethyl)carbamate (170 mg) and cyclohexanecarbonyl chloride (99.0 mg).

MS (API+): [M+H]$^+$ 313.1.

$^1$H NMR (300 MHz, CD$_3$OD) δ 0.41 (2H, q, J=5.0 Hz), 0.65-0.76 (2H, m), 1.03-1.17 (1H, m), 1.33-1.60 (7H, m), 1.67-1.76 (1H, m), 1.78-1.90 (4H, m), 2.27-2.50 (2H, m), 2.94 (1H, dt, J=7.8, 4.0 Hz), 3.06 (2H, dd, J=7.5, 2.1 Hz), 7.11 (2H, d, J=8.5 Hz), 7.50 (2H, d, J=8.7 Hz).

Example 142

N-{4-[trans-2-{[2-(dimethylamino)benzyl]amino}cyclopropyl]phenyl}-3-(trifluoromethyl)benzamide hydrochloride

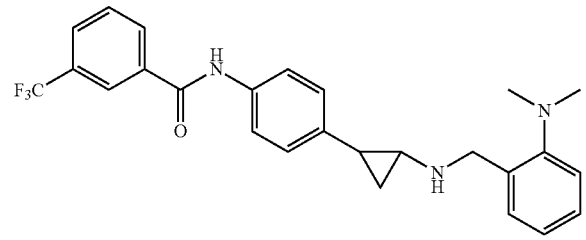 [SMILES: CN(C)c1ccccc1CNC1CC1c1ccc(NC(=O)c2cccc(C(F)(F)F)c2)cc1]

By a method similar to Example 65, the title compound (40 mg) was obtained from N-[4-(trans-2-aminocyclopropyl)phenyl]-3-(trifluoromethyl)benzamide hydrochloride (100 mg) and 2-(dimethylamino)benzaldehyde (41.8 mg).

MS (API+): [M+H]$^+$ 454.0.

$^1$H NMR (300 MHz, DMSO-d$_6$) δ 1.22-1.34 (1H, m), 1.56-1.71 (1H, m), 2.54-2.64 (1H, m), 2.82 (6H, s), 2.98-3.11 (1H, m), 4.52 (2H, brs), 7.13 (2H, d, J=8.5 Hz), 7.24-7.38 (1H, m), 7.42-7.57 (2H, m), 7.67-7.82 (4H, m), 7.97 (1H, d, J=7.7 Hz), 8.22-8.33 (2H, m), 9.84 (2H, brs), 10.52 (1H, s).

Example 143

2-(4-{trans-2-[(cyclopropylmethyl)amino]cyclopropyl}phenyl)-1H-isoindole-1,3(2H)-dione hydrochloride

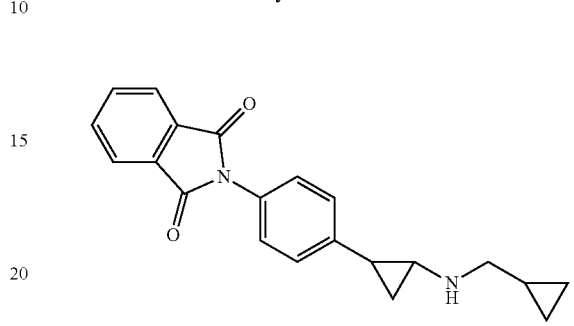

A) tert-butyl(cyclopropylmethyl){trans-2-[4-(1,3-dioxo-1,3-dihydro-2H-isoindol-2-yl)phenyl]cyclopropyl}carbamate To a solution of tert-butyl [trans-2-(4-aminophenyl)cyclopropyl](cyclopropylmethyl)carbamate (177.9 mg) and triethylamine (98 μL) in THF (2.94 mL) was added phthalic anhydride (105 mg). The mixture was stirred at room temperature overnight and the solvent was evaporated under reduced pressure. The residue was dissolved in acetic anhydride (3 mL), and the mixture was stirred at 80° C. for 5 hr. The solvent was evaporated under reduced pressure. The residue was purified by silica gel column chromatography (hexane/ethyl acetate) to give the title compound (252.7 mg).

$^1$H NMR (300 MHz, DMSO-d$_6$) δ 0.07-0.18 (1H, m), 0.19-0.31 (1H, m), 0.33-0.56 (2H, m), 0.90-1.07 (1H, m), 1.25-1.34 (2H, m), 1.38 (9H, s), 2.10-2.24 (1H, m), 2.75-2.85 (1H, m), 3.01 (1H, dd, J=14.4, 6.7 Hz), 3.22 (1H, dd, J=14.4, 6.7 Hz), 7.22-7.39 (4H, m), 7.85-7.99 (4H, m).

B) 2-(4-{trans-2-[(cyclopropylmethyl)amino]cyclopropyl}phenyl)-1H-isoindole-1,3(2H)-dione hydrochloride tert-Butyl(cyclopropylmethyl){trans-2-[4-(1,3-dioxo-1,3-dihydro-2H-isoindol-2-yl)phenyl]cyclopropyl}carbamate (252.7 mg) was dissolved in 4N hydrochloric acid/cyclopentyl methyl ether solution (3 mL), and the mixture was stirred at room temperature for 2 hr. The solvent was evaporated under reduced pressure. The residue was recrystallized from methanol/diisopropyl ether to give the title compound (176.2 mg).

MS (API+): [M+H]$^+$ 333.2.

$^1$H NMR (300 MHz, DMSO-d$_6$) δ 0.34-0.43 (2H, m), 0.55-0.64 (2H, m), 1.02-1.16 (1H, m), 1.31-1.43 (1H, m), 1.53-1.66 (1H, m), 2.54-2.63 (1H, m), 2.90-3.07 (3H, m), 7.21-7.50 (4H, m), 7.84-8.03 (4H, m), 9.37 (2H, brs).

Example 144

2-(4-{trans-2-[(cyclopropylmethyl)amino]cyclopropyl}phenyl)isoindolin-1-one hydrochloride

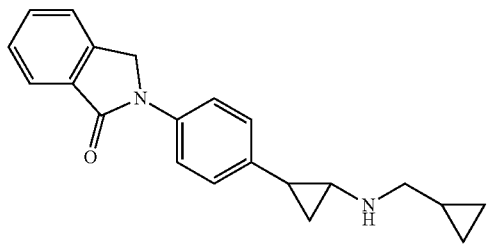 [SMILES: O=C1c2ccccc2CN1c1ccc(C2CC2NCC2CC2)cc1]

A) tert-butyl(cyclopropylmethyl){trans-2-[4-(1-oxo-1,3-dihydro-2H-isoindol-2-yl)phenyl]cyclopropyl}carbamate To a solution of tert-butyl [trans-2-(4-aminophenyl)cyclopropyl](cyclopropylmethyl)carbamate (126.8 mg) and triethylamine (70.1 µL) in THF (2.1 mL) was added 2-(chloromethyl)benzoyl chloride (95 mg). The mixture was stirred at room temperature overnight, and saturated aqueous ammonium chloride solution was added. The mixture was extracted with ethyl acetate, and the extract was washed successively with saturated aqueous sodium hydrogen carbonate solution and saturated brine, and dried over anhydrous magnesium sulfate. The solvent was evaporated under reduced pressure to give a mixture (260.5 mg) containing the title compound and tert-butyl [trans-2-(4-{[2-(chloromethyl)benzoyl]amino}phenyl)cyclopropyl]-(cyclopropylmethyl)carbamate. To a solution of this mixture and tetrabutylammonium iodide (15.51 mg) in DMF (4.2 mL) was added sodium hydride (20.16 mg). The mixture was stirred at room temperature for 2 hr and poured into water. The mixture was extracted with ethyl acetate, and the extract was washed with saturated brine, and dried over anhydrous magnesium sulfate. The solvent was evaporated under reduced pressure. The residue was purified by silica gel column chromatography (hexane/ethyl acetate) to give the title compound (123.7 mg).

$^1$H NMR (300 MHz, DMSO-$d_6$) δ 0.07-0.17 (1H, m), 0.18-0.28 (1H, m), 0.33-0.53 (2H, m), 0.90-1.08 (1H, m), 1.14-1.27 (2H, m), 1.37 (9H, s), 2.07 (1H, ddd, J=9.4, 6.5, 3.2 Hz), 2.65-2.78 (1H, m), 3.00 (1H, dd, J=14.4, 6.8 Hz), 3.20 (1H, dd, J=14.4, 6.8 Hz), 5.49 (2H, s), 7.09 (2H, d, J=8.5 Hz), 7.17 (2H, d, J=8.5 Hz), 7.50-7.73 (4H, m).

B) 2-(4-{trans-2-[(cyclopropylmethyl)amino]cyclopropyl}phenyl)isoindolin-1-one hydrochloride tert-Butyl(cyclopropylmethyl){trans-2-[4-(1-oxo-1,3-dihydro-2H-isoindol-2-yl)phenyl]cyclopropyl}carbamate (123.7 mg) was dissolved in 4N hydrochloric acid/cyclopentyl methyl ether solution (1.5 mL), and the mixture was stirred at room temperature for 4 hr. The solvent was evaporated under reduced pressure. The residue was recrystallized from methanol/diisopropyl ether to give the title compound (76.4 mg).

MS (API+): [M+H]$^+$ 319.3.

$^1$H NMR (300 MHz, DMSO-$d_6$) δ 0.32-0.42 (2H, m), 0.52-0.64 (2H, m), 0.99-1.17 (1H, m), 1.22-1.36 (1H, m), 1.45-1.63 (1H, m), 2.53-2.59 (1H, m), 2.82-3.06 (3H, m), 5.65 (2H, brs), 7.08-7.44 (4H, m), 7.46-7.84 (3H, m), 7.98-8.41 (1H, m), 9.33 (2H, brs).

Example 145

N-(4-{trans-2-[(cyclopropylmethyl)amino]cyclopropyl}phenyl)-3-sulfamoylbenzamide hydrochloride

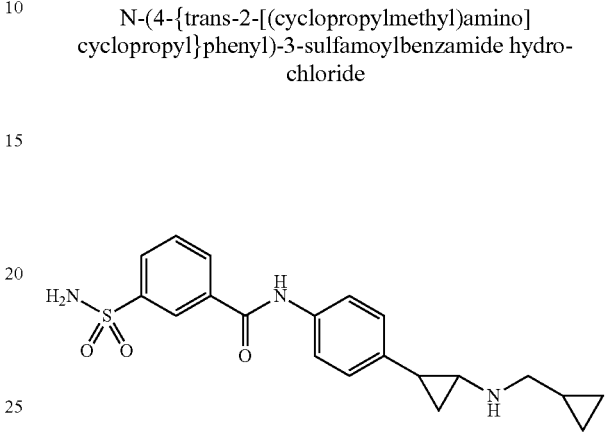

A) tert-butyl(cyclopropylmethyl)(trans-2-{4-[(3-sulfamoylbenzoyl)amino]phenyl}cyclopropyl)carbamate By a method similar to Example 80, Step A, the title compound (125.0 mg) was obtained from tert-butyl [trans-2-(4-aminophenyl)cyclopropyl](cyclopropylmethyl)carbamate (76.0 mg) and 3-sulfamoylbenzoic acid (60.7 mg).

$^1$H NMR (300 MHz, DMSO-$d_6$) δ 0.07-0.16 (1H, m), 0.18-0.28 (1H, m), 0.33-0.51 (2H, m), 1.02 (1H, brs), 1.20-1.28 (2H, m), 1.37 (9H, s), 2.07 (1H, ddd, J=9.6, 6.5, 3.1 Hz), 2.69-2.76 (1H, m), 3.00 (1H, dd, J=14.4, 6.7 Hz), 3.20 (1H, dd, J=14.4, 6.7 Hz), 7.14 (2H, d, J=8.6 Hz), 7.47-7.51 (2H, m), 7.67 (2H, d, J=8.6 Hz), 7.73 (1H, dd, J=7.7, 7.6 Hz), 7.98-8.08 (1H, m), 8.10-8.22 (1H, m), 8.38 (1H, t, J=1.6 Hz), 10.43 (1H, s).

B) N-(4-{trans-2-[(cyclopropylmethyl)amino]cyclopropyl}phenyl)-3-sulfamoylbenzamide hydrochloride tert-Butyl(cyclopropylmethyl)(trans-2-{4-[(3-sulfamoylbenzoyl)amino]phenyl}cyclopropyl)carbamate (125.0 mg) was dissolved in 4N hydrochloric acid/ethyl acetate solution (1.25 mL), and the mixture was stirred at room temperature overnight. The solvent was evaporated under reduced pressure. The residue was recrystallized from methanol/diisopropyl ether to give the title compound (69.5 mg).

MS (API+): [M+H]$^+$ 386.3.

$^1$H NMR (300 MHz, DMSO-$d_6$) δ 0.28-0.40 (2H, m), 0.54-0.62 (2H, m), 0.95-1.11 (1H, m), 1.17-1.34 (1H, m), 1.35-1.52 (1H, m), 2.34-2.45 (1H, m), 2.86-3.02 (3H, m), 7.18 (2H, d, J=8.5 Hz), 7.49 (2H, s), 7.67-7.79 (3H, m), 8.00-8.04 (1H, m), 8.14-8.19 (1H, m), 8.37 (1H, t, J=1.7 Hz), 8.90 (2H, s), 10.48 (1H, s).

Example 146

N-(4-{trans-2-[(cyclopropylmethyl)amino]cyclopropyl}phenyl)-3-(1H-imidazol-1-ylmethyl)benzamide hydrochloride

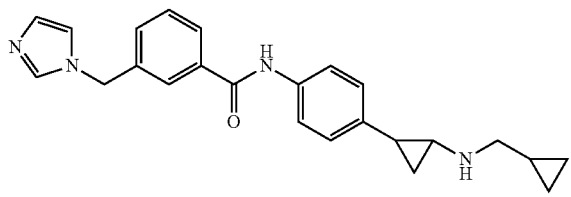 [SMILES: O=C(Nc1ccc(C2CC2NCC2CC2)cc1)c1cccc(Cn2ccnc2)c1]

By a method similar to Example 145, the title compound (21.0 mg) was obtained from tert-butyl [trans-2-(4-aminophenyl)cyclopropyl](cyclopropylmethyl)carbamate (76.6 mg) and 3-(1H-imidazol-1-ylmethyl)benzoic acid (61.5 mg).

MS (API+): [M+H]$^+$ 387.4.

$^1$H NMR (300 MHz, DMSO-d$_6$) δ 0.29-0.45 (2H, m), 0.53-0.62 (2H, m), 1.05-1.12 (1H, m), 1.21-1.31 (1H, m), 1.47-1.60 (1H, m), 2.42-2.47 (1H, m), 2.85-3.00 (3H, m), 5.52 (2H, s), 7.17 (2H, d, J=8.3 Hz), 7.52-7.65 (2H, m), 7.67-7.76 (3H, m), 7.81-7.88 (1H, m), 7.94-8.08 (2H, m), 9.22-9.45 (3H, m), 10.37 (1H, s).

Example 147

N-(4-{trans-2-[(cyclopropylmethyl)amino]cyclopropyl}phenyl)-3-(1H-1,2,4-triazol-1-ylmethyl)benzamide hydrochloride

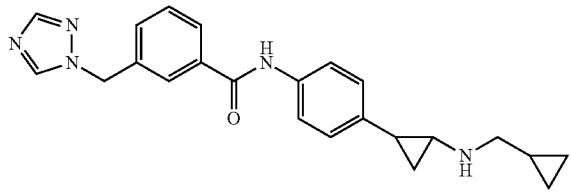 [SMILES: O=C(Nc1ccc(C2CC2NCC2CC2)cc1)c1cccc(Cn2cncn2)c1]

By a method similar to Example 145, the title compound (15.3 mg) was obtained from tert-butyl [trans-2-(4-aminophenyl)cyclopropyl](cyclopropylmethyl)carbamate (76.6 mg) and 3-(1H-1,2,4-triazol-1-ylmethyl)benzoic acid (61.8 mg).

MS (API+): [M+H]$^+$ 388.3.

$^1$H NMR (300 MHz, DMSO-d$_6$) δ 0.33-0.40 (2H, m), 0.55-0.62 (2H, m), 1.00-1.12 (1H, m), 1.23-1.33 (1H, m), 1.42-1.54 (1H, m), 2.40-2.46 (1H, m), 2.87-3.03 (3H, m), 5.51 (2H, s), 7.17 (2H, d, J=8.7 Hz), 7.45-7.58 (2H, m), 7.69 (2H, d, J=8.7 Hz), 7.82-7.94 (2H, m), 8.01 (1H, s), 8.72 (1H, s), 9.08 (2H, brs), 10.27 (1H, s).

Example 148

N-(4-{trans-2-[(cyclopropylmethyl)amino]cyclopropyl}phenyl)-3-(1H-imidazol-1-yl)benzamide hydrochloride

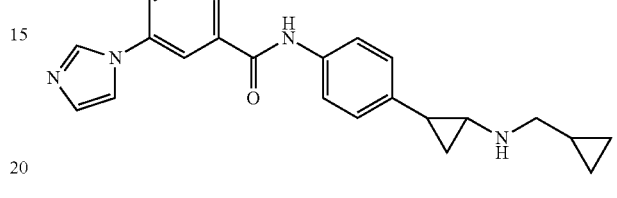

By a method similar to Example 145, the title compound (48.2 mg) was obtained from tert-butyl [trans-2-(4-aminophenyl)cyclopropyl](cyclopropylmethyl)carbamate (77.3 mg) and 3-(1H-imidazol-1-yl)benzoic acid (48.1 mg).

MS (API+): [M+H]$^+$ 373.3.

$^1$H NMR (300 MHz, DMSO-d$_6$) δ 0.38 (2H, m), 0.53-0.62 (2H, m), 1.08-1.15 (1H, m), 1.22-1.32 (1H, m), 1.50-1.60 (1H, m), 2.52-2.58 (1H, m), 2.88-3.01 (3H, m), 7.19 (2H, d, J=8.6 Hz), 7.76-7.85 (3H, m), 7.90 (1H, s), 8.03 (1H, dd, J=8.1, 1.6 Hz), 8.12 (1H, d, J=8.1 Hz), 8.48 (2H, d, J=19.1 Hz), 9.42 (2H, brs), 9.81 (1H, brs), 10.68 (1H, s).

Example 149

N-(4-{trans-2-[(8-methyl-8-azabicyclo[3.2.1]oct-3-yl)amino]cyclopropyl}phenyl)-3-(trifluoromethyl)benzamide dihydrochloride

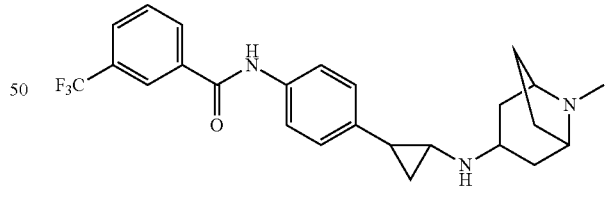

By a method similar to Example 65, the title compound (50 mg) was obtained from N-[4-(trans-2-aminocyclopropyl)phenyl]-3-(trifluoromethyl)benzamide hydrochloride (100 mg) and 8-methyl-8-azabicyclo[3.2.1]octan-3-one (50.7 mg).

MS (API+): [M+H]$^+$ 444.1.

$^1$H NMR (300 MHz, CD$_3$OD) δ 1.44-1.61 (3H, m), 1.66-1.78 (3H, m), 2.21-2.26 (1H, m), 2.37-2.56 (3H, m), 2.68-2.76 (1H, m), 2.80-2.86 (3H, m), 3.15-3.25 (1H, m), 3.80-

4.30 (3H, m), 7.25 (2H, d, J=7.9 Hz), 7.65-7.78 (3H, m), 7.90 (1H, d, J=7.8 Hz), 8.18-8.28 (2H, m).

Example 150

N-methyl-N-(4-{trans-2-[(1-methylpiperidin-4-yl)amino]cyclopropyl}phenyl)-3-(trifluoromethyl)benzamide dihydrochloride

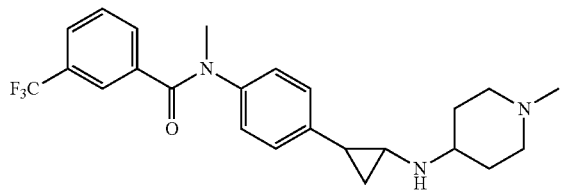 [SMILES: CN1CCC(NC2CC2c2ccc(N(C)C(=O)c3cccc(C(F)(F)F)c3)cc2)CC1]

By a method similar to Example 64, the title compound (3 mg) was obtained from N-(4-{trans-2-[(1-methylpiperidin-4-yl)amino]cyclopropyl}phenyl)-3-(trifluoromethyl)benzamide hydrochloride (160 mg).

MS (API+): [M+H]$^+$ 432.1.

$^1$H NMR (300 MHz, CD$_3$OD) δ 1.18-1.43 (2H, m), 1.48-1.62 (1H, m), 1.91-2.11 (2H, m), 2.31-2.58 (3H, m), 2.84-3.21 (5H, m), 3.46 (3H, s), 3.56-3.73 (3H, m), 7.05-7.19 (4H, m), 7.37-7.48 (1H, m), 7.51-7.63 (3H, m).

Example 151

N-(4-{trans-2-[(1,1-dioxidotetrahydro-2H-thiopyran-4-yl)amino]cyclopropyl}phenyl)-3-(trifluoromethyl)benzamide hydrochloride

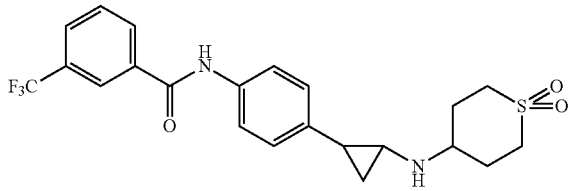 [SMILES: O=C(Nc1ccc(C2CC2NC2CCS(=O)(=O)CC2)cc1)c1cccc(C(F)(F)F)c1]

To a solution of N-[4-(trans-2-aminocyclopropyl)phenyl]-3-(trifluoromethyl)benzamide hydrochloride (75 mg), tetrahydro-4H-thiopyran-4-one 1,1-dioxide (37.4 mg) and acetic acid (0.2 mL) in methanol (2 mL) was added 2-picoline-borane complex (38.2 mg). The mixture was stirred at room temperature overnight, and saturated aqueous sodium hydrogen carbonate solution was added under ice-cooling. The mixture was m extracted with ethyl acetate, and the extract was washed with water and saturated brine, and dried over anhydrous magnesium sulfate. The solvent was evaporated under reduced pressure. The residue was purified by silica gel column chromatography (hexane/ethyl acetate, ethyl acetate/methanol) and 10% hydrochloric acid methanol solution was added. The solvent was evaporated under reduced pressure. The residue was recrystallized from methanol/diisopropyl ether to give the title compound (32.0 mg).

MS (API+): [M+H]$^+$ 453.1.

$^1$H NMR (300 MHz, CD$_3$OD) δ 1.39-1.61 (2H, m), 2.25 (2H, d, J=12.8 Hz), 2.43-2.63 (3H, m), 3.03 (1H, dt, J=7.7, 4.1 Hz), 3.14-3.25 (2H, m), 3.32-3.42 (2H, m), 3.61-3.76 (1H, m), 7.22 (2H, d, J=8.5 Hz), 7.65-7.78 (3H, m), 7.89 (1H, d, J=7.7 Hz), 8.15-8.26 (2H, m).

Example 152

N-(4-{(1R,2S) or (1S,2R)-2-[(1-methylpiperidin-4-yl)amino]cyclopropyl}phenyl)-3-(trifluoromethyl)benzamide dihydrochloride

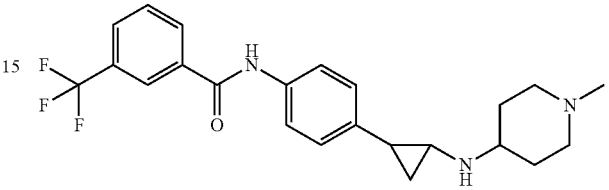

N-(4-{trans-2-[(1-Methylpiperidin-4-yl)amino]cyclopropyl}phenyl)-3-(trifluoromethyl)benzamide dihydrochloride (113 mg) was fractionated by HPLC (CHIRALCEL (registered trademark) OD (CA002), 50 mmID×500 mmL, manufactured by Daicel Corporation, mobile phase: hexane/ethanol/diethylamine=900/100/0.5), a fraction containing the object product and having a shorter retention time was concentrated under reduced pressure, and the residue was ice-cooled to 0° C. 4N Hydrochloric acid/cyclopentyl methyl ether solution (3.0 mL) was added, and the mixture was concentrated under reduced pressure to give the title compound (43 mg).

optical purity: 99.9% ee, retention time: 9.284 min (CHIRACEL (registered trademark) OD3 (NL022), 4.6 mmID×250 mmL, manufactured by Daicel Corporation, mobile phase: hexane/ethanol/diethylamine=900/100/0.1)

$^1$H NMR (300 MHz, CD$_3$OD) δ 1.41-1.52 (1H, m), 1.54-1.64 (1H, m), 2.00-2.19 (2H, m), 2.38-2.63 (3H, m), 2.91 (3H, s), 2.99-3.06 (1H, m), 3.10-3.27 (2H, m), 3.59-3.75 (3H, m), 7.23 (2H, d, J=8.5 Hz), 7.64-7.77 (3H, m), 7.90 (1H, d, J=7.9 Hz), 8.17-8.27 (2H, m).

Example 153

N-(4-{(1S,2R) or (1R,2S)-2-[(1-methylpiperidin-4-yl)amino]cyclopropyl}phenyl)-3-(trifluoromethyl)benzamide dihydrochloride

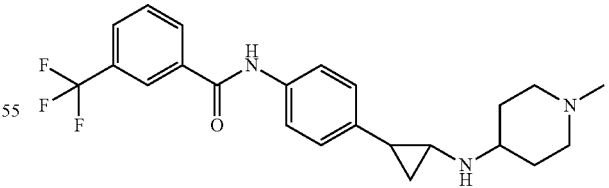

N-(4-{trans-2-[(1-Methylpiperidin-4-yl)amino]cyclopropyl}phenyl)-3-(trifluoromethyl)benzamide dihydrochloride (113 mg) was fractionated by HPLC (CHIRALCEL (registered trademark) OD (CA002), 50 mmID×500 mmL, manufactured by Daicel Corporation, mobile phase: hexane/ethanol/diethylamine=900/100/0.5), a fraction containing the object product and having a longer retention time was concentrated under reduced pressure, and the residue was ice-cooled to 0° C. 4N Hydrochloric acid/cyclopentyl methyl ether solution (3.0 mL) was added, and the mixture was concentrated under reduced pressure to give the title compound (46 mg).
optical purity: 99.1% ee, retention time: 12.724 min (CHIRACEL (registered trademark) OD3 (NL022), 4.6 mmID×250 mmL, manufactured by Daicel Corporation, mobile phase: hexane/ethanol/diethylamine=900/100/0.1)
$^1$H NMR (300 MHz, CD$_3$OD) δ 1.43-1.52 (1H, m), 1.54-1.64 (1H, m), 1.98-2.19 (2H, m), 2.37-2.61 (3H, m), 2.91 (3H, s), 3.00-3.25 (3H, m), 3.59-3.76 (3H, m), 7.23 (2H, d, J=8.7 Hz), 7.67-7.77 (3H, m), 7.90 (1H, d, J=7.3 Hz), 8.16-8.27 (2H, m).

Example 154

N-(4-{trans-2-[(4,4-difluorocyclohexyl)amino]cyclopropyl}phenyl)-3-(trifluoromethyl)benzamide hydrochloride

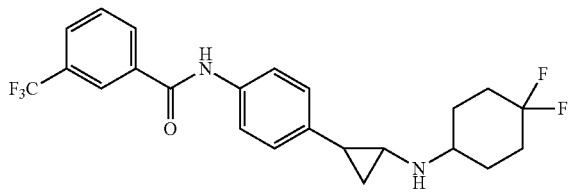 [SMILES: O=C(Nc1ccc(C2CC2NC2CCC(F)(F)CC2)cc1)c1cccc(C(F)(F)F)c1]

By a method similar to Example 151, the title compound (45 mg) was obtained from N-[4-(trans-2-aminocyclopropyl)phenyl]-3-(trifluoromethyl)benzamide hydrochloride (75 mg) and 4,4-difluorocyclohexanone (33.8 mg).
MS (API+): [M+H]$^+$ 439.0.
$^1$H NMR (300 MHz, CD$_3$OD) δ 1.39-1.55 (2H, m), 1.73 (2H, q, J=12.2 Hz), 1.83-2.08 (2H, m), 2.11-2.32 (4H, m), 2.44 (1H, ddd, J=10.1, 6.7, 3.6 Hz), 2.95-3.03 (1H, m), 3.40-3.55 (1H, m), 7.20 (2H, d, J=8.7 Hz), 7.65-7.77 (3H, m), 7.89 (1H, d, J=7.9 Hz), 8.15-8.27 (2H, m).

Example 155

N-{4-[trans-2-{[(1-methylpiperidin-4-yl)methyl]amino}cyclopropyl]phenyl}-3-(trifluoromethyl)benzamide dihydrochloride

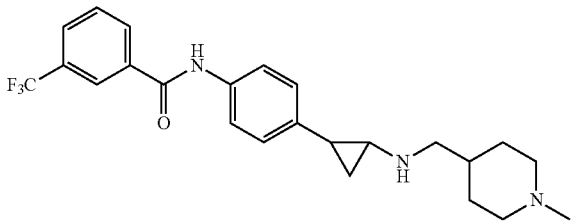 [SMILES: CN1CCC(CNC2CC2c2ccc(NC(=O)c3cccc(C(F)(F)F)c3)cc2)CC1]

By a method similar to Example 65, the title compound (20 mg) was obtained from N-[4-(trans-2-aminocyclopropyl)phenyl]-3-(trifluoromethyl)benzamide hydrochloride (80 mg) and 1-methylpiperidine-4-carbaldehyde (28.5 mg).
MS (API+): [M+H]$^+$ 432.1.
$^1$H NMR (300 MHz, CD$_3$OD) 1.35-1.46 (1H, m), 1.51-1.73 (3H, m), 2.04-2.16 (3H, m), 2.51-2.61 (1H, m), 2.86-2.92 (3H, m), 2.97-3.11 (3H, m), 3.20 (2H, d, J=6.6 Hz), 3.52-3.63 (2H, m), 7.21 (2H, d, J=8.7 Hz), 7.64-7.77 (3H, m), 7.89 (1H, d, J=7.9 Hz), 8.15-8.29 (2H, m).

Example 156

N-(4-{trans-2-[(cyclopropylmethyl)amino]cyclopropyl}phenyl)-1,3-dimethyl-1H-pyrazole-5-carboxamide dihydrochloride

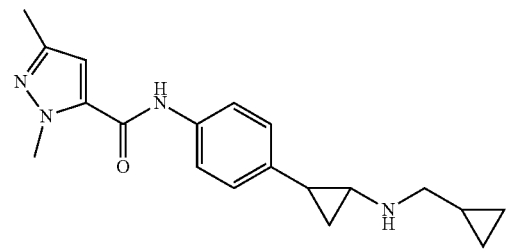 [SMILES: Cc1cc(C(=O)Nc2ccc(C3CC3NCC3CC3)cc2)n(C)n1]

By a method similar to Example 145, the title compound (89.6 mg) was obtained from tert-butyl [trans-2-(4-aminophenyl)cyclopropyl](cyclopropylmethyl)carbamate (88.6 mg) and 1,3-dimethyl-1H-pyrazole-5-carboxylic acid (49.3 mg).
MS (API+): [M+H]$^+$ 325.3.
$^1$H NMR (300 MHz, DMSO-d$_6$) δ 0.32-0.40 (2H, m), 0.52-0.64 (2H, m), 0.98-1.14 (1H, m), 1.22-1.32 (1H, m), 1.42-1.55 (1H, m), 2.19 (3H, s), 2.40-2.47 (1H, m), 2.87-3.03 (3H, m), 3.99 (3H, s), 6.82 (1H, s), 7.16 (2H, d, J=8.6 Hz), 7.65 (2H, d, J=8.6 Hz), 9.18 (2H, brs), 10.11 (1H, s).

Example 157

N-(4-{trans-2-[(cyclopropylmethyl)amino]cyclopropyl}phenyl)-1,5-dimethyl-1H-pyrazole-3-carboxamide dihydrochloride

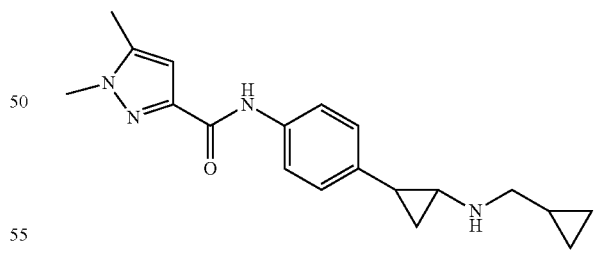

By a method similar to Example 145, the title compound (60.0 mg) was obtained from tert-butyl [trans-2-(4-aminophenyl)cyclopropyl](cyclopropylmethyl)carbamate (87.2 mg) and 1,5-dimethyl-1H-pyrazole-3-carboxylic acid (48.5 mg).
MS (API+): [M+H]$^+$ 325.3.
$^1$H NMR (300 MHz, DMSO-d$_6$) δ 0.31-0.41 (2H, m), 0.53-0.63 (2H, m), 0.98-1.11 (1H, m), 1.18-1.33 (1H, m), 1.41-1.52 (1H, m), 2.30 (3H, s), 2.37-2.47 (1H, m), 2.85-3.03

(3H, m), 3.83 (3H, s), 6.53 (1H, s), 7.12 (2H, d, J=8.7 Hz), 7.74 (2H, d, J=8.6 Hz), 9.11 (2H, brs), 9.89 (1H, s).

Example 158

N-(4-{trans-2-[(cyclopropylmethyl)amino]cyclopropyl}phenyl)-1-methyl-3-(trifluoromethyl)-1H-pyrazole-4-carboxamide hydrochloride

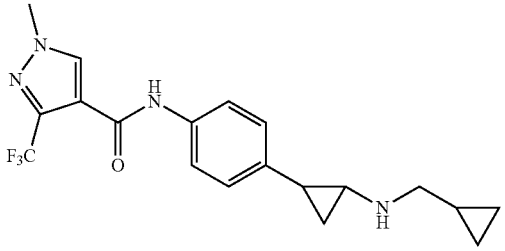 [SMILES: Cn1cc(C(=O)Nc2ccc(C3CC3NCC3CC3)cc2)c(C(F)(F)F)n1]

By a method similar to Example 145, the title compound (40.8 mg) was obtained from tert-butyl [trans-2-(4-aminophenyl)cyclopropyl](cyclopropylmethyl)carbamate (87.1 mg) and 1-methyl-3-(trifluoromethyl)-1H-pyrazole-4-carboxylic acid (67.1 mg).

MS (API+): [M+H]+ 379.3.

1H NMR (300 MHz, DMSO-d6) δ 0.29-0.39 (2H, m), 0.52-0.62 (2H, m), 0.95-1.11 (1H, m), 1.17-1.30 (1H, m), 1.35-1.52 (1H, m), 2.31-2.45 (1H, m), 2.81-3.01 (3H, m), 3.98 (3H, s), 7.14 (2H, d, J=8.6 Hz), 7.60 (2H, d, J=8.6 Hz), 8.53 (1H, s), 8.95 (2H, brs), 10.11 (1H, s).

Example 159

N-(4-{trans-2-[(cyclopropylmethyl)amino]cyclopropyl}phenyl)-1-methyl-5-(trifluoromethyl)-1H-pyrazole-4-carboxamide hydrochloride

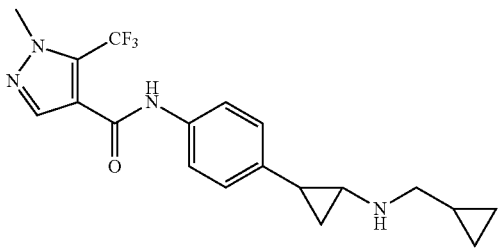 [SMILES: Cn1ncc(C(=O)Nc2ccc(C3CC3NCC3CC3)cc2)c1C(F)(F)F]

By a method similar to Example 80, the title compound (56.1 mg) was obtained from tert-butyl [trans-2-(4-aminophenyl)cyclopropyl](cyclopropylmethyl)carbamate (82.8 mg) and 1-methyl-5-(trifluoromethyl)-1H-pyrazole-4-carboxylic acid (63.8 mg).

MS (API+): [M+H]+ 379.3.

1H NMR (300 MHz, DMSO-d6) δ 0.29-0.40 (2H, m), 0.52-0.62 (2H, m), 0.95-1.11 (1H, m), 1.18-1.30 (1H, m), 1.39-1.52 (1H, m), 2.32-2.47 (1H, m), 2.82-3.02 (3H, m), 3.98 (3H, s), 7.14 (2H, d, J=8.6 Hz), 7.61 (2H, d, J=8.6 Hz), 8.54 (1H, s), 9.01 (2H, brs), 10.12 (1H, s).

Example 160

N-(4-{trans-2-[(imidazo[2,1-b][1,3]thiazol-6-ylmethyl)amino]cyclopropyl}phenyl)-3-(trifluoromethyl)benzamide dihydrochloride

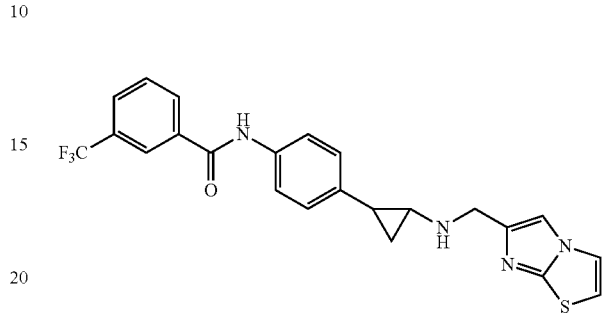

By a method similar to Example 65, the title compound (17 mg) was obtained from N-[4-(trans-2-aminocyclopropyl)phenyl]-3-(trifluoromethyl)benzamide hydrochloride (75 mg) and imidazo[2,1-b][1,3]thiazole-6-carbaldehyde (41.6 mg).

MS (API+): [M+H]+ 457.0.

1H NMR (300 MHz, CD3OD) δ 1.35 (1H, q, J=6.8 Hz), 1.53-1.65 (1H, m), 2.50 (1H, s), 3.00-3.11 (1H, m), 4.60-4.66 (2H, m), 7.01 (2H, d, J=8.3 Hz), 7.51-7.69 (4H, m), 7.80 (1H, d, J=7.7 Hz), 8.00-8.26 (4H, m).

Example 161

N-(4-{trans-2-[(thieno[2,3-b]pyridin-2-ylmethyl)amino]cyclopropyl}phenyl)-3-(trifluoromethyl)benzamide hydrochloride

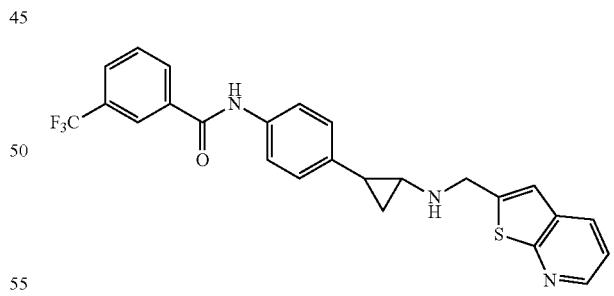

By a method similar to Example 65, the title compound (10 mg) was obtained from N-[4-(trans-2-aminocyclopropyl)phenyl]-3-(trifluoromethyl)benzamide hydrochloride (75 mg) and thieno[2,3-b]pyridine-2-carbaldehyde (44.6 mg).

MS (API+): [M+H]+ 468.0.

1H NMR (300 MHz, CD3OD) δ 1.36-1.57 (2H, m), 2.41 (1H, ddd, J=10.2, 6.5, 3.7 Hz), 3.01 (1H, dt, J=7.6, 4.0 Hz), 4.73 (2H, s), 7.07 (2H, d, J=8.7 Hz), 7.44-7.54 (2H, m), 7.61 (2H, d, J 25=8.7 Hz), 7.70-7.79 (1H, m), 7.90 (1H, d, J=7.9 Hz), 8.15-8.30 (3H, m), 8.58 (1H, dd, J=4.7, 1.5 Hz).

Example 162

N-(4-{trans-2-[(1,8-naphthyridin-2-ylmethyl)amino]cyclopropyl}phenyl)-3-(trifluoromethyl)benzamide hydrochloride

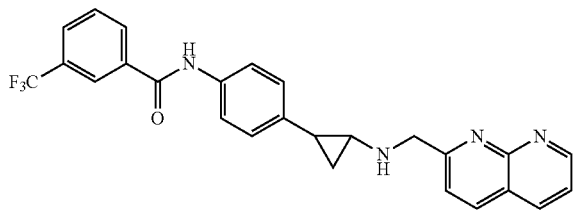 [SMILES: O=C(Nc1ccc(C2CC2NCc2ccc3cccnc3n2)cc1)c1cccc(C(F)(F)F)c1]

By a method similar to Example 65, the title compound (16 mg) was obtained from N-[4-(trans-2-aminocyclopropyl)phenyl]-3-(trifluoromethyl)benzamide hydrochloride (75 mg) and 1,8-naphthyridine-2-carbaldehyde(43.2 mg).

MS (API+): [M+H]$^+$ 463.0.

$^1$H NMR (300 MHz, CD$_3$OD) δ 1.42-1.53 (1H, m), 1.63-1.73 (1H, m), 2.59-2.70 (1H, m), 3.20-3.28 (1H, m), 4.95 (2H, s), 7.20 (2H, d, J=8.7 Hz), 7.64-7.77 (3H, m), 7.83-7.97 (3H, m), 8.16-8.27 (2H, m), 8.69 (1H, d, J=8.5 Hz), 8.85 (1H, dd, J=8.3, 1.7 Hz), 9.19-9.32 (1H, m).

Example 163

N-(4-{trans-2-[(cyclopropylmethyl)amino]cyclopropyl}phenyl)-1-methyl-1H-pyrazole-4-carboxamide hydrochloride

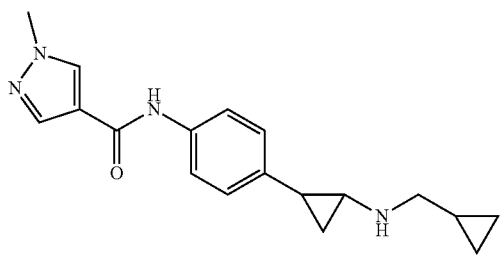 [SMILES: Cn1cc(C(=O)Nc2ccc(C3CC3NCC3CC3)cc2)cn1]

A) tert-butyl(cyclopropylmethyl)[trans-2-(4-{[(1-methyl-1H-pyrazol-4-yl)carbonyl]amino}phenyl)cyclopropyl]carbamate To a solution of tert-butyl [trans-2-(4-aminophenyl)cyclopropyl](cyclopropylmethyl)carbamate (85.8 mg) and 1-methyl-1H-pyrazole-4-carboxylic acid (42.9 mg) in DMF (1.42 mL) was added N-ethyl-N'-(3-dimethylaminopropyl)carbodiimide hydrochloride (82 mg). The mixture was stirred at room temperature overnight, and poured into water. The mixture was extracted with ethyl acetate, and the extract was washed successively with saturated aqueous sodium hydrogen carbonate solution and saturated brine, and dried over anhydrous magnesium sulfate. The solvent was evaporated under reduced pressure to give the title compound (114.8 mg).

$^1$H NMR (300 MHz, DMSO-d$_6$) δ 0.05-0.16 (1H, m), 0.16-0.28 (1H, m), 0.32-0.52 (2H, m), 0.89-1.05 (1H, m), 1.09-1.26 (2H, m), 1.36 (9H, s), 2.00-2.10 (1H, m), 2.65-2.72 (1H, m), 2.98 (1H, dd, J=14.2, 6.9 Hz), 3.19 (1H, dd, J=14.2, 6.9 Hz), 3.88 (3H, s), 7.10 (2H, d, J=8.5 Hz), 7.59 (2H, d, J=8.7 Hz), 7.99 (1H, s), 8.28 (1H, s), 9.74 (1H, s).

B) N-(4-{trans-2-[(cyclopropylmethyl)amino]cyclopropyl}phenyl)-1-methyl-1H-pyrazole-4-carboxamide hydrochloride tert-Butyl(cyclopropylmethyl)[trans-2-(4-{[(1-methyl-1H-pyrazol-4-yl)carbonyl]amino}phenyl)cyclopropyl]carbamate (114.8 mg) was dissolved in 4N hydrochloric acid/cyclopentyl methyl ether solution (1 mL), and the mixture was stirred at room temperature for 1.5 hr. The solvent was evaporated under reduced pressure. The residue was recrystallized from methanol/diisopropyl ether to give the title compound (51.1 mg).

MS (API+): [M+H]$^+$ 311.3.

$^1$H NMR (300 MHz, DMSO-d$_6$) δ 0.32-0.41 (2H, m), 0.51-0.62 (2H, m), 1.01-1.15 (1H, m), 1.19-1.30 (1H, m), 1.47-1.58 (1H, m), 2.43-2.49 (1H, m), 2.80-3.01 (3H, m), 3.89 (3H, s), 7.13 (2H, d, J=8.7 Hz), 7.66 (2H, d, J=8.7 Hz), 8.02 (1H, s), 8.33 (1H, s), 9.41 (2H, brs), 9.86 (1H, s).

Example 164

1-tert-butyl-N-(4-{trans-2-[(cyclopropylmethyl)amino]cyclopropyl}phenyl)-1H-pyrazole-4-carboxamide hydrochloride

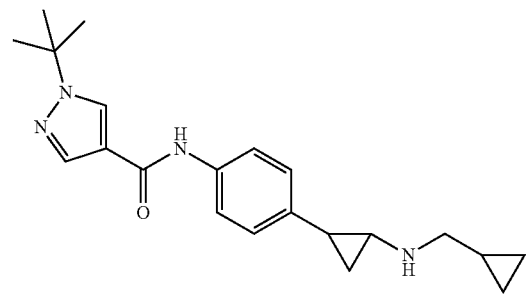 [SMILES: CC(C)(C)n1cc(C(=O)Nc2ccc(C3CC3NCC3CC3)cc2)cn1]

By a method similar to Example 163, the title compound (30.7 mg) was obtained from tert-butyl [trans-2-(4-aminophenyl)cyclopropyl](cyclopropylmethyl)carbamate (76.5 mg) and 1-(tert-butyl)-1H-pyrazole-4-carboxylic acid (51.1 mg).

MS (API+): [M+H]$^+$ 353.2.

$^1$H NMR (300 MHz, DMSO-d$_6$) δ 0.27-0.42 (2H, m), 0.53-0.61 (2H, m), 0.99-1.13 (1H, m), 1.19-1.30 (1H, m), 1.42-1.51 (1H, m), 1.55 (9H, s), 2.36-2.47 (1H, m), 2.84-2.98 (3H, m), 7.14 (2H, d, J=8.5 Hz), 7.64 (2H, d, J=8.5 Hz), 8.01 (1H, s), 8.48 (1H, s), 9.09 (2H, brs), 9.79 (1H, s).

Example 165

N-(4-{(1R,2S) or (1S,2R)-2-[(cyclopropylmethyl)amino]cyclopropyl}phenyl)biphenyl-4-carboxamide hydrochloride

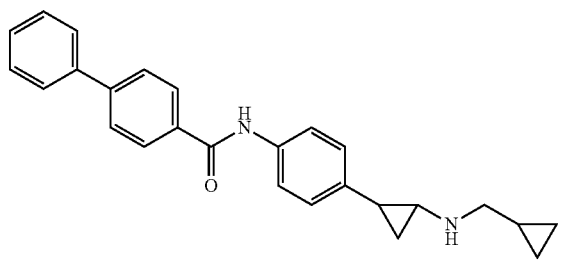 [SMILES: O=C(Nc1ccc(C2CC2NCC2CC2)cc1)c1ccc(-c2ccccc2)cc1]

N-(4-{trans-2-[(Cyclopropylmethyl)amino]
cyclopropyl}phenyl)biphenyl-4-carboxamide hydrochloride
(273 mg) was fractionated by HPLC (CHIRALPAK (registered trademark) AD (JG001), 50 mmID×500 mmL, manufactured by Daicel Corporation, mobile phase: ethanol), a fraction containing the object product and having a shorter retention time was concentrated under reduced pressure, and the residue was ice-cooled to 0° C. 4N Hydrochloric acid/cyclopentyl methyl ether solution (3.0 mL) was added, and the mixture was concentrated under reduced pressure to give the title compound (116 mg).

optical purity: 99.7% ee, retention time: 13.684 min (CHIRALPAK (registered trademark) AD (KF053), 4.6 mmID×250 mmL, manufactured by Daicel Corporation, mobile phase: ethanol)

$^1$H NMR (300 MHz, CD$_3$OD) δ 0.39-0.48 (2H, m), 0.69-0.78 (2H, m), 1.06-1.23 (1H, m), 1.31-1.55 (2H, m), 2.47 (1H, ddd, J=10.3, 6.7, 3.6 Hz), 2.95-3.03 (1H, m), 3.06-3.13 (2H, m), 7.21 (2H, d, J=9.8 Hz), 7.36-7.53 (3H, m), 7.66-7.73 (4H, m), 7.78 (2H, d, J=8.1 Hz), 8.01 (2H, d, J=9.0 Hz).

Example 166

N-(4-{(1S,2R) or (1R,2S)-2-[(cyclopropylmethyl)
amino]cyclopropyl}phenyl)biphenyl-4-carboxamide
hydrochloride

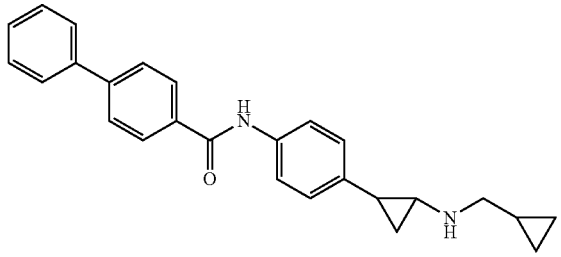 [SMILES: O=C(Nc1ccc(C2CC2NCC2CC2)cc1)c1ccc(-c2ccccc2)cc1]

N-(4-{trans-2-[(Cyclopropylmethyl)amino]
cyclopropyl}phenyl)biphenyl-4-carboxamide hydrochloride
(273 mg) was fractionated by HPLC (CHIRALPAK (registered trademark) AD (JG001), 50 mmID×500 mmL, manufactured by Daicel Corporation, mobile phase: ethanol), a fraction containing the object product and having a longer retention time was concentrated under reduced pressure, and the residue was ice-cooled to 0° C. 4N Hydrochloric acid/cyclopentyl methyl ether solution (3.0 mL) was added, and the mixture was concentrated under reduced pressure to give the title compound (128 mg).

optical purity: 99.1% ee, retention time: 16.256 min (CHIRALPAK (registered trademark) AD (KF053), 4.6 mmID×250 mmL, manufactured by Daicel Corporation, mobile phase: ethanol)

$^1$H NMR (300 MHz, CD$_3$OD) δ 0.38-0.48 (2H, m), 0.69-0.79 (2H, m), 1.04-1.21 (1H, m), 1.36-1.55 (2H, m), 2.47 (1H, ddd, J=10.2, 6.6, 3.4 Hz), 2.95-3.02 (1H, m), 3.09 (2H, dd, J=7.5, 2.3 Hz), 7.21 (2H, d, J=8.7 Hz), 7.36-7.44 (1H, m), 7.44-7.53 (2H, m), 7.66-7.73 (4H, m), 7.78 (2H, d, J=8.9 Hz), 8.02 (2H, d, J=8.5 Hz).

Experimental Example 1

The genetic engineering method described below was performed according to the method described in a book (Maniatis et al., Molecular Cloning, Cold Spring Harbor Laboratory, 1989) or the method described in the protocol attached to the reagent.

(1) Construction of GST-Tagged Expression Vector Having TEV Protease Cleavage Sequence A GST-tagged expression vector having TEV Protease cleavage sequence was constructed by successive 2 times of PCR method. Firstly, PCR was performed using pGEX6P1 (GE Healthcare) as a template, two primers

```
GST-Sw-F:
                                        [SEQ ID NO: 1]
5'-AGAATCATTTAAATGGTGATCATGTAACCCATCCT-3'

GST-Tv-R1:
                                        [SEQ ID NO: 2]
5'-CGCCCTGAAAGTACAGGTTCTCATCCGATTTTGGAGGATGGTCG-3'
``` and PrimeStar GXL DNA Polymerase (Takara Bio Inc.). Template DNA 0.5 μL, 5× Buffer 10 μL, 2.5 mM dNTP solution 4 μL, 10 μM primer solution each 1.5 μL, PrimeStar GXL DNA Polymerase 1 μL, and sterilized distilled water 31.5 μL were mixed. After a treatment at 98° C. for 1 min, the PCR reaction was started with repeats of a treatment at 98° C. for 10 seconds, at 65° C. for 5 seconds, and at 72° C. for 25 seconds, followed by a treatment at 72° C. for 1 min. Then, PCR was performed using the obtained PCR product as a template, two primers

```
GST-Sw-F:
                                        [SEQ ID NO: 1]
5'-AGAATCATTTAAATGGTGATCATGTAACCCATCCT-3'

GST-Tv-R2:
                                        [SEQ ID NO: 3]
5'-ATAATAGGATCCGCCCTGAAAGTACAGGTTCTC-3'
``` and PrimeStar GXL DNA Polymerase. Template DNA 0.5 μL, 5× Buffer 10 μL, 2.5 mM dNTP solution 4 μL, 10 μM primer solution each 1.5 μL, PrimeStar GXL DNA Polymerase 1 μL, and sterilized distilled water 31.5 μL were mixed. After a treatment at 98° C. for 1 min, the PCR reaction was started with 25 repeats of a treatment at 98° C. for 10 seconds, at 65° C. for 5 seconds, and at 72° C. for 25 seconds, followed by a treatment at 72° C. for 1 min.

The obtained PCR product was electrophoresed on agarose gel (1%), and an about 0.3 kbp DNA fragment containing a part of GST gene was recovered from the gel. The recovered DNA fragment was cleaved with restriction enzymes Swa I (New England Biolabs) and Bam HI (Takara Bio Inc.), and inserted into the Swa I/Bam HI site of pGEX6P1 to prepare an expression vector pGEX7V1.

(2) Cloning of Human LSD1 (AOF2) Gene

Human LSD1 gene was cloned by PCR method using brain cDNA Library (Takara Bio Inc.) as a template, two primers

```
hLSD1-NheI-ko-F:
                                        [SEQ ID NO: 4]
5'-TATTATGCTAGCGCCACCATGTTATCTGGGAAGAAGGCGGCAGC-3' hLSD1-St-NotI-R:
                                        [SEQ ID NO: 5]
5'-TATTATGCGGCCGCTCACATGCTTGGGGACTGCTGTGC-3'
``` and Pyrobest DNA Polymerase (Takara Bio Inc.). Template DNA 0.5 μL, 10× Buffer 5 μL, 2.5 mM dNTP solution 4 μL, 10 μM primer solution each 2.5 μL, Pyrobest DNA Polymerase 0.5 μL, and sterilized distilled water 34 μL were mixed. After a treatment at 98° C. for 1 min, the PCR reaction was started with repeats of a treatment at 98° C. for 10 seconds, at 68° C. for 5 seconds, and at 72° C. for 2.5 min, followed by a treatment at 72° C. for 1 min. The obtained PCR product was electrophoresed on agarose gel (1%), and an about 2.5 kbp DNA fragment containing human LSD1 gene was recovered from the gel. The recovered DNA fragment was cleaved with restriction enzymes Nhe I and Not I (Takara Bio Inc.), and inserted into the Nhe I/Not I site of pcDNA3.1 (+) (Invitrogen) to prepare an expression plasmid pcDNA3.1/hLSD1.

(3) Construction of Expression Plasmid for Human LSD1 (171-852) in *Escherichia coli*

A plasmid for expression of human LSD1(171-852) in *Escherichia coli* was produced by PCR method using pcDNA3.1/hLSD1 as a template, two primers

```
hLSD1-171aa-Bgl2-F:
                                        [SEQ ID NO: 6]
5'-TATTATAGATCTCCATCGGGTGTGGAGGGCGCA-3' hLSD1-St-NotI-R:
                                        [SEQ ID NO: 5]
5'-TATTATGCGGCCGCTCACATGCTTGGGGACTGCTGTGC-3'
``` and PrimeStar MAX DNA Polymerase (Takara Bio Inc.). Template DNA 1 μL, 2× Enzyme PreMix 25 μL, 10 μM primer solution each 1.5 μL, and sterilized distilled water 21 μL were mixed. After a treatment at 98° C. for 1 min, the PCR reaction was started with 25 repeats of a treatment at 98° C. for 10 seconds and at 68° C. for 10 seconds, followed by a treatment at 72° C. for 1 min. The obtained PCR product was electrophoresed on agarose gel (1%), and an about 2 kbp DNA fragment containing human LSD1(171-852) gene was recovered from the gel. The recovered DNA fragment was cleaved with restriction enzymes Bgl II and Not I (Takara Bio Inc.), and inserted into the Bam HI/Not I site of pGEX7V1 to prepare expression plasmid pGEX7V1/GST-hLSD1(171-852).

(4) Preparation of LSD1

*Escherichia coli* C43(DE3) pLysS was transformed with the expression plasmid pGEX7V1/GST-hLSD1(171-852) prepared in (3). The obtained recombinant *Escherichia coli* was inoculated in a TB medium (1.2% tryptone, 2.4% yeast extract, 0.4% glycerol, 0.5% glucose, 17 mM potassium dihydrogen phosphate and 72 mM dipotassium hydrogen phosphate) added with 100 mg/L ampicillin and 30 mg/L chloramphenicol, and cultured at 37° C. When the turbidity reached 600 Klett units, the culture temperature was changed to 16° C., IPTG having a final concentration of 0.5 mM was added to induce expression, and the cells were cultured further for 21 hr. The culture medium was centrifuged at 9,000 g for 10 min, and *Escherichia coli* pellets were recovered.

*Escherichia coli* pellets in 9 L of the culture medium were suspended in 1340 mL of an extraction buffer (PBS, 5%(V/V) Glycerol), and 6700 units of Benzonase (Merck) were added. Using Branson ultrasonic disintegrator, the suspension was disrupted by ultrasonication for 3 min, and centrifuged at 33,000 g for 20 min, and the supernatant was recovered. To the supernatant was added 5 M NaCl solution to a final concentration of 0.15 M, and the mixture was applied to two GSTrap 4B 5 mL columns (GE Healthcare) equilibrated in advance with PBS, 0.15 M NaCl, 5%(V/V) Glycerol (Buffer A), and the columns were each washed with 25 mL of Buffer A. GST-hLSD1(171-852) was eluted from each column with 20 mL of 0.1 M Tris (pH 8.0), 10 mM GSH, 0.15 M NaCl, 5%(V/V) Glycerol. The eluate (14 mL) containing GST-hLSD1(171-852) was applied to HiLoad 26/60 Superdex 200 pg column (GE Healthcare) equilibrated with Buffer A, and eluted with 300 mL of Buffer A. The fraction containing GST-hLSD1(171-852) was concentrated to 9 mL with AmiconUltra 15 (Japan Millipore) having a molecular weight cutoff of 30K to give purified GST-hLSD1(171-852). 1 mg of His-TEV protease was added relative to about 36 mg of GST-hLSD1(171-852), and the mixture was treated with 50 mM Tris (pH 8.0), 0.5 mM EDTA, 1 mM DTT at 4° C. for 16 hr to cleave the GST tag. The reaction mixture after the cleavage reaction was applied to GSTrap 4B 5 mL column (GE Healthcare) equilibrated in advance with Buffer A, and a flow-through fraction containing hLSD1(171-852) free of GST tag was recovered. It was concentrated to 9 mL with AmiconUltra 15 (Japan Millipore), and purified with HiLoad 26/60 Superdex 200 pg column (GE Healthcare) equilibrated with Buffer A again to give hLSD1(171-852) purified product. The protein concentration of hLSD1(171-852) was measured by BCA Protein Assay Kit (Thermo Fisher Scientific K.K.) using bovine serum albumin as the standard.

(5) Measurement of LSD1 Inhibitory Activity

A test compound dissolved in 2.5% DMSO was added by 4 μL to 3 μL reaction solution (50 mM Tris-HCl (pH 8.0), 0.1% BSA, 1 mM DTT) containing 2.8 ng of LSD1, and the mixture was reacted at room temperature for 15 min. Biotin-histone H3 mono methylated K4 peptide solution (NH2-ART(me-K)QTARKSTGGKAPRKQLAGGK(Biotin)-CONH2) (3.3 μM) was added by 3 μL to start the reaction. After reaction at room temperature for 20 min, 1 mM 2-PCPA solution (5 μL) was added to terminate the reaction. A detection solution (800 mM potassium fluoride, 0.1% BSA) containing europium-labeled antihistone H3 antibody (Wako Pure Chemical Industries, Ltd.) and Streptavidin-XL665 (Cisbio) was further added by 5 μL, and the mixture was left standing for 60 min. A time-resolved fluorescence (excitation 320 nm, emission 615 nm, 665 nm) was measured by Envision (PerkinElmer). The LSD1 inhibitory rate (%) of the test compound was calculated by the following formula.

inhibitory rate (%)=(1−(test compound count−blank)÷(control−blank)×100

The count of the LSD1 enzyme reaction mixture under compound non-addition conditions is indicated as control, and the count under compound non-addition and LSD1 enzyme non-addition conditions is indicated as blank. The results are shown in Table 2.

Experimental Example 2

(1) Measurement of MAO-A Inhibitory Activity

The MAO-A inhibitory activity evaluation described below followed the protocol of MAO-Glo (registered trademark) Assay of Promega KK.

A test compound dissolved in 4% DMSO was added by 12.5 μL to 25 μL reaction solution (100 mM HEPES (pH 7.5), 5% glycerol) containing 400 ng of MAO-A enzyme (Sigma-Aldrich Co. LLC.), and the mixture was reacted at room temperature for 10 min. MAO substrate (Promega KK) (160 μM) was added by 12.5 μL to start the reaction. After reaction at room temperature for 60 min, Luciferine detection reagent (Promega KK) (50 μL) was added to terminate the reaction. After reaction at room temperature for 20 min with stirring, the luminescence was measured by Envision (PerkinElmer). The MAO-A inhibitory rate (%) of the test compound was calculated by the following formula.

inhibitory rate (%)=(1−(test compound count−blank)÷(control−blank)×100

The count of the MAO-A enzyme reaction mixture under compound non-addition conditions is indicated as control, and the count under compound non-addition and MAO-A enzyme non-addition conditions is indicated as blank. The results are shown in Table 2.

(2) Measurement of MAO-B Inhibitory Activity

The MAO-B inhibitory activity evaluation described below followed the protocol of MAO-Glo (registered trademark) Assay of Promega KK.

A test compound dissolved in 4% DMSO was added by 12.5 μL to 25 μL reaction solution (100 mM HEPES (pH 7.5), 5% glycerol, 10% DMSO) containing 400 ng of MAO-B enzyme (Sigma-Aldrich Co. LLC.), and the mixture was reacted at room temperature for 10 min. MAO substrate (Promega KK) (16 μM) was added by 12.5 μL to start the reaction. After reaction at room temperature for 60 min, Luciferine detection reagent (Promega KK) (50 μL) was added to terminate the reaction. After reaction at room temperature for 20 min with stirring, the luminescence was measured by Envision (PerkinElmer). The MAO-B inhibitory rate (%) of the test compound was calculated by the following formula.

inhibitory rate (%)=(1−(test compound count−blank)÷(control−blank)×100

The count of the MAO-B enzyme reaction mixture under compound non-addition conditions is indicated as control, and the count under compound non-addition and MAO-B enzyme non-addition conditions is indicated as blank. The results are shown in Table 2.

TABLE 2

| Ex. No. | LSD1 IC$_{50}$ value (μM) | MAO-A IC$_{50}$ value (μM) | MAO-B IC$_{50}$ value (μM) |
|---|---|---|---|
| 1 | <0.1 | 3.8 | 9.7 |
| 2 | 0.2 | 9.3 | >10 |
| 3 | <0.1 | 4.4 | 9 |
| 4 | 0.24 | >10 | >10 |
| 5 | <0.1 | 7.7 | >10 |
| 6 | <0.1 | >10 | >10 |
| 7 | <0.1 | 5.6 | >10 |
| 8 | <0.1 | 5.8 | >10 |
| 9 | 0.28 | >10 | >10 |
| 10 | 0.14 | 3.3 | >10 |
| 11 | 0.15 | 2.4 | >10 |
| 12 | <0.1 | 4.7 | >10 |
| 13 | <0.1 | >10 | >10 |
| 14 | <0.1 | >10 | >10 |
| 15 | <0.1 | 6 | >10 |
| 16 | <0.1 | 4.7 | >10 |
| 17 | <0.1 | >10 | >10 |
| 18 | <0.1 | 2.6 | >10 |
| 19 | <0.1 | >10 | 3.2 |
| 20 | <0.1 | >10 | >10 |
| 21 | <0.1 | >10 | >10 |
| 22 | 0.41 | 3.6 | 2.6 |
| 23 | <0.1 | >10 | >10 |
| 24 | <0.1 | >10 | >10 |
| 25 | <0.1 | >10 | >10 |
| 26 | <0.1 | 9.2 | >10 |
| 28 | <0.1 | 3.5 | >10 |
| 29 | 0.11 | 5.2 | >10 |
| 30 | 0.58 | 1.7 | >10 |
| 31 | <0.1 | >10 | >10 |
| 32 | <0.1 | >10 | >10 |
| 33 | <0.1 | >10 | >10 |
| 34 | 0.19 | >10 | >10 |
| 35 | 0.13 | 1.3 | >10 |
| 36 | <0.1 | 4.6 | >10 |
| 38 | <0.1 | 9.1 | >10 |
| 39 | <0.1 | >10 | >10 |
| 40 | <0.1 | — | — |
| 41 | 0.11 | 5.8 | 5.1 |
| 42 | <0.1 | >10 | >10 |
| 43 | 0.11 | 3.3 | 4.7 |
| 44 | <0.1 | >10 | 9.3 |
| 45 | 0.29 | >10 | >10 |
| 46 | <0.1 | >10 | >10 |
| 47 | 0.19 | 1.8 | 1.7 |
| 48 | <0.1 | 4.3 | 3.8 |
| 49 | <0.1 | >10 | >10 |
| 50 | <0.1 | >10 | >10 |
| 51 | 0.1 | >10 | >10 |
| 52 | 0.16 | >10 | >10 |
| 53 | 0.23 | 4 | 3.4 |
| 54 | <0.1 | 0.85 | 1.5 |
| 55 | 0.13 | >10 | >10 |
| 56 | 0.26 | >10 | >10 |
| 57 | 0.48 | >10 | >10 |
| 58 | 0.41 | >10 | >10 |
| 59 | <0.1 | 7.1 | >10 |
| 60 | 1.9 | >10 | >10 |
| 61 | <0.1 | 2.2 | 3.3 |
| 62 | <0.1 | >10 | >10 |
| 63 | <0.1 | >10 | >10 |
| 64 | 0.2 | 8.5 | >10 |
| 65 | <0.1 | 8.6 | 9.6 |
| 66 | <0.1 | >10 | >10 |
| 67 | <0.1 | >10 | >10 |
| 68 | <0.1 | >10 | >10 |
| 69 | <0.1 | >10 | >10 |
| 70 | <0.1 | >10 | >10 |
| 71 | <0.1 | >10 | >10 |
| 72 | <0.1 | 3.1 | >10 |
| 73 | <0.1 | 10.0 | 8.1 |
| 74 | <0.1 | >10 | >10 |
| 75 | <0.1 | >10 | >10 |
| 76 | <0.1 | >10 | >10 |
| 77 | <0.1 | 9.9 | >10 |
| 78 | <0.1 | >10 | >10 |
| 79 | <0.1 | >10 | >10 |
| 80 | <0.1 | >10 | >10 |
| 81 | <0.1 | >10 | >10 |
| 82 | <0.1 | >10 | >10 |
| 83 | <0.1 | >10 | >10 |
| 84 | <0.1 | >10 | >10 |
| 85 | <0.1 | 9.1 | 4.9 |
| 86 | 1.0 | >10 | >10 |
| 87 | <0.1 | >10 | >10 |
| 88 | <0.1 | >10 | >10 |
| 89 | 0.1 | >10 | >10 |
| 90 | <0.1 | >10 | >10 |
| 91 | <0.1 | >10 | >10 |
| 92 | <0.1 | 7.9 | >10 |
| 93 | <0.1 | >10 | >10 |
| 94 | <0.1 | >10 | >10 |
| 95 | <0.1 | >10 | >10 |
| 96 | <0.1 | >10 | >10 |
| 97 | <0.1 | >10 | >10 |
| 98 | <0.1 | >10 | >10 |
| 99 | <0.1 | >10 | >10 |
| 100 | <0.1 | >10 | >10 |
| 101 | <0.1 | >10 | >10 |
| 102 | 0.2 | >10 | >10 |
| 103 | <0.1 | >10 | >10 |
| 104 | <0.1 | >10 | >10 |
| 105 | <0.1 | >10 | >10 |
| 106 | <0.1 | >10 | >10 |
| 107 | <0.1 | 4.3 | >10 |
| 108 | <0.1 | >10 | >10 |
| 109 | <0.1 | >10 | >10 |
| 110 | <0.1 | >10 | >10 |
| 111 | <0.1 | >10 | >10 |
| 112 | <0.1 | >10 | >10 |
| 113 | <0.1 | 5.7 | >10 |
| 114 | <0.1 | >10 | >10 |
| 115 | <0.1 | >10 | >10 |
| 116 | 1.8 | >10 | >10 |
| 117 | <0.1 | 7.5 | >10 |
| 118 | 0.1 | >10 | >10 |

TABLE 2-continued

| Ex. No. | LSD1 IC$_{50}$ value (μM) | MAO-A IC$_{50}$ value (μM) | MAO-B IC$_{50}$ value (μM) |
|---|---|---|---|
| 119 | <0.1 | 0.1 | >10 |
| 120 | 1.6 | >10 | >10 |
| 121 | <0.1 | >10 | >10 |
| 122 | <0.1 | >10 | >10 |
| 123 | <0.1 | 5.0 | >10 |
| 124 | <0.1 | >10 | >10 |
| 125 | <0.1 | 2.5 | >10 |
| 126 | <0.1 | >10 | >10 |
| 127 | 0.1 | >10 | >10 |
| 128 | <0.1 | 5.3 | >10 |
| 129 | <0.1 | 8.2 | >10 |
| 130 | <0.1 | >10 | >10 |
| 131 | <0.1 | >10 | >10 |
| 132 | <0.1 | 8.3 | >10 |
| 133 | <0.1 | >10 | >10 |
| 134 | <0.1 | >10 | >10 |
| 135 | 0.1 | >10 | >10 |
| 136 | <0.1 | >10 | >10 |
| 137 | <0.1 | 4.2 | >10 |
| 138 | <0.1 | >10 | >10 |
| 139 | <0.1 | 8.2 | >10 |
| 140 | <0.1 | >10 | >10 |
| 141 | <0.1 | >10 | >10 |
| 142 | 0.1 | >10 | >10 |
| 143 | <0.1 | 4.5 | >10 |
| 144 | 0.2 | >10 | >10 |
| 145 | <0.1 | >10 | >10 |
| 146 | <0.1 | 6.7 | >10 |
| 147 | <0.1 | >10 | >10 |
| 148 | <0.1 | 8.3 | >10 |
| 149 | <0.1 | >10 | >10 |
| 150 | <0.1 | >10 | >10 |
| 151 | <0.1 | >10 | >10 |
| 152 | <0.1 | >10 | >10 |
| 153 | <0.1 | >10 | >10 |
| 154 | <0.1 | >10 | >10 |
| 155 | <0.1 | >10 | >10 |
| 156 | <0.1 | >10 | >10 |
| 157 | 0.1 | >10 | >10 |
| 158 | <0.1 | >10 | >10 |
| 159 | <0.1 | >10 | >10 |
| 160 | <0.1 | 5.1 | >10 |
| 161 | <0.1 | 4.1 | >10 |
| 162 | <0.1 | 2.1 | >10 |
| 163 | 0.1 | >10 | >10 |
| 164 | 0.2 | >10 | >10 |
| 165 | <0.1 | >10 | >10 |
| 166 | <0.1 | >10 | >10 |

As shown in Table 2, the compound of the present invention has a superior LSD1 inhibitory activity. In addition, the MAO-A inhibitory activity and MAO-B inhibitory activity of the compound of the present invention are low, and the compound of the present invention has a selective LSD1 inhibitory activity.

Experimental Example 3

Tumor Growth Suppressive Effect Test Using HEL92.1.7 Acute Myeloid Leukemia Cell 6-Week-old SCID mice were subcutaneously transplanted with $5 \times 10^6$ cells/100 μL of HEL92.1.7 acute myeloid leukemia cells, and the mice were grouped according to the body weight and tumor volume after 15 to 17 days. Vehicle (0.5% methylcellulose) or compound A, compound B or compound C was administered orally to mice (5 mice per group). The administration was once per day and performed continuously during the dosing period. Setting the change in tumor volume of the vehicle-treated group as 100%, the change rate in tumor volume of the compound-treated group (T/C %) was calculated. The tumor volume was determined by measuring the long diameter m and short diameter of the tumor with a vernier caliper, and calculating by the following calculation formula: (long diameter)×(short diameter)×(short diameter)/2. The results are shown in Table 3.

Compound A: N-(4-{trans-2-[(cyclopropylmethyl)amino]cyclopropyl}phenyl)biphenyl-4-carboxamide hydrochloride Compound B: N-(4-{trans-2-[(1-methylpiperidin-4-yl)amino]cyclopropyl}phenyl)-3-(trifluoromethyl)benzamide dihydrochloride Compound C: N-(4-{trans-2-[(cyclopropylmethyl)amino]cyclopropyl}phenyl)-1H-pyrazole-4-carboxamide hydrochloride

TABLE 3

| compound | T/C (%) | dose (mg/kg) | dosing period (days) |
|---|---|---|---|
| A | 12.54 | 30 mg/kg | 14 |
| B | −8.08 | 30 mg/kg | 7 |
| C | 46.42 | 30 mg/kg | 14 |

As shown in Table 3, the compound of the present invention has a superior antitumor growth activity.

Formulation Example 1

A medicament containing the compound of the present invention as an active ingredient can be produced, for example, according to the following formulation.

1. Capsule

| (1) | compound obtained in Example 1 | 10 mg |
|---|---|---|
| (2) | lactose | 90 mg |
| (3) | crystalline cellulose | 70 mg |
| (4) | magnesium stearate | 10 mg |
| | 1 capsule | 180 mg |

The total amount of the above-mentioned (1), (2) and (3) and 5 mg of (4) are blended, and the mixture is granulated. Thereto is added the remaining 5 mg of (4), and the whole is sealed in a gelatin capsule.

2. Tablet

| (1) | compound obtained in Example 1 | 10 mg |
|---|---|---|
| (2) | lactose | 35 mg |
| (3) | cornstarch | 150 mg |
| (4) | crystalline cellulose | 30 mg |
| (5) | magnesium stearate | 5 mg |
| | 1 tablet | 230 mg |

The total amount of the above-mentioned (1), (2) and (3), mg of (4) and 2.5 mg of (5) are blended, and the mixture is granulated. Thereto are added the remaining 10 mg of (4) and 2.5 mg of (5), and the mixture is compression-molded to give a tablet.

Industrial Applicability

The compound of the present invention has a superior LSD1 inhibitory action, and is useful as a medicament such as a prophylactic or therapeutic agent for cancer, schizophrenia, Alzheimer's disease, Parkinson's disease and Huntington's chorea, and the like.

This application is based on patent application No. 2011-174305 filed in Japan, the entire contents of which are incorporated by reference herein.

The invention claimed is:

1. N-(4-{trans-2-[(cyclopropylmethyl)amino]cyclopropyl}phenyl)biphenyl-4-carboxamide or a salt thereof.

2. N-(4-{trans-2-[(1-methylpiperidin-4-yl)amino]cyclopropyl}phenyl)-3-(trifluoromethy)benzamide or a salt thereof.

3. N-(4-{trans-2-[(cyclopropylmethy)amino]cyclopropyl}phenyl)-1H-pyrazole-4-carboxamide or a salt thereof.

4. A compound selected from the group consisting of
   (1) N-(4-{trans-2-[(cyclopropylmethyl)amino]cyclopropyl}-2-methylphenyl)benzamide,
   (2) N-(4-{trans-2-[(cyclopropylmethyl)amino]cyclopropyl}phenyl)-3-(trifluoromethoxy)benzamide,
   (3) N-(4-{trans-2-[(cyclopropylmethyl)amino]cyclopropyl}phenyl)benzamide,
   (4) N-(4-{trans-2-[(cyclopropylmethyl)amino]cyclopropyl}phenyl)-cyclohexanecarboxamide,
   (5) N-(4-{trans-2-[(1,1-dioxidotetrahydro-2H-thiopyran-4-yl)amino]cyclopropyl}phenyl)-3-(trifluoromethyl)benzamide,
   (6) N-(4-{trans-2-[(cyclopropylmethyl)amino]cyclopropyl}phenyl)-1,3-dimethyl-1H-pyrazole-5-carboxamide,
   (7) N-(4-{trans-2-[(cyclopropylmethyl)amino]cyclopropyl}phenyl)-1,5-dimethyl-1H-pyrazole-3-carboxamide,
   (8) N-(4-{trans-2-[(cyclopropylmethyl)amino]cyclopropyl}phenyl)-1-methyl-3-(trifluoromethyl)-1H-pyrazole-4-carboxamide,
   (9) N-(4-{trans-2-[(cyclopropylmethyl)amino]cyclopropyl}phenyl)-1-methyl-5-(trifluoromethyl)-1H-pyrazole-4-carboxamide, and
   (10) N-(4-{trans-2-[(cyclopropylmethyl)amino]cyclopropyl}phenyl)-1-methyl-1H-pyrazole-4-carboxamide,
or a salt thereof.

5. A medicament comprising: an effective amount of the compound according to claim 4 or a salt thereof; and a pharmaceutically acceptable carrier.

6. The medicament according to claim 5, which is a therapeutic agent for cancer.

7. The medicament according to claim 5, which is an LSD1 inhibitor.

8. The medicament according to claim 5, which is a therapeutic agent for schizophrenia, Alzheimer's disease, Parkinson's disease or Huntington's chorea.

9. A method for a treatment of schizophrenia, Alzheimer's disease, Parkinson's disease or Huntington's chorea, comprising administering an effective amount of the compound according to claim 4 or a salt thereof to a mammal in need thereof.

10. A method of inhibiting LSD1, comprising administering an effective amount of the compound according to claim 4 or a salt thereof to a mammal.

11. A method for a treatment of cancer, comprising administering an effective amount of the compound according to claim 4 or a salt thereof to a mammal in need thereof.

12. The compound according to claim 4, which is N-(4-{trans-2-[(cyclopropylmethyl)amino]cyclopropyl}-2-methylphenyl)benzamide or a salt thereof.

13. The compound according to claim 4, which is N-(4-{trans-2-[(cyclopropylmethyl)amino]cyclopropyl}phenyl)-3-(trifluoromethoxy)benzamide or a salt thereof.

14. The compound according to claim 4 which is N-(4-{trans-2-[(cyclopropylmethyl)amino]cyclopropyl}phenyl)benzamide or a salt thereof.

15. The compound according to claim 4, which is N-(4-{trans-2-[(cyclopropylmethyl)amino]cyclopropyl}phenyl)cyclohexanecarboxamide or a salt thereof.

16. The compound according to claim 4, which is N-(4-{trans-2-[(1,1-dioxidotetrahydro-2H-thiopyran-4-yl)amino]cyclopropyl}phenyl)-3-(trifluoromethyl)benzamide or a salt thereof.

17. The compound according to claim 4, which is N-(4-{trans-2-[(cyclopropylmethyl)amino]cyclopropyl}phenyl)-1,3-dimethyl-1H-pyrazole-5-carboxamide or a salt thereof.

18. The compound according to claim 4, which is N-(4-{trans-2-[(cyclopropylmethyl)amino]cyclopropyl}phenyl)-1,5-dimethyl-1H-pyrazole-3-carboxamide or a salt thereof.

19. The compound according to claim 4, which is N-(4-{trans-2-[(cyclopropylmethyl)amino]cyclopropyl}phenyl)-1-methyl-3-(trifluoromethyl)-1H-pyrazole-4-carboxamide or a salt thereof.

20. The compound according to claim 4, which is N-(4-{trans-2-[(cyclopropylmethyl)amino]cyclopropyl}phenyl)-1-methyl-5-(trifluoromethyl)-1H-pyrazole-4-carboxamide or a salt thereof.

21. The compound according to claim 4, which is N-(4-{trans-2-[(cyclopropylmethyl)amino]cyclopropyl}phenyl)-1-methyl-1H-pyrazole-4-carboxamide or a salt thereof.

* * * * *

SEQUENCE LISTING

```
<160> NUMBER OF SEQ IDS NOS: 6

<210> SEQ ID NO 1
<211> LENGTH: 35
<212> TYPE: DNA
<213> ORGANISM: Artificial Sequence
<220> FEATURE:
<223> OTHER INFORMATION: primer

<400> SEQUENCE: 1
agaatcattt aaatggtgat catgtaaccc atcct                         35

<210> SEQ ID NO 2
<211> LENGTH: 44
<212> TYPE: DNA
<213> ORGANISM: Artificial Sequence
<220> FEATURE:
<223> OTHER INFORMATION: primer

<400> SEQUENCE: 2
cgccctgaaa gtacaggttc tcatccgatt ttggaggatg gtcg               44

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
ataataggat ccgccctgaa agtacaggtt ctc                           33

<210> SEQ ID NO 4
<211> LENGTH: 44
<212> TYPE: DNA
<213> ORGANISM: Artificial Sequence
<220> FEATURE:
<223> OTHER INFORMATION: primer

<400> SEQUENCE: 4
tattatgcta gcgccaccat gttatctggg aagaaggcgg cagc               44

<210> SEQ ID NO 5
<211> LENGTH: 38
<212> TYPE: DNA
<213> ORGANISM: Artificial Sequence
<220> FEATURE:
<223> OTHER INFORMATION: primer

<400> SEQUENCE: 5
tattatgcgg ccgctcacat gcttggggac tgctgtgc                      38

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
tattatagat ctccatcggg tgtggagggc gca                           33
```